United States Patent
Barraja et al.

(10) Patent No.: US 12,410,164 B2
(45) Date of Patent: Sep. 9, 2025

(54) HETEROCYCLIC COMPOUNDS AND MEDICAL USE THEREOF

(71) Applicants: FONDAZIONE TELETHON, Rome (IT); UNIVERSITA DEGLI STUDI DI PALERMO, Palermo (IT)

(72) Inventors: Paola Barraja, Palermo (IT); Ilaria Musante, Rome (IT); Luis Juan Vicente Galietta, Rome (IT); Virginia Spano', Palermo (IT)

(73) Assignees: FONDAZIONE TELETHON, Rome (IT); UNIVERSITA DEGLI STUDI DI PALERMO, Palermo (IT)

( * ) Notice: Subject to any disclaimer, the term of this patent is extended or adjusted under 35 U.S.C. 154(b) by 1035 days.

(21) Appl. No.: 17/295,728

(22) PCT Filed: Nov. 20, 2019

(86) PCT No.: PCT/EP2019/081988
§ 371 (c)(1),
(2) Date: May 20, 2021

(87) PCT Pub. No.: WO2020/104558
PCT Pub. Date: May 28, 2020

(65) Prior Publication Data
US 2022/0002295 A1    Jan. 6, 2022

(30) Foreign Application Priority Data
Nov. 20, 2018   (IT) .................. 102018000010466

(51) Int. Cl.
| | | |
|---|---|---|
| *C07D 471/04* | (2006.01) | |
| *C07D 471/14* | (2006.01) | |
| *C07D 487/04* | (2006.01) | |

(52) U.S. Cl.
CPC ......... *C07D 471/04* (2013.01); *C07D 471/14* (2013.01); *C07D 487/04* (2013.01)

(58) Field of Classification Search
CPC ... C07D 471/04; C07D 471/14; C07D 487/04
See application file for complete search history.

(56) References Cited

U.S. PATENT DOCUMENTS

2011/0257223 A1   10/2011  Goor et al.
2012/0129884 A1*   5/2012  Dall'Acqua ....... A61K 31/4745
                                                                514/300

FOREIGN PATENT DOCUMENTS

WO       2011/013159 A1     2/2011

OTHER PUBLICATIONS

Cleveland Clinic, Cystic Fibrosis, obtained from https://my.clevelandclinic.org/health/diseases/9358-cystic-fibrosis#overview accessed on Jun. 20, 2024 (Year: 2024).*
Ceders-Sinai, Chronic Pancreatitis, obtained from https://www.cedars-sinai.org/health-library/diseases-and-conditions/c/chronic-pancreatitis.html on Jun. 21, 2024 (Year: 2024).*
BrightFocus, Prevention of Age Related Macular Degeneration, obtained from https://www.brightfocus.org/macular/article/prevention-age-related-macular on Jun. 21, 2024 (Year: 2024).*
American Lung Association, Treating and Preventing Aspergillosis , obtained from https://www.lung.org/lung-health-diseases/lung-disease-lookup/aspergillosis/treatment#:~:text=Though%20it%20can%20be%20difficult,drugs%20as%20a%20preventive%20measure on Jun. 20, 2024 (Year: 2024).*
Donate et al. (Expert review of clinical immunology. 2014. 10(4): 469-481. (Year: 2014).*
Kogure, Yasunori, and Keisuke Kataoka. Cancer science 108.9 (2017): 1719-1725. (Year: 2017).*
Spano, Virginia; et al, "Pyrrolo[3',2':6,7]cyclohepta[1,2-b]pyridines with potent photo-antiproliferative activity", European Journal of Medicinal Chemistry, Editions Scientifique Elsevier, Paris, FR, vol. 128, Feb. 7, 2017 (Feb. 7, 2017), pp. 300-318.
Barraja, P; et al, "Synthesis of pyrrolo[3,2-h]quinolinones with good photochemotherapeutic activity and no DNA damage", BIOORGANIC & Medicinal Chemistry, Jul. 1, 2010 (Jul. 1, 2010), vol. 18, No. 13, pp. 4830-4843.
ISA/EP, "PCT International Search Report and Written Opinion", issued in connection with PCT International Application No. PCT/EP2019/081988 and mailed May 12, 2020 (10 pages).

* cited by examiner

*Primary Examiner* — Joseph K McKane
*Assistant Examiner* — Quincy McKoy
(74) *Attorney, Agent, or Firm* — Lucas & Mercanti, LLP

(57) ABSTRACT

The present invention relates to heterocyclic nitrogen compounds, use thereof as a medicament and pharmaceutical compositions thereof. Furthermore, the invention provides combinations of compounds of general formula (I) with therapeutic agents, such as correctors, potentiators and amplifiers of dysfunctional proteins.

19 Claims, 5 Drawing Sheets

HETEROCYCLIC COMPOUNDS AND MEDICAL USE THEREOF

CROSS-REFERENCE TO RELATED APPLICATIONS

Figure 1:
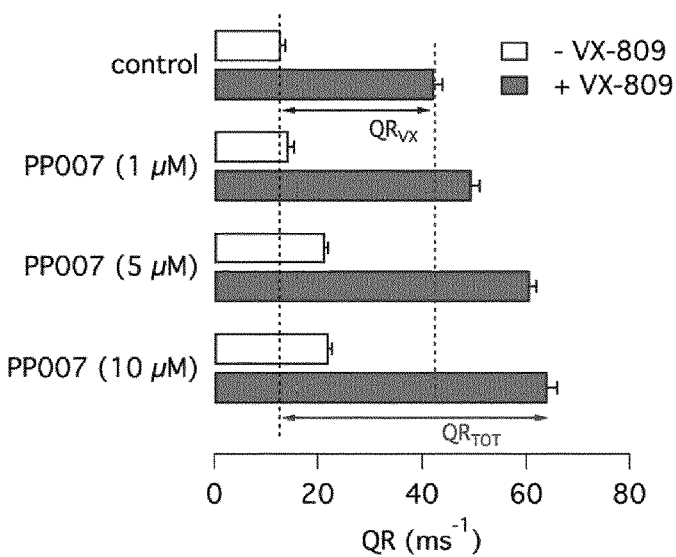

This application is a 371 of PCT/EP2019/081988, filed Nov. 20, 2019, which claims the benefit of Italian Patent Application No. 102018000010466, filed Nov. 20, 2018.

FIELD OF THE INVENTION

The present invention relates to heterocyclic nitrogen compounds, use thereof as a medicament and pharmaceutical compositions thereof. Furthermore, the invention provides combinations of compounds of general formula (I) with therapeutic agents, such as correctors, potentiators, and amplifiers of dysfunctional proteins.

BACKGROUND OF THE INVENTION

Cystic fibrosis (CF), one of the most frequent genetic diseases, is caused by mutations in the Cystic Fibrosis Transmembrane Conductance Regulator (CFTR) protein (Elborn J S. Lancet 2016, 388, 2519-2531). CFTR (Accession number NCBI: NP_000483; version: NP_000483.3), a member of the ABC-transporter protein family, is a channel permeable to chloride and other anions expressed in the apical membrane of epithelial cells of the respiratory, gastrointestinal and reproductive tract. In CF, mutations in the CFTR gene impair protein function. The result is the alteration of chloride and bicarbonate secretion with production and stagnation of a very dense mucus, resulting in damage to various organs, mainly lungs and pancreas. In the lungs, the problem is mostly the appearance and progressive persistence of respiratory infections, leading to irreversible damage to the airways caused by said infections and the consequent inflammation. In addition to respiratory dysfunction, mutations in the CFTR gene have an impact on other organs such as pancreas, intestine, biliary tract, vas deferens.

The known mutations of the CFTR gene are divided into six classes: class I comprises mutations that insert a premature stop codon (premature termination codon, PTC) resulting in production of a truncated protein, e.g. W1281X, R553X, G542X. Class II comprises missense mutations and deletions leading to altered folding of the protein, with consequent altered positioning on the cell surface, e.g. F508del, N1303K; class III comprises missense mutations leading to defective channel opening, known as gating mutations, e.g. G551D, G551S, G1349D; class IV comprises missense mutations leading to changes in the structure of the channel, which forms a distort pore with consequent defective movement of the ions, known as a conductance defect, e.g. R117H, R334W, R347P. Class V comprises missense mutations that cause RNA splicing alterations with production of aberrant mRNA molecules and therefore defect of synthesis of a functional CFTR protein, e.g. 2789+5G>A, 3849+10 kb C>T. Class VI comprises different types of mutations that increase protein turnover at the cell surface: although the protein is expressed, it is unstable hence it is removed and degraded (e.g. 120del123, Q1412X).

In addition to CF, mutations in the CFTR gene and/or malfunctioning of the chloride-permeable channel are implicated in other pathologies, e.g. congenital bilateral absence of vas deferens (CBAVD), polycystic kidney syndrome, acute, chronic and/or recurrent pancreatitis, disseminated bronchiectasis, asthma, allergic pulmonary aspergillosis, smoking-related lung diseases such as chronic obstructive pulmonary disease, dry eye syndrome, Sjogren's syndrome, chronic sinusitis, cholestatic jaundice (Sloane et al. 2012, PLoS ONE 7, e39809.doi: 10.1371/journal.pone.0039809; Bombieri et al. 2011, J Cyst Fibros 2011, 10 Suppl 2, S86-S102; Albert et al. 2008, Clinical Respiratory Medicine, Third Ed., Mosby Inc.; Levin et al. 2005, Invest Ophthalmol Vis Sci 46, 1428-1434; Froussard 2007, Pancreas 35, 94-95; Son et al. 2017, J Med Chem 60, 2401-2410).

Loss-of-function of CFTR can occur in different ways depending on the type of mutation (Elborn J S. Lancet 2016, 388, 2519-2531). For example the F508del mutation, which is the most frequent among CF patients, affects a critical region of the CFTR protein causing multiple problems: intrinsic instability of the NBD1 domain (nucleotide binding domain 1) and alteration of the interaction between NBD1 and another domain of same protein called ICL4 (Lukacs G L, Verkman A S. Trends Mol Med 2012, 18, 81-91; Okiyoneda T, et al. Nat Chem Biol 2013, 9, 444-454). The F508del-CFTR protein is therefore recognized as defective by cellular quality control systems and degraded early.

The defect caused by F508del can be partially counteracted by molecules called "correctors" such as the compound VX-809, developed by Vertex Pharmaceuticals.

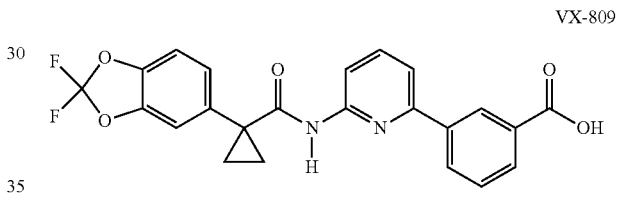

VX-809

The effect of VX-809 (also known as lumacaftor) on CFTR function can be increased through co-treatment with a potentiator compound such as VX-770 (ivacaftor) which stimulates the CFTR channel activity.

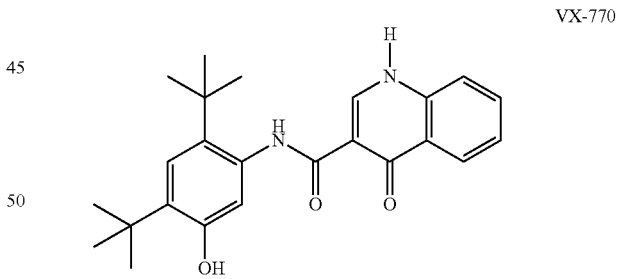

VX-770

However, the combined treatment VX-770-VX-809 (a drug known as Orkambi) does not produce a marked effect in CF patients (Wainwright C E, et al. N Engl J Med 2015, 373, 220-231). This is due to the fact that VX-809 only partially corrects the stability and maturation defect caused by F508del (Okiyoneda T, et al. Nat Chem Biol 2013, 9, 444-454). In particular, it is considered that VX-809 acts on the interaction defect between NBD1 and ICL4, but not on the instability of NBD1. Therefore, only the combination of VX-809 (or similar compound) with a second type of corrector provided with a complementary mechanism can generate a significant effect from a therapeutic point of view. In this respect, a triple combination including the potentiator VX-770, VX-661 (a corrector acting similarly to VX-809), and VX-445 (a new type of corrector, commercial name Elexacaftor) has recently shown efficacy on patients with a single or double F508del mutation (Keating D, et al. N Engl J Med 2018, 379, 1612-1620).

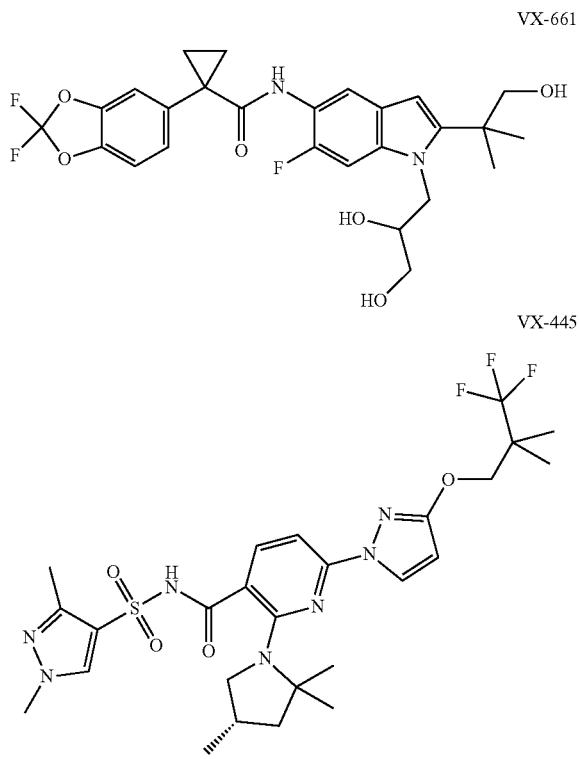

Combinational pharmacotherapy is an already established concept for the correction of the basic defect in CF (Veit G, et al. Mol Biol Cell 2016, 27, 424-433). Treatment with combinations of compounds that act at different levels on the stability, maturation and function of the CFTR protein can have a synergistic effect on the end-result, i.e. the CFTR-mediated secretion of chloride and bicarbonate.

There is evidence that some CFTR pharmacological correctors are effective in vitro on other proteins with congenital defects of folding and stability (Sampson H M, et al. Orphanet J Rare Dis. 2013, 8, 11), hence said compounds are useful in correcting diseases due to defects in protein folding, degradation, and/or maturation where the mutant protein is recognized by the quality control systems, retained in the endoplasmic reticulum (ER), and degraded by the proteasome. For example, class 4 and 5 correctors (corr-4a, corr-4c, corr-4d, corr-5a, corr-5c) described below (Pedemonte N, et al. J Clin Invest. 2005, 115, 2564-2571) have proved to be active on mutated forms of the alpha-sarcoglycan protein that cause muscular dystrophy of the cinguli (Carotti M, et al. Hum Mol Genet. 2018, 27, 969-984). In addition to VX-809 and VX-770, there are several compounds that act as correctors and potentiators of the mutated CFTR protein (Galietta L J. Paediatr Drugs 2013, 15, 393-402).

These include furocoumarins, tricyclic aromatic compounds of natural or synthetic origin that have various types of biological activity: upon photoactivation with light of a suitable wavelength, they can covalently bind the pyrimidine DNA bases and find application in the treatment of hyperproliferative and/or autoimmune dermatological disorders, such as psoriasis, vitiligo, or lymphomas (Dall'Acqua F, et al. CRC Handbook of Organic Photochemistry and Photobiology (2004) WM Hoorspool, F. Lenci, and CRC Press). Some furocoumarin derivatives, have been characterized as potentiators of the mutated CFTR protein and as anti-inflammatory agents (Devor D C, et al. Am J Physiol 1997, 272, C976-C988). In particular, 5-methoxypsoralene (5-MOP) and analogues thereof have shown the ability to inhibit the production of IL-8 induced by *Pseudomonas aeruginosa* (Nicolis E, et al., Int Immunopharmacol 2009, 9, 1411-1422). Among the angular isomers, the 4,6,4'-trimethylangelicin (TMA) emerged in different cell lines both as potent NF-cB inhibitor, and potentiator and corrector of CFTR (Tamanini A, et al. Am J Physiol 2011, 300, L380-L390; Favia M, et al. Am J Physiol 2014, 307, L48-L61).

Further tricyclic compounds with photosensitizing properties and antiproliferative activity are described in Spanò V, et al. Eur J Med Chem 2017, 128, 300-318, which describes pyrrolo[3',2':6,7]cyclohepta[1,2-b]pyridines.

Patent application WO 2011/013159 describes pyrrolo[3,2-h]quinoline compounds as photochemotherapeutic agents useful in the treatment of neoplastic diseases.

Despite the promising results obtained with triple combinations of compounds, there is a significant fraction of patients carrying the F508del mutation that do not respond well to the treatment (Keating D, et al. N Engl J Med 2018, 379, 1612-1620; Heijerman H G M, et al. Lancet 2019, pii: S0140-6736(19)32597-8). Furthermore, there is a need for compounds and combinations of compounds to treat patients carrying less common mutations that do not respond well to currently available therapies. Therefore, there is still need for additional pharmacological agents acting as correctors. These molecules may also be useful for other diseases involving ABC-transporters, other diseases (particularly other chronic respiratory diseases) involving altered CFTR function, and diseases involving misfolding, instability, and mistrafficking of mutant proteins.

SUMMARY OF THE INVENTION

The present invention is based on the finding that nitrogenated heterocyclic compounds of formula I as described below can act as correctors of members of the ABC-transporter protein family, such as CFTR. The compounds of the invention can advantageously rescue the function of malfunctioning members of the ABC-transporter protein family, such as F508del-CFTR. In particular, these compounds produce a remarkable synergistic effect if combined with other compounds such as the known corrector VX-809. Advantageously, compounds of the invention can improve efficacy of read-through agents for Class I mutations like the G542X mutation (eg mutations with a premature stop codon in the CFTR gene) by stabilizing the full length CFTR protein. Moreover, the compounds of the invention can improve maturation and trafficking to the plasma membrane of members of the ABC-transporter protein family, especially when combined with known correctors. Further, compounds of the invention can advantageously rescue the function of malfunctioning intracellular proteins due to defects in protein folding, degradation, and/or maturation.

The compounds of the invention have therefore a very promising therapeutic potential on patients suffering from a disease associated with a defect in an ABC-transporter and/or a disease caused by and/or involving a defect in protein folding, degradation, and/or maturation, preferably said defect is caused by a genetic mutation. Preferably the compounds of the invention can treat patients having CF, preferably having CF with one or more copies of the mutation F508del which compromise stability and maturation of the CFTR protein.

Compounds of the present invention can further be used for the treatment of CF patients with mutations belonging to other classes that act with mechanisms that do not involve a maturation defect. Indeed, an increase in biosynthesis and CFTR membrane transport would provide more substrate for other therapeutic agents, such as potentiator agents. A particular example of another possible application relates to class I mutations. In these cases, treatment with the so-called "read-through agents" (RTA) is required, which favour the by-passing of the premature stop codon allowing complete synthesis of the CFTR protein. The mechanism of action of such agents, however, implies the insertion of a random amino acid at the mutated codon and therefore the possible production of a partially defective protein. The compounds of the present invention therefore increase the efficacy of the RTAs by improving the stability and maturation of the protein produced.

The most promising derivatives in terms of biological activity belong to heterocyclic systems with a general 1 and 2 pyrrolo[3,2-h]quinoline structure, known for their marked abilities as drugs useful in neoplastic pathologies upon photoactivation (WO 2011/013159; Spanò V, et al. Eur J Med Chem. 2017, 128, 300-318).

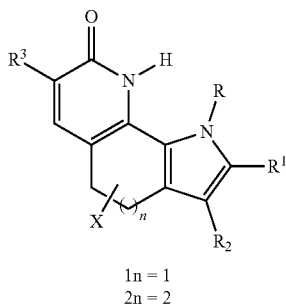

1n = 1
2n = 2

An object of the present invention therefore comprises the identification of further compounds, capable of correcting the basic defect of a ABC-transporter family protein, e.g. CFTR, in particular F508del-CFTR, as demonstrated by functional assays carried out both on cells having the expression of the mutated protein, and directly on primary epithelial cells obtained from patients with the mutation F508del.

The compounds object of the present invention show high efficacy in combination with further therapeutic agents, e.g. already known corrector agents, such as the compound VX-809. This result is of considerable importance as the clinical efficacy of first-generation correctors such as VX-809 (lumacaftor) and VX-661 (tezacaftor) is limited and it is therefore commonly believed that the treatment of patients with combinations of correctors having complementary mechanisms is necessary (Lukacs G L, et al. Trends Mol Med. 2012, 18, 81-91; Okiyoneda T, et al. Nat Chem Biol. 2013, 9, 444-454).

An object of the present invention is therefore a compound of general formula (I):

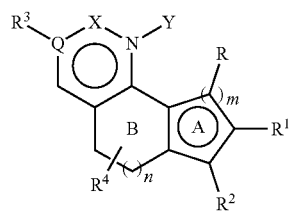

wherein:
A is a pentatomic or hexatomic aromatic heterocyclic ring, comprising one, two or three heteroatoms selected from nitrogen, oxygen and sulfur;
R is selected from the group consisting of: hydrogen, linear or branched C1-C6 alkyl, cycloalkyl, heterocycloalkyl, aryl, arylalkyl, heteroaryl, heteroarylalkyl, arylsulfonyl, halogen and alkylamine, wherein said linear or branched C1-C6 alkyl, cycloalkyl, heterocycloalkyl, aryl, arylalkyl, heteroaryl, arylsulfonyl or alkylamine is optionally substituted with one or more substituents independently selected from: linear or branched C1-C6 alkyl, nitro, amino, halogen, haloalkyl and alkoxy;
$R^1$ and $R^2$ are independently selected from the group consisting of: hydrogen, carboxylic acid, carboxylic ester, carboxamide from primary, secondary or tertiary amine, halogen, nitro, amine, azide, alkylamine, arylalkyl and trifluoroalkyl, wherein said carboxylic acid, carboxylic ester, carboxamide from primary, secondary or tertiary amine, halogen, nitro, amine, azide, alkylamine or trifluorolalkyl is optionally substituted with one or more substituents independently selected from: linear or branched C1-C6 alkyl, cycloalkyl, nitro, amino, halogen, arylsulfonyl, optionally substituted heteroaryl and haloalkyl;
$R^3$ is absent or present and is selected from the group consisting of: carbonitrile, carboxylic ester, carboxamide, alkylsulfonyl, arylsulfonyl, wherein said carboxylic ester, carboxamide, alkylsulfonyl or arylsulfonyl is optionally substituted with one or more substituents independently selected from: linear or branched C1-C6 alkyl, nitro, amino, halogen and haloalkyl;
B is a cycloalkyl, aryl, heterocycloalkyl or heteroaryl ring, wherein said heterocycloalkyl or heteroaryl ring comprises at least one heteroatom selected from nitrogen, oxygen and sulfur;
$R^4$ is selected from the group consisting of: hydrogen, alkyl, aryl, arylalkyl and heteroaryl;
X is selected from the group consisting of: C=O, C—O-alkyl, and C—NR$^a$R$^b$;
$R^a$ and $R^b$ are independently selected from the group consisting of: hydrogen, alkyl, cycloalkane, aryl, arylalkyl, heteroaryl, heteroarylalkyl, acetyl, arylsulfonyl; wherein said alkyl, cycloalkane, aryl, arylalkyl, heteroaryl, heteroarylalkyl, acetyl or arylsulfonyl is optionally substituted with one or more substituents independently selected from: C1-C6 alkyl, nitro, amino, halogen and haloalkyl;
Y is absent or present and is selected from the group consisting of: hydrogen, alkyl, aryl and alkylamine; wherein when X is C—O-alkyl or C—NR$^a$R$^b$, Y is absent;
Q is a carbon or nitrogen atom, wherein when Q is a nitrogen atom, R3 is absent;

n is 0, 1, 2 or 3;

m is 1 or 2;

or a pharmaceutically acceptable salt, tautomer, stereoisomer, deuterated derivative, active metabolite thereof for use in the treatment and/or prevention of a pathology associated with a defect in an ABC (ATP-binding cassette) transporter and/or for use in the treatment and/or prevention of a pathology associated with at least one of the following: protein mutation, protein misfolding, protein degradation, protein maturation, protein trafficking.

In a preferred embodiment, the present invention provides a compound of general formula (I):

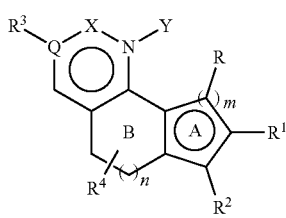

(I)

wherein:

A is a pentatomic or hexatomic aromatic heterocyclic ring, comprising one, two or three heteroatoms selected from nitrogen, oxygen and sulfur;

R is selected from the group consisting of: hydrogen, linear or branched C1-C6 alkyl, cycloalkyl, heterocycloalkyl, aryl, arylalkyl, heteroaryl, arylsulfonyl and alkylamine, wherein said linear or branched C1-C6 alkyl, cycloalkyl, heterocycloalkyl, aryl, arylalkyl, heteroaryl, arylsulfonyl or alkylamine is optionally substituted with one or more substituents independently selected from: linear or branched C1-C6 alkyl, nitro, amino, halogen, haloalkyl and alkoxy;

$R^1$ and $R^2$ are independently selected from the group consisting of: hydrogen, carboxylic acid, carboxylic ester, carboxamide from primary, secondary or tertiary amine, halogen, nitro, amine, azide, alkylamine and trifluoroalkyl, wherein said carboxylic acid, carboxylic ester, carboxamide from primary, secondary or tertiary amine, halogen, nitro, amine, azide, alkylamine or trifluorolalkyl is optionally substituted with one or more substituents independently selected from: linear or branched C1-C6 alkyl, nitro, amino, halogen and haloalkyl;

$R^3$ is selected from the group consisting of: carbonitrile, carboxylic ester, carboxamide, alkylsulfonyl, arylsulfonyl, wherein said carboxylic ester, carboxamide, alkylsulfonyl or arylsulfonyl is optionally substituted with one or more substituents independently selected selected from: linear or branched C1-C6 alkyl, nitro, amino, halogen and haloalkyl;

B is an aromatic or non-aromatic cycloalkyl, aryl, heterocycloalkyl or heteroaryl ring, wherein said heterocycloalkyl or heteroaryl ring comprises at least one heteroatom selected from nitrogen, oxygen and sulfur;

$R^4$ is selected from the group consisting of: hydrogen, alkyl, aryl, arylalkyl and heteroaryl;

X is selected from the group consisting of: C=O, C—O-alkyl and C—$NR^aR^b$;

$R^a$ and $R^b$ are independently selected from the group consisting of: hydrogen, alkyl, cycloalkane, aryl, arylalkyl, heteroaryl, heteroarylalkyl, acetyl; wherein said alkyl, cycloalkane, aryl, arylalkyl, heteroaryl, heteroarylalkyl or acetyl is optionally substituted with one or more substituents independently selected from: C1-C6 alkyl, nitro, amino, halogen and haloalkyl;

Y is absent or present and is selected from the group consisting of: hydrogen, alkyl, aryl and alkylamine; wherein when X is C—O-alkyl or C—$NR^aR^b$, Y is absent;

Q is a carbon or nitrogen atom; wherein when Q is a nitrogen atom, X is not C—O-alkyl o C—$NR^aR^b$ and Y is absent;

n is 0, 1, 2 or 3;

m is 1 or 2;

or a pharmaceutically acceptable salt, tautomer, stereoisomer, deuterated derivative, active metabolite thereof for use in the treatment and/or prevention of a pathology associated with a defect in an ABC (ATP-binding cassette) transporter.

Preferred compounds of the present invention include:

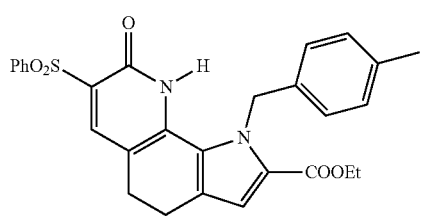

PP007

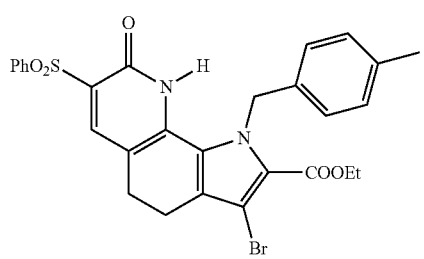

PP008

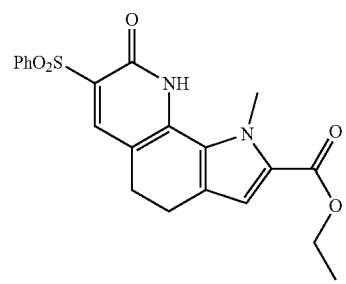

PP010

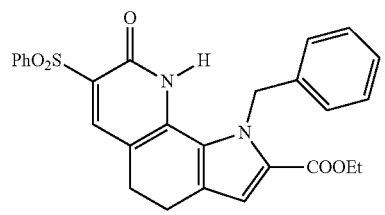

PP011

PP015 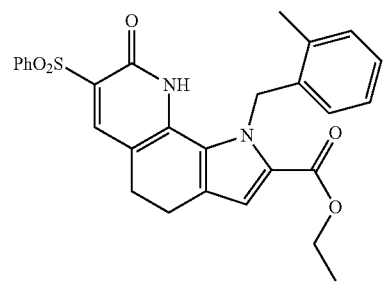
PP016 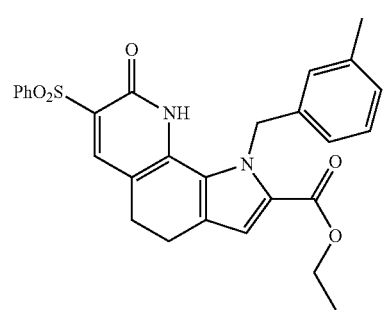
PP017 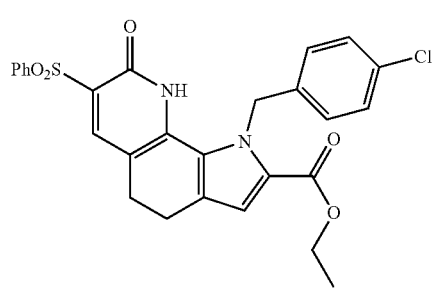
PP019 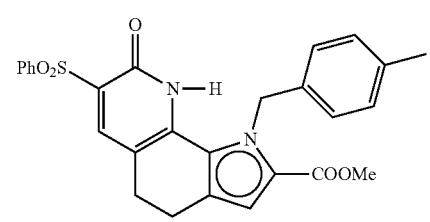
PP020 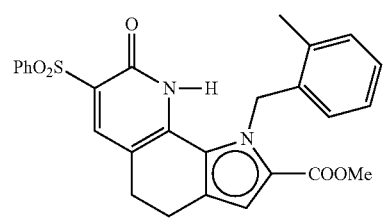
PP021 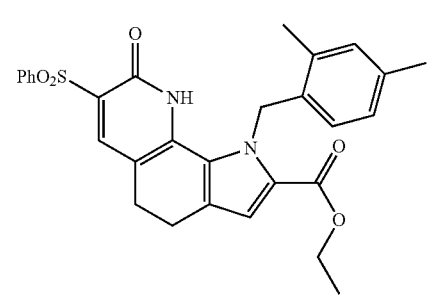
PP022 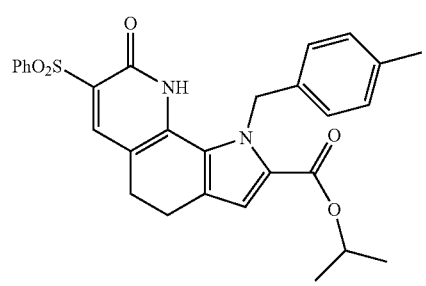
PP023 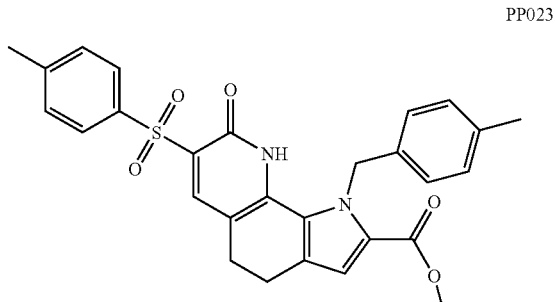
PP024 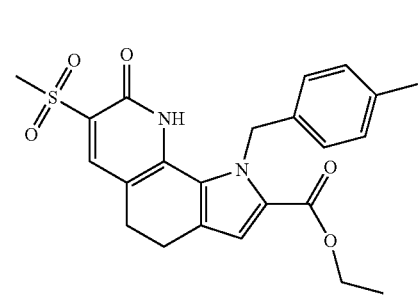
PP025 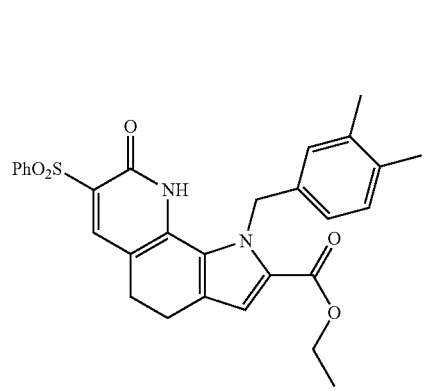
PP027 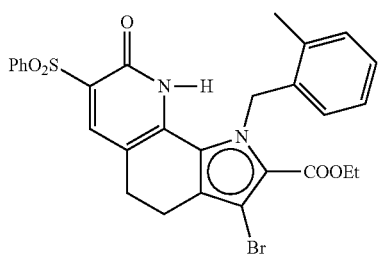

-continued
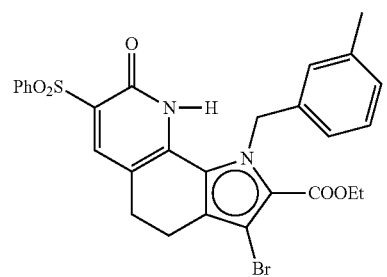
PP028
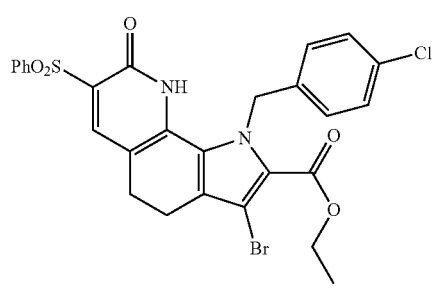
PP029
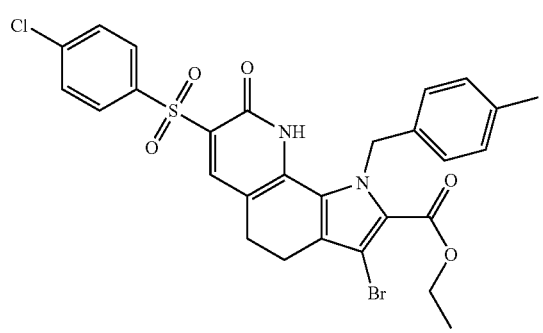
PP030
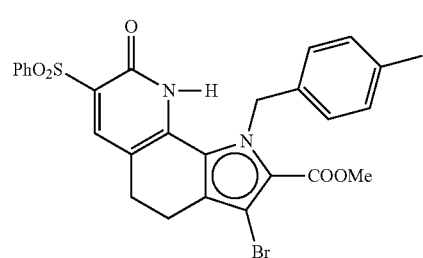
PP031
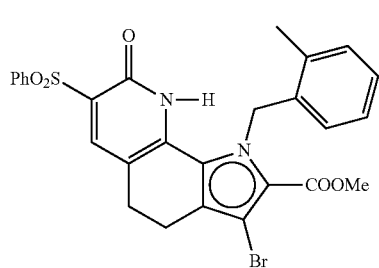
PP032
-continued
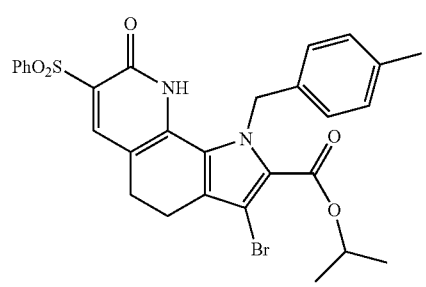
PP033
PP034
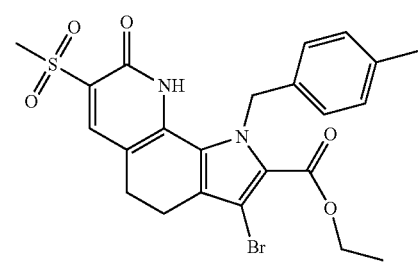
PP035
PP036
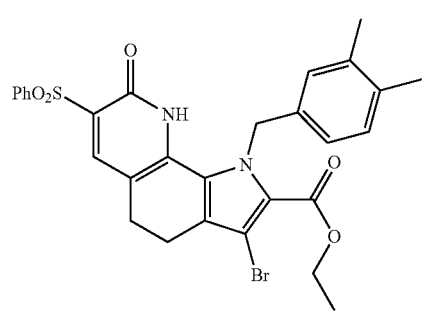
PP037

-continued
PP057
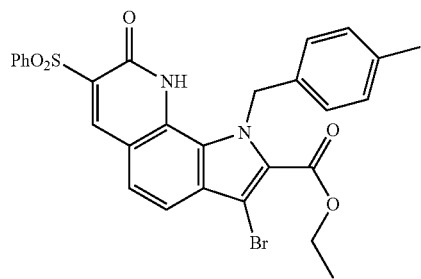
PP058
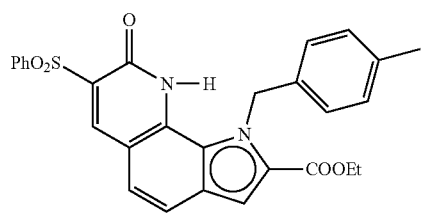
PP060
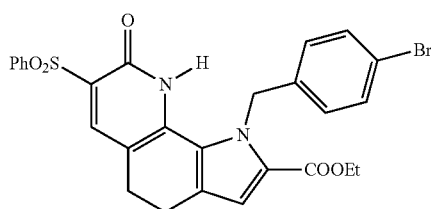
PP062
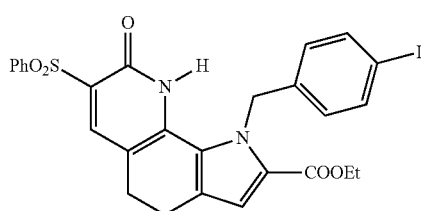
PP063
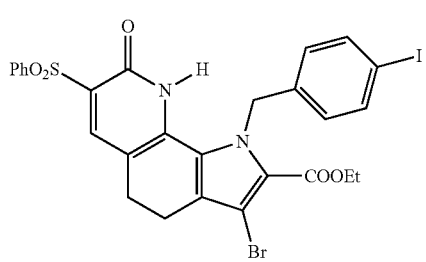
PP064
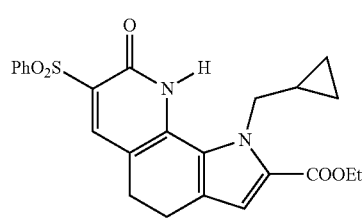
-continued
PP065
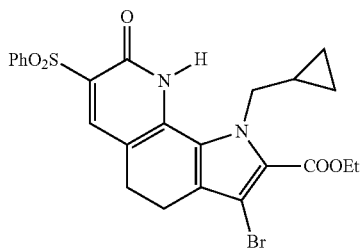
PP066
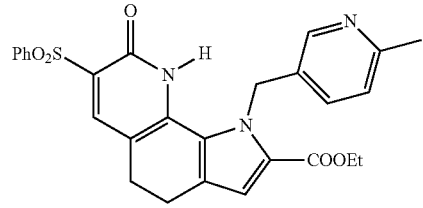
PP067
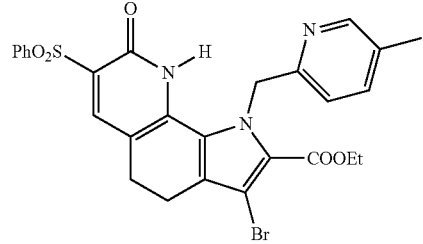
PP068
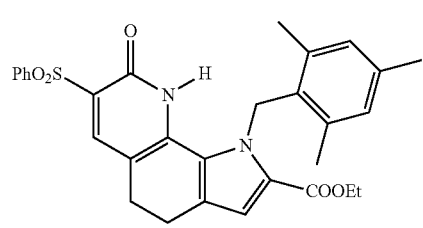
PP069
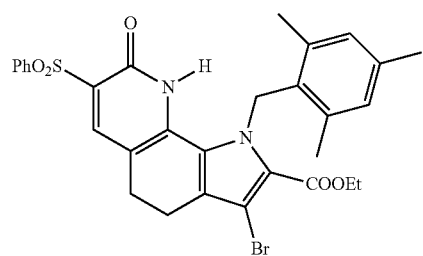
PP070
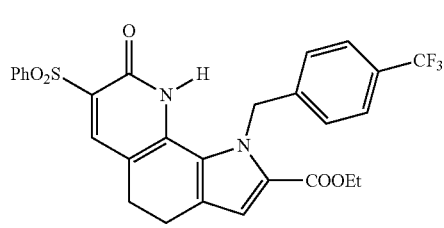

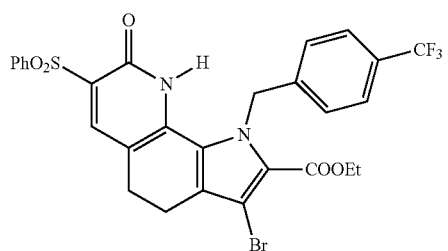
PP071
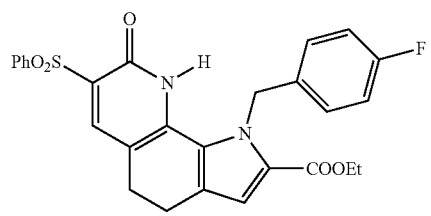
PP072
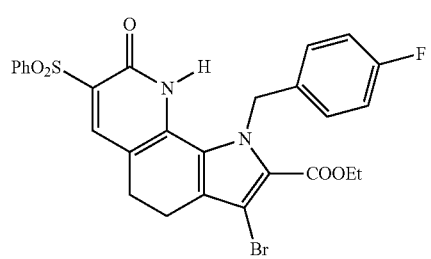
PP073
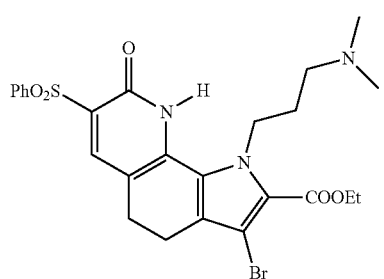
PP075
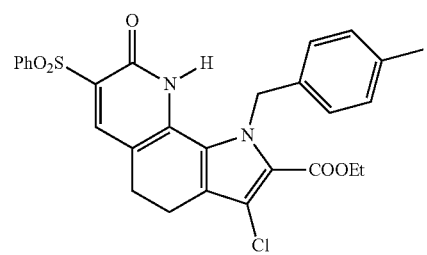
PP076
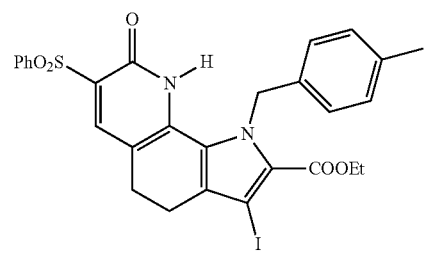
PP077
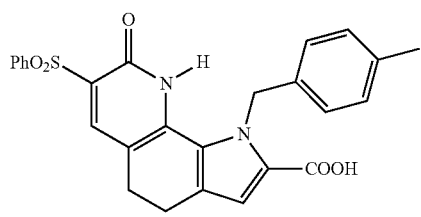
PP078
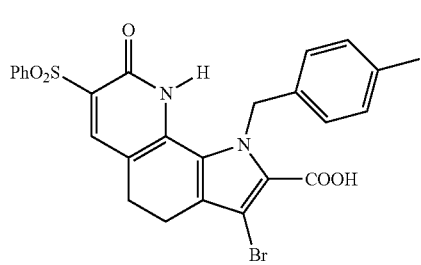
PP079
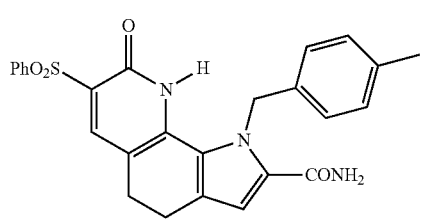
PP080
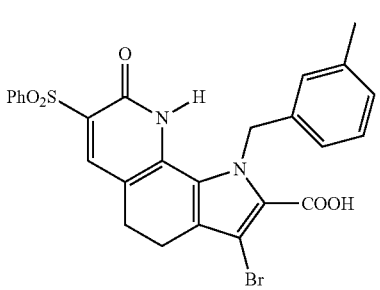
PP081
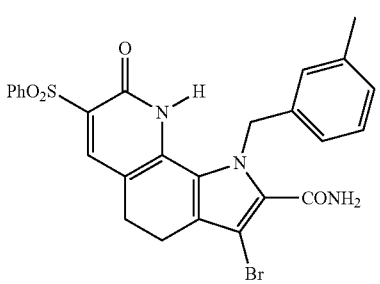
PP082
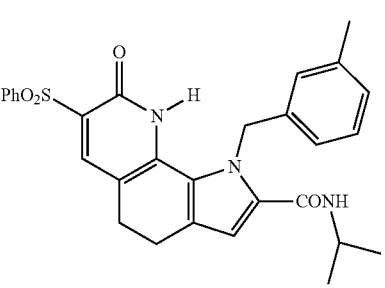
PP083

PP084
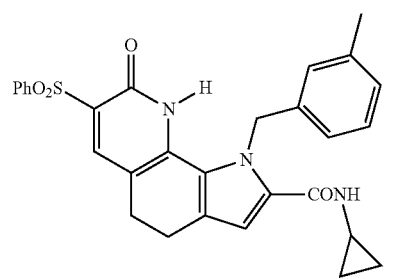
PP086
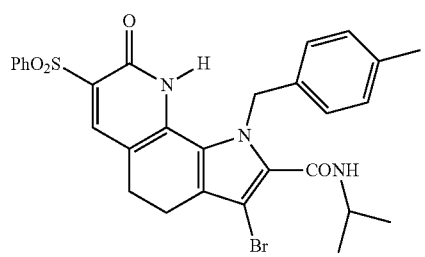
PP089
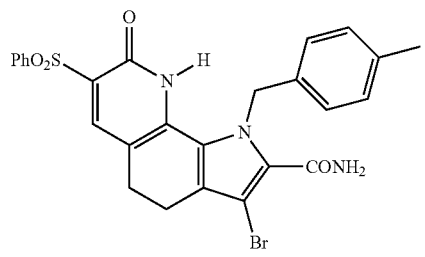
PP090
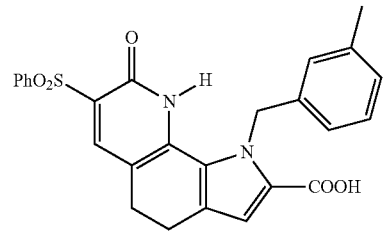
PP091
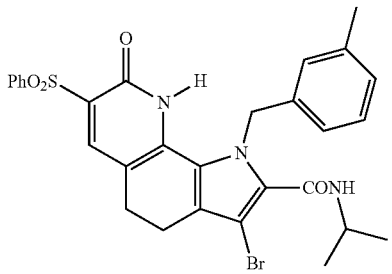
PP092
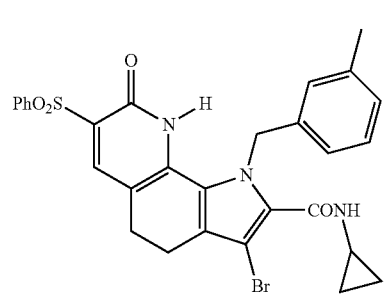
PP093
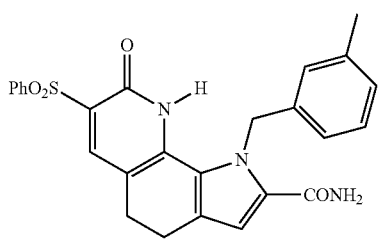
PP094
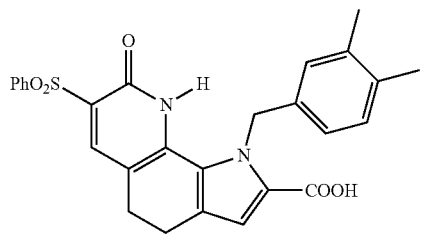
PP095
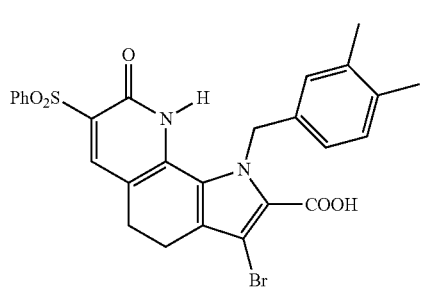
PP096
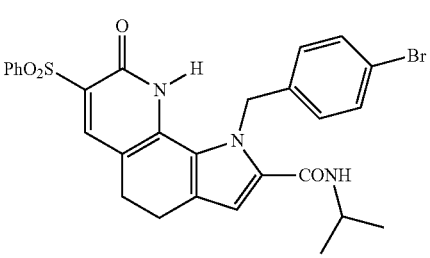
PP097
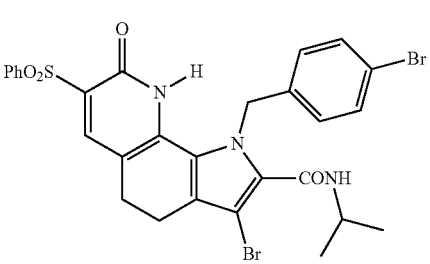
PP098
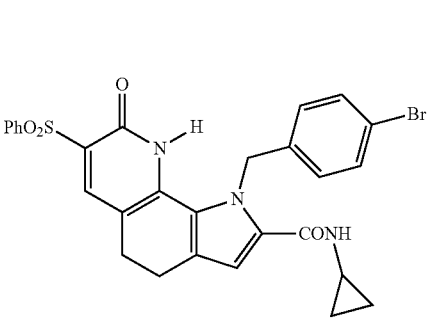

-continued
PP099
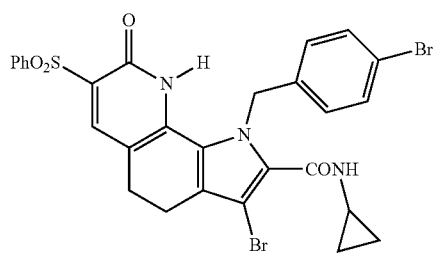
PP100
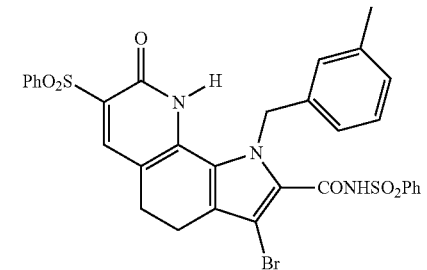
PP101
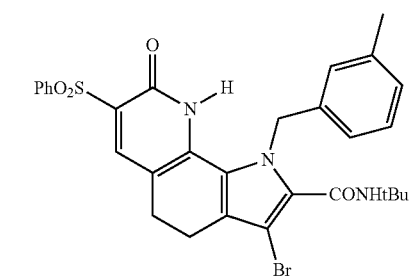
PP102
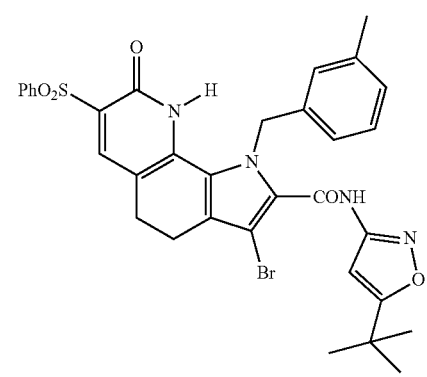
PP103
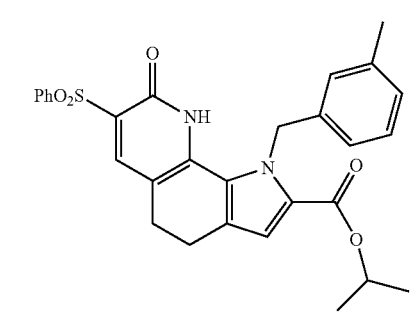
-continued
PP104
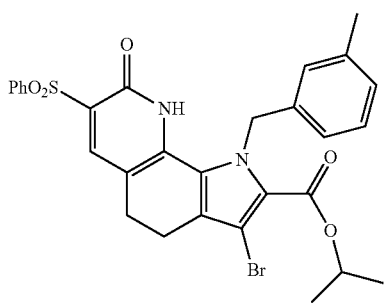
PP105
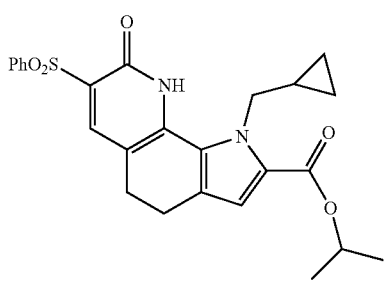
PP106
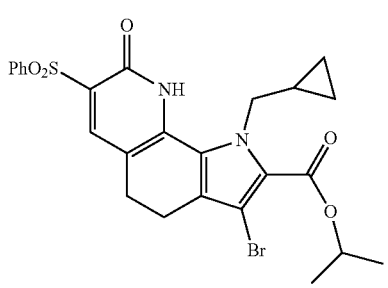
PP107
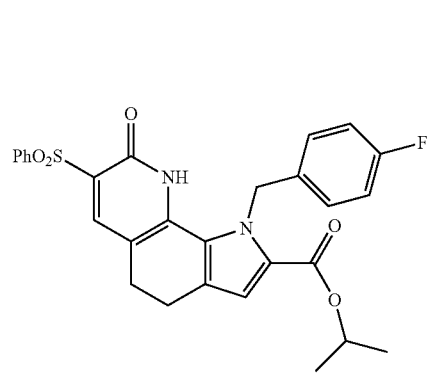
PP108
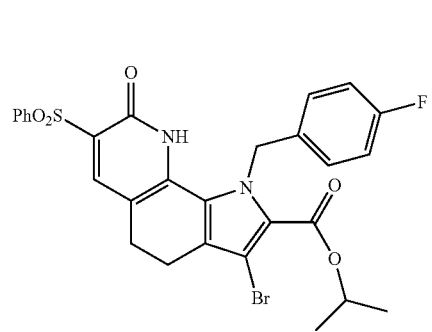

-continued

PP048

PP056

SVQ4

SVQ9

SVQ10

SVQ11

-continued

SVQ12

SVQ13

SVQ14

SVQ15

SVQ16

QZN2

-continued
QZN5
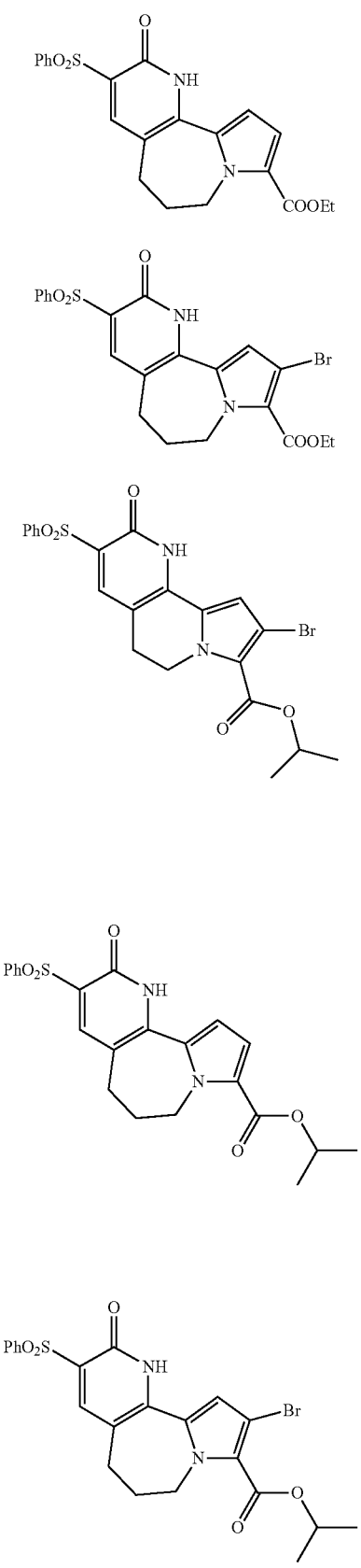
QZN6
QZN10
QZN13
QZN14
-continued
QZQ14
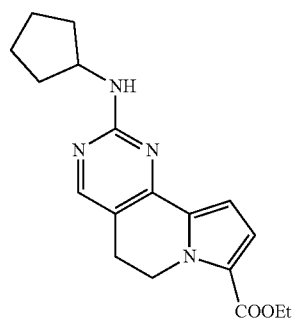
QZQ20
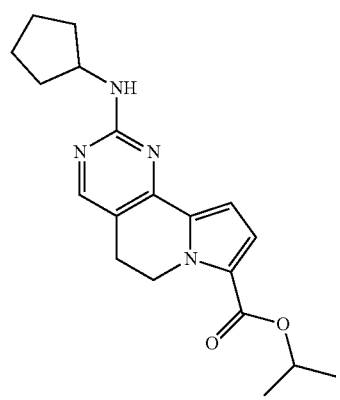
QZQ21
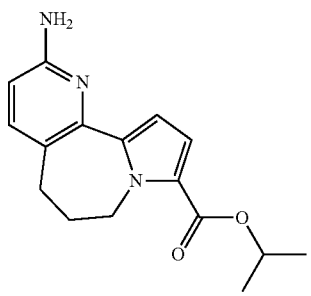
QZQ26
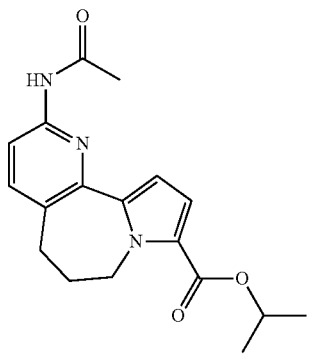
PZ1
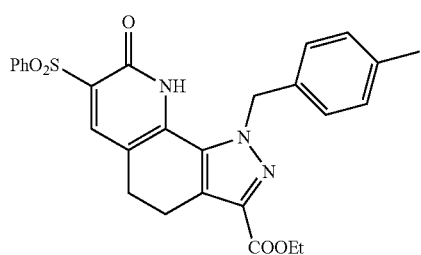

PZ3
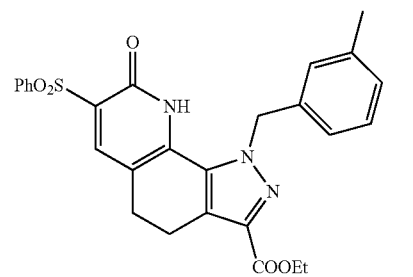
PZ5
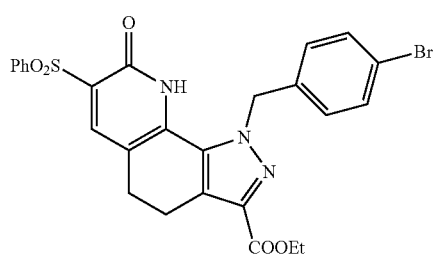
PZ7
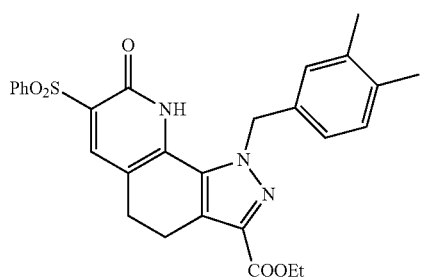
PZ8
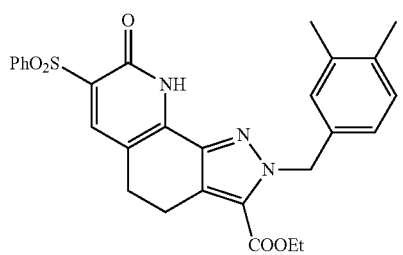
Also preferably, compounds of the present invention include:
PP007
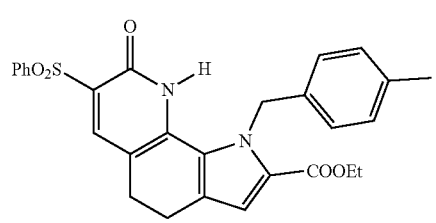
PP010
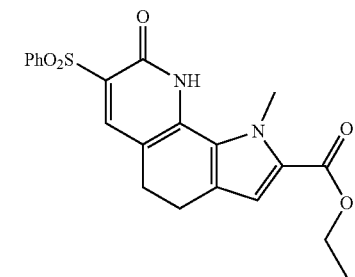
PP048
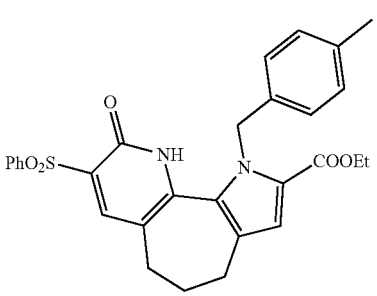
PP014
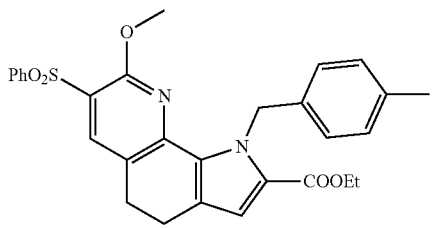
PP008
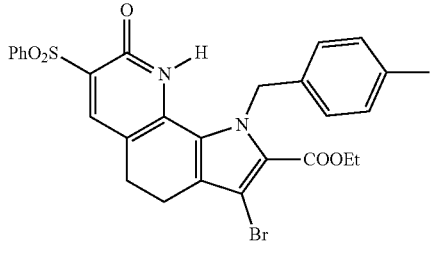
PP011
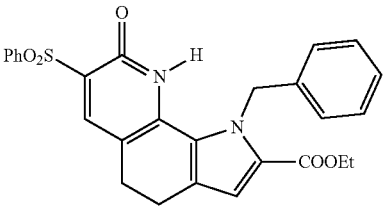
PP056
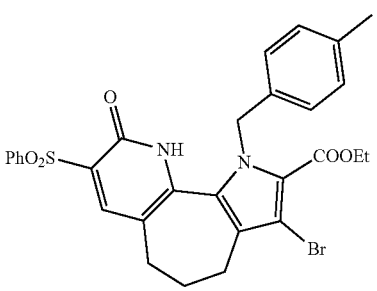

-continued

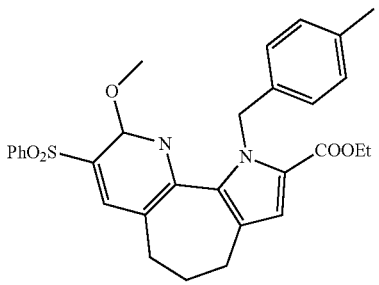
PP055

A further object of the present invention is a pharmaceutical composition comprising the compound as defined above and a pharmaceutically acceptable carrier for use in the treatment and/or prevention of a pathology associated with a defect in an ABC (ATP-binding cassette) transporter and/or for use in the treatment and/or prevention of a pathology associated with at least one of the following: protein mutation, protein misfolding, protein degradation, protein maturation, protein trafficking.

Preferably, said ABC (ATP-binding cassette) transporter is CFTR (Cystic Fibrosis Transmembrane Conductance Regulator).

Preferably, said pathology is selected from the group consisting of: cystic fibrosis, Limb-Girdle muscular dystrophy (LGMD), Congenital Bilateral Absence of Vas Deferens (CBAVD), acute, chronic, recurrent and/or autoimmune pancreatitis, disseminated bronchiectasis, asthma, allergic pulmonary aspergillosis, smoking-related lung pathology, dry eye syndrome, Sjogren's syndrome, chronic sinusitis, cholestatic jaundice, emphysema, idiopathic chronic pancreatitis, isolated obstructive azoospermia, sclerosing cholangitis, panbronchiolite, neonatal hypertripsinemia, adrenoleukodystrophy, Stargardt disease, Tangier disease, progressive familial intrahepatic cholestasis, Dubin-Johnson syndrome, elastic pseudoxantoma, persistent hyperinsulinemic hypoglycemia of infancy due to focal adenomatous hyperplasia, senile macular degeneration, retinitis pigmentosa and "cone-rod" retinal dystrophy. Still preferably, said smoking-related lung disease is chronic obstructive pulmonary disease.

More preferably, said pathology is cystic fibrosis.

Still preferably, the CFTR (Cystic Fibrosis Transmembrane conductance Regulator) protein bears the F508del mutation and/or the G542X premature stop codon mutation. More preferably, said pathology is caused by a mutation in the CFTR gene, in particular the F508del mutation and/or the G542X premature stop codon mutation.

In a preferred embodiment, the present invention provides a combination of a compound of general formula (I) or a pharmaceutically acceptable salt, tautomer, stereoisomer, deuterated derivative, active metabolite thereof as defined above and at least one further therapeutic agent.

Preferably, said further therapeutic agent is useful for use in the treatment and/or prevention of a pathology associated with a defect in an ABC (ATP-binding cassette) transporter and/or for use in the treatment and/or prevention of a pathology associated with at least one of the following: protein mutation, protein misfolding, protein degradation, protein maturation, protein trafficking.

Still preferably, said further therapeutic agent is selected from the group consisting of: a corrector, a potentiator, an amplifier, an agent that increases the read-through of the stop codons, a furocoumarin, an antibiotic or anti-infective, an anti-inflammatory agent, a mucolytic and a bronchodilator.

Preferably, said corrector is selected from: VX809 (3-(6-(1-(2,2-difluorobenzo[d][1,3]dioxol-5-yl)cyclopropanecarboxamido)-3-methylpyridin-2-yl)benzoic acid, lumacaftor), VX770 (ivacaftor), VX770-VX809 (orkambi), VX661 (tezacaftor), VX445, VX659, VX983, VX152, VX440, ABBV-2737, GLPG2222, GLPG2851, GLPG2665, GLPG2737, GLPG3221, PTI-801, FDL169, bisaminomethylthiazole (corr-4a), W1282Xcorr-B09, W1282Xcorr-A23 and a furocoumarin.

Preferably, said potentiator is selected from: VX770 (ivacaftor), VX561, GLPG1837, GLPG2545, GLPG3067, genistein, phenylglycine (PG-01), PTI-808, 1,4-dihydropyridine, tetrahydrobenzothiophene, benzofuran, anthraquinone and sulphonamide.

Preferably, said amplifier is PTI-428.

Preferably, said agent that increases the "read-through" of the stop codons is Ataluren (PTC124) (3-[5-(2-fluorophenyl)-1,2,4-oxadiazol-3-yl]benzoic acid).

Preferably, said furocoumarin is selected from: 5-methoxypsoralene (5-MOP), 4,6,4'-trimethylangelicin (TMA), 8-methoxypsoralene (8-MOP), Angelicin and a pyrrolo[3',2':6,7]cyclohepta[1,2-b]pyridine.

Preferably, said antibiotic or anti-infective is selected from: penicillins, preferably amoxicillin, clavulanic acid, cloxacillin, dicloxacillin, ticarcillin; cephalosporins, preferably cephalexin, cefdinir, cefprozil, cefaclor, cefuroxime; sulfamethoxazole, trimethoprim, erythromycin, sulfisoxazole, macrolides, preferably erythromycin, clarithromycin, azithromycin; tetracyclines, preferably tetracycline, doxycycline, minocycline, and tigecycline; vancomycin; imipenem; meropenem; colistimethate; aminoglycosides, preferably tobramycin, amikacin, gentamicin; quinolones, preferably ciprofloxacin or levofloxacin; aztreonam; linezolid upon oral, inhalation, intravenous, intra-muscular administration.

Preferably, said anti-inflammatory is selected from: corticosteroids, preferably by inhalation or oral route, preferably Budesonide or Clenil, and non-steroidal drugs, preferably ibuprofen.

Preferably, said mucolytic is selected from: dornase alfa (Pulmozyme), N-acetylcysteine (Fluimucil), saline hypertonic, mannitol (Bronchitol).

Preferably, said bronchodilator is selected from: salbutamol, albuterol and levalbuterol.

Preferably, the combination comprises as the at least one further therapeutic agent: one corrector, one potentiator, two correctors and one potentiator, or one corrector and one potentiator. More preferably, the combination comprises as the at least one further therapeutic agent:

VX-809, VX770, VX661 or VX445, or

VX770, VX661 and VX445, or genistein and VX809.

In a preferred embodiment, the present invention provides a pharmaceutical composition comprising the combination as defined above and a pharmaceutically acceptable carrier.

In a further preferred embodiment, the present invention provides the combination as defined above for use as a medicament.

A further object of the present invention is the combination as defined above or the pharmaceutical composition as defined above for use in the treatment and/or prevention of a pathology associated with a defect in an ABC (ATP-binding cassette) transporter and/or for use in the treatment and/or prevention of a pathology associated with at least one of the following: protein mutation, protein misfolding, protein degradation, protein maturation, protein trafficking. Preferably, said ABC transporter is CFTR (Cystic Fibrosis Transmembrane Conductance Regulator). Preferably, said pathology is selected from the group consisting of: cystic fibrosis, Limb-Girdle muscular dystrophy (LGMD), Congenital Bilateral Absence of Vas Deferens (CBAVD), acute, chronic, recurrent and/or autoimmune pancreatitis, disseminated bronchiectasis, asthma, allergic pulmonary aspergillosis, smoking-related lung pathology, dry eye syndrome, Sjogren's syndrome, chronic sinusitis, cholestatic jaundice, emphysema, idiopathic chronic pancreatitis, isolated obstructive azoospermia, sclerosing cholangitis, panbronchiolite, neonatal hypertripsinemia, adrenoleukodystrophy, Stargardt disease, Tangier disease, progressive familial intrahepatic cholestasis, Dubin-Johnson syndrome, elastic pseudoxantoma, persistent hyperinsulinemic hypoglycemia of infancy due to focal adenomatous hyperplasia, senile macular degeneration, retinitis pigmentosa and "cone-rod" retinal dystrophy. Still preferably, said smoking-related lung disease is chronic obstructive pulmonary disease.

In a preferred embodiment, the present invention provides a compound of general formula (I):

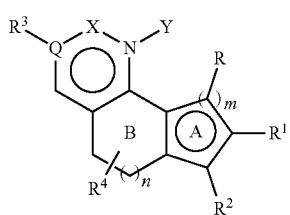

(I)

wherein:
A is a pentatomic or hexatomic aromatic heterocyclic ring, comprising one, two or three heteroatoms selected from nitrogen, oxygen and sulfur;
R is selected from the group consisting of: hydrogen, linear or branched C1-C6 alkyl, cycloalkyl, heterocycloalkyl, aryl, arylalkyl, heteroaryl, heteroarylalkyl, arylsulfonyl, halogen and alkylamine, wherein said linear or branched C1-C6 alkyl, cycloalkyl, heterocycloalkyl, aryl, arylalkyl, heteroaryl, arylsulfonyl or alkylamine is optionally substituted with one or more substituents independently selected from: linear or branched C1-C6 alkyl, nitro, amino, halogen, haloalkyl and alkoxy;
$R^1$ and $R^2$ are independently selected from the group consisting of: hydrogen, carboxylic acid, carboxylic ester, carboxamide from primary, secondary or tertiary amine, halogen, nitro, amine, azide, alkylamine, arylalkyl and trifluoroalkyl, wherein said carboxylic acid, carboxylic ester, carboxamide from primary, secondary or tertiary amine, halogen, nitro, amine, azide, alkylamine or trifluorolalkyl is optionally substituted with one or more substituents independently selected from: linear or branched C1-C6 alkyl, cycloalkyl, nitro, amino, halogen, arylsulfonyl, optionally substituted heteroaryl and haloalkyl;
$R^3$ is absent or present and is selected from the group consisting of: carbonitrile, carboxylic ester, carboxamide, alkylsulfonyl, arylsulfonyl, wherein said carboxylic ester, carboxamide, alkylsulfonyl or arylsulfonyl is optionally substituted with one or more substituents independently selected from: linear or branched C1-C6 alkyl, nitro, amino, halogen and haloalkyl;

B is a cycloalkyl, aryl, heterocycloalkyl or heteroaryl ring, wherein said heterocycloalkyl or heteroaryl ring comprises at least one heteroatom selected from nitrogen, oxygen and sulfur;
$R^4$ is selected from the group consisting of: hydrogen, alkyl, aryl, arylalkyl and heteroaryl;
X is selected from the group consisting of: C=O, C—O-alkyl, and C—$NR^aR^b$;
$R^a$ and $R^b$ are independently selected from the group consisting of: hydrogen, alkyl, cycloalkane, aryl, arylalkyl, heteroaryl, heteroarylalkyl, acetyl, arylsulfonyl; wherein said alkyl, cycloalkane, aryl, arylalkyl, heteroaryl, heteroarylalkyl, acetyl or arylsulfonyl is optionally substituted with one or more substituents independently selected from: C1-C6 alkyl, nitro, amino, halogen and haloalkyl;
Y is absent or present and is selected from the group consisting of: hydrogen, alkyl, aryl and alkylamine; wherein when X is C—O-alkyl or C—$NR^aR^b$, Y is absent;
Q is a carbon or nitrogen atom, wherein when Q is a nitrogen atom, R3 is absent;
n is 0, 1, 2 or 3;
m is 1 or 2;
or a pharmaceutically acceptable salt, tautomer, stereoisomer, deuterated derivative, active metabolite thereof. Preferably, when X is C=O, $R^2$ is different from hydrogen.

In another preferred embodiment, the present invention provides a compound of general formula (I):

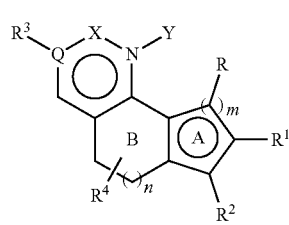

(I)

wherein:
A is a pentatomic or hexatomic aromatic heterocyclic ring, comprising one, two or three heteroatoms selected from nitrogen, oxygen and sulfur;
R is selected from the group consisting of: hydrogen, linear or branched C1-C6 alkyl, cycloalkyl, heterocycloalkyl, aryl, arylalkyl, heteroaryl, arylsulfonyl and alkylamine, wherein said linear or branched C1-C6 alkyl, cycloalkyl, heterocycloalkyl, aryl, arylalkyl, heteroaryl, arylsulfonyl or alkylamine is optionally substituted with one or more substituents independently selected from: linear or branched C1-C6 alkyl, nitro, amino, halogen, haloalkyl and alkoxy;
$R^1$ and $R^2$ are independently selected from the group consisting of: hydrogen, carboxylic acid, carboxylic ester, carboxamide from primary, secondary or tertiary amine, halogen, nitro, amine, azide, alkylamine and trifluoroalkyl, wherein said carboxylic acid, carboxylic ester, carboxamide from primary, secondary or tertiary amine, halogen, nitro, amine, azide, alkylamine or trifluorolalkyl is optionally substituted with one or more substituents independently selected from: linear or branched C1-C6 alkyl, nitro, amino, halogen and haloalkyl;

R³ is selected from the group consisting of: carbonitrile, carboxylic ester, carboxamide, alkylsulfonyl, arylsulfonyl, wherein said carboxylic ester, carboxamide, alkylsulfonyl or arylsulfonyl is optionally substituted with one or more substituents independently selected selected from: linear or branched C1-C6 alkyl, nitro, amino, halogen and haloalkyl; B is an aromatic or non-aromatic cycloalkyl, aryl, heterocycloalkyl or heteroaryl ring, wherein said heterocycloalkyl or heteroaryl ring comprises at least one heteroatom selected from nitrogen, oxygen and sulfur;

R⁴ is selected from the group consisting of: hydrogen, alkyl, aryl, arylalkyl and heteroaryl;

X is selected from the group consisting of: C=O, C—O-alkyl and C—NR$^a$R$^b$;

R$^a$ and R$^b$ are independently selected from the group consisting of: hydrogen, alkyl, cycloalkane, aryl, arylalkyl, heteroaryl, heteroarylalkyl, acetyl; wherein said alkyl, cycloalkane, aryl, arylalkyl, heteroaryl, heteroarylalkyl or acetyl is optionally substituted with one or more substituents independently selected from: C1-C6 alkyl, nitro, amino, halogen and haloalkyl;

Y is absent or present and is selected from the group consisting of: hydrogen, alkyl, aryl and alkylamine; wherein when X is C—O-alkyl or C—NR$^a$R$^b$, Y is absent;

Q is a carbon or nitrogen atom; wherein when Q is a nitrogen atom, X is not C—O-alkyl o C—NR$^a$R$^b$ and Y is absent;

n is 0, 1, 2 or 3;

m is 1 or 2;

or a pharmaceutically acceptable salt, tautomer, stereoisomer, deuterated derivative, active metabolite thereof, preferably wherein when X is C=O, R² is different from hydrogen.

Preferred compounds according to the latter two embodiments are:

Ethyl 1-(2-methylbenzyl)-8-oxo-7-(phenylsulfonyl)-4,5,8,9-tetrahydro-1H-pyrrolo[3,2-h]quinoline-2-carboxylate (PP015);

Ethyl 1-(3-methylbenzyl)-8-oxo-7-(phenylsulfonyl)-4,5,8,9-tetrahydro-1H-pyrrolo[3,2-h]quinoline-2-carboxylate (PP016);

Ethyl 1-(4-chlorobenzyl)-8-oxo-7-(phenylsulfonyl)-4,5,8,9-tetrahydro-1H-pyrrolo[3,2-h]quinoline-2-carboxylate (PP017);

Ethyl 7-[(4-chlorophenyl)sulfonyl]-1-(4-methylbenzyl)-8-oxo-4,5,8,9-tetrahydro-1H-pyrrolo[3,2-h]quinoline-2-carboxylate (PP018);

Ethyl 7-(benzenesulfonyl)-1-[(2,4-dimethylphenyl)methyl]-8-oxo-4,5,8,9-tetrahydro-1H-pyrrolo[3,2-h]quinoline-2-carboxylate (PP021);

Ethyl 7-(benzenesulfonyl)-1-[(3,4-dimethylphenyl)methyl]-8-oxo-4,5,8,9-tetrahydro-1H-pyrrolo[3,2-h]quinoline-2-carboxylate (PP025);

Propan-2-yl 7-(benzenesulfonyl)-1-[(4-methylphenyl)methyl]-8-oxo-4,5,8,9-tetrahydro-1H-pyrrolo[3,2-h]quinoline-2-carboxylate (PP022);

Ethyl 7-(4-methylbenzene-1-sulfonyl)-1-[(4-methylphenyl)methyl]-8-oxo-4,5,8,9-tetrahydro-1H-pyrrolo[3,2-h]quinoline-2-carboxylate (PP023);

Ethyl 7-(metansulfonyl)-1-[(4-methylphenyl)methyl]-8-oxo-4,5,8,9-tetrahydro-1H-pyrrolo[3,2-h]quinoline-2-carboxylate (PP024);

Methyl 1-(4-methylbenzyl)-8-oxo-7-(phenylsulfonyl)-4,5,8,9-tetrahydro-1H-pyrrolo[3,2-h]quinoline-2-carboxylate (PP019);

Methyl 1-(2-methylbenzyl)-8-oxo-7-(phenylsulfonyl)-4,5,8,9-tetrahydro-1H-pyrrolo[3,2-h]quinoline-2-carboxylate (PP020);

Ethyl 8-(benzenesulfonyl)-1-[(4-methylphenyl)methyl]-9-oxo-1,4,5,6,9,10-hexahydropyrrolo[3',2':6,7]cyclohepta[1,2-b]pyridine-2-carboxylate (PP048);

Ethyl 7-(benzenesulfonyl)-1-[(4-bromophenyl)methyl]-8-oxo-4,5,8,9-tetrahydro-1H-pyrrolo[3,2-h]quinoline-2-carboxylate (PP060);

Ethyl 7-(benzenesulfonyl)-1-[(4-iodophenyl)methyl]-8-oxo-4,5,8,9-tetrahydro-1H-pyrrolo[3,2-h]quinoline-2-carboxylate (PP062);

Ethyl 7-(benzenesulfonyl)-1-(cyclopropylmethyl)-8-oxo-4,5,8,9-tetrahydro-1H-pyrrolo[3,2-h]quinoline-2-carboxylate (PP064);

Ethyl 7-(benzenesulfonyl)-1-[(6-methylpyridin-3-yl)methyl]-8-oxo-4,5,8,9-tetrahydro-1H-pyrrolo[3,2-h]quinoline-2-carboxylate (PP066);

Ethyl 7-(benzenesulfonyl)-8-oxo-1-[(2,4,6-trimethylphenyl)methyl]-4,5,8,9-tetrahydro-1H-pyrrolo[3,2-h]quinoline-2-carboxylate (PP068);

Ethyl 7-(benzenesulfonyl)-8-oxo-1-{[4-(trifluoromethyl)phenyl]methyl}-4,5,8,9-tetrahydro-1H-pyrrolo[3,2-h]quinoline-2-carboxylate (PP070);

Ethyl 7-(benzenesulfonyl)-1-[(4-fluorophenyl)methyl]-8-oxo-4,5,8,9-tetrahydro-1H-pyrrolo[3,2-h]quinoline-2-carboxylate (PP072);

Ethyl 7-(benzenesulfonyl)-1-[3-(dimethylamino)propyl]-8-oxo-4,5,8,9-tetrahydro-1H-pyrrolo[3,2-h]quinoline-2-carboxylate (PP074);

Propan-2-yl 7-(benzenesulfonyl)-1-[(3-methylphenyl)methyl]-8-oxo-4,5,8,9-tetrahydro-1H-pyrrolo[3,2-h]quinoline-2-carboxylate (PP103);

Propan-2-yl 7-(benzenesulfonyl)-1-(cyclopropylmethyl)-8-oxo-4,5,8,9-tetrahydro-1H-pyrrolo[3,2-h]quinoline-2-carboxylate (PP105);

Propan-2-yl 7-(benzenesulfonyl)-1-[(4-fluorophenyl)methyl]-8-oxo-4,5,8,9-tetrahydro-1H-pyrrolo[3,2-h]quinoline-2-carboxylate (PP107);

7-(Benzenesulfonyl)-1-[(3-methylphenyl)methyl]-8-oxo-N-(propan-2-yl)-4,5,8,9-tetrahydro-1H-pyrrolo[3,2-h]quinoline-2-carboxamide (PP083);

7-(Benzenesulfonyl)-N-cyclopropyl-1-[(3-methylphenyl)methyl]-8-oxo-4,5,8,9-tetrahydro-1H-pyrrolo[3,2-h]quinoline-2-carboxamide (PP084);

7-(Benzenesulfonyl)-1-[(4-methylphenyl)methyl]-8-oxo-N-(propan-2-yl)-4,5,8,9-tetrahydro-1H-pyrrolo[3,2-h]quinoline-2-carboxamide (PP085);

7-(Benzenesulfonyl)-N-cyclopropyl-1-[(4-methylphenyl)methyl]-8-oxo-4,5,8,9-tetrahydro-1H-pyrrolo[3,2-h]quinoline-2-carboxamide (PP087);

7-(Benzenesulfonyl)-1-[(4-bromophenyl)methyl]-8-oxo-N-(propan-2-yl)-4,5,8,9-tetrahydro-1H-pyrrolo[3,2-h]quinoline-2-carboxamide (PP096);

7-(Benzenesulfonyl)-1-[(4-bromophenyl)methyl]-N-cyclopropyl-8-oxo-4,5,8,9-tetrahydro-1H-pyrrolo[3,2-h]quinoline-2-carboxamide (PP098);

Ethyl 7-(benzenesulfonyl)-3-chloro-1-[(4-methylphenyl)methyl]-8-oxo-4,5,8,9-tetrahydro-1H-pyrrolo[3,2-h]quinoline-2-carboxylate (PP076);

Ethyl 7-(benzenesulfonyl)-3-iodo-1-[(4-methylphenyl)methyl]-8-oxo-4,5,8,9-tetrahydro-1H-pyrrolo[3,2-h]quinoline-2-carboxylate (PP077);

) allowing the isolation of N-methyl derivatives and O-methyl derivatives as pure products.

Ethyl 7-(benzenesulfonyl)-8-methoxy-1-[(4-methylphenyl)methyl]-4,5-dihydro-1H-pyrrolo[3,2-h]quinoline-2-carboxylate (PP014);

Ethyl 8-(benzenesulfonyl)-9-methoxy-1-[(4-methylphenyl)methyl]-1,4,5,6-tetrahydropyrrolo[3',2':6,7]cyclohepta[1,2-b]pyridine-2-carboxylate (PP055);

Ethyl 7-(benzenesulfonyl)-3-bromo-1-[(4-methylphenyl)methyl]-8-oxo-4,5,8,9-tetrahydro-1H-pyrrolo[3,2-h]quinoline-2-carboxylate (PP008);

Ethyl 8-(benzenesulfonyl)-3-bromo-1-[(4-methylphenyl)methyl]-9-oxo-1,4,5,6,9,10-hexahydropyrrolo[3',2':6,7]cyclohepta[1,2-b]pyridine-2-carboxylate (PP056);

Ethyl 3-bromo 1-(2-methylbenzyl)-8-oxo-7-(phenylsulfonyl)-4,5,8,9-tetrahydro-1H-pyrrolo[3,2-h]quinoline-2-carboxylate (PP027);

Ethyl 3-bromo 1-(3-methylbenzyl)-8-oxo-7-(phenylsulfonyl)-4,5,8,9-tetrahydro-1H-pyrrolo[3,2-h]quinoline-2-carboxylate (PP028);

Ethyl 3-bromo 1-(4-chlorobenzyl)-8-oxo-7-(phenylsulfonyl)-4,5,8,9-tetrahydro-1H-pyrrolo[3,2-h]quinoline-2-carboxylate (PP029);

Methyl 3-bromo-1-(4-methylbenzyl)-8-oxo-7-(phenylsulfonyl)-4,5,8,9-tetrahydro-1H-pyrrolo[3,2-h]quinoline-2-carboxylate (PP031);

Methyl 3-bromo-1-(2-methylbenzyl)-8-oxo-7-(phenylsulfonyl)-4,5,8,9-tetrahydro-1H-pyrrolo[3,2-h]quinoline-2-carboxylate (PP032);

Ethyl 3-bromo-7-[(4-chlorophenyl)sulfonyl]-1-(3-methylbenzyl)-8-oxo-4,5,8,9-tetrahydro-1H-pyrrolo[3,2-h]quinoline-2-carboxylate (PP030);

Ethyl 7-(benzenesulfonyl)-3-bromo-1-[(2,4-dimethylphenyl)methyl]-8-oxo-4,5,8,9-tetrahydro-1H-pyrrolo[3,2-h]quinoline-2-carboxylate (PP033);

Ethyl 7-(benzenesulfonyl)-3-bromo-1-[(3,4-dimethylphenyl)methyl]-8-oxo-4,5,8,9-tetrahydro-1H-pyrrolo[3,2-h]quinoline-2-carboxylate (PP037);

Propan-2-yl 7-(benzenesulfonyl)-3-bromo-1-[(4-methylphenyl)methyl]-8-oxo-4,5,8,9-tetrahydro-1H-pyrrolo[3,2-h]quinoline-2-carboxylate (PP034);

Ethyl 3-bromo-7-(4-methylbenzene-1-sulfonyl)-1-[(4-methylphenyl)methyl]-8-oxo-4,5,8,9-tetrahydro-1H-pyrrolo[3,2-h]quinoline-2-carboxylate (PP035);

Ethyl 3-bromo-7-(metansulfonyl)-1-[(4-methylphenyl)methyl]-8-oxo-4,5,8,9-tetrahydro-1H-pyrrolo[3,2-h]quinoline-2-carboxylate (PP036);

Ethyl 7-(benzenesulfonyl)-3-bromo-1-[(4-methylphenyl)methyl]-8-oxo-8,9-dihydro-1H-pyrrolo[3,2-h]quinoline-2-carboxylate (14, PP057);

Ethyl 7-(benzenesulfonyl)-3-bromo-1-[(4-bromophenyl)methyl]-8-oxo-4,5,8,9-tetrahydro-1H-pyrrolo[3,2-h]quinoline-2-carboxylate (PP061);

Ethyl 7-(benzenesulfonyl)-3-bromo-1-[(4-iodophenyl)methyl]-8-oxo-4,5,8,9-tetrahydro-1H-pyrrolo[3,2-h]quinoline-2-carboxylate (PP063);

Ethyl 7-(benzenesulfonyl)-3-bromo-1-(cyclopropylmethyl)-8-oxo-4,5,8,9-tetrahydro-1H-pyrrolo[3,2-h]quinoline-2-carboxylate (PP065);

Ethyl 7-(benzenesulfonyl)-3-bromo-1-[(6-methylpyridin-3-yl)methyl]-8-oxo-4,5,8,9-tetrahydro-1H-pyrrolo[3,2-h]quinoline-2-carboxylate (PP067);

Ethyl 7-(benzenesulfonyl)-3-bromo-8-oxo-1-[(2,4,6-trimethylphenyl)methyl]-4,5,8,9-tetrahydro-1H-pyrrolo[3,2-h]quinoline-2-carboxylate (PP069);

Ethyl 7-(benzenesulfonyl)-3-bromo-8-oxo-1-{[4-(trifluoromethyl)phenyl]methyl}-4,5,8,9-tetrahydro-1H-pyrrolo[3,2-h]quinoline-2-carboxylate (PP071);

Ethyl 7-(benzenesulfonyl)-3-bromo-1-[(4-fluorophenyl)methyl]-8-oxo-4,5,8,9-tetrahydro-1H-pyrrolo[3,2-h]quinoline-2-carboxylate (PP073);

Ethyl 7-(benzenesulfonyl)-1-[3-(dimethylamino)propyl]-8-oxo-4,5,8,9-tetrahydro-1H-pyrrolo[3,2-h]quinoline-2-carboxylate (PP075);

Propan-2-yl 7-(benzenesulfonyl)-3-bromo-1-[(3-methylphenyl)methyl]-8-oxo-4,5,8,9-tetrahydro-1H-pyrrolo[3,2-h]quinoline-2-carboxylate (PP104);

Propan-2-yl 7-(benzenesulfonyl)-3-bromo-1-(cyclopropylmethyl)-8-oxo-4,5,8,9-tetrahydro-1H-pyrrolo[3,2-h]quinoline-2-carboxylate (PP106);

Propan-2-yl 7-(benzenesulfonyl)-3-bromo-1-[(4-fluorophenyl)methyl]-8-oxo-4,5,8,9-tetrahydro-1H-pyrrolo[3,2-h]quinoline-2-carboxylate (PP108);

7-(Benzenesulfonyl)-3-bromo-1-[(3-methylphenyl)methyl]-8-oxo-N-(propan-2-yl)-4,5,8,9-tetrahydro-1H-pyrrolo[3,2-h]quinoline-2-carboxamide (PP091);

7-(Benzenesulfonyl)-N-cyclopropyl-1-[(3-methylphenyl)methyl]-8-oxo-4,5,8,9-tetrahydro-1H-pyrrolo[3,2-h]quinoline-2-carboxamide (PP092);

7-(Benzenesulfonyl)-3-bromo-1-[(4-methylphenyl)methyl]-8-oxo-N-(propan-2-yl)-4,5,8,9-tetrahydro-1H-pyrrolo[3,2-h]quinoline-2-carboxamide (PP086);

7-(Benzenesulfonyl)-3-bromo-N-cyclopropyl-1-[(4-methylphenyl)methyl]-8-oxo-4,5,8,9-tetrahydro-1H-pyrrolo[3,2-h]quinoline-2-carboxamide (PP088);

7-(Benzenesulfonyl)-3-bromo-1-[(4-bromophenyl)methyl]-8-oxo-N-(propan-2-yl)-4,5,8,9-tetrahydro-1H-pyrrolo[3,2-h]quinoline-2-carboxamide (PP097);

7-(Benzenesulfonyl)-3-bromo-1-[(4-bromophenyl)methyl]-N-cyclopropyl-8-oxo-4,5,8,9-tetrahydro-1H-pyrrolo[3,2-h]quinoline-2-carboxamide (PP099);

7-(Benzenesulfonyl)-1-[(3-methylphenyl)methyl]-8-oxo-4,5,8,9-tetrahydro-1H-pyrrolo[3,2-h]quinoline-2-carboxylic acid (PP090);

7-(Benzenesulfonyl)-3-bromo-1-[(3-methylphenyl)methyl]-8-oxo-4,5,8,9-tetrahydro-1H-pyrrolo[3,2-h]quinoline-2-carboxylic acid (PP081);

7-(Benzenesulfonyl)-1-[(4-methylphenyl)methyl]-8-oxo-4,5,8,9-tetrahydro-1H-pyrrolo[3,2-h]quinoline-2-carboxylic acid (PP078);

7-(Benzenesulfonyl)-3-bromo-1-[(4-methylphenyl)methyl]-8-oxo-4,5,8,9-tetrahydro-1H-pyrrolo[3,2-h]quinoline-2-carboxylic acid (PP079);

7-(Benzenesulfonyl)-1-[(3,4-dimethylphenyl)methyl]-8-oxo-4,5,8,9-tetrahydro-1H-pyrrolo[3,2-h]quinoline-2-carboxylic acid (PP094);

7-(Benzenesulfonyl)-3-bromo-1-[(3,4-dimethylphenyl)methyl]-8-oxo-4,5,8,9-tetrahydro-1H-pyrrolo[3,2-h]quinoline-2-carboxylic acid (PP095);

7-(Benzenesulfonyl)-1-[(3-methylphenyl)methyl]-8-oxo-4,5,8,9-tetrahydro-1H-pyrrolo[3,2-h]quinoline-2-carboxamide (PP093);

7-(Benzenesulfonyl)-1-[(3-methylphenyl)methyl]-8-oxo-4,5,8,9-tetrahydro-1H-pyrrolo[3,2-h]quinoline-2-carboxamide (PP082);

7-(Benzenesulfonyl)-3-bromo-1-[(4-methylphenyl)methyl]-8-oxo-4,5,8,9-tetrahydro-1H-pyrrolo[3,2-h]quinoline-2-carboxamide (PP080);

7-(Benzenesulfonyl)-3-bromo-1-[(4-methylphenyl)methyl]-8-oxo-4,5,8,9-tetrahydro-1H-pyrrolo[3,2-h]quinoline-2-carboxamide (PP089);

N,7-di(benzenesulfonyl)-3-bromo-1-[(3-methylphenyl)methyl]-8-oxo-4,5,8,9-tetrahydro-1H-pyrrolo[3,2-h]quinoline-2-carboxamide (PP100);

7-(Benzenesulfonyl)-3-bromo-N-tert-butyl-1-[(3-methylphenyl)methyl]-8-oxo-4,5,8,9-tetrahydro-1H-pyrrolo[3,2-h]quinoline-2-carboxamide (PP101);

7-(Benzenesulfonyl)-3-bromo-N-(5-tert-butyl-1,2-oxazol-3-yl)-1-[(3-methylphenyl)methyl]-8-oxo-4,5,8,9-tetrahydro-1H-pyrrolo[3,2-h]quinoline-2-carboxamide (PP102);

Ethyl 1-(4-methylbenzyl)-8-oxo-7-(phenylsulfonyl)-8,9-dihydro-1H-pyrrolo[3,2-h]quinoline-2-carboxylate (13, PP058);

Ethyl 2-amino-9-[(4-methylphenyl)methyl]-6,9-dihydro-5H-pyrrolo[3,2-h]quinazoline-8-carboxylate (SVQ1);

Ethyl 2-amino-9-[(3-methylphenyl)methyl]-6,9-dihydro-5H-pyrrolo[3,2-h]quinazoline-8-carboxylate (SVQ3);

Ethyl 2-amino-9-[(3,4-dimethylphenyl)methyl]-6,9-dihydro-5H-pyrrolo[3,2-h]quinazoline-8-carboxylate (SVQ5);

Ethyl 2-amino-9-[(4-bromophenyl)methyl]-6,9-dihydro-5H-pyrrolo[3,2-h]quinazoline-8-carboxylate (SVQ7);

Ethyl 2-[(benzenesulfonyl)amino]-9-[(4-methylphenyl)methyl]-6,9-dihydro-5H-pyrrolo[3,2-h]quinazoline-8-carboxylate (SVQ9);

Ethyl 2-[(benzenesulfonyl)amino]-9-[(3-methylphenyl)methyl]-6,9-dihydro-5H-pyrrolo[3,2-h]quinazoline-8-carboxylate (SVQ11);

Ethyl 2-[(benzenesulfonyl)amino]-9-[(3,4-dimethylphenyl)methyl]-6,9-dihydro-5H-pyrrolo[3,2-h]quinazoline-8-carboxylate (SVQ13);

Ethyl 2-[(benzenesulfonyl)amino]-9-[(4-bromophenyl)methyl]-6,9-dihydro-5H-pyrrolo[3,2-h]quinazoline-8-carboxylate (SVQ15);

Ethyl 2-amino-7-bromo-9-[(4-methylphenyl)methyl]-6,9-dihydro-5H-pyrrolo[3,2-h]quinazoline-8-carboxylate (SVQ2);

Ethyl 2-amino-7-bromo-9-[(3-methylphenyl)methyl]-6,9-dihydro-5H-pyrrolo[3,2-h]quinazoline-8-carboxylate (SVQ4);

Ethyl 2-amino-7-bromo-9-[(3,4-dimethylphenyl)methyl]-6,9-dihydro-5H-pyrrolo[3,2-h]quinazoline-8-carboxylate (SVQ6);

Ethyl 2-amino-7-bromo-9-[(4-bromophenyl)methyl]-6,9-dihydro-5H-pyrrolo[3,2-h]quinazoline-8-carboxylate (SVQ8);

Ethyl 2-[(benzenesulfonyl)amino]-7-bromo-9-[(4-methylphenyl)methyl]-6,9-dihydro-5H-pyrrolo[3,2-h]quinazoline-8-carboxylate (SVQ10);

Ethyl 2-[(benzenesulfonyl)amino]-7-bromo-9-[(3-methylphenyl)methyl]-6,9-dihydro-5H-pyrrolo[3,2-h]quinazoline-8-carboxylate (SVQ12);

Ethyl 2-[(benzenesulfonyl)amino]-7-bromo-9-[(3,4-dimethylphenyl)methyl]-6,9-dihydro-5H-pyrrolo[3,2-h]quinazoline-8-carboxylate (SVQ14);

Ethyl 2-[(benzenesulfonyl)amino]-7-bromo-9-[(4-bromophenyl)methyl]-6,9-dihydro-5H-pyrrolo[3,2-h]quinazoline-8-carboxylate (SVQ16);

Ethyl 3-(benzenesulfonyl)-2-oxo-1,2,5,6-tetrahydropyrrolo[1,2-h][1,7]naphthyridine-8-carboxylate (QZN1);

Ethyl 3-(benzenesulfonyl)-2-oxo-1,5,6,7-tetrahydro-2H-pyrido[2,3-c]pyrrolo[1,2-a]azepine-9-carboxylate (QZN5);

Propan-2-yl 3-(benzenesulfonyl)-2-oxo-1,2,5,6-tetrahydropyrrolo[1,2-h][1,7]naphthyridine-8-carboxylate (QZN9);

Propan-2-yl 3-(benzenesulfonyl)-2-oxo-1,5,6,7-tetrahydro-2H-pyrido[2,3-c]pyrrolo[1,2-a]azepine-9-carboxylate (QZN13);

Ethyl 3-(benzenesulfonyl)-2-methoxy-5,6-dihydropyrrolo[1,2-h][1,7]naphthyridine-8-carboxylate (QZN3);

Ethyl 3-(benzenesulfonyl)-1-methyl-2-oxo-1,2,5,6-tetrahydropyrrolo[1,2-h][1,7]naphthyridine-8-carboxylate (QZN4);

Ethyl 3-(benzenesulfonyl)-2-methoxy-6,7-dihydro-5H-pyrido[2,3-c]pyrrolo[1,2-a]azepine-9-carboxylate (QZN7);

Ethyl 3-(benzenesulfonyl)-1-methyl-2-oxo-1,5,6,7-tetrahydro-2H-pyrido[2,3-c]pyrrolo[1,2-a]azepine-9-carboxylate (QZN8);

Propan-2-yl 3-(benzenesulfonyl)-2-methoxy-5,6-dihydropyrrolo[1,2-h][1,7]naphthyridine-8-carboxylate (QZN11);

Propan-2-yl 3-(benzenesulfonyl)-1-methyl-2-oxo-1,2,5,6-tetrahydropyrrolo[1,2-h][1,7]naphthyridine-8-carboxylate (QZN12);

Propan-2-yl 3-(benzenesulfonyl)-2-methoxy-6,7-dihydro-5H-pyrido[2,3-c]pyrrolo[1,2-a]azepine-9-carboxylate (QZN15);

Propan-2-yl 3-(benzenesulfonyl)-1-methyl-2-oxo-1,5,6,7-tetrahydro-2H-pyrido[2,3-c]pyrrolo[1,2-a]azepine-9-carboxylate (QZN16);

Ethyl 3-(benzenesulfonyl)-9-bromo-2-oxo-1,2,5,6-tetrahydropyrrolo[1,2-h][1,7]naphthyridine-8-carboxylate (QZN2);

Ethyl 3-(benzenesulfonyl)-10-bromo-2-oxo-1,5,6,7-tetrahydro-2H-pyrido[2,3-c]pyrrolo[1,2-a]azepine-9-carboxylate (QZN6);

Propan-2-yl 3-(benzenesulfonyl)-9-bromo-2-oxo-1,2,5,6-tetrahydropyrrolo[1,2-h][1,7]naphthyridine-8-carboxylate (QZN10);

Propan-2-yl 3-(benzenesulfonyl)-10-bromo-2-oxo-1,5,6,7-tetrahydro-2H-pyrido[2,3-c]pyrrolo[1,2-a]azepine-9-carboxylate (QZN14);

Ethyl 2-amino-5,6-dihydropyrimido[5,4-g]indolizine-8-carboxylate (QZQ1);

Ethyl 2-amino-6,7-dihydro-5H-pyrimido[4,5-c]pyrrolo[1,2-a]azepine-9-carboxylate (QZQ5);

Propan-2-yl 2-amino-5,6-dihydropyrimido[5,4-g]indolizine-8-carboxylate (QZQ17);

Propan-2-yl 2-amino-6,7-dihydro-5H-pyrimido[4,5-c]pyrrolo[1,2-a]azepine-9-carboxylate (QZQ21);

Ethyl 2-anilino-5,6-dihydropyrimido[5,4-g]indolizine-8-carboxylate (QZQ2);

Ethyl 2-(cyclohexylamino)-5,6-dihydropyrimido[5,4-g]indolizine-8-carboxylate (QZQ3);

Ethyl 2-anilino-6,7-dihydro-5H-pyrimido[4,5-c]pyrrolo[1,2-a]azepine-9-carboxylate (QZQ6);

Ethyl 2-(cyclohexylamino)-6,7-dihydro-5H-pyrimido[4,5-c]pyrrolo[1,2-a]azepine-9-carboxylate (QZQ7);

Propan-2-yl 2-anilino-5,6-dihydropyrimido[5,4-g]indolizine-8-carboxylate (QZQ18);

Propan-2-yl 2-(cyclohexylamino)-5,6-dihydropyrimido[5,4-g]indolizine-8-carboxylate (QZQ19);

Propan-2-yl 2-anilino-6,7-dihydro-5H-pyrimido[4,5-c]pyrrolo[1,2-a]azepine-9-carboxylate (QZQ22);

Propan-2-yl 2-(cyclohexylamino)-6,7-dihydro-5H-pyrimido[4,5-c]pyrrolo[1,2-a]azepine-9-carboxylate (QZQ23);

Ethyl 2-(cyclopentylamino)-5,6-dihydropyrimido[5,4-g]indolizine-8-carboxylate (QZQ14);

Ethyl 2-(cyclopentylamino)-6,7-dihydro-5H-pyrimido[4,5-c]pyrrolo[1,2-a]azepine-9-carboxylate (QZQ15);

Propan-2-yl 2-(cyclopentylamino)-5,4-g]indolizine-8-carboxylate (QZQ20);

Propan-2-yl 2-(cyclopentylamino)-6,7-dihydro-5H-pyrimido[4,5-c]pyrrolo[1,2-a]azepine-9-carboxylate (QZQ24);

Ethyl 2-acetamido-5,6-dihydropyrimido[5,4-g]indolizine-8-carboxylate (QZQ4);
Ethyl 2-acetamido-6,7-dihydro-5H-pyrimido[4,5-c]pyrrolo[1,2-a]azepine-9-carboxylate (QZQ8);
Propan-2-yl 2-acetamido-5,6-dihydropyrimido[5,4-g]indolizine-8-carboxylate (QZQ25);
Propan-2-yl 2-acetamido-6,7-dihydro-5H-pyrimido[4,5-c]pyrrolo[1,2-a]azepine-9-carboxylate (QZQ26);
Ethyl 7-(benzenesulfonyl)-1-[(4-methylphenyl)methyl]-8-oxo-4,5,8,9-tetrahydro-1H-pyrazolo[4,3-h]quinoline-3-carboxylate (PZ1);
Ethyl 7-(benzenesulfonyl)-2-[(4-methylphenyl)methyl]-8-oxo-4,5,8,9-tetrahydro-2H-pyrazolo[4,3-h]quinoline-3-carboxylate (PZ2);
Ethyl 7-(benzenesulfonyl)-1-[(3-methylphenyl)methyl]-8-oxo-4,5,8,9-tetrahydro-1H-pyrazolo[4,3-h]quinoline-3-carboxylate (PZ3);
Ethyl 7-(benzenesulfonyl)-2-[(3-methylphenyl)methyl]-8-oxo-4,5,8,9-tetrahydro-2H-pyrazolo[4,3-h]quinoline-3-carboxylate (PZ4);
Ethyl 7-(benzenesulfonyl)-1-[(4-bromophenyl)methyl]-8-oxo-4,5,8,9-tetrahydro-1H-pyrazolo[4,3-h]quinoline-3-carboxylate (PZ5);
Ethyl 7-(benzenesulfonyl)-2-[(4-bromophenyl)methyl]-8-oxo-4,5,8,9-tetrahydro-2H-pyrazolo[4,3-h]quinoline-3-carboxylate (PZ6);
Ethyl 7-(benzenesulfonyl)-1-[(3,4-dimethylphenyl)methyl]-8-oxo-4,5,8,9-tetrahydro-1H-pyrazolo[4,3-h]quinoline-3-carboxylate (PZ7);
Ethyl 7-(benzenesulfonyl)-2-[(3,4-dimethylphenyl)methyl]-8-oxo-4,5,8,9-tetrahydro-2H-pyrazolo[4,3-h]quinoline-3-carboxylate (PZ8).

Further objects of the invention are:
a pharmaceutical composition comprising the compound as defined in the two latter preferred embodiments and a pharmaceutically acceptable carrier;
a compound as defined in the two latter preferred embodiments for use as a medicament. Preferably, the invention provides said compound or pharmaceutical composition for use in the treatment and/or prevention of a pathology associated with a defect in an ABC (ATP-binding cassette) transporter and/or for use in the treatment and/or prevention of a pathology associated with at least one of the following: protein mutation, protein misfolding, protein degradation, protein maturation, protein trafficking. Preferably, said ABC transporter is CFTR (Cystic Fibrosis Transmembrane Conductance Regulator). Preferably, said pathology is selected from the group consisting of: cystic fibrosis, Limb-Girdle muscular dystrophy (LGMD), Congenital Bilateral Absence of Vas Deferens (CBAVD), acute, chronic, recurrent and/or autoimmune pancreatitis, disseminated bronchiectasis, asthma, allergic pulmonary aspergillosis, smoking-related lung pathology, dry eye syndrome, Sjogren's syndrome, chronic sinusitis, cholestatic jaundice, emphysema, idiopathic chronic pancreatitis, isolated obstructive azoospermia, sclerosing cholangitis, panbronchiolite, neonatal hypertripsinemia, adrenoleukodystrophy, Stargardt disease, Tangier disease, progressive familial intrahepatic cholestasis, Dubin-Johnson syndrome, elastic pseudoxantoma, persistent hyperinsulinemic hypoglycemia of infancy due to focal adenomatous hyperplasia, senile macular degeneration, retinitis pigmentosa and "cone-rod" retinal dystrophy. Still preferably, said smoking-related lung disease is chronic obstructive pulmonary disease.

The following definitions of preferred substituents apply to all above-defined embodiments of the present invention.
Preferably, when X is C=O, $R^2$ is different from hydrogen.
Preferably, $R^2$ is halogen, preferably bromine.
Preferably, A is a pentatomic aromatic heterocyclic ring comprising one or two nitrogen atoms. More preferably, A is selected from the group consisting of:

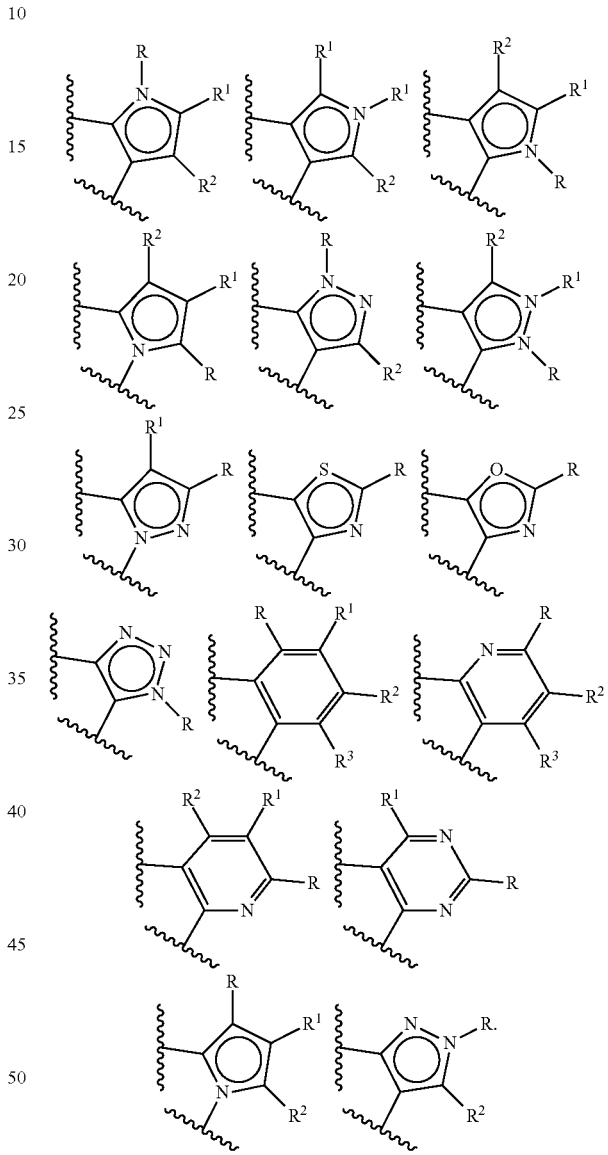

Preferably, R is selected from the group consisting of: hydrogen, linear or branched C1-C6 alkyl, aryl, arylalkyl, heteroarylalkyl, arylsulfonyl and alkylamine. Still preferably, R is a benzyl or a methylpyridinyl optionally substituted with one or more substituents independently selected from: linear or branched C1-C6 alkyl, haloalkyl, halogen (preferably chlorine) and alkoxy. Even more preferably, R is selected from the group consisting of: $SO_2Ph$, hydrogen, methyl, benzyl, phenyl, methylpyridinyl, methylbenzyl, dimethylbenzyl, methoxybenzyl, halobenzyl (preferably chlorobenzyl) and $CH_2CH_2CH_2(NMe)_2$.
Preferably, $R^1$ is hydrogen, carboxylic acid, carboxylic ester, carboxamide from primary, secondary or tertiary amine or halogen. Still preferably, $R^1$ is hydrogen, COOEt, COOMe, COOiPr, COOtBu, COOH, CONH$_2$, CONHiPr, CONHcyclopropyl, CONHSO$_2$Ph, CONHtBu, CONHtButisoxazole or Br.

Preferably, $R^2$ is hydrogen, carboxylic ester or halogen. Still preferably, $R^2$ is hydrogen, bromine, iodine, chlorine, COOEt, COOMe, COOiPr or COOtBu.

More preferably, $R^1$ and/or $R^2$ is a carboxylic ester or a carboxamide from primary, secondary or tertiary amine.

Preferably, $R^3$ is carbonitrile, alkylsulfonyl or arylsulfonyl, preferably SO$_2$Ph, optionally substituted with one or more substituents independently selected from: linear or branched C1-C6 alkyl and halogen, preferably chlorine. Still preferably, $R^3$ is SO$_2$Ph, 4-Cl—SO$_2$Ph, SO$_2$Ph-4-Me, SO$_2$Me, or CN.

Preferably, $R^3$ is arylsulfonyl or $R^3$ is absent, Q is a nitrogen atom, X is C—NR$^a$R$^b$, R$^a$ is H and R$^b$ is arylsulfonyl.

Preferably, B is a cycloalkyl or aryl ring. Still preferably, B is cyclohexyl, cycloheptyl, phenyl, or cycloheptadienyl.

Preferably, $R^4$ is hydrogen.

Preferably, X is C=O, C—OMe, C—NH$_2$ or C—NHR$^a$.

Preferably,

Q is a carbon atom, X is C=O and Y is hydrogen or alkyl, or

Q is a carbon atom, X is C—Oalkyl and Y is absent, or

Q is a nitrogen atom, X is C—NR$^a$R$^b$ and Y is absent.

Preferably R$^a$ and R$^b$ are independently selected from the group consisting of: hydrogen, arylsulfonyl, acetyl, aryl and cycloalkane. More preferably, R$^a$ and R$^b$ are independently selected from the group consisting of: SO$_2$Ph, Ph, cyclohexyl and cyclopentyl.

Preferably, when X is C=O, Y is hydrogen or alkyl or when X is C—O-alkyl, preferably C—OMe, Y is absent. Still preferably, when X is C=O, Y is hydrogen or methyl or when X is C—O-alkyl, preferably C—OMe, Y is absent.

Preferably, Y is absent or present and is hydrogen or alkyl (e.g. methyl).

Preferably, Q is a carbon atom.

Preferably, n is 1 or 2.

Preferably, m is 1.

Preferably, the compound or the pharmaceutically acceptable salt, tautomer, stereoisomer, deuterated derivative, active metabolite thereof as defined above has one of the following general formulas:

(II)

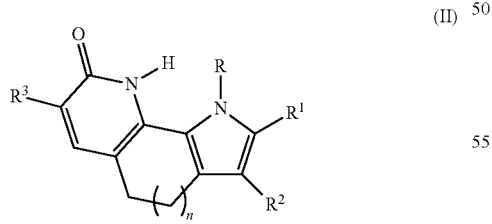

(III)

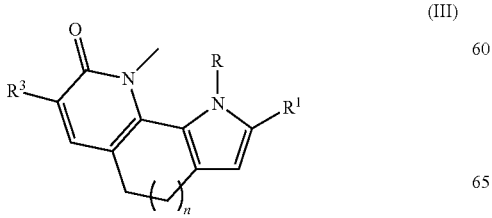

(IV)

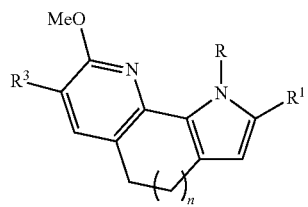

(V)

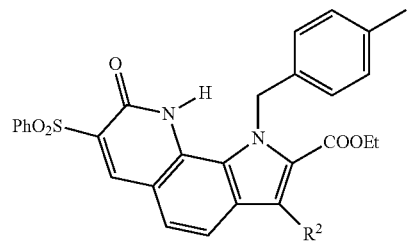

(VI)

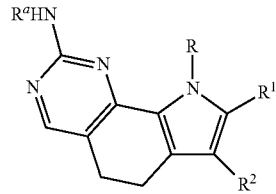

(VII)

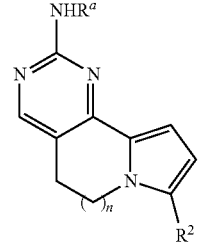

(VIII)

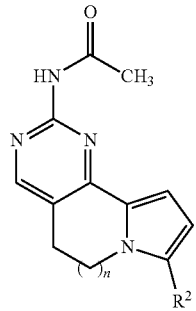

(IX)

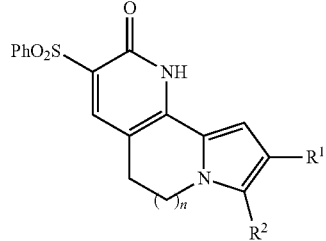

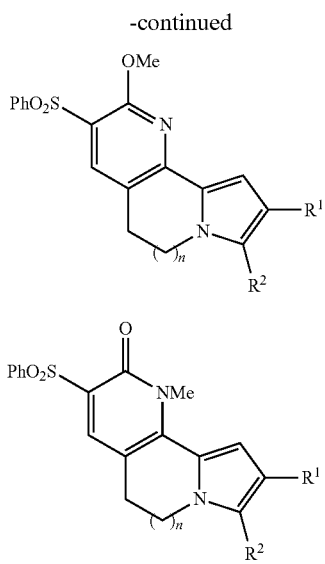

Furthermore, the compounds of the invention are also for use in the treatment and/or prevention of a disease caused by and/or involving a maturation defect of at least one protein, e.g. alpha-sarcoglycan.

As defined herein, a "pathology associated with a protein mutation" is a disease caused by a mutation in a gene encoding a protein. Such mutation causes loss of function of the protein because the protein synthesis is arrested, the resulting protein is unstable and/or misfolded, or the structure of a critical region of the protein involved in activity is significantly altered. Said diseases are generally Mendelian diseases or diseases due to complex genetic defects. Examples of pathologies associated with protein mutation are cystic fibrosis, Duchenne muscular dystrophy, spinal muscular atrophy, sickle cell disease, Tay-Sachs disease.

As defined herein, a "pathology associated with protein misfolding" is a disease in which a protein is structurally abnormal assuming a tridimensional conformation significantly different from the structure of the wild type protein. When a protein fails to fold correctly, it may lose its normal function or it may become noxious to the cell as a result of a gain of toxic function. Protein misfolding may be the result of changes in the primary amino acid sequence of the protein (due for instance to a gene mutation or post-translational modifications such as hyperphosphorylation), changes in temperature or pH, an increase in production of a protein, or a decrease in its clearance. Advancing age is a strong risk factor, as is traumatic brain injury. Diseases associated to protein misfolding include but are not limited to prion diseases, Alzheimer's disease, Parkinson's disease, amyloidosis, amyotrophic lateral sclerosis, trinucleotide repeat disorders (e.g. hungtinton's disease), retinitis pigmentosa with rhodopsin mutations.

As defined herein, a "pathology associated with protein degradation" is a disease in which cell protein degradation pathways, the protein quality control responsible for protein degradation through the ubiquitin-proteasome system (UPS), recognize mutated/misfolded proteins and degrade them. In case of diseases related to protein misfolding, a protein may misfold but does not necessarily lose entirely its functional activity. Nevertheless it is recognized as potentially toxic and degraded, thereby causing a loss of protein function of what would otherwise have been a partially active protein.

As defined herein, "pathology associated with a protein maturation" is a disease in which a protein, due to mutations affecting the protein itself or other factors, is unable to undergo the modifications (e.g. glycosylation) that are required to generate the normal and mature form of the protein. The inability to mature can be due to misfolding or other types of modifications of the protein structure. Defective maturation can result in altered subcellular localization of the protein. Examples of pathologies associated with protein maturation defect are cystic fibrosis (class 2 mutations), Wilson's disease, progressive familial intrahepatic cholestasis, nephrogenic diabetes insipidus due to vasopressin receptor mutations.

As defined herein, a "pathology associated with protein trafficking" is a disease in which a protein, due to mutations affecting the protein itself or other factors, remains trapped in an intermediate cellular compartment (e.g. the endoplasmic reticulum) and therefore does not reach its final destination (e.g. plasma membrane). Mistrafficking may be the consequence of misfolding that leads to detection by the quality control systems resulting in early degradation by the proteasome. Mistrafficking may be also due to defective interaction with ancillary proteins required for coordinated trafficking. Examples of pathologies associated with protein maturation defect are cystic fibrosis (class 2 mutations), Wilson's disease, progressive familial intrahepatic cholestasis, nephrogenic diabetes insipidus due to vasopressin receptor mutations.

Preferred pathologies that may be treated with the compounds of the present invention are summarised in the following table:

| Defect | Pathology | Comment |
|---|---|---|
| Pathology associated with a defect in an ABC (ATP-binding cassette) transporter | | |
| I. Genetic and non genetic diseases associated with altered CFTR activity in the lungs and/or other organs | | |
| CFTR mutations | Cystic fibrosis | |
| CFTR mutations | Congenital Bilateral Absence of Vas Deferens (CBAVD) | More than half of all men with CBAVD have mutations in the CFTR gene. Mutations in this gene also cause cystic fibrosis. When CBAVD occurs with CFTR mutations, it is considered a form of atypical cystic fibrosis. |
| CFTR mutations | obstructive azoospermia | Obstructive azoospermia (OA) results from mechanical blockage, which can occur anywhere along the reproductive tract, including the vas deferens, epididymis, and ejaculatory. Link to CFTR mutations |

-continued

| Defect | Pathology | Comment |
|---|---|---|
| Pathology associated with a defect in an ABC (ATP-binding cassette) transporter ||||
| CFTR Mutations, polymorphisms, dysfunction | disseminated bronchiectasis | Obstructive multifactorial disorder belonging to the category of cystic fibrosis monosymptomatic diseases (or CFTR-opathies) Association of bronchiectasis with cystic fibrosis gene mutations and polymorphisms. The cystic fibrosis gene is also associated with bronchiectasis due to rheumatoid arthritis and allergic bronchopulmonary aspergillosis; see Semin Respir Crit Care Med. 2003 April; 24(2): 179-84. |
| CFTR Mutations | asthma | See Can Respir J. 2012 January-February; 19(1): 44-45. |
| CFTR mutations | allergic pulmonary aspergillosis | Increased risk in CF patients. |
| CFTR mutations | acute, chronic and/or recurrent and/or autoimmune pancreatitis | Subjects with non-functional CFTR protein show clinical features of cystic fibrosis. Those with less severe mutations in the CFTR gene risk developing pancreatitis, which is estimated to be 40 to 80 times that in the general population. Heterozygotes for CFTR mutations are generally healthy but still have a 3 to 4-fold risk over the general population for pancreatitis; see World J Gastroenterol. 2014 Dec. 7; 20(45): 16891-16901. |
| | chronic sinusitis | Cystic fibrosis related, see Am J Rhinol Allergy. 2013 September-October; 27(5): 387-395. |
| | smoking-related lung pathology | Beneficial effect due to thinning of mucus not directly linked to CFTR mutations. Correctors/potentiators may have beneficial effect in diseases characterized by mucus stasis, like smoke related lung disease and COPD |
| CFTR expression related (not necessarily with mutation) | Sjogren's syndrome | Disorders with decreased function of salivary, lacrimal glands, and the exocrine pancreas; CFTR expression found to be altered and Transgene expression as well as Treatment with VX770 and, in particular, C18 restored salivation, rescued CFTR expression and localization, and nearly eliminated the inflammation and tissue damage; see Gastroenterology. 2017 October; 153(4): 1148-1159. doi: 10.1053/j.gastro.2017.06.011. Epub 2017 Jun. 19. |
| CFTR-related disorder | sclerosing cholangitis | Abnormalities in CFTR function/CFTR-mediated ion transport dysfunction |
| CFTR related | panbronchiolites | |
| CFTR-related disorder | neonatal hypertripsinemia | |
| | Pulmonary emphysema | Emphysema, as a consequence of chronic obstructive lung disease, could benefit from stabilization and enhanced function of CFTR protein |
| II. Genetic diseases in which a defective ABC transporter is involved ||||
| ABC transporter defect | adrenoleukodystrophy | |
| ABC transporter defect | Stargardt disease | |
| ABC transporter defect | senile macular degeneration | |
| ABC transporter defect | Tangier disease | |
| ABC transporter defect | progressive familial intrahepatic cholestasis | |
| ABC transporter defect | Dubin-Johnson syndrome | |

| Defect | Pathology | Comment |
|---|---|---|
| | Pathology associated with a defect in an ABC (ATP-binding cassette) transporter | |
| ABC transporter defect | elastic pseudoxanthoma | |
| ABC transporter defect | persistent hyperinsulinemic hypoglycaemia of infancy due to focal adenomatous hyperplasia | |
| III. Genetic diseases caused by folding, degradation, and/or maturation defects leading to instability of a mutant protein | | |
| | Limb-Girdle muscular dystrophy (LGMD) | Application of small molecules developed to rescue F508del-CFTR trafficking- CFTR correctors- improved the maturation of several α-sarcoglycan mutants that were consequently rescued at the plasma membrane. Remarkably, in myotubes from a patient with LGMD2D, treatment with CFTR correctors induced the proper re-localization of the whole sarcoglycan complex; see Carotti et al., Human Molecular Genetics, Volume 27, Issue 6, 15 Mar. 2018, Pages 969-984. Autosomal dominant LGMD is known as LGMD1 and there are currently recognized eight subtypes (LGMD1A-1H). Autosomal recessive LGMD is known as LGMD2 and has 17 subtypes (LGMDA-Q). Additional terminology has been used in the past to describe forms of muscular dystrophy that are now classified under LGMD. These terms are no longer widely used and include scapulohumeral (Erb) muscular dystrophy, pelvifemoral (Leyden-Mobius) muscular dystrophy, and severe childhood autosomal recessive muscular dystrophy (SCARMD) |
| | muscular dystrophy of the cinguli | See Carotti M, et al. Hum Mol Genet. 2018, 27, 969-984 |
| | nephrogenic diabetes insipidus | See Sampson H M, et al. Orphanet J Rare Dis. 2013, 8, 11- cited at page 4 |
| | LQTS2 | See Sampson H M, et al. Orphanet J Rare Dis. 2013, 8, 11- cited at page 4 |
| | congenital hyperinsulinism retinitis pigmentosa and "cone-rod" retinal dystrophy | See Sampson H M, et al. Orphanet J Rare Dis. 2013, 8, 11- cited at page 4 |

Although many eukaryotic ABC-transporters use the energy derived from ATP hydrolysis to carry out an active transport of substances, others work differently. In the CFTR protein and in the sulfonylurea receptor (SUR), the ATP hydrolysis is associated with the regulation of the opening and closure of the same channel-protein (CFTR) or $K^+$ channels (SUR). Human ABC-transporters are involved in several diseases resulting from polymorphisms in the ABC genes, and rarely due to the complete loss of function of the individual ABC proteins. Of particular relevance are diseases due to ER-associated degradation (ERAD) of mutant ABC proteins. Misfolding and premature degradation caused by missense mutations has been reported to be a significant cause of membrane protein deficiencies. Disease causing mutations in several human ABC proteins, including among others ABCA1 (Tangier disease), ABCB4 (progressive familial intrahepatic cholestasis type 3), ABCB11 (progressive familial intrahepatic cholestasis type 2), ABCC2 (Dubin-Johnson syndrome), ABCC7 (cystic fibrosis), ABCC8 (hyperinsulinemic hypoglycemia of infancy) and ABCG2 (gout), have been linked to aberrant folding, retrotranslocation of proteins into the cytoplasm and subsequent proteasomal degradation (Rudashevskaya E L, et al. Drug Discov Today Technol 2014, 12, e87-e94).

Further ABC-related diseases include adrenoleukodystrophy, Stargardt's disease, immune deficiencies, elastic Pseudoxanthoma, persistent hyperinsulinemic hypoglycaemia of childhood. The human family ABCB (MDR/TAP) is responsible for multiresistance (MDR) against a variety of structurally unrelated drugs. Glycoprotein P ABCB1 or MDR1 is also involved in other biological processes, for which lipid transport is the main function. It mediates the secretion of aldosterone steroids from the adrenal glands and its inhibition has blocked the migration of dendritic immune cells, probably related to the transport outwardly of the lipidic platelet activating factor (PAF).

The compounds of the present invention can also increase the activity of mutated forms of CFTR gene, such as S549N, G542X, G551D, R117H, N1303K, W1282X, R553X, I507del, R1162X, G85E, D1152H, R560T, R347P, A455E, R334W, Q493X, E56K, P67L, R74W, D110E, D110H, R117C, G178R, E193K, L206W, R347H, R352Q, A455E, S549R, G551S, D579G, S945L, S997F, F1052V, K1060T, R1070, F1074L, G1244E, S1251N, S 1255P, D1270N, G1349D.

In a preferred embodiment, the compounds of the invention are intended for use in the treatment of patients carrying CFTR gene mutations of one or more classes, e.g. class I, class II, class III, class IV, class V, or class VI mutations. The subjects can carry mutations in a homozygosity (e.g. F508del/F508del), or compounded heterozygosity condition (e.g. F508del/G542X or F508del/N1303K). In fact, the chemical compounds of the present invention, although they are provided with a mechanism of action which is typical for the correctors, can operate on different mutation classes, since they are able to increase the production of mature CFTR protein. Preferably, in the specific case of class I mutations (e.g. G542X, or W1282X), the ability of combination with agents promoting the "read through" of the premature stop mutation is referred to.

In one embodiment, the compounds defined above are part of combinations designed specifically for recovering the function of a mutated protein.

In a preferred embodiment, the compounds of the present invention produce a synergistic effect on the recovery of F508del-CFTR if combined with class 1 correctors, such as VX-809 (3-(6-(1-(2,2-difluorobenzo[d][1,3]dioxol-5-yl)cyclopropanecarboxamido)-3-methylpyridin-2-yl)benzoic acid), according to the terminology created by Okiyoneda et al. (Okiyoneda T, et al. Nat Chem Biol 2013, 9, 444-454). This synergistic action is also expected for combinations including other correctors, e.g. but not limited to VX-661 (1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide), VX-445, VX-659, VX-983, VX-152, VX-440 (Olacaftor, N-(benzenesulfonyl)-6-[3-fluoro-5-(2-methylpropoxy)phenyl]-2-[(4S)-2,2,4-trimethylpyrrolidin-1-yl]pyridine-3-carboxamide) developed by Vertex Pharmaceuticals; ABBV-2737, GLPG2222 (Wang X, et al. J Med Chem. 2018, 61, 1436-1449), GLPG2851, GLPG2665, GLPG2737, GLPG3221 developed by Galapagos/AbbVie; PTI-801 developed by Proteostasis Therapeutics; FDL169 developed by Flatley Discovery Lab; bisaminomethylthiazole known as corr-4a (Pedemonte N, et al. J Clin Invest. 2005, 115, 2564-2571); W1282Xcorr-B09 and W1282Xcorr-A23 (Haggie et al., J Biol Chem 2017, 292, 771-785).

In particular, a synergistic effect is expected for combinations which include one of the active compounds described herein and one of the following correctors: VX-661 (tezacaftor), VX-809 or GLPG-2222 (Galapagos/AbbVie).

Positive effects are also expected from combinations comprising potentiators and/or amplifiers (Giuliano K A et al., SLAS Discov 2018, 23, 111-121; Molinski S V, et al. EMBO Mol Med. 2017, 9, 1224-1243). The potentiators increase the probability of opening the CFTR channels carried in the plasma membrane by the effect of the correctors. The amplifiers instead increase the synthesis of the CFTR protein, regardless of the type of mutation, and therefore provide more "substrate" for the corrector activity (Giuliano K A et al., SLAS Discov 2018, 23, 111-121).

Potentiators of interest for the present invention include, e.g., VX-770 (Ivacaftor), VX-561 (deuterated form of VX-770), GLPG1837 (Van der Plas S E, et al. J Med Chem. 2018, 61, 1425-1435), GLPG 2545, GLPG 3067, genistein, phenylglycine (PG-01), PTI-808 (Proteostasis Therapeutics). Other potentiators, belonging to the families of 1,4-dihydropyridines, tetrahydrobenzothiophenes, benzofurans, anthraquinones, sulphonamides and phenylglycines, have been previously identified by academic laboratories by screening chemical "libraries" (Yang H, et al. J Biol Chem 2003, 278, 35079-35085; Pedemonte N, et al. Mol Pharmacol 2005, 67, 1797-1807; Pedemonte N, et al. Mol Pharmacol 2005, 68, 1736-1746).

Amplifiers of interest for the present invention include, e.g., PTI-428, (Proteostasis Therapeutics).

The combination of compounds of the invention and drugs that increase the read-through of the premature stop codons, such as Ataluren (PTC124) (3-[5-(2-fluorophenyl)-1,2,4-oxadiazol-3-yl]benzoic acid) is also of interest for the present invention.

Correctors, potentiators, amplifiers of interest for the present invention are known in the art and, in particular, described in WO 2017173274 (which is herein incorporated by reference). Compounds of the present invention may also be combined to inhibitors of HDAC which have shown significant benefit in correcting protein misfolding diseases that occur in response to both familial and somatic mutation (see as a reference Angles, F., Hutt, D. M., & Balch, W. E. (2019). HDAC Inhibitors Rescue Multiple Disease-Causing CFTR Variants. Human Molecular Genetics. doi:10.1093/hmg/ddz02). HDAC inhibitors belinostat (PXD-101), panobinostat (LBH-589) and romidepsin (FK-228) have shown efficacy in improving the stability, trafficking and function of CFTR variants alone or in combination with the CFTR corrector, VX-809. In particular, HDAC inhibitors can correct the trafficking defect associated with Class II (ER export defective) and III/IV (gating/channel function defective) CFTR variants and restore cell surface chloride channel activity in primary bronchial epithelial (hBE) cells homozygous for F508del.

Further, relevant for the present invention is the combination of compounds of the invention and gene therapy for replacing the mutated gene with a functioning gene (classical gene therapy), or repairing the mutated gene through, e.g., "gene editing" protocols.

The compounds described herein can also be combined with drugs that act on targets other than CFTR, but equally relevant for the multi-organ pathology features of cystic fibrosis, especially for respiratory manifestations. Among these drugs we can include:

i) antibiotics and anti-infectives such as penicillins (amoxicillin, clavulanic acid, cloxacillin, dicloxacillin, ticarcillin), cephalosporins (cephalexin, cefdinir, cefprozil, cefaclor, cefuroxime), sulfamethoxazole, trimethoprim, erythromycin, sulfisoxazole, azithromycin), tetracycline (tetracycline, doxycycline, minocycline, and tigecycline); vancomycin; imipenem, meropenem; colistimethate; aminoglycosides (tobramycin, amikacin, gentamicin); quinolones (ciprofloxacin, levofloxacin), aztreonam, linezolid upon oral, inhalation, intravenous, intramuscular administration;

ii) anti-inflammatories: corticosteroids (inhaled or orally; e.g. budesonide, Clenil) and non-steroidal drugs (ibuprofen);

iii) mucolytics: dornase alfa (Pulmozyme), N-acetylcysteine (Fluimucil), saline hypertonic, mannitol (Bronchitol);

iv) bronchodilators: salbutamol, albuterol, levalbuterol.

An "active metabolite" is a modified form of a drug occurring when a drug is metabolized by the body into a form which continues to produce effects in the body.

As used herein, the term "deuterated derivative" refers to an identical chemical structure, in which one or more hydrogen atoms are replaced by a deuterium atom.

As used herein, the term "modulator" refers to a compound that increases the activity of a biological molecule, such as a protein, preferably a mutated protein. For example, a protein modulator is a compound that increases the activity of that protein. The increase in activity resulting from a modulator includes but is not limited to compounds that correct, enhance, stabilize and/or amplify the protein.

As used herein, the term "corrector" refers to an agent that promotes the processing and trafficking of a biological molecule, such as a protein, preferably a mutated protein, to increase the amount of such biological molecule on the surface of the cell. Preferably, the compounds of the invention as defined above act as correctors, in particular of the CFTR mutated protein.

As used herein, the term "potentiator" refers to an agent that increases the activity of a channel-protein, preferably in its mutated form, located on the surface of the cell, preferably resulting in an increase in ion transport.

In the present invention, the term "potentiator" also refers to an agent that increases the probability of opening the channels of a biological molecule, such as a protein, preferably a mutated protein. For mutations which cause a defect in protein maturation (e.g. F508del), the action of potentiators is preferably favoured by the correctors' effect.

As used herein, the term "active pharmaceutical ingredient" ("API") refers to a biologically active compound.

In the present invention, the term "amplifier" refers to an agent that increases the synthesis of a biological molecule, preferably a protein, preferably a mutated protein, preferably regardless of the type of mutation, thus providing more "substrate" for the activity of correctors and potentiators.

The term "aryl" includes carbocyclic or heterocyclic hydrocarbons containing one to two rings, either fused or bound by a single bond, in which at least at least one of the rings is aromatic. Preferably, each heterocyclic aromatic hydrocarbon, also referred to as heteroaryl group, comprises a 5- or 6-membered ring containing 1-3 heteroatoms selected from N, O or S.

Examples of aryl groups according to the invention are, e.g., phenyl, biphenyl α- or β-naphthyl, dihydronaphthyl, thienyl, benzothienyl, furyl, benzofuranyl, pyrrolyl, imidazolyl, pyrazolyl, tiazolyl, isothiazolyl, oxazolyl, isoxazolyl, pyridyl, pyrazinyl, pyrimidyl, pyridazinil, indolyl, isoindolyl, purinyl, quinolyl, isoquinolyl, dihydroquinolyl, quinoxalinil, benzodioxolyl, indanil, indenyl, triazolyl, and the like. Preferably, aryl is phenyl.

As used herein, the term "heterocyclic" (also known as "heterocycloalkyl") refers to a ring, preferably having 5 or 6 members, containing one or more heteroatoms from N, O, S. In particular, it is meant a saturated or partially unsaturated 3- to 7-membered carbocyclic ring, where one or more carbon atoms are replaced by heteroatoms, such as nitrogen, oxygen and sulphur. Examples not limited to the heterocyclic groups are, e.g., piran, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine, and the like.

The term "cycloalkyl", unless otherwise specified, means a monocyclic ring comprising 5 to 8 carbon atoms, which may contain one or more double bonds even if it does not have a completely conjugated π system. Examples of cycloalkyl groups, without limitation, are cyclopropane, cyclobutane, cyclopentane, cyclopentene, cyclohexane, cyclohexene, cyclohexadiene, cycloheptane, cycloheptene, cycloheptadiene.

The term "linear or branched C1-C6 alkyl", thus including C1-C4 alkyls, is understood to mean any group such as, e.g., methyl, ethyl, n-propyl, isopropyl, n-butyl, isobutyl, tertbutyl, secbutyl, n-pentyl, n-hexyl, and the like. Preferably, alkyl is methyl.

The term "linear or branched C2-C6 alkenyl" is understood to mean any group such as, e.g., vinyl, allyl, 1-propenyl, isopropenyl, 1-butenyl, 2-butenyl, 3-butenyl, 2-pentenyl, 1-hexenyl, and the like.

The term "linear or branched C2-C6 alkynyl" is understood to mean any group such as, e.g., ethinyl, 2-propinyl, 4-pentinyl, and the like.

Preferably, arylalkyl is benzyl. Preferably, arylsulfonyl is phenylsulfonyl. Preferred examples of carboxylic ester include: COOEt, COOMe, COOiPr, COOtBu.

Preferred halogens include bromine, chlorine and iodine. More preferably, halogen is bromine.

The salts of the compounds of the present invention are also included within the scope of the invention. Due to their potential use in medicine, the salts of the compounds of formula (I) are preferably pharmaceutically acceptable. Pharmaceutically acceptable salts comprise the conventional non-toxic salts obtained by saltification of a compound of formula (I) with inorganic acids (e.g. hydrochloric, hydrobromic, sulfuric or phosphoric acid), or with organic acids (e.g. acetic, propionic, succinic acid, benzoic, sulfanylic, 2-acetoxy-benzoic, cinnamic, mandelic, salicylic, glycolic, lactic, oxalic, malic, maleic, malonic, fumaric, tartaric, citric, p-toluene sulphonic, methanesulphonic, ethanesulphonic, or naphthalensulphonic). For a review on suitable pharmaceutical salts, see: Berge S. M. et al., *J. Pharm. Sci.* 1977, 66, 1-19; Gould P. L. *Int. J. Pharm* 1986, 33, 201-217 and Bighley et al. *Encyclopedia of Pharmaceutical Technology*, Marcel Dekker Inc, New York 1996, Volume 13, page 453-497. Other pharmaceutically acceptable salts include pharmaceutically acceptable alkali or alkaline earth metal salts such as sodium, potassium, calcium or magnesium salts; in particular pharmaceutically acceptable salts of one or more carboxylic acid groups which may be present in the compound of formula (I). Other salts, which are not pharmaceutically acceptable, e.g. the trifluoroacetate salt, may be useful in the preparation of compounds of the present invention and these form a further aspect of the invention. The invention comprises in its scope all the possible stoichiometric and non-stoichiometric forms of the salts of the compounds of formula (I).

Furthermore, the compounds of formula (I) can exist in unsolvated forms as well as in solvated form with pharmaceutically acceptable solvents such as water, EtOH and the like. Some compounds of formula (I) may exist in stereoisomeric forms (e.g., they may contain one or more asymmetric carbon atoms). The individual stereoisomers (enantiomers and diastereoisomers) and mixtures thereof are included in the scope of the present invention. The present invention also covers the individual isomers of the compounds represented by the formula (I) as mixtures with isomers in which one or more chiral centres are inverted. Racemic mixtures can be separated to give their individual enantiomer using preparative HPLC using a column with chiral stationary phase or resolved to produce individual enantiomers using methods known to those skilled in the art. Furthermore, chiral intermediates can be resolved and used to prepare single enantiomers.

Similarly, it is understood that the compounds of formula (I) can exist in tautomeric forms different from those shown in the formula and these are included in the scope of the present invention.

The invention also includes all suitable isotopic variations of a compound of the invention. An isotopic variation of a compound of the invention is defined as that in which at least one atom is replaced by an atom having the same atomic number but an atomic mass different from the atomic mass which is usually found in nature. Examples of isotopes that can be incorporated into the compounds of the invention include isotopes such as $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl respectively. Some isotopic variations of the invention, e.g., those in which a radioactive isotope such as $^3$I or $^{14}$C is incorporated, are useful in tissue delivery studies of the drug and/or substrate. Furthermore, replacement with isotopes such as deuterium $^2$H, can provide certain therapeutic advantages resulting from greater metabolic stability. The isotopic variations of the compounds of the invention can generally be prepared by conventional procedures as well as with the illustrative methods or with the preparations described in the examples below by using suitable isotopic variations of the suitable reagents.

It will be appreciated by those skilled in the art that certain protected derivatives of the compounds of the invention, which can be made prior to a final deprotection step, cannot possess pharmacological activity as such, but can, in certain cases, be administered orally or parenterally and then metabolized in the body to form compounds defined in the first aspect that are pharmacologically active. These derivatives can therefore be described as "prodrugs". All protected derivatives, prodrugs, solvates, clathrates, pharmaceutically acceptable salts of compounds defined in the first aspect are included in the scope of the invention. Examples of prodrugs suitable for the compounds of the present invention are described in Drug of Today, Volume 19, Number 9, 1983, pp. 499-538 and in Topics in Chemistry, Chapter 31, pp. 306-316 and in "Design of Prodrugs" by H. Bundgaard, Elsevier, 1985, Chapter 1 (the disclosure of which the document is incorporated therein by reference). It will be further appreciated by those skilled in the art that certain moieties, known to those skilled in the art as "pro-moieties", are described by H. Bundgaard, in "Design of Prodrugs" (the disclosure of which the document is incorporated therein by reference) can be positioned on appropriate functionalities when these features are present within the compound defined in the first aspect.

The pharmaceutical compositions of the present invention can be selected based on the treatment requirements. These compositions are prepared by admixing and are suitably adapted for oral or parenteral administration, and as such they can be administered in the form of tablets, capsules, oral preparations, powders, granules, pills, injectable or infusible liquid solutions, suspensions, suppositories, preparation for inhalation.

In particular, a pharmaceutical composition comprising a compound of formula (I) or a pharmaceutically acceptable salt, solvate, clathrate, prodrug, tautomer, stereoisomer, deuterated derivative, active metabolite thereof can be administered in a variety of ways, including parenteral, oral, pulmonary, ophthalmic, nasal, rectal, vaginal, auditory, topical, buccal, transdermal, intravenous, intramuscular, subcutaneous, intradermal, intraocular, intracerebral, intralymphatic, intraarticular, intrathecal and intraperitoneal routes. The pharmaceutical compositions of the present invention are particularly suitable for pulmonary, intranasal and/or ocular administration.

In addition to the common meaning attributed to the routes described herein for administration to any part, tissue or organ whose primary function is the gas exchange with the external environment, for the purposes of the present invention, "pulmonary" also includes a tissue or a cavity which it is contingent on the respiratory tract, particularly breasts, even more particularly paranasal sinuses. For pulmonary administration, an aerosol formulation comprising the compound of the invention, a manual pump spray, a nebulizer or a pressurized dose inhaler (meter-dose inhaler) as well as dry powder formulations are provided by way of non-limiting example. Suitable formulations of this type may also include other agents, such as antistatic agents, to keep the described compounds in the form of effective aerosols.

A drug delivery device for dispensing and delivering an aerosol can comprise an aerosol container with a dosage valve containing a pharmaceutical aerosol formulation as described and a housing for an actuator adapted to contain the container and allow the delivery and delivery of the drug. The container in said device can have a head space that represents more than about 15% of the total volume of the container. Often, the compound intended for pulmonary administration is dissolved, suspended or emulsified in a mixture of solvent, surfactant and propellant. The mixture can be kept under pressure in a sealed container with a metering valve.

Tablets and capsules for oral administration are generally presented in unit dosage form and contain conventional excipients such as binders, fillers (including cellulose, mannitol, lactose), diluents, tablet agents, lubricants (including magnesium stearate), detergents, disintegrants (e.g. polyvinylpyrrolidone and starch derivatives such as sodium starch glycolate), dyes, flavourings and wetting agents (e.g. sodium lauryl sulphate).

The oral solid compositions can be prepared by conventional mixing, filling or pelleting methods. The mixing operation can be repeated to distribute the active ingredient in all the compositions containing large quantities of fillers. These operations are conventional.

Oral liquid preparations may be in the form of, e.g., aqueous or oily suspensions, solutions, emulsions, syrups or elixirs, or may be presented as a dry product to be reconstituted with water or with a suitable vehicle before use. Such liquid preparations may contain conventional additives such as suspending agents, e.g. sorbitol, syrup, methylcellulose, gelatine, hydroxyethyl cellulose, carboxymethylcellulose, aluminium stearate gel or hydrogenated edible fats; emulsifying agents, e.g. lecithin, sorbitan monooleate, or acacia; non-aqueous vehicles (which may include edible oils) such as almond oil, fractionated coconut oil, oily esters such as glycerine esters, propylene glycol, or ethyl alcohol; preservatives, such as methyl or propyl p-hydroxybenzoate or sorbic acid, and if desired, conventional flavouring or colouring agents. Oral formulations also include conventional slow release formulations such as coated gastro-resistant tablets or granules.

The pharmaceutical preparation for administration via inhalation can be provided by an insufflator or a pressure nebulizer.

For parenteral administration the fluid unit dosage can be prepared, comprising the compound and a sterile vehicle. The compound can be suspended or dissolved, depending on the vehicle and concentration. Parenteral solutions are normally prepared by dissolving the compound in a vehicle, sterilization by filtration of the latter, filling of suitable bottles and sealing. Advantageously, adjuvants such as local anaesthetics, preservatives and buffering agents can be dissolved in the vehicle. To increase stability, the composition can be frozen after filling the vials and removing the water under vacuum. The parenteral suspensions are prepared in substantially the same way, except that the compound may be suspended in the vehicle instead of being dissolved and sterilized by exposure to ethylene oxide prior to suspension in the sterile vehicle. Conveniently, a surfactant or a wetting agent may be included in the composition to promote uniform distribution of the compound of the invention.

For oral or sublingual administration, the compositions can be tablets, pastilles, or gels.

The compounds can be pharmaceutically formulated as suppositories or retention enemas, e.g. suppositories containing conventional bases such as cocoa butter, polyethylene glycol, or other glycerides, for rectal administration.

Another route of administration of the compounds of the present invention relates to topical treatment. Topical formulations may contain, e.g., ointments, creams, lotions, gels, solutions, pastes and/or may contain liposomes, micelles and/or microspheres. Examples of ointments comprise oily ointments such as vegetable oils, animal fats, semisolid hydrocarbons, emulsifiable ointments such as hydroxystearin sulphate, anhydrous lanolin, hydrophilic petrolatum, cetyl alcohol, glycerol monostearate, stearic acid, water-soluble ointments containing polyethylene glycols of various molecular weight. The creams, as known to the experts in the formulation, are viscous liquids or semisolid emulsions, and contain an oily phase, an emulsifier and an aqueous phase. The oily phase generally contains petrolatum and an alcohol such as cetyl or stearic alcohol. The formulations suitable for topical ocular administration also include eye drops, in which the active ingredient is dissolved or suspended in a suitable vehicle, in particular in an aqueous solvent for the active ingredient.

A further way of administering the compounds of the invention concerns transdermal delivery. Typical transdermal formulations comprise conventional aqueous and non-aqueous vectors, such as creams, oils, lotions or pastes or they can be in the form of medicated membranes or plasters.

In order to increase bioavailability, the compounds can be formulated pharmaceutically in liposomes or in nanoparticles. Acceptable liposomes can be neutral, negatively or positively charged, the charge being a function of the charge of the liposome components and of the pH of the liposomal solution. Liposomes can normally be prepared using a mixture of phospholipids and cholesterol. Suitable phospholipids include phosphatidylcholine, phosphatidylethanolamine, phosphatidic acid, phosphotidylglycerol, phosphatidylinositol. Polyethylene glycol can be added to improve the blood circulation time of liposomes.

Acceptable nanoparticles include albumin nanoparticles and gold nanoparticles.

A reference for the formulations is the book by Remington (Remington "*The Science and Practice of Pharmacy*", Lippincott Williams & Wilkins, 2000).

The compounds of the present invention can be used for use in the treatment and/or prevention of the above-mentioned pathologies as a sole therapy or in combination with further therapeutic agents. The combination can be administered as a separate (simultaneous, sequential) composition of the individual components of the treatment or as a single dosage form containing both agents. When the compounds of the present invention are in combination with other active principles, the active ingredients can be formulated separately in preparations for a single ingredient of one of the forms described above, and then given as combined preparations, which are administered simultaneously or several times, or can be formulated together in a two or more ingredient preparation.

The compounds of general formula (I) can be administered to a patient at a total daily dose of, e.g., from 0.001 to 1000 mg/kg of body weight per day. The compositions of the dosage units can contain quantities of sub-multiples thereof to compensate for the daily dose. The compound can also be administered weekly or any other day. Determining the optimal dosages for a particular patient is well known to those skilled in the art. As is common practice, compositions are normally accompanied by instructions for use written or printed in the treatment in question.

The present invention will be described by non-limiting examples, with reference to the following figures:

FIG. 1. Evaluation of the corrective efficacy of a compound of the invention, PP007. The plot shows an example of an experiment where the activity of F508del-CFTR was evaluated in CFBE41o– cells with the HS-YFP fluorescent probe. Activity is reported as "quenching rate" (QR) of cellular fluorescence following the addition of iodide in the extracellular saline solution. The extent of the iodide flow, which occurs through the CFTR protein, reflects the efficacy of the corrective treatment. The figure also shows the two parameters ($QR_{TOT}$ and $QR_{VX}$) used to calculate the "additivity index" (AI) reported in the various tables to describe the compounds' efficacy. The cells were treated for 24 h with PP007 at the indicated concentrations, with and without VX-809 (1 µM). As control, cells were treated for 24 h with vehicle alone (dimethylsufoxide, DMSO) at the same concentration (0.1%) used to add test compounds.

Figure 2:
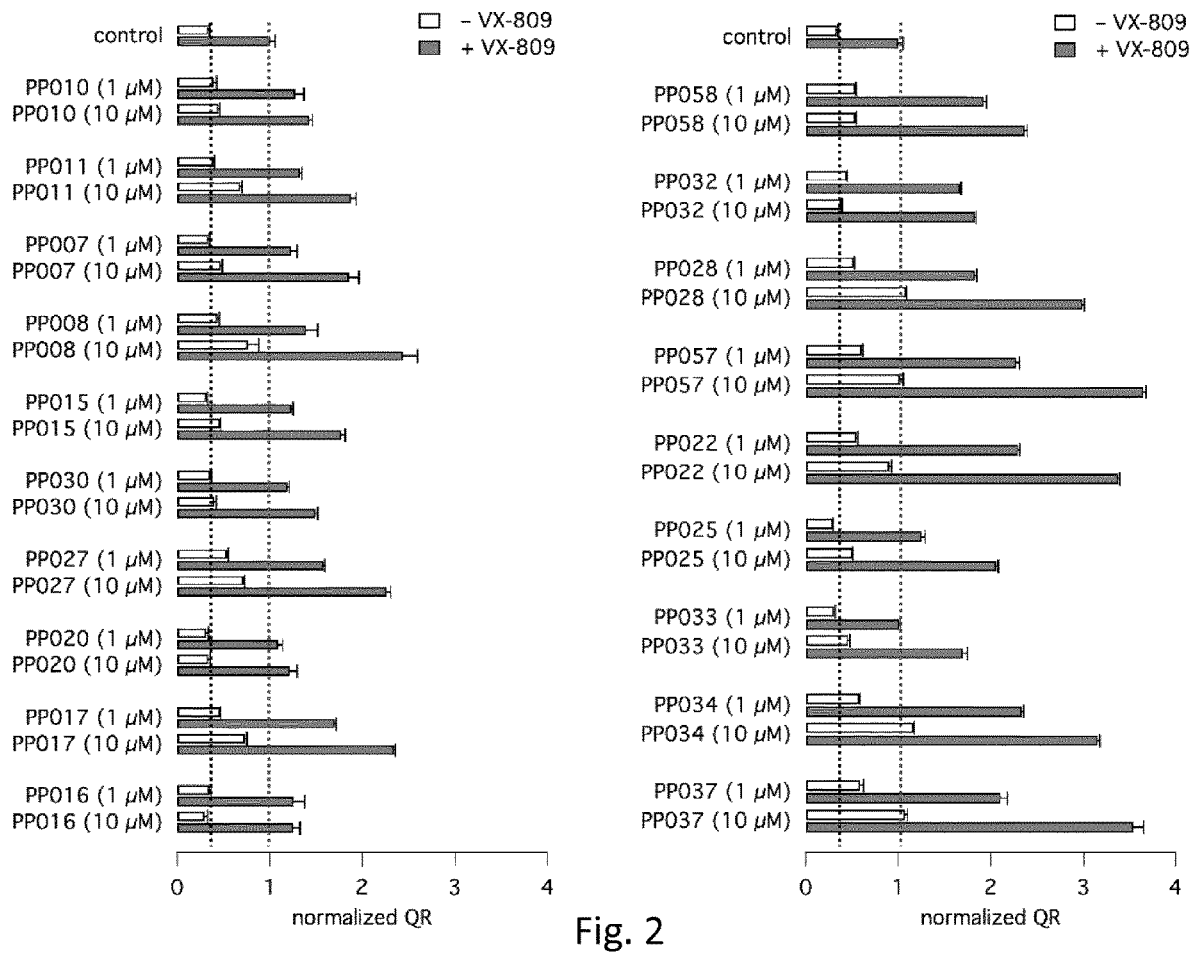

FIG. 2. Comparison of analogues of the compound PP007. The corrective activity was evaluated in CFBE41o– cells as described in FIG. 1. The cells were treated for 24 hours with the compounds indicated at two concentrations (1 and 10 µM) in the presence and absence of the corrector VX-809 (1 µM). As control, cells were treated for 24 h with vehicle alone (dimethylsufoxide, DMSO) at the same concentration (0.1%) used to add test compounds.

Figure 3:
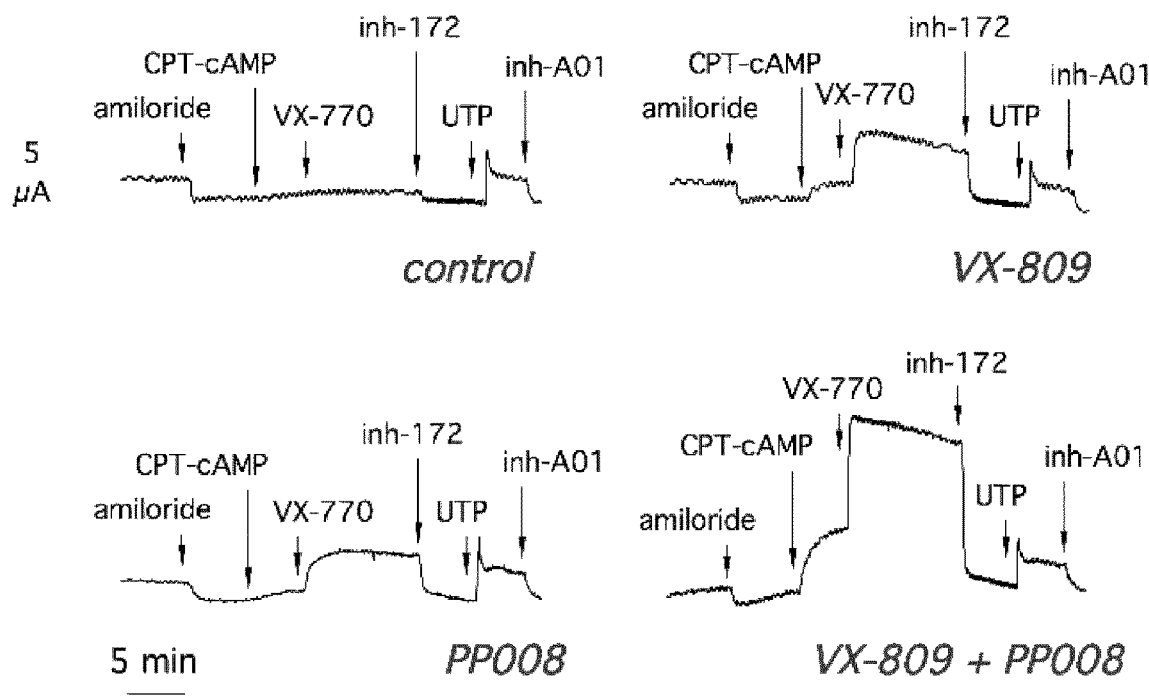
Figure 3:
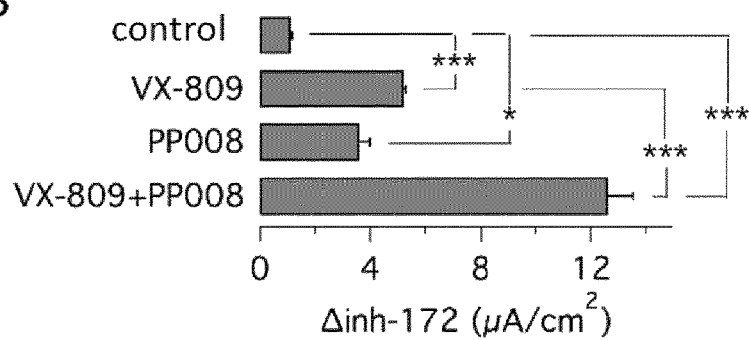
Figure 3:
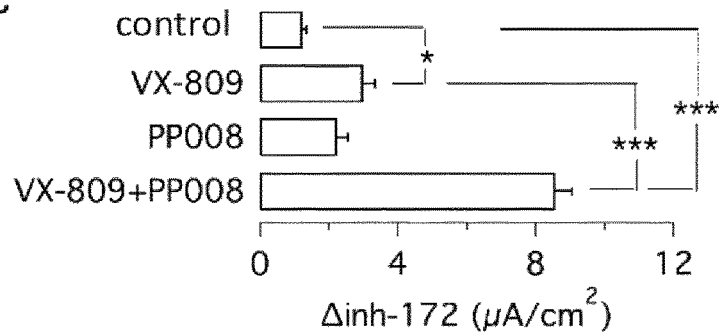

FIG. 3. PP008 corrective activity on primary epithelial cells. (A) The representative plots and (B) the bar chart show the results obtained by treating bronchial epithelial cells from a patient homozygous for the mutation F508del with PP008 (10 µM) in the presence and absence of VX-809 (1 µM). As control, cells were treated for 24 h with vehicle alone (dimethylsufoxide, DMSO) at the same concentration (0.1%) used to add test compounds. The activity of F508del-CFTR, represented by the response to the specific inhibitor inh-172, is significantly increased by treatment with PP008, especially in combination with VX-809. *, $p<0.05$; ***, $p<0.001$. As shown at the bottom of the plot in panel A, treatment with PP008 does not modify the calcium-dependent chloride secretion, activated and inhibited with UTP and inh-A01, respectively. (C) Results obtained on nasal epithelial cells of a homozygous F508del patient. *, $p<0.05$; ***, $p<0.001$.

Figure 4:
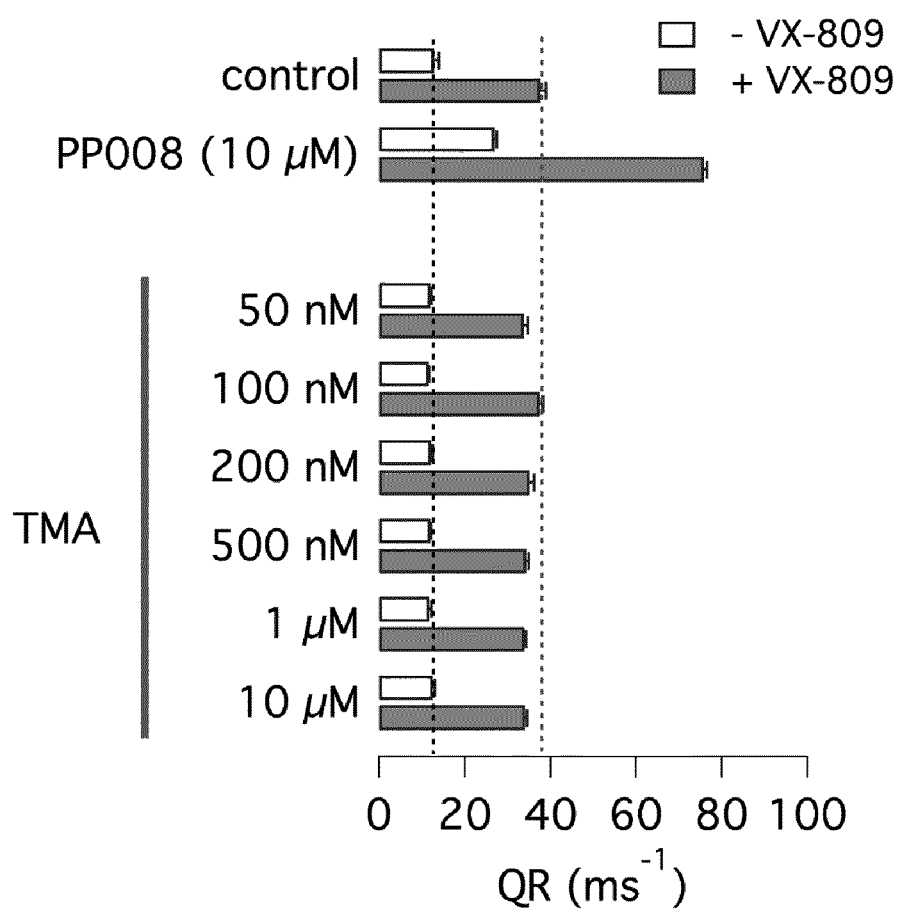

FIG. 4. Evaluation of trimethylangelicin (TMA) corrective activity. The assay (HS-YFP) was performed on CFBE41o– cells treated with TMA and PP008 (with and without VX-809 1 µM) at the indicated concentrations. As control, cells were treated for 24 h with vehicle alone (dimethylsufoxide, DMSO) at the same concentration (0.1%) used to add test compounds.

Figure 5:
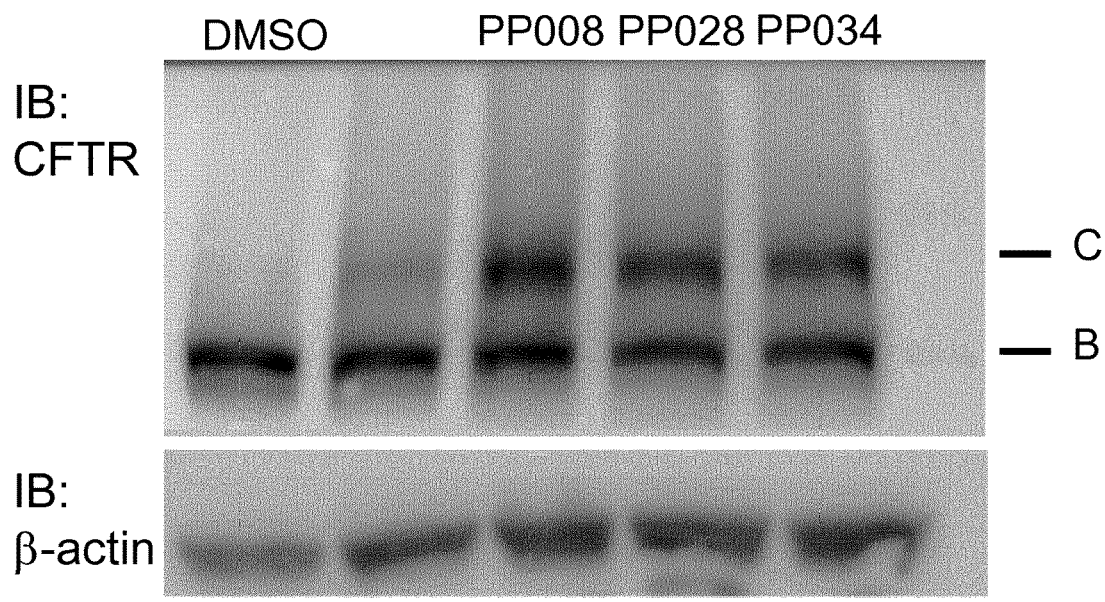

FIG. 5. Analysis of F508del-CFTR maturation by immunoblot (IB). The image shows a representative experiment where electrophoretic mobility of F508del-CFTR was determined in lysates of CFBE41o– cells treated for 24 hr with vehicle (DMSO), VX-809 (1 µM) alone, or VX-809 (1 µM) combined with PP008, PP028 or PP034 (10 µM). The protein migrates as band B (150 kDa, core-glycosylated immature form) or band C (170 kDa, fully-glycosylated mature form). Detection of beta-actin from the same samples is also shown. Treatment of cells with PP008, PP028, or PP034 markedly enhances the abundance of the mature form of the protein with respect to VX-809 alone.

Figure 6:
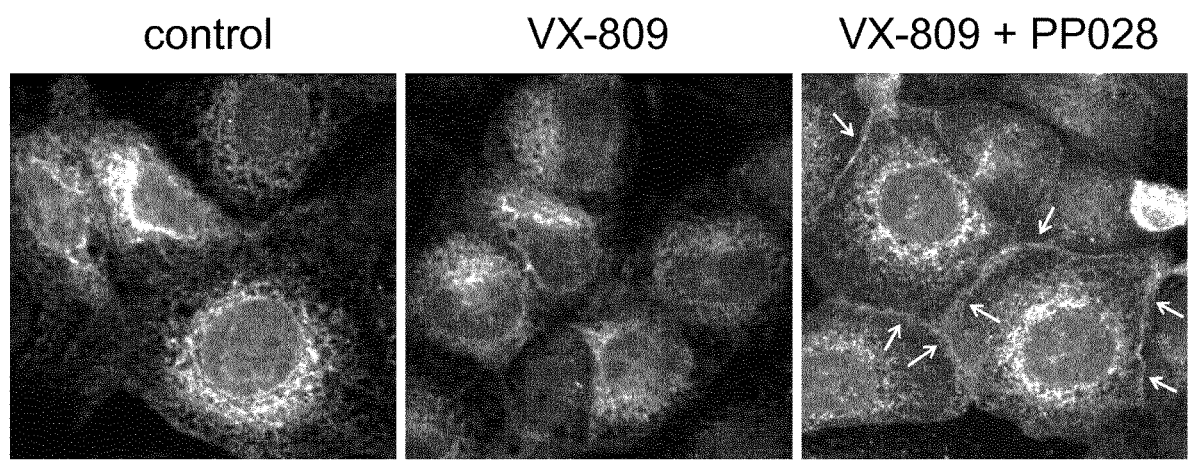

FIG. 6. Analysis of F508del-CFTR localization by immunofluorescence. CFBE41o− cells were treated for 24 hr vehicle (DMSO, control), with VX-809 (1 μM), or with VX-809 (1 μM) plus PP028 (10 μM). Cells were then fixed and stained with an antibody against CFTR. Arrows show regions where CFTR signal appears at the cell periphery in agreement with plasma membrane localization.

Figure 7:
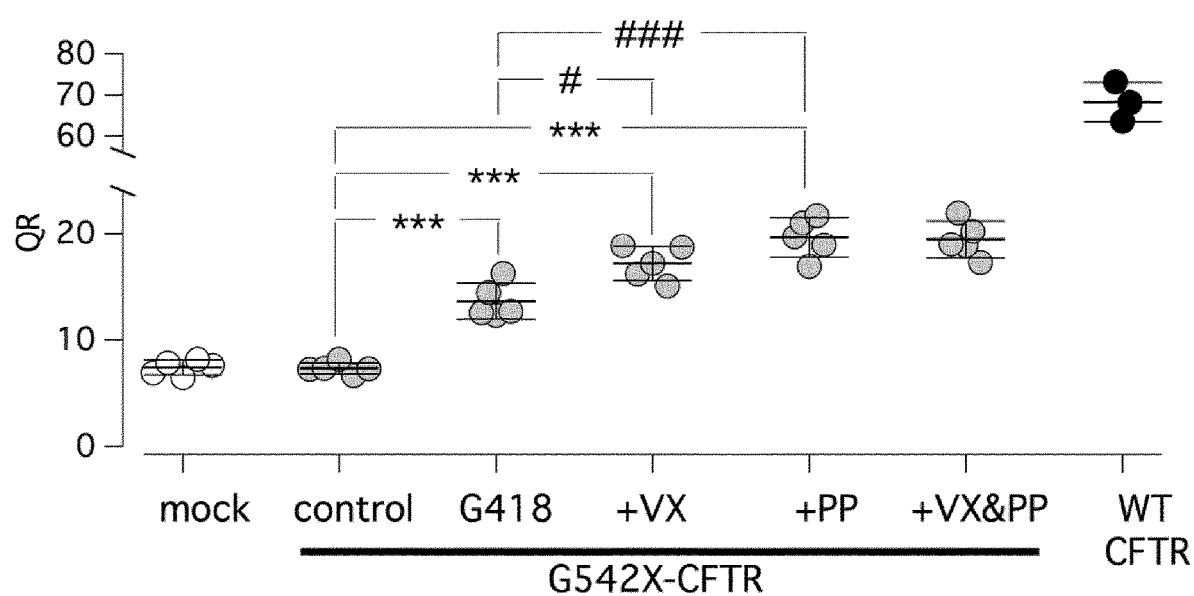

FIG. 7. Effect of a compound of the invention on the G542X premature stop codon mutation. The scatter dot plot shows data obtained with the HS-YFP assay in null CFBE41o− cells (cells with negligible expression of F508del-CFTR). Cells were cotransfected with HS-YFP and one of the following plasmids: empty (mock), G542X-CFTR, wild type CFTR. Where indicated, cells expressing G542X-CFTR were also treated with DMSO (control), G418 0.5 mg/ml alone, or G418 in combination with VX-809 (1 μM), with PP028 (10 μM), or with VX-809 plus PP028 (1 and 10 μM, respectively). Each dot reports the activity from a separate experiment. Mean and SD are also reported for each group of data. ***, p<0.001 vs. untreated cells. #, p<0.05 vs. G418 alone. ###, p<0.001 vs. G418 alone.

DETAILED DESCRIPTION OF THE INVENTION

Chemical Synthesis
General

According to a further aspect of the invention there is provided a process for the preparation of compounds of formula (I). The following schemes are examples of synthetic schemes that may be used to synthesise the compounds of the invention. In the following schemes reactive groups can be protected with protecting groups and deprotected according to well established techniques. In the following schemes substituents are as defined herein above for formula (I), unless otherwise indicated. It will be understood by those skilled in the art that certain compounds of the invention can be converted into other compounds of the invention according to standard chemical methods.

A synthetic route optimized for the synthesis of the compounds of the invention containing the pyrrole core and the corresponding ketone precursors is described in general schemes 1 and 2 below. Ketones of formula 6 and 7, which can be functionalised at the α-carbonyl position, are ideal precursors for the synthesis of the compounds of the invention. In particular the 1,4,5,6-tetrahydro-7H-indolones (6a n=1) and 4,5,6,7-tetrahydrocyclohepta[b]pyrrol-8 (1H)-ones (6b n=2) can be obtained according to synthetic pathways previously reported by the inventors, via multistep sequences that involve the anellation of the carbocyclic portion of substituted pyrroles of formula 3 (Spanò V, et al. Eur J Med Chem 2017, 128, 300-318; Spanò V, et al. Eur J Med Chem 2016, 123, 447-461; P. Barraja, et al. Bioorg Med Chem 2010, 18, 4830-4843). In particular, the compounds of formula 4, 5 and 6 and some compounds of formula 7-12 can be prepared according to methods previously reported by the authors.

By means of a selective acylation with $AlCl_3$ and succinic or glutaric anhydride derivatives 4a (n=2) (90-100%) and 4b (n=3) (80-95%) are obtained. The reduction of the carbonyl to methylene according to the Clemmensen method or with triethylsilane in trifluoroacetic acid allows the isolation of pyrrole of formula 5a (n=3) (70-75%) and 5b (n=4) (75-94%). The closure of the hexa- or hepta-cyclic ring on the free position 5 of the pyrrole, with trifluoroacetic anhydride leads to the compounds 6a,b with excellent yields (85-90%) (Scheme 1).

The alkyl- or aralkyl-substituted derivatives 7a,b, can be prepared by alkylation reactions starting from the corresponding NH-type derivatives 6a,b, carried out in solvents such as anhydrous THF or DMF and alkyl- or arylalkyl-halides as electrophiles.

Compounds of formula 7a with $R^1$=COOEt and 7b with $R^1$=COOEt can be subjected to hydrolysis in basic media in ethanol generating the carboxyacid derivatives 7c ($R^1$=COOH) which can be converted into isopropyl esters 7d (e.g. $R^1$=COOiPr) in isopropanol, 4-dimethylaminopyridine (DMAP) and N-ethyl-N'-(3-dimethylaminopropyl)carbodiimide hydrochloride (EDC). Alternatively compounds 7c ($R^1$=COOH) can be transformed into the corresponding carboxyamide derivatives 7e ($R^1$=CONHR$^a$) by activation of the carboxyacid functionality with N-ethyl-N'-(3-dimethylaminopropyl)carbodiimide hydrochloride (EDC) and subsequent reaction with the proper amine in the presence of N,N-diisopropylethylamine (DIPEA) and 1-hydroxybenzotriazole (HOBt). Compounds of formula 7a ($R^1$=ester such as COOEt) can also be subjected to chlorination or iodination using N-chlorosuccinimide (NCS) or N-iodosuccinimide (NIS).

Scheme 1. Synthesis of 1,4,5,6-tetrahydro-7H-indol-7-ones 7a,c-e and 1,4,5,6,78-hexa-hydrocylohepta[b]pyrrolo-2-carboxylates 7b.

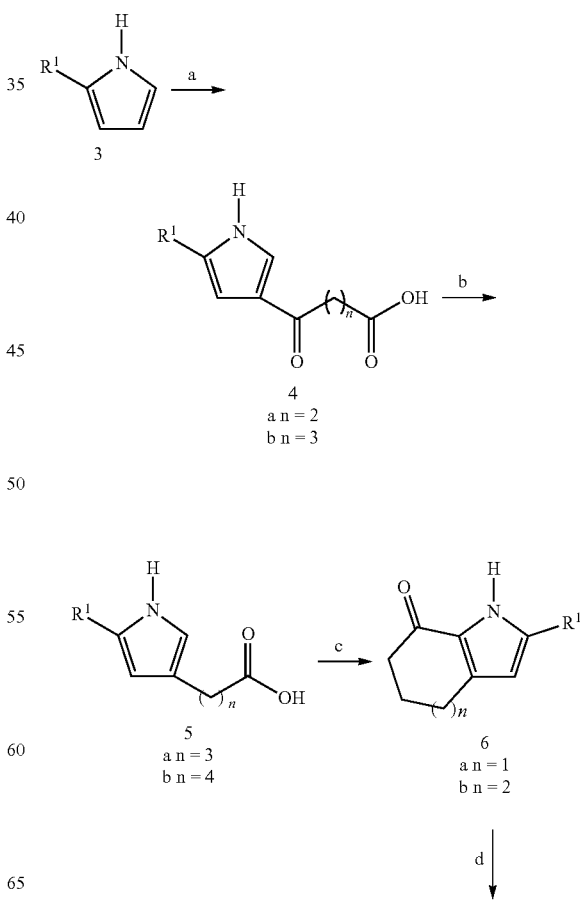

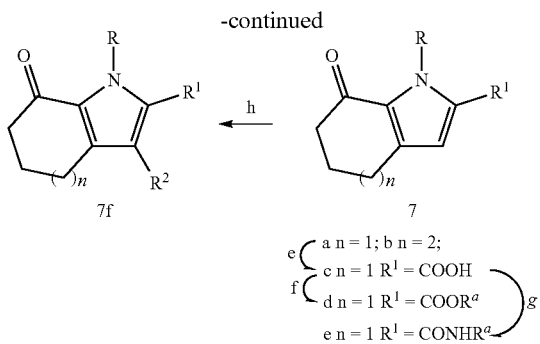

e ( a n = 1; b n = 2;
f ( c n = 1 R¹ = COOH
  d n = 1 R¹ = COORᵃ  ) g
  e n = 1 R¹ = CONHRᵃ

(a) AlCl₃, succinic or glutaric anhydride, DCM, rt, 1 h then 3: (b) Clemmensen method (R¹ = H) or triethylsilane (R¹ = H) or triethylsilane (R¹ = COOEt), trifluoroacetic acid, rt; (c) trifluoroacetic anhydride, DCM, rt; (d) NaH, THF or DMF, 0° C. to rt, 90 min then substituted alkyl- or arylalkyl-halides, 0° C. at rt; (e) NaOH, EtOH, reflux; (f) i-propanol, EDC, DMAP, rt, 16 h; (g) HOBt, DIPEA, EDC, DMF, rt, 10 min then amine, rt, 16 h; (h) AcOH, NCS or NIS (stoichiometric ratio 1:1), rt, 16 h.

Scheme 2 refers to the synthesis of pyrrolo[3,2-h]quinolin-2-ones (n=1), pyrrolo[3,2-h]quinolinones 13 and 14 and cyclohepta[b]pyrrol-8 (1H)-one (n=2) as reported in Tables 1, 1a and 2. Functionalization in α-carbonyl position of compounds of formula 7 can be obtained by direct introduction of the enaminic group using acetal amides such as dimethylformamide dimethylacetale (DMFDMA) or t-butoxy-bis(dimethylamino)methane (TBDMAM) with conventional reflux-heating in solvents such as toluene or DMF (Method A) or with the aid of microwave irradiation (Method B) (Power 50 W; Time 20-40 min; 100 psi; Temperature 120° C.) in dimethyl formamide (DMF) to give the corresponding enamino ketones 8. Prolonging heating time (24 h) in dimethyl formamide dimethylacetale (DMFDMA) (Method C), in the case of 4-methylbenzyl ketones (compound 7 with R=4-MeBn) and 2-methylbenzyl (compound 7 with R=2-MeBn), leads to transesterification of the 2-ethoxycarbonyl function to 2-methoxycarbonyl. Carboxymethyl-substituted enaminone derivatives 8 (R¹=COOMe) thus obtained, can then be subjected to the same cyclization conditions described below allowing to obtain the corresponding tricyclic compounds of formula 9⁽#⁾ (Scheme 2).

Intermediates 8 reacted with cyanomethylene compounds selected as 1,3 dinucleophiles, in particular benzene sulfonyl acetonitriles, cyclize after prolonged reflux to give tricyclic derivatives of formula 9, see Table 1 and 2. The subsequent methylation of the annular amidic function leads to the N-methyl (10) and O-methyl substituted derivatives (11) formed in the same reaction mixture, indicating the existence of the tautomeric equilibrium between the ketonic and enolic form in the reaction solvent. The introduction of halogen atoms (e.g. R2=Br, I) at position R² can be obtained by reaction with Br₂, in anhydrous dichloromethane (DCM) or I₂ in anhydrous N,N-dimethylformamide in the presence of potassium hydroxide. In the latter case instead of the iodo derivative 12⁽^⁾, the oxidation compound of the tricyclic scaffold was isolated from the reaction mixture after chromatographic purification 13 (PP058, Table 1a), which was subsequently subjected to bromination to give the derivative 14 (PP057, Table 1a).

Compounds 9⁽#⁾ and 12⁽^⁾ where R¹ is an ester can be converted into the corresponding carboxyacid derivatives (R¹=COOH) by basic hydrolysis and then transformed into the corresponding carboxyamide derivatives (R¹=CONHRᵃ) by activation of the carboxyacid functionality with N-ethyl-N'-(3-dimethylaminopropyl)carbodiimide hydrochloride (EDC) and subsequent reaction with ammonium carbonate or the proper amine in the presence of N,N-diisopropylethylamine (DIPEA) and 1-hydroxybenzotriazole (HOBt).

Scheme 2. Synthesis of pyrrolo[3,2-h]quinolin-2-ones (n = 1) and cyclohepta[b]pyrrol-8 (1H)-one (n = 2).

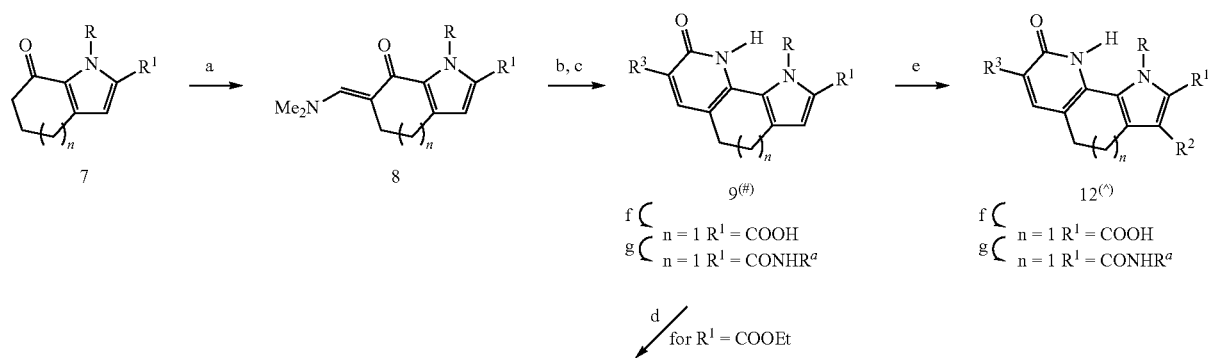

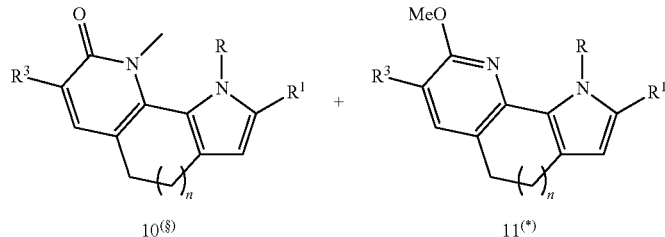

(a) DMFDMA (1:10), DMF, reflux 3 h or TBDMAM (1:3), toluene, reflux 3 h (Method A), DMFDMA (1:1) or TBDMAM (1:1.5), DMF, MW (50 W, 100° C.) (Method B); DMFDMA (1:10), DMF, reflux 24 h (Method C); (b) R³SO₂CH₂CN, ethanol, reflux 24 h (c) Acetic acid (1:1), toluene, reflux with Dean-Stark apparatus 24 h; (d) NaH, DMF, 0° C. to rt, 3 h then iodomethane, 0° C. to rt; (e) DCM, Br₂, rt 24 h, (1:2) or DMF, KOH, 15 minutes at rt then I₂ (1:1), 24 h at 40° C.; (f) KOH, EtOH, reflux; (g) HOBt, DIPEA, EDC, DMF, rt, 10 min then amine, rt, 16 h.

An exemplary set of derivatives synthesised according to Schemes 1-2 is shown in Tables 1-2 below, along with their additivity index (AI %), which was measured as described in the Materials and Methods section. Table 1 refers to compounds of formula 9-12 in which n=1, while Table 2 refers to compounds of formula 9-12 in which n=2. The compound PP058 and its brominated analogue PP057, reported as compounds of formula 13 and 14 in Scheme 2, are reported in Table 1a.

TABLE 1

Pyrrolo[3,2-h]quinolinones

| CPD | R | R¹ | R² | R³ | AI$^a$ (%) |
|---|---|---|---|---|---|
| PP007(#) | 4-MeBn | COOEt | — | SO2Ph | 169 |
| PP008(^) | 4-MeBn | COOEt | Br | SO2Ph | 207 |
| PP010(#) | Me | COOEt | — | SO2Ph | 95 |
| PP011(#) | Bn | COOEt | — | SO2Ph | 150 |
| PP015(^) | 2-MeBn | COOEt | H | SO2Ph | 124 |
| PP016(^) | 3-MeBn | COOEt | H | SO2Ph | 42 |
| PP017(^) | 4-ClBn | COOEt | H | SO2Ph | 203 |
| PP019(^) | 4-MeBn | COOMe | H | SO2Ph | 29 |
| PP020(^) | 2-MeBn | COOMe | H | SO2Ph | 33 |
| PP021(^) | 2,4-diMeBn | COOEt | H | SO2Ph | 40 |
| PP022(^) | 4-MeBn | COOi-Pr | H | SO2Ph | 279 |
| PP023(^) | 4-MeBn | COOEt | H | SO2Ph-4-Me | 89 |
| PP024(^) | 4-MeBn | COOEt | H | SO2Me | 11 |
| PP025(^) | 3,4-diMeBn | COOEt | H | SO2Ph | 178 |
| PP027(^) | 2-MeBn | COOEt | Br | SO2Ph | 185 |
| PP028(^) | 3-MeBn | COOEt | Br | SO2Ph | 278 |
| PP029(^) | 4-ClBn | COOEt | Br | SO2Ph | 46 |
| PP030(^) | 4-MeBn | COOEt | Br | 4-ClSO2Ph | 96 |
| PP031(^) | 4-MeBn | COOMe | Br | SO2Ph | 39 |
| PP032(^) | 2-MeBn | COOMe | Br | SO2Ph | 133 |
| PP033(^) | 2,4-diMeBn | COOEt | Br | SO2Ph | 114 |
| PP034(^) | 4-MeBn | COOi-Pr | Br | SO2Ph | 261 |
| PP035(^) | 4-MeBn | COOEt | Br | SO2Ph-4-Me | 56 |
| PP036(^) | 4-MeBn | COOEt | Br | SO2Me | 23 |
| PP037(^) | 3,4-diMeBn | COOEt | Br | SO2Ph | 335 |
| PP060(#) | 4-BrBn | COOEt | H | SO2Ph | 148 |
| PP062(#) | 4-IBn | COOEt | H | SO2Ph | 95 |
| PP063(^) | 4-IBn | COOEt | Br | SO2Ph | 146 |
| PP064(#) | cyclopropylmethyl | COOEt | H | SO2Ph | 235 |
| PP065(^) | cyclopropylmethyl | COOEt | Br | SO2Ph | 284 |
| PP066(#) | 6-methylpyridin-(3-yl)methyl | COOEt | H | SO₂Ph | 62 |
| PP068(#) | 2,4,6-(Me)3Bn | COOEt | H | SO₂Ph | 116 |
| PP070(#) | 4-CF₃Bn | COOEt | H | SO₂Ph | 101 |
| PP072(#) | 4-FBn | COOEt | H | SO₂Ph | 420 |
| PP075(^) | CH₂CH₂CH₂—N(Me)₂ | COOEt | Br | SO₂Ph | 34 |
| PP076(^) | 4-MeBn | COOEt | Cl | SO2Ph | 244 |
| PP077(^) | 4-MeBn | COOEt | I | SO2Ph | 202 |
| PP078(#) | 4-MeBn | COOH | H | SO2Ph | 37 |
| PP079(^) | 4-MeBn | COOH | Br | SO2Ph | 38 |
| PP080(#) | 4-MeBn | CONH2 | H | SO2Ph | 2 |
| PP081(^) | 3-MeBn | COOH | Br | SO2Ph | 20 |
| PP082(^) | 3-MeBn | CONH2 | Br | SO2Ph | 31 |
| PP083(#) | 3-MeBn | CONHiPr | H | SO2Ph | 53 |

TABLE 1-continued

Pyrrolo[3,2-h]quinolinones

| CPD | R | R$^1$ | R$^2$ | R$^3$ | AI$^a$ (%) |
|---|---|---|---|---|---|
| PP084(#) | 3-MeBn | CONHcyclopropyl | H | SO2Ph | 10 |
| PP086(^) | 4-MeBn | CONHiPr | Br | SO2Ph | 116 |
| PP089(^) | 4-MeBn | CONH2 | Br | SO2Ph | 11 |
| PP090(#) | 3-MeBn | COOH | H | SO2Ph | 36 |
| PP091(^) | 3-MeBn | CONHiPr | Br | SO2Ph | 208 |
| PP092(^) | 3-MeBn | CONHcyclopropyl | Br | SO2Ph | 52 |
| PP093(#) | 3-MeBn | CONH2 | H | SO2Ph | 25 |
| PP094(#) | 3,4-Me2Bn | COOH | H | SO2Ph | 47 |
| PP095(^) | 3,4-Me2Bn | COOH | Br | SO2Ph | 11 |
| PP096(#) | 4-BrBn | CONHiPr | H | SO2Ph | 3 |
| PP097(^) | 4-BrBn | CONHiPr | Br | SO2Ph | 99 |
| PP098(#) | 4-BrBn | CONHcyclopropyl | H | SO2Ph | 4 |
| PP099(^) | 4-BrBn | CONHcyclopropyl | Br | SO2Ph | 82 |
| PP100(^) | 3-MeBn | CONHSO2Ph | Br | SO2Ph | 47 |
| PP101(^) | 3-MeBn | CONHt-But | Br | SO2Ph | 249 |
| PP102(^) | 3-MeBn | CONHt-Butisoxzole | Br | SO2Ph | 103 |
| PP103(#) | 3-MeBn | COOiPr | H | SO2Ph | 284 |
| PP104(^) | 3-MeBn | COOiPr | Br | SO2Ph | 374 |
| PP105(#) | cyclopropylmethyl | COOiPr | H | SO2Ph | 174 |
| PP106(^) | cyclopropylmethyl | COOiPr | Br | SO2Ph | 277 |
| PP107(#) | 4-FBn | COOiPr | H | SO2Ph | 335 |
| PP108(^) | 4-FBn | COOiPr | Br | SO2Ph | 257 |
| PP067(^) | 6-methylpyridin-(3-yl)methyl | COOEt | Br | SO$_2$Ph | 81 |
| PP069(^) | 2,4,6-(Me)3Bn | COOEt | Br | SO$_2$Ph | 175 |
| PP071(^) | 4-CF$_3$Bn | COOEt | Br | SO$_2$Ph | 35 |
| PP073(^) | 4-FBn | COOEt | Br | SO$_2$Ph | 442 |

(#)Compounds of formula 9 in Scheme 2;
(§) Compounds of formula 10 in Scheme 2;
(*) Compounds of formula 11 in Scheme 2;
(^)Compounds of formula 12 in Scheme 2
$^a$Activity of compounds (at 10 μM) was expressed as additivity index (AI %) which is calculated as (QR$_{TOT}$ − QR$_{VX}$)/QR$_{VX}$ where QR$_{TOT}$ is the quenching rate (HS-YFP assay) in the presence of test compound plus VX-809 and QR$_{VX}$ is the quenching rate with VX-809 alone.

TABLE 1a

Pyrrolo[3,2-h]quinolinones corresponding to compounds of formula 13 and 14 in Scheme 2

| CPD | R | R$^1$ | R$^2$ | R$^3$ | AI$^a$ |
|---|---|---|---|---|---|
| 13 (PP057) | 4-MeBn | COOEt | H | SO$_2$Ph | 272% |
| 14 (PP058) | 4-MeBn | COOEt | Br | SO$_2$Ph | 177% |

$^a$Activity of compounds (at 10 μM) was expressed as additivity index (AI %) which is calculated as (QR$_{TOT}$ − QR$_{VX}$)/QR$_{VX}$ where QR$_{TOT}$ is the quenching rate (HS-YFP assay) in the presence of test compound plus VX-809 and QR$_{VX}$ is the quenching rate with VX-809 alone.

TABLE 2

Pyrrolo[3',2':6,7]cyclohepta[1,2-6]pyridin-9(1H)-ones

| CPD | R | R$^1$ | R$^2$ | R$^3$ | AI$^a$ |
|---|---|---|---|---|---|
| PP048(#) | 4-MeBn | COOEt | — | SO$_2$Ph | 22% |
| PP056(^) | 4-MeBn | COOEt | Br | SO$_2$Ph | 60% |

(#)Compounds of formula 9 in Scheme 2;
(^)Compounds of formula 12 in Scheme 2
$^a$Activity of compounds (at 10 μM) was expressed as additivity index (AI %) which is calculated as (QR$_{TOT}$ − QR$_{VX}$)/QR$_{VX}$ where QR$_{TOT}$ is the quenching rate (HS-YFP assay) in the presence of test compound plus VX-809 and QR$_{VX}$ is the quenching rate with VX-809 alone.

A detailed description of the synthesis of exemplary compounds produced according to Schemes 1 and 2 is provided hereinbelow.

General Procedure for the Synthesis of 1,4,5,6-tetrahydro-7H-indolones (7a n=1) e 4,5,6,7-tetrahydrocyclohepta[b]pyrrole-8 (1H)-ones (7b n=2) 1-Substituted To a solution of the suitable ketones 6a,b (15 mmol) in anhydrous THF or DMF (20 mL), NaH (0.64 g, 16 mmol) was added at 0° C. and the reaction mixture was stirred at room temperature for 1 h. Then the suitable alkyl or aralkyl halide was added at (16 mmol). The reaction mixture was stirred at room temperature or heated at reflux up to completeness (TLC). Then the reaction mixture was poured onto crushed ice and the precipitate was filtered off and dried, in absence the solution was extracted with DCM (3×30 mL). The organic layer was dried over Na$_2$SO$_4$ and the solvent was removed under reduced pressure. The crude product was purified by chromatography (DCM) giving the desired ketones.

Ethyl 1-(2-methylbenzyl)-7-oxo-4,5,6,7-tetrahydro-1H-indole-2-carboxylate. This compound was obtained by reaction of ethyl 7-oxo-4,5,6,7-tetrahydro-1H-indole-2-carboxylate 6a (R$^1$=COOEt) with 2-methylbenzyl chloride in DMF after 24 h at room temperature: light brown solid; yield: 80%; m.p.: 123-124° C.; IR: 1709 (CO), 1653 (CO) cm$^{-1}$; $^1$H nmr (CDCl$_3$) (ppm): 1.31 (3H, t, J=7.1 Hz, CH$_3$), 2.00-2.13 (2H, m, CH$_2$), 2.27 (3H, s, CH$_3$), 2.52 (2H, t, J=6.0 Hz, CH$_2$), 2.75 (2H, t, J=6.0 Hz, CH$_2$), 4.27 (2H, q, J=7.1 Hz, CH$_2$), 6.07 (2H, s, CH$_2$), 6.78 (1H, s, H-3), 6.97-7.08 (4H, m, H-3', H-4', H-5' and H-6'); $^{13}$C nmr (CDCl$_3$) (ppm): 14.3 (q), 21.1 (q), 23.7 (t), 24.6 (t), 40.2 (t), 49.1 (t), 60.7 (t), 115.1 (d), 126.7 (2×d), 128.0 (s), 129.0 (2×d), 130.2 (s), 135.6 (s), 135.9 (s), 136.5 (s), 161.0 (s), 190.5 (s). Anal calcd for $C_{19}H_{21}NO_3$: C, 73.29; H, 6.80; N, 4.50. Found: C, 73.41; H, 6.65; N, 4.43.

Ethyl 1-(3-methylbenzyl)-7-oxo-4,5,6,7-tetrahydro-1H-indole-2-carboxylate. This compound was obtained by reaction of ethyl 7-oxo-4,5,6,7-tetrahydro-1H-indole-2-carboxylate 6a ($R^1$=COOEt) with 3-methylbenzyl chloride in DMF after 24 h at room temperature: colorless oil; yield: 65%; IR: 1711 (CO), 1656 (CO) $cm^{-1}$; $^1$H nmr (CDCl$_3$) (ppm): 1.30 (3H, t, J=7.1 Hz, CH$_3$), 2.01-2.14 (2H, m, CH$_2$), 2.28 (3H, s, CH$_3$), 2.53 (2H, t, J=6.0 Hz, CH$_2$), 2.76 (2H, t, J=6.0 Hz, CH$_2$), 4.26 (2H, q, J=7.1 Hz, CH$_2$), 6.08 (2H, s, CH$_2$), 6.80-7.16 (4H, m, H-3, H-2', H-4', H-5' and H-6'); $^{13}$C nmr (CDCl$_3$) (ppm): 14.2 (q), 21.5 (q), 23.7 (t), 24.6 (t), 40.2 (t), 49.3 (t), 60.7 (t), 115.1 (d), 123.5 (d), 127.3 (d), 127.7 (d), 128.1 (s), 128.2 (d), 130.3 (s), 135.6 (s), 137.8 (s), 138.8 (s), 160.9 (s), 190.5 (s). Anal calcd for $C_{19}H_{21}NO_3$: C, 73.29; H, 6.80; N, 4.50. Found: C, 73.14; H, 6.53; N, 4.69.

Ethyl 1-(4-chlorobenzyl)-7-oxo-4,5,6,7-tetrahydro-1H-indole-2-carbossilato. This compound was obtained by reaction of ethyl 7-oxo-4,5,6,7-tetrahydro-1H-indole-2-carboxylate 6a ($R^1$=COOEt) with 4-chlorobenzyl chloride in DMF after 3 h at room temperature: white solid; yield: 70%; m.p.: 91-92° C.; IR: 1710 (CO), 1653 (CO) $cm^{-1}$; $^1$H nmr (CDCl$_3$) (ppm): 1.31 (3H, t, J=7.1 Hz, CH$_3$), 2.02-2.14 (2H, m, CH$_2$), 2.53 (2H, t, J=6.0 Hz, CH$_2$), 2.76 (2H, t, J=6.0 Hz, CH$_2$), 4.27 (2H, q, J=7.1 Hz, CH$_2$), 6.06 (2H, s, CH$_2$), 6.81 (1H, s, H-3), 7.04 (2H, d, J=8.5 Hz, H-2' and H-6'), 7.22 (2H, d, J=8.5 Hz, H-3' and H-4'); $^{13}$C nmr (CDCl$_3$) (ppm): 14.2 (q), 23.6 (t), 24.5 (t), 40.1 (t), 48.8 (t), 60.8 (t), 115.3 (d), 127.9 (s), 128.2 (2×d), 128.5 (2×d), 130.1 (s), 132.7 (s), 135.8 (s), 137.3 (s), 160.9 (s), 190.6 (s). Anal calcd for $C_{18}H_{18}ClNO_3$: C, 65.16; H, 5.47; N, 4.22. Found: C, 65.01; H, 5.69; N, 4.09.

Ethyl 1-(2,4-dimethylbenzyl)-7-oxo-4,5,6,7-tetrahydro-1H-indole-2-carboxylate. This compound was obtained by reaction of ethyl 7-oxo-4,5,6,7-tetrahydro-1H-indole-2-carboxylate 6a ($R^1$=COOEt) with 2,4-dimethylbenzyl chloride in DMF after 24 h at room temperature: white solid; yield: 65%; m.p.: 102-103° C.; IR: 1712 (CO), 1653 (CO) $cm^{-1}$; $^1$H nmr (DMSO-d$_6$) (ppm): 1.18 (3H, t, J=7.1 Hz, CH$_3$), 1.93-2.05 (2H, m, CH$_2$), 2.19 (3H, s, CH$_3$), 2.29 (3H, s, CH$_3$), 2.44 (2H, t, J=5.6 Hz, CH$_2$), 2.76 (2H, t, J=5.6 Hz, CH$_2$), 4.15 (2H, q, J=7.1 Hz, CH$_2$), 5.88-5.92 (3H, m, CH$_2$ and H), 6.79 (1H, d, J=7.9 Hz, Ar), 6.88 (1H, s, Ar), 6.98 (1H, s, Ar); $^{13}$C nmr (DMSO-d$_6$) (ppm): 13.9 (q), 18.5 (q), 20.4 (q), 22.9 (t), 24.1 (t), 39.5 (t), 47.0 (t), 60.4 (t), 114.9 (d), 123.0 (d), 126.5 (d), 127.4 (s), 129.9 (s), 130.3 (d), 133.7 (s), 134.4 (s), 135.1 (s), 135.3 (s), 160.0 (s), 189.9 (s). Anal calcd for $C_{20}H_{23}NO_3$: C, 73.82; H, 7.12; N, 4.30. Found: C, 73.99; H, 7.01; N, 4.44.

Ethyl 1-(3,4-dimethylbenzyl)-7-oxo-4,5,6,7-tetrahydro-1H-indole-2-carboxylate. This compound was obtained by reaction of ethyl 7-oxo-4,5,6,7-tetrahydro-1H-indole-2-carboxylate 6a ($R^1$=COOEt) with 3,4-dimethylbenzyl chloride in DMF after 24 h at room temperature: light yellow oil; yield: 60%; IR: 1710 (CO), 1654 (CO) $cm^{-1}$; $^1$H nmr (DMSO-d$_6$) (ppm): 1.23 (3H, t, J=6.0 Hz, CH$_3$), 1.92-2.04 (2H, m, CH$_2$), 2.13 (6H, s, 2×CH$_3$), 2.47 (2H, t, J=6.0 Hz, CH$_2$), 2.73 (2H, t, J=6.0 Hz, CH$_2$), 4.21 (2H, q, J=6.0 Hz, CH$_2$), 5.93 (2H, s, CH$_2$), 6.60 (1H, d, J=8.0 Hz, Ar), 6.79-6.82 (2H, m, Ar), 6.99 (1H, d, J=8.0 Hz, Ar); $^{13}$C nmr (DMSO-d$_6$) (ppm): 14.0 (q), 18.9 (q), 19.5 (q), 22.9 (t), 24.1 (t), 39.6 (t), 48.3 (t), 60.5 (t), 115.0 (d), 123.3 (d), 127.1 (s), 127.3 (d), 129.4 (d), 129.7 (s), 134.6 (s), 135.3 (s), 135.9 (s), 136.1 (s), 160.2 (s), 190.0 (s). Anal calcd for $C_{20}H_{23}NO_3$: C, 73.82; H, 7.12; N, 4.30. Found: C, 73.75; H, 6.95; N, 4.59.

Ethyl 1-[(4-methylphenyl)methyl]-8-oxo-1,4,5,6,7,8-hexahydrocyclohepta[b]pyrrole-2-carboxylate. This compound was obtained by reaction of ethyl 8-oxo-1,4,5,6,7,8-hexahydrocyclohepta[b]pyrrole-2-carboxylate 6b ($R^1$=COOEt) with 4-methylbenzyl chloride in DMF after 24 h at room temperature: white solid; yield 67%; m.p.: 72-73° C.; IR: 1715 (CO), 1649 (CO) $cm^{-1}$; $^1$H nmr (CDCl$_3$) (ppm): 1.30 (3H, t, J=7.1 Hz, CH$_3$), 1.77-1.84 (4H, m, 2×CH$_2$), 2.27 (3H, s, CH$_3$), 2.60-2.66 (2H, m, CH$_2$), 2.77-2.83 (2H, m, CH$_2$), 4.25 (2H, q, J=7.1 Hz, CH$_2$), 6.07 (2H, s, CH$_2$), 6.80 (1H, s, H-3), 6.88 (2H, d, J=8.0 Hz, H-3" and H-5"), 7.04 (2H, d, J=8.0 Hz, H-2" and H-6"); $^{13}$C nmr (CDCl$_3$) (ppm): 14.2 (q), 21.1 (q), 21.3 (t), 24.8 (t), 25.8 (t), 42.0 (t), 48.8 (t), 60.6 (t), 117.7 (d), 126.2 (2×d), 127.0 (s), 129.0 (2×d), 133.5 (s), 134.0 (s), 136.2 (s), 136.3 (s), 160.8 (s), 194.6 (s). Anal calcd for $C_{20}H_{23}NO_3$: C, 73.82; H, 7.12; N, 4.30. Found: C, 73.64; H, 7.38; N, 4.22.

Ethyl 1-[(4-bromophenyl)methyl]-7-oxo-4,5,6,7-tetrahydro-1H-indole-2-carboxylate. This compound was obtained by reaction of ethyl 7-oxo-4,5,6,7-tetrahydro-1H-indole-2-carboxylate 6a ($R^1$=COOEt) with 4-bromobenzyl chloride in DMF after 24 h at room temperature: white solid; yield: 78%; m.p.: 75-76° C.; IR: 1715 (CO), 1658 (CO) $cm^{-1}$; $^1$H nmr (DMSO-d$_6$) (ppm): 1.21 (3H, t, J=7.1 Hz, CH$_3$), 1.90-2.05 (2H, m, CH$_2$), 2.47 (2H, t, J=5.8 Hz, CH$_2$), 2.73 (2H, t, J=5.8 Hz, CH$_2$), 4.20 (2H, q, J=7.1 Hz, CH$_2$), 5.94 (2H, s, CH$_2$), 6.85 (1H, s, H-3), 6.91 (2H, d, J=8.3 Hz, H-2' and H-6'), 7.47 (2H, d, J=8.3 Hz, H-3' and H-5'); $^{13}$C nmr (DMSO-d$_6$) (ppm): 14.0 (q), 22.8 (t), 24.1 (t), 39.5 (t), 48.3 (t), 60.6 (t), 115.1 (d), 119.9 (s), 127.0 (s), 128.3 (2×d), 129.7 (s), 131.2 (2×d), 135.5 (s), 138.2 (s), 161.1 (s), 190.1 (s). Anal calcd for $C_{18}H_{18}BrNO_3$: C, 57.46; H, 4.82; N, 3.72. Found: C, 57.33; H, 4.69; N, 3.84.

Ethyl 1-[(4-iodophenyl)methyl]-7-oxo-4,5,6,7-tetrahydro-1H-indole-2-carboxylate. This compound was obtained by reaction of ethyl 7-oxo-4,5,6,7-tetrahydro-1H-indole-2-carboxylate 6a ($R^1$=COOEt) with 4-iodobenzyl chloride in DMF after 24 h at room temperature: white solid; yield: 55%; m.p.: 95-96° C.; IR: 1709 (CO), 1658 (CO) $cm^{-1}$; $^1$H nmr (DMSO-d$_6$) (ppm): 1.22 (3H, t, J=7.1 Hz, CH$_3$), 1.92-2.09 (2H, m, CH$_2$), 2.47 (2H, t, J=5.5 Hz, CH$_2$), 2.73 (2H, t, J=5.5 Hz, CH$_2$), 4.20 (2H, q, J=7.1 Hz, CH$_2$), 5.93 (2H, s, CH$_2$), 6.77 (2H, d, J=8.3 Hz, H-2' and H-6'), 6.85 (1H, s, H-3), 7.63 (2H, d, J=8.3 Hz, H-3' and H-5'); $^{13}$C nmr (DMSO-d$_6$) (ppm): 14.0 (q), 22.9 (t), 24.1 (t), 39.5 (t), 48.4 (t), 60.6 (t), 92.7 (s), 115.1 (d), 127.0 (s), 128.4 (2×d), 129.7 (s), 135.5 (s), 137.0 (2×d), 138.6 (s), 160.1 (s), 190.1 (s). Anal calcd for $C_{18}H_{18}INO_3$: C, 51.08; H, 4.29; N, 3.31. Found: C, 50.92; H, 4.11; N, 3.47.

Ethyl 1-(cyclopropylmethyl)-7-oxo-4,5,6,7-tetrahydro-1H-indole-2-carboxylate. This compound was obtained by reaction of ethyl 7-oxo-4,5,6,7-tetrahydro-1H-indole-2-carboxylate 6a ($R^1$=COOEt) with (chloromethyl)cyclopropane in DMF after 5 h at room temperature: yellow oil; yield: 60%; IR: 1715 (CO), 1664 (CO) $cm^{-1}$; $^1$H nmr (DMSO-d$_6$) (ppm): 0.31-0.38 (4H, m, 2×CH$_2$), 1.14-1.32 (4H, m, CH$_3$ e CH), 1.91-2.03 (2H, m, CH$_2$), 2.48 (2H, t, J=6.1 Hz, CH$_2$), 2.70 (2H, t, J=6.1 Hz, CH$_2$), 4.26 (2H, q, J=7.1 Hz, CH$_2$), 4.64 (2H, d, J=7.1 Hz, CH$_2$), 6.75 (1H, s, H-3); $^{13}$C nmr (DMSO-d$_6$) (ppm): 3.0 (2×t), 12.8 (d), 14.0 (q), 22.9 (t), 24.1 (t), 39.7 (t), 49.1 (t), 60.5 (t), 114.7 (d), 126.7 (s), 129.4 (s), 135.2 (s), 160.5 (s), 190.0 (s). Anal calcd for $C_{15}H_{19}NO_3$: C, 68.94; H, 7.33; N, 5.36. Found: C, 69.08; H, 7.21; N, 5.24.

Ethyl 1-[(6-methylpyridin-3-yl)methyl]-7-oxo-4,5,6,7-tetrahydro-1H-indole-2-carboxylate. This compound was obtained by reaction of ethyl 7-oxo-4,5,6,7-tetrahydro-1H- indole-2-carboxylate 6a ($R^1$=COOEt) with 5-(chloromethyl)-2-methylpyridine in DMF after 8 h at room temperature: light brown solid; yield: 65%; m.p.: 64-65° C.; IR: 1715 (CO), 1658 (CO) cm$^{-1}$; $^1$H nmr (DMSO-d$_6$) (ppm): 1.23 (3H, t, J=7.1 Hz, CH$_3$), 1.94-2.06 (2H, m, CH$_2$), 2.40-2.49 (5H, m, CH$_3$ and CH$_2$), 2.73 (2H, t, J=5.9 Hz, CH$_2$), 4.22 (2H, q, J=7.1 Hz, CH$_2$), 5.95 (2H, s, CH$_2$), 6.84 (1H, s, H-3), 7.12-7.28 (2H, m, H-4' and H-5'), 8.15 (1H, s, H-2'); $^{13}$C nmr (DMSO-d$_6$) (ppm): 14.0 (q), 22.8 (t), 23.6 (q), 24.0 (t), 39.5 (t), 46.4 (t), 60.6 (t), 115.2 (d), 122.7 (d), 127.0 (s), 129.6 (s), 131.0 (s), 134.4 (d), 135.6 (s), 147.1 (d), 156.5 (s), 160.2 (s), 190.2 (s). Anal calcd for $C_{18}H_{20}N_2O_3$: C, 69.21; H, 6.45; N, 8.97. Found: C, 69.14; H, 6.64; N, 9.09.

Ethyl 7-oxo-1-[(2,4,6-trimethylphenyl)methyl]-4,5,6,7-tetrahydro-1H-indole-2-carboxylate. This compound was obtained by reaction of ethyl 7-oxo-4,5,6,7-tetrahydro-1H-indole-2-carboxylate 6a ($R^1$=COOEt) with 2,4,6-trimetthylbenzyl chloride in DMF after 24 h at room temperature: yellow oil; yield: 67%; IR: 1715 (CO), 1652 (CO) cm$^{-1}$; $^1$H nmr (DMSO-d$_6$) (ppm): 1.08 (3H, t, J=7.1 Hz, CH$_3$), 1.85-2.03 (8H, m, 2×CH$_3$ and CH$_2$), 2.15 (3H, s, CH$_3$), 2.46 (2H, t, J=6.2 Hz, CH$_2$), 2.72 (2H, t, J=6.2 Hz, CH$_2$), 4.06 (2H, q, J=7.1 Hz, CH$_2$), 5.76 (1H, s, H-3), 5.94 (2H, s, CH$_2$), 6.72 (2H, s, H-3' and H-5'); $^{13}$C nmr (DMSO-d$_6$) (ppm): 13.8 (q), 19.1 (2×q), 20.2 (q), 23.0 (t), 24.2 (t), 39.6 (t), 45.8 (t), 60.4 (t), 114.2 (d), 128.8 (s), 129.3 (2×d), 130.4 (s), 131.4 (s), 135.0 (s), 135.2 (s), 135.6 (2×s), 160.4 (s), 190.3 (s). Anal calcd for $C_{21}H_{25}NO_3$: C, 74.31; H, 7.42; N, 4.13. Found: C, 74.22; H, 7.61; N, 3.95.

Ethyl 7-oxo-1-{[4-(trifluoromethyl)phenyl]methyl}-4,5,6,7-tetrahydro-1H-indole-2-carboxylate. This compound was obtained by reaction of ethyl 7-oxo-4,5,6,7-tetrahydro-1H-indole-2-carboxylate 6a ($R^1$=COOEt) with 4-trifluoromethylbenzyl chloride in DMF after 24 h at room temperature: white solid; yield: 78%; m.p.: 56-57° C.; IR: 1709 (CO), 1652 (CO) cm$^{-1}$; $^1$H nmr (DMSO-d$_6$) (ppm): 1.20 (3H, t, J=7.1 Hz, CH$_3$), 1.97-2.08 (2H, m, CH$_2$), 2.44 (2H, t, J=5.5 Hz, CH$_2$), 2.75 (2H, t, J=5.5 Hz, CH$_2$), 4.19 (2H, q, J=7.1 Hz, CH$_2$), 6.06 (2H, s, CH$_2$), 6.88 (1H, s, H-3), 7.14 (2H, d, J=8.1 Hz, H-2' and H-6'), 7.65 (2H, d, J=8.1 Hz, H-3' and H-5'); $^{13}$C nmr (DMSO-d$_6$) (ppm): 13.9 (q), 22.8 (t), 24.0 (t), 39.4 (t), 48.7 (t), 60.6 (t), 115.2 (d), 125.3 (2×d), 125.3 (s), 126.6 (2×d), 127.1 (s), 127.7 (s), 129.7 (s), 135.6 (s), 145.5 (d, $J_{C-F}$=284.0 Hz), 161.2 (s), 190.1 (s). Anal calcd for $C_{19}H_{18}F_3NO_3$: C, 62.46; H, 4.97; N, 3.83. Found: C, 62.60; H, 5.09; N, 3.77.

Ethyl 1-[(4-fluorophenyl)methyl]-7-oxo-4,5,6,7-tetrahydro-1H-indole-2-carboxylate. This compound was obtained by reaction of ethyl 7-oxo-4,5,6,7-tetrahydro-1H-indole-2-carboxylate 6a ($R^1$=COOEt) with 4-fluorobenzyl chloride in DMF after 24 h at room temperature: white solid; yield: 62%; m.p.: 72-73° C.; IR: 1726 (CO), 1658 (CO) cm$^{-1}$; $^1$H nmr (DMSO-d$_6$) (ppm): 1.22 (3H, t, J=7.1 Hz, CH$_3$), 1.89-2.07 (2H, m, CH$_2$), 2.47 (2H, t, J=5.8 Hz, CH$_2$), 2.72 (2H, t, J=5.8 Hz, CH$_2$), 4.20 (2H, q, J=7.1 Hz, CH$_2$), 5.96 (2H, s, CH$_2$), 6.83 (1H, s, H-3), 7.00-7.12 (4H, m, H-2', H-3', H-5' and H-6'); $^{13}$C nmr (DMSO-d$_6$) (ppm): 14.4 (q), 23.3 (t), 24.5 (t), 40.0 (t), 48.5 (t), 61.0 (t), 115.4 (d), 115.6 (2×d, $J_{C3'-F}$=16.2 Hz), 127.5 (s), 128.7 (2×d, $J_{C2'-F}$=8.2 Hz), 130.1 (s), 135.3 (s), 136.0 (s), 160.0 (s), 161.9 (d, $J_{C4'-F}$=191.5 Hz), 190.6 (s). Anal calcd for $C_{18}H_{18}FNO_3$: C, 68.56; H, 5.75; N, 4.44. Found: C, 68.69; H, 5.51; N, 4.31.

Ethyl 1-[3-(dimethylamino)propyl]-7-oxo-4,5,6,7-tetrahydro-1H-indole-2-carboxylate. This compound was obtained by reaction of ethyl 7-oxo-4,5,6,7-tetrahydro-1H-indole-2-carboxylate 6a ($R^1$=COOEt) with 4-fluorobenzyl chloride in DMF after 3-chloro-N,N-dimethylpropan-1-amine in DMF after 16 h at 60° C.: yellow oil; yield: 50%; IR: 1709 (CO), 1652 (CO) cm$^{-1}$; $^1$H nmr (DMSO-d$_6$) (ppm): 1.28 (3H, t, J=7.1 Hz, CH$_3$), 1.76-1.80 (2H, m, CH$_2$), 1.90-2.02 (2H, m, CH$_2$), 2.10-2.30 (8H, m, 2×CH$_3$ and CH$_2$), 2.46 (2H, t, J=6.0 Hz, CH$_2$), 2.68 (2H, t, J=6.0 Hz, CH$_2$), 4.26 (2H, q, J=7.1 Hz, CH$_2$), 4.61-4.68 (2H, m, CH$_2$), 6.71 (1H, s, H-3); $^{13}$C nmr (DMSO-d$_6$) (ppm): 14.1 (q), 22.9 (t), 24.1 (t), 29.0 (t), 39.5 (t), 44.6 (t), 45.0 (2×q), 56.4 (t), 60.4 (t), 114.2 (d), 127.1 (s), 129.5 (s), 134.9 (s), 160.2 (s), 189.7 (s). Anal calcd for $C_{16}H_{24}N_2O_3$: C, 65.73; H, 8.27; N, 9.58. Found: C, 65.57; H, 8.16; N, 9.69.

General Procedure for the Synthesis of 1-substituted-7-oxo-4,5,6,7-tetrahydro-1H-indole-2-carboxylic acid 7c ($R^1$=COOH)

To a solution of ethyl 1-substituted-7-oxo-4,5,6,7-tetrahydro-1H-indole-2-carboxylate (6.4 mmol) in ethanol (25 mL) an aqueous solution of KOH 50% (4.8 mL) was added and the reaction mixture was heated at reflux up to completeness (TLC). After cooling, the solvent was removed under reduced pressure The residue was added of water and the solution was acidified with HCl 6M. The solid formed was filtered off and dried.

1-(4-Methylbenzyl)-7-oxo-4,5,6,7-tetrahydro-1H-indole-2-carboxylic acid. This compound was obtained by reaction of ethyl 1-(4-methylbenzyl)-7-oxo-4,5,6,7-tetrahydro-1H-indole-2-carboxylate 7a ($R^1$=COOEt) after 3 h: white solid; yield: 98%; m.p.: 191-192° C.; IR: 3136 (OH), 1722 (CO), 1613 (CO) cm$^{-1}$; $^1$H nmr (DMSO-d$_6$) (ppm): 1.89-2.06 (2H, m, CH$_2$), 2.23 (3H, s, CH$_3$), 2.45 (2H, t, J=6.0 Hz, CH$_2$), 2.72 (2H, t, J=6.0 Hz, CH$_2$), 5.98 (2H, s, CH$_2$), 6.78 (1H, s, H-3), 6.85 (2H, d, J=8.0 Hz, H-2' and H-6'), 7.06 (1H, d, J=8.0 Hz, H-3' and H-5'), 13.04 (1H, s, OH); $^{13}$C nmr (DMSO-d$_6$) (ppm): 20.6 (q), 22.9 (t), 24.1 (t), 39.5 (t), 48.1 (t), 114.9 (d), 126.1 (2×d), 128.1 (s), 128.8 (2×d), 129.4 (s), 135.4 (s), 135.8 (s), 136.0 (s), 161.9 (s), 189.9 (s). Anal calcd for $C_{17}H_{17}NO_3$: C, 72.07; H, 6.05; N, 4.94. Found: C, 72.19; H, 5.89; N, 4.76.

1-[(3-Methylphenyl)methyl]-7-oxo-4,5,6,7-tetrahydro-1H-indole-2-carboxylic acid. This compound was obtained by reaction of ethyl 1-(3-methylbenzyl)-7-oxo-4,5,6,7-tetrahydro-1H-indole-2-carboxylate 7a ($R^1$=COOEt) after 2 h: white solid; yield: 99%; m.p: 154-155° C.; IR: 3131 (OH), 1692 (CO), 1658 (CO) cm$^{-1}$; $^1$H nmr (DMSO-d$_6$) (ppm): 1.89-2.23 (2H, m, CH$_2$), 2.45 (2H, t, J=6.0 Hz, CH$_2$), 2.73 (2H, t, J=6.0 Hz, CH$_2$), 5.99 (2H, s, CH$_2$), 6.65-6.79 (3H, m, H-3 and Ar), 7.02-7.14 (2H, m, Ar), 13.05 (1H, s, OH); $^{13}$C nmr (DMSO-d$_6$) (ppm): 21.4 (q), 22.9 (t), 24.2 (t), 39.5 (t), 48.4 (t), 114.9 (d), 123.0 (d), 126.7 (d), 127.4 (d), 128.1 (s), 128.2 (d), 129.5 (s), 135.3 (s), 137.3 (s), 139.0 (s), 161.9 (s), 189.9 (s). Anal calcd for $C_{17}H_{17}NO_3$: C, 72.07; H, 6.05; N, 4.94. Found: C, 72.22; H, 6.16; N, 4.82.

1-[(4-Bromophenyl)methyl]-7-oxo-4,5,6,7-tetrahydro-1H-indole-2-carboxylic acid. This compound was obtained by reaction of ethyl 1-[(4-bromophenyl)methyl]-7-oxo-4,5,6,7-tetrahydro-1H-indole-2-carboxylate 7a ($R^1$=COOEt) after 1 h: white solid; yield: 99%; m.p.: 195-196° C.; IR: 3131 (OH), 1723 (CO), 1614 (CO) cm$^{-1}$; $^1$H nmr (DMSO-d$_6$) (ppm): 1.91-2.06 (2H, m, CH$_2$), 2.45 (2H, t, J=6.0 Hz, CH$_2$), 2.72 (2H, t, J=6.0 Hz, CH$_2$), 5.96 (2H, s, CH$_2$), 6.80 (1H, s, H-3), 6.91 (2H, d, J=8.3 Hz, H-2' and H-6'), 7.47 (2H, d, J=8.3 Hz, H-3' and H-6'), 13.13 (1H, s, OH); $^{13}$C nmr (DMSO-d$_6$) (ppm): 22.9 (t), 24.1 (t), 39.5 (t), 48.1 (t), 115.0 (d), 119.8 (s), 128.0 (s), 128.3 (2×d), 129.4 (s), 131.2 (2×d), 135.5 (s), 138.4 (s), 161.8 (s), 189.9 (s). Anal calcd for C$_{16}$H$_{14}$BrNO$_3$: C, 55.19; H, 4.05; N, 4.02. Found: C, 55.33; H, 4.17; N, 3.90.

1-(Cyclopropylmethyl)-7-oxo-4,5,6,7-tetrahydro-1H-indole-2-carboxylic acid. This compound was obtained by reaction of ethyl 1-(cyclopropylmethyl)-7-oxo-4,5,6,7-tetrahydro-1H-indole-2-carboxylate 7a (R$^1$=COOEt) after 1 h: white solid; yield: 99%; m.p.: 173-174° C.; IR: 3096 (OH), 1692 (CO), 1664 (CO) cm$^{-1}$; $^1$H nmr (DMSO-d$_6$) (ppm): 0.29-0.39 (4H, m, 2×CH$_2$), 1.14-1.27 (1H, m, CH), 1.93-2.01 (2H, m, CH$_2$), 2.46 (2H, t, J=6.1 Hz, CH$_2$), 2.69 (2H, t, J=6.1 Hz, CH$_2$), 4.65 (2H, d, J=7.0 Hz, CH$_2$), 6.70 (1H, s, H-3), 13.01 (1H, s, OH); $^{13}$C nmr (DMSO-d$_6$) (ppm): 3.5 (2×t), 13.4 (d), 23.4 (t), 24.6 (t), 40.2 (t), 49.4 (t), 115.1 (d), 128.3 (s), 129.7 (s), 135.6 (s), 162.6 (s), 190.4 (s). Anal calcd for C$_{13}$H$_{15}$NO$_3$: C, 66.94; H, 6.48; N, 6.00. Found: C, 67.08; H, 6.60; N, 5.88.

1-[(4-Fluorophenyl)methyl]-7-oxo-4,5,6,7-tetrahydro-1H-indole-2-carboxylic acid. This compound was obtained by reaction of ethyl 1-[(4-fluorophenyl)methyl]-7-oxo-4,5,6,7-tetrahydro-1H-indole-2-carboxylate 7a (R$^1$=COOEt) after 2 h: white solid; yield: 99%; m.p.: 205-206° C.; IR: 3136 (OH), 1715 (CO), 1623 (CO) cm$^{-1}$; $^1$H nmr (DMSO-d$_6$) (ppm): 1.88-2.07 (2H, m, CH$_2$), 2.46 (2H, t, J=5.6 Hz, CH$_2$), 2.72 (2H, t, J=5.6 Hz, CH$_2$), 5.99 (2H, s, CH$_2$), 6.79 (1H, s, H-3), 7.01-7.12 (4H, m, H-2', H-3', H-5' and H-6'), 13.08 (1H, s, OH); $^{13}$C nmr (DMSO-d$_6$) (ppm): 23.4 (t), 24.6 (t), 40.0 (t), 48.3 (t), 115.4 (d), 115.6 (2×d, J$_{C3'-F}$=12.7 Hz), 128.5 (s), 128.7 (2×d, J$_{C2'-F}$=8.2 Hz), 129.9 (s), 135.6 (s), 136.0 (s), 161.1 (d, J$_{C4'-F}$=179.0 Hz), 163.2 (s), 190.4 (s). Anal calcd for C$_{16}$H$_{14}$FNO$_3$: C, 66.89; H, 4.91; N, 4.88. Found: C, 67.01; H, 5.05; N, 4.73.

Synthesis of propan-2-yl 1-(4-methylbenzyl)-7-oxo-4,5,6,7-tetrahydro-1H-indole-2-carboxylate To a solution of 1-(4-methylbenzyl)-7-oxo-4,5,6,7-tetrahydro-1H-indole-2-carboxylic acid (0.71 mmol) in a mixture of 2-propanol (10 mL) and xylene (10 mL) concentrated H$_2$SO$_4$ (0.8 mL) was added and the reaction mixture was heated at reflux for 48 h. After cooling, the solvent was removed under reduced pressure. The crude product was purified by chromatography (DCM) to give the desired ketone. White solid; yield: 89%; m.p.: 79-80° C.; IR: 1708 (CO), 1654 (CO) cm$^{-1}$; $^1$H nmr (CDCl$_3$) (ppm): 1.18 (3H, s, CH$_3$), 1.21 (3H, s, CH$_3$), 1.89-2.04 (2H, m, CH$_2$), 2.19 (3H, s, CH$_3$), 2.43 (2H, t, J=5.8 Hz, CH$_2$), 2.66 (2H, t, J=5.8 Hz, CH$_2$), 5.00-5.12 (1H, m, CH), 5.98 (2H, s, CH$_2$), 6.69 (1H, s, H-3), 6.89-7.00 (4H, m, H-2', H-3', H-5' and H-6'); $^{13}$C nmr (CDCl$_3$) (ppm): 21.1 (q), 21.9 (q), 23.7 (t), 24.6 (t), 40.2 (t), 49.1 (t), 68.3 (d), 115.0 (d), 126.7 (2×d), 128.5 (s), 129.0 (2×d), 130.1 (s), 135.6 (s), 135.9 (s), 136.4 (s), 160.5 (s), 190.5 (s). Anal calcd for C$_{20}$H$_{23}$NO$_3$: C, 73.82; H, 7.12; N, 4.30. Found: C, 73.99; H, 7.01; N, 4.55.

General Procedure for the Synthesis of propan-2-yl 1-substituted-7-oxo-4,5,6,7-tetrahydro-1H-indole-2-carboxylate 7d To a solution of the suitable acid derivatives 7c (5.3 mmol) in i-propanol (50 mL), DMAP (2.72 g, 22.3 mmol) and EDC (1.5 g, 7.8 mmol) were added and the reaction mixture was stirred at room temperature for 16 h. Then the solvent was removed under reduced pressure and water and crushed ice were added. The aqueous solution was extracted with ethyl acetate (3×50 mL). The organic layers were dried over Na$_2$SO$_4$ and the solvent removed under reduced pressure. The crude product was purified by chromatography column (DCM).

Propan-2-yl 1-[(3-methylphenyl)methyl]-7-oxo-4,5,6,7-tetrahydro-1H-indole-2-carboxylate. This compound was obtained by reaction of 1-[(3-methylphenyl)methyl]-7-oxo-4,5,6,7-tetrahydro-1H-indole-2-carboxylic acid 7c (R$^1$=COOH): white solid; yield: 87%; m.p.: 81-82° C.; IR: 1715 (CO), 1658 (CO) cm$^{-1}$; $^1$H nmr (DMSO-d$_6$) (ppm): 1.18 (6H, d, J=5.7 Hz, 2×CH$_3$), 1.95-2.04 (2H, m, CH$_2$), 2.22 (3H, s, CH$_3$), 2.37-2.48 (2H, m, CH$_2$), 2.63-2.79 (2H, m, CH$_2$), 4.95-5.11 (1H, m, CH), 5.96 (2H, s, CH$_2$), 6.64-7.20 (5H, m, H-3, H-2', H-4', H-5' and H-6'); $^{13}$C nmr (DMSO-d$_6$) (ppm): 21.0 (q), 21.4 (2×q), 22.9 (t), 24.1 (t), 39.6 (t), 48.6 (t), 68.0 (d), 115.0 (d), 122.9 (d), 126.6 (d), 127.4 (d), 127.6 (s), 128.2 (d), 129.6 (s), 135.4 (s), 137.3 (s), 138.8 (s), 159.7 (s), 190.0 (s). Anal calcd for C$_{20}$H$_{23}$NO$_3$: C, 73.82; H, 7.12; N, 4.30. Found: C, 73.97; H, 7.01; N, 4.46.

Propan-2-yl 1-(cyclopropylmethyl)-7-oxo-4,5,6,7-tetrahydro-1H-indole-2-carboxylate. This compound was obtained by reaction of 1-(cyclopropylmethyl)-7-oxo-4,5,6,7-tetrahydro-1H-indole-2-carboxylic acid 7c (R$^1$=COOH): colorless oil; yield: 56%; IR: 1709 (CO), 1652 (CO) cm$^{-1}$; $^1$H nmr (DMSO-d$_6$) (ppm): 0.28-0.39 (4H, m, 2×CH$_2$), 1.14-1.29 (7H, m, 2×CH$_3$ and CH), 1.92-2.00 (2H, m, CH$_2$), 2.46 (2H, t, J=5.9 Hz, CH$_2$), 2.69 (2H, t, J=5.9 Hz, CH$_2$), 4.63 (2H, d, J=7.1 Hz, CH$_2$), 5.04-5.13 (1H, m, CH), 6.71 (1H, s, H-3); $^{13}$C nmr (DMSO-d$_6$) (ppm): 3.4 (2×t), 13.3 (d), 22.0 (2×q), 23.4 (t), 24.6 (t), 40.2 (t), 49.5 (t), 68.4 (d), 115.1 (d), 127.7 (s), 129.8 (s), 135.6 (s), 160.5 (s), 190.4 (s). Anal calcd for C$_{16}$H$_{21}$NO$_3$: C, 69.79; H, 7.69; N, 5.09. Found: C, 69.64; H, 7.51; N, 4.93.

Propan-2-yl 1-[(4-fluorophenyl)methy]-7-oxo-4,5,6,7-tetrahydro-1H-indole-2-carboxylate. This compound was obtained by reaction of 1-[(4-fluorophenyl)methyl]-7-oxo-4,5,6,7-tetrahydro-1H-indole-2-carboxylic acid 7c (R$^1$=COOH): white solid; yield: 84%; m.p.: 100-101° C.; IR: 1715 (CO), 1658 (CO) cm$^{-1}$; $^1$H nmr (DMSO-d$_6$) (ppm): 1.21 (6H, d, J=6.1 Hz, 2×CH$_3$), 1.91-2.04 (2H, m, CH$_2$), 2.47 (2H, t, J=5.6 Hz, CH$_2$), 2.71 (2H, t, J=5.6 Hz, CH$_2$), 4.90-5.17 (1H, m, CH), 5.97 (2H, s, CH$_2$), 6.81 (1H, s, H-3), 6.99-7.13 (4H, m, H-2', H-3', H-5' and H-6'); $^{13}$C nmr (DMSO-d$_6$) (ppm): 21.9 (2×q), 23.4 (t), 24.6 (t), 40.0 (t), 48.5 (t), 68.6 (d), 115.4 (d), 115.5 (2×d, J$_{C3'-F}$=16.3 Hz), 127.8 (s), 128.6 (2×d, J$_{C2'-F}$=8.1 Hz), 130.0 (s), 135.4 (s), 136.0 (s), 161.7 (d, J$_{C4'-F}$=225.2 Hz), 190.5 (s). Anal calcd for C$_{19}$H$_{20}$FNO$_3$: C, 69.29; H, 6.12; N, 4.25. Found: C, 69.38; H, 6.01; N, 4.17.

General Procedure for the Synthesis of 1-substituted-7-oxo-N-substituted-4,5,6,7-tetrahydro-1H-indole-2-carboxamide 7e To a suspension of the suitable acid derivatives 7c (1.9 mmol) in anhydrous DMF (6 mL) N,N-diisopropylethylamine (1.9 mL, 10.9 mmol), 1-hydroxybenzotriazole hydrate (0.41 g, 3.0 mmol), and EDC (0.53 g, 2.8 mmol) were added. The reaction mixture was stirred at room temperature for 10 min. Then the proper amine (7.6 mmol) was added in one portion, and the resulting suspension was stirred at room temperature up to completeness (TLC). Then the reaction mixture was poured onto crushed ice and the solid formed was filtered off, dried and used in the next step without further purification.

1-[(3-Methylphenyl)methyl]-7-oxo-N-(propan-2-yl)-4,5,6,7-tetrahydro-1H-indole-2-carboxamide. This compound was obtained by reaction of 1-[(3-methylphenyl)methyl]-7- oxo-4,5,6,7-tetrahydro-1H-indole-2-carboxylic acid 7c ($R^1$=COOH) with isopropyl amine after 1 h: white solid; yield: 55%; m.p.: 181-182° C.; IR: 3291 (NH), 1653 (CO), 1632 (CO) cm$^{-1}$; $^1$H nmr (DMSO-d$_6$) (ppm): 1.08 (6H, d, J=6.2 Hz, 2×CH$_3$), 1.90-2.03 (2H, m, CH$_2$), 2.22 (3H, s, CH$_3$), 2.42 (2H, t, J=6.0 Hz, CH$_2$), 2.70 (2H, t, J=6.0 Hz, CH$_2$), 3.90-4.08 (1H, m, CH), 5.95 (2H, s, CH$_2$), 6.59 (1H, s, H-3), 6.77-7.16 (4H, m, H-2', H-4', H-5' and H-6'), 8.24 (1H, d, J=7.2 Hz, NH); $^{13}$C nmr (DMSO-d$_6$) (ppm): 21.0 (q), 22.1 (2×q), 23.1 (t), 24.3 (t), 39.4 (t), 40.5 (d), 47.8 (t), 110.4 (d), 123.8 (d), 127.3 (d), 127.4 (d), 127.5 (s), 128.1 (d), 132.6 (s), 135.6 (s), 137.2 (s), 139.2 (s), 160.2 (s), 189.2 (s). Anal calcd for C$_{20}$H$_{24}$N$_2$O$_2$: C, 74.04; H, 7.46; N, 8.64. Found: C, 74.18; H, 7.37; N, 8.55.

N-cyclopropyl-1-[(3-methylphenyl)methyl]-7-oxo-4,5,6, 7-tetrahydro-1H-indole-2-carboxamide. This compound was obtained by reaction of 1-[(3-methylphenyl)methyl]-7-oxo-4,5,6,7-tetrahydro-1H-indole-2-carboxylic acid 7c ($R^1$=COOH) with cyclopropylamine after 2 h: white solid; yield: 50%; m.p.: 184-185° C.; IR: 3385 (NH), 1652 (CO), 1635 (CO) cm$^{-1}$; $^1$H nmr (DMSO-d$_6$) (ppm): 0.41-0.73 (4H, m, 2×CH$_2$), 1.93-2.05 (2H, m, CH$_2$), 2.23 (3H, s, CH$_3$), 2.42 (2H, t, J=6.0 Hz, CH$_2$), 2.67-2.81 (3H, m, CH$_2$ and CH), 5.96 (2H, s, CH$_2$), 6.60 (1H, s, H-3), 6.74 (2H, t, J=7.5 Hz, Ar), 6.85 (1H, s, H-2'), 6.98-7.17 (2H, m, Ar), 8.45 (1H, d, J=3.8 Hz, NH); $^{13}$C nmr (DMSO-d$_6$) (ppm): 5.7 (2×t), 21.1 (q), 22.6 (d), 23.1 (t), 24.3 (t), 39.4 (t), 47.9 (t), 110.6 (d), 123.5 (d), 127.1 (d), 127.4 (d), 127.8 (s), 128.1 (d), 132.0 (s), 135.5 (s), 137.2 (s), 139.2 (s), 162.1 (s), 189.2 (s). Anal calcd for C$_{20}$H$_{22}$N$_2$O$_2$: C, 74.51; H, 6.88; N, 8.69. Found: C, 74.67; H, 6.97; N, 8.54.

1-[(4-Methylphenyl)methyl]-7-oxo-N-(propan-2-yl)-4,5, 6,7-tetrahydro-1H-indole-2-carboxamide. This compound was obtained by reaction of 1-(4-methylbenzyl)-7-oxo-4,5, 6,7-tetrahydro-1H-indole-2-carboxylic acid 7c ($R^1$=COOH) with isopropylamine after 2 h: white solid; yield: 50%; m.p.: 183-184° C.; IR: 3245 (NH), 1671 (CO), 1645 (CO) cm$^{-1}$; $^1$H nmr (DMSO-d$_6$) (ppm): 1.09 (6H, d, J=6.6 Hz, 2×CH$_3$), 1.89-2.03 (2H, m, CH$_2$), 2.22 (3H, s, CH$_3$), 2.42 (2H, t, J=5.8 Hz, CH$_2$), 2.69 (2H, t, J=5.8 Hz, CH$_2$), 3.91-4.08 (1H, m, CH), 5.94 (2H, s, CH$_2$), 6.61 (1H, s, H-3), 6.92 (2H, d, J=7.9 Hz, H-3' and H-5'), 7.04 (2H, d, J=7.9 Hz, H-2' and H-6'), 8.27 (1H, d, J=7.9 Hz, NH); $^{13}$C nmr (DMSO-d$_6$) (ppm): 20.6 (q), 22.1 (2×q), 23.1 (t), 24.3 (t), 39.4 (t), 40.5 (d), 47.6 (t), 110.5 (d), 126.7 (2×d), 127.5 (s), 128.7 (2×d), 132.5 (s), 135.6 (s), 135.9 (s), 136.3 (s), 160.1 (s), 189.1 (s). Anal calcd for C$_{20}$H$_{24}$N$_2$O$_2$: C, 74.04; H, 7.46; N, 8.64. Found: C, 73.92; H, 7.31; N, 8.79.

N-cyclopropyl-1-[(4-methylphenyl)methyl]-7-oxo-4,5,6, 7-tetrahydro-1H-indole-2-carboxamide. This compound was obtained by reaction of 1-(4-methylbenzyl)-7-oxo-4,5, 6,7-tetrahydro-1H-indole-2-carboxylic acid 7c ($R^1$=COOH) with cyclopropylamine after 1 h: white solid; yield: 51%; m.p.: 186-187° C.; IR: 3268 (NH), 1669 (CO), 1641 (CO) cm$^{-1}$; $^1$H nmr (DMSO-d$_6$) (ppm): 0.49-0.53 (2H, m, CH$_2$), 0.62-0.71 (2H, m, CH$_2$), 1.93-1.98 (2H, m, CH$_2$), 2.23 (3H, s, CH$_3$), 2.42 (2H, t, J=5.8 Hz, CH$_2$), 2.66-2.80 (3H, m, CH$_2$ and CH), 5.95 (2H, s, CH$_2$), 6.60 (1H, s, H-3), 6.91 (2H, d, J=7.9 Hz, H-3' and H-5'), 7.05 (2H, d, J=7.9 Hz, H-2' and H-6'), 8.44 (1H, d, J=3.9 Hz, NH); $^{13}$C nmr (DMSO-d$_6$) (ppm): 5.7 (2×t), 20.6 (q), 22.6 (d), 23.6 (t), 24.3 (t), 39.4 (t), 47.7 (t), 110.7 (d), 126.6 (2×d), 127.8 (s), 128.7 (2×d), 131.9 (s), 135.5 (s), 135.9 (s), 136.3 (s), 162.1 (s), 189.2 (s). Anal calcd for C$_{20}$H$_{22}$N$_2$O$_2$: C, 74.51; H, 6.88; N, 8.69. Found: C, 74.77; H, 6.79; N, 8.54

1-[(4-Bromophenyl)methyl]-7-oxo-N-(propan-2-yl)-4,5, 6,7-tetrahydro-1H-indole-2-carboxamide. This compound was obtained by reaction of 1-[(4-bromophenyl)methyl]-7-oxo-4,5,6,7-tetrahydro-1H-indole-2-carboxylic acid 7c ($R^1$=COOH) with isopropylamine after 1 h: white solid; yield: 77%; m.p.: 170-171° C.; IR: 3291 (NH), 1652 (CO), 1636 (CO) cm$^{-1}$; $^1$H nmr (DMSO-d$_6$) (ppm): 1.08 (6H, d, J=6.5 Hz, 2×CH$_3$), 1.91-2.03 (2H, m, CH$_2$), 2.42 (2H, t, J=5.5 Hz, CH$_2$), 2.70 (2H, t, J=5.5 Hz, CH$_2$), 3.90-4.03 (1H, m, CH), 5.93 (2H, s, CH$_2$), 6.67 (1H, s, H-3), 6.97 (2H, d, J=8.3 Hz, H-2' and H-6'), 7.46 (2H, d, J=8.3 Hz, H-3' and H-5'), 8.26 (1H, d, J=7.6 Hz, NH); $^{13}$C nmr (DMSO-d$_6$) (ppm): 22.1 (2×q), 23.1 (t), 24.3 (t), 39.3 (t), 40.6 (d), 47.7 (t), 110.6 (d), 119.9 (s), 127.6 (s), 128.8 (2×d), 131.0 (2×d), 132.2 (s), 135.7 (s), 138.7 (s), 159.9 (s), 189.2 (s). Anal calcd for C$_{19}$H$_{21}$BrN$_2$O$_2$: C, 58.62; H, 5.44; N, 7.20. Found: C, 58.55; H, 5.31; N, 7.33.

1-[(4-Bromophenyl)methyl]-N-cyclopropyl-7-oxo-4,5,6, 7-tetrahydro-1H-indole-2-carboxamide. This compound was obtained by reaction of 1-[(4-bromophenyl)methyl]-7-oxo-4,5,6,7-tetrahydro-1H-indole-2-carboxylic acid 7c ($R^1$=COOH) with cyclopropylamine after 1 h: white solid; yield: 77%; m.p.: 178-179° C.; IR: 3296 (NH), 1669 (CO), 1629 (CO) cm$^{-1}$; $^1$H nmr (DMSO-d$_6$) (ppm): 0.46-0.70 (4H, m, 2×CH$_2$), 1.12-1.23 (1H, m, CH), 1.91-2.00 (2H, m, CH$_2$), 2.42 (2H, t, J=6.3 Hz, CH$_2$), 2.66 (2H, t, J=6.3 Hz, CH$_2$), 5.94 (2H, s, CH$_2$), 6.68 (1H, s, H-3), 6.95 (2H, d, J=8.3 Hz, H-2' and H-6'), 7.46 (2H, d, J=8.3 Hz, H-3' and H-5'), 8.49 (1H, d, J=4.0 Hz, NH); $^{13}$C nmr (DMSO-d$_6$) (ppm): 5.7 (2×t), 22.6 (d), 23.0 (t), 24.2 (t), 39.3 (t), 47.7 (t), 110.8 (d), 119.8 (s), 127.8 (s), 128.7 (2×d), 131.1 (2×d), 131.6 (s), 135.7 (s), 138.7 (s), 161.9 (s), 189.3 (s). Anal calcd for C$_{19}$H$_{19}$BrN$_2$O$_2$: C, 58.93; H, 4.95; N, 7.23. Found: C, 59.02; H, 5.06; N, 7.11.

General Procedure for the Synthesis of ethyl 3-substituted-1-[(4-methylphenyl)methyl]-7-oxo-4,5,6,7-tetrahydro-1H-indole-2-carboxylate 7f To a solution 1-(4-methylbenzyl)-7-oxo-4,5,6,7-tetrahydro-1H-indole-2-carboxylate (4.5 mmol) in acetic acid (12 mL) NCS or NIS (4.5 mmol) was added and the reaction mixture was stirred at room temperature or at 60° C. up to completeness (TLC). Then the reaction mixture was poured onto crushed ice and the aqueous solution was extracted with ethyl acetate (3×50 mL). The organic layers were dried over Na$_2$SO$_4$ and the solvent removed under reduced pressure. The crude product was purified by chromatography column (Petroleum ether/AcOEt 95:5).

Ethyl 3-chloro-1-[(4-methylphenyl)methyl]-7-oxo-4,5,6, 7-tetrahydro-1H-indole-2-carboxylate. This compound was obtained by reaction of ethyl 1-(4-methylbenzyl)-7-oxo-4, 5,6,7-tetrahydro-1H-indole-2-carboxylate 7a ($R^1$=COOEt) with N-chlorosuccinimide after 5 h at 60° C.: white solid; yield: 50%; m.p.: 54-55° C.; IR: 1709 (CO), 1669 (CO) cm$^{-1}$; $^1$H nmr (DMSO-d$_6$) (ppm): 1.21 (3H, t, J=7.1 Hz, CH$_3$), 1.95-2.07 (2H, m, CH$_2$), 2.23 (3H, s, CH$_3$), 2.52 (2H, t, J=5.9 Hz, CH$_2$), 2.67 (2H, t, J=5.9 Hz, CH$_2$), 4.24 (2H, q, J=7.1 Hz, CH$_2$), 5.93 (2H, s, CH$_2$), 6.84 (2H, d, J=8.0 Hz, H-3' and H-5'), 7.08 (2H, d, J=8.0 Hz, H-2' and H-6'); $^{13}$C nmr (DMSO-d$_6$) (ppm): 13.8 (q), 20.6 (q), 20.9 (t), 23.1 (t), 39.4 (t), 48.9 (t), 61.1 (t), 115.8 (s), 123.7 (s), 126.0 (2×d), 127.7 (s), 128.9 (2×d), 133.2 (s), 135.2 (s), 136.2 (s), 159.3 (s), 189.9 (s). Anal calcd for C$_{19}$H$_{20}$ClNO$_3$: C, 65.99; H, 5.83; N, 4.05. Found: C, 66.11; H, 5.69; N, 3.91.

Ethyl 3-iodo-1-[(4-methylphenyl)methyl]-7-oxo-4,5,6,7-tetrahydro-1H-indole-2-carboxylate. This compound was obtained by reaction of ethyl 1-(4-methylbenzyl)-7-oxo-4, 5,6,7-tetrahydro-1H-indole-2-carboxylate 7a ($R^1$=COOEt)

with N-iodosuccinimide after 3 h at room temperature: light yellow solid; yield: 67%; m.p.: 61-62° C.; IR: 1715 (CO), 1658 (CO) cm$^{-1}$; $^1$H nmr (DMSO-d$_6$) (ppm): 1.24 (3H, t, J=7.0 Hz, CH$_3$), 1.91-2.07 (2H, m, CH$_2$), 2.23 (3H, s, CH$_3$), 2.56-2.62 (4H, m, 2×CH$_2$), 4.24 (2H, q, J=7.0 Hz, CH$_2$), 5.93 (2H, s, CH$_2$), 6.83 (2H, d, J=8.0 Hz, H-3' and H-5'), 7.07 (2H, d, J=8.0 Hz, H-2' and H-6'); $^{13}$C nmr (DMSO-d$_6$) (ppm): 13.8 (q), 20.6 (q), 23.2 (t), 25.3 (t), 39.3 (t), 49.3 (t), 61.2 (t), 73.8 (s), 126.0 (2×d), 128.4 (s), 128.9 (2×d), 129.3 (s), 135.4 (s), 136.1 (s), 139.8 (s), 159.8 (s), 189.9 (s). Anal calcd for C$_{19}$H$_{20}$INO$_3$: C, 52.19; H, 4.61; N, 3.20. Found: C, 52.03; H, 4.77; N, 3.14.

Method A for the Synthesis of 6-[(dimethylamino) methylidene]-7-oxo-4,5,6,7-tetrahydro-1H-indole-2-carboxylate of type 8a and 7-[(dimethylamino) methylidene]-8-oxo-1,4,5,6,7,8-hexahydrocyclohepta[b]pyrrole 1-Substituted of type 8b To a solution of 7a,b (1.3 mmol) in anhydrous DMF (2.5 mL) DMFDMA (1.73 mL, 13 mmol) was added and the reaction mixture was heated at reflux for 3 h. Then the reaction mixture was poured onto crushed ice and the precipitate was filtered off and dried, in absence the solution was extracted with ethyl acetate (3×30 mL). The organic layer was dried over Na$_2$SO$_4$ and the solvent was removed under reduced pressure. Some derivatives of type 8 are used in the next step without further purification, those isolated and characterized are shown below.

Method B for the Synthesis of 6-[(dimethylamino) methylidene]-7-oxo-4,5,6,7-tetrahydro-1H-indole-2-carboxylate of Type 8a and 7-[(dimethylamino) methylidene]-8-oxo-1,4,5,6,7,8-hexahydrocyclohepta[b]pyrrole 1-Substituted of Type 8b To a solution of 7a,b (1.3 mmol) in anhydrous DMF (2.5 ml) DMFDMA (0.19 mL, 1.4 mmol) was added and the reaction mixture was irradiated under microwave conditions (Power 50 W; Pressure (max) 100 psi; Temperature (max) 100° C.) up to completeness (TLC). Then the reaction mixture was poured onto crushed ice and the precipitate was filtered off and dried, in absence the solution was extracted with ethyl acetate (3×30 mL). The organic layer was dried over Na$_2$SO$_4$ and the solvent was removed under reduced pressure.

Method C for the Synthesis of 6-[(dimethylamino) methylidene]-7-oxo-4,5,6,7-tetrahydro-1H-indole-2-carboxylate of Type 8a and 7-[(dimethylamino) methylidene]-8-oxo-1,4,5,6,7,8-hexahydrocyclohepta[b]pyrrole 1-Substituted of Type 8b To a solution of 7a,b (1.3 mmol) in anhydrous DMF (2.5 mL) DMFDMA (1.73 mL, 13 mmol) was added and the reaction mixture was heated at reflux for 24 h. Then the reaction mixture was poured onto crushed ice and the precipitate was filtered off and dried, in absence the solution was extracted with ethyl acetate (3×30 mL). The organic layer was dried over Na$_2$SO$_4$ and the solvent was removed under reduced pressure.

Method D for the Preparation of 1-Substituted 6-[(dimethylamino)methylidene]-1,4,5,6-tetrahydro-7H-indole-7-ones of Type 8a and 1-substituted-7-[(dimethylamino)methylidene]-8-oxo-1,4,5,6,7,8-hexahydrocyclohepta[b]pyrrole of Type 8b To a solution of 7a-e (1.3 mmol) in anhydrous toluene (3 mL) TBDMAM (0.80 mL, 3.9 mmol) was added and the reaction mixture was heated at reflux up to completeness (TLC). After cooling, the solvent was removed under reduced pressure.

Ethyl 6-[(dimethylamino)methylidene]-1-(2-methylbenzyl)-7-oxo-4,5,6,7-tetrahydro-1H-indole-2-carboxylate.

This compound was obtained by reaction of ethyl 1-(2-methylbenzyl)-7-oxo-4,5,6,7-tetrahydro-1H-indole-2-carboxylate 7a (R$^1$=COOEt) with METHOD A and used in the next step without further purification.

Ethyl 6-[(dimethylamino)methylidene]-1-(3-methylbenzyl)-7-oxo-4,5,6,7-tetrahydro-1H-indole-2-carboxylate.

This compound was obtained by reaction of ethyl 1-(3-methylbenzyl)-7-oxo-4,5,6,7-tetrahydro-1H-indole-2-carboxylate 7a (R$^1$=COOEt) with METHOD A. Dark brown solid; yield: 85%; m.p.: 118-119° C.; IR: 1704 (CO), 1634 (CO) cm$^{-1}$; $^1$H nmr (DMSO-d$_6$) (ppm): 1.21 (3H, t, J=7.1 Hz, CH$_3$), 2.22 (3H, s, CH$_3$), 2.61 (2H, t, J=6.6 Hz, CH$_2$), 2.85 (2H, t, J=6.6 Hz, CH$_2$), 4.17 (2H, q, J=7.1 Hz, CH$_2$), 3.07 (6H, s, 2×CH$_3$), 6.11 (2H, s, CH$_2$), 6.65 (1H, d, J=7.5 Hz, Ar), 6.78-6.80 (2H, m, H-3 and Ar), 6.98 (1H, d, J=7.5 Hz, Ar), 7.15 (1H, t, J=7.5 Hz, Ar), 7.38 (1H, s, CH); $^{13}$C nmr (DMSO-d$_6$) (ppm): 14.1 (q), 21.1 (q), 22.4 (t), 24.0 (t), 43.3 (2×q), 48.1 (t), 59.9 (t), 103.5 (s), 114.7 (d), 123.0 (d), 125.0 (s), 126.6 (d), 127.2 (d), 128.1 (d), 130.1 (s), 131.9 (s), 137.1 (s), 139.7 (s), 149.1 (d), 160.3 (s), 178.6 (s). Anal calcd for C$_{22}$H$_{26}$N$_2$O$_3$: C, 72.11; H, 7.15; N, 7.64. Found: C, 71.97; H, 7.29; N, 7.76.

Ethyl 6-[(dimethylamino)methylidene]-1-(4-chlorobenzyl)-7-oxo-4,5,6,7-tetrahydro-1H-indole-2-carboxylate.

This compound was obtained by reaction of ethyl 1-(4-chlorobenzyl)-7-oxo-4,5,6,7-tetrahydro-1H-indole-2-carboxylate 7a (R$^1$=COOEt) with METHOD A. Dark brown solid; yield: 78%; m.p.: 149-150° C.; IR: 1705 (CO), 1635 (CO) cm$^{-1}$; $^1$H nmr (DMSO-d$_6$) (ppm): 1.20 (3H, t, J=7.0 Hz, CH$_3$), 2.60 (2H, t, J=6.0 Hz, CH$_2$), 2.82 (2H, t, J=6.0 Hz, CH$_2$), 4.16 (2H, q, J=7.0 Hz, CH$_2$), 3.07 (6H, s, 2×CH$_3$), 6.09 (2H, s, CH$_2$), 6.79 (1H, s, H-3), 6.98 (2H, d, J=7.9 Hz, H-2' and H-6'), 7.31-7.38 (3H, s, H-3', H-4' and CH); $^{13}$C nmr (DMSO-d$_6$) (ppm): 14.1 (q), 22.3 (t), 24.0 (t), 43.3 (2×q), 47.7 (t), 60.0 (t), 103.4 (s), 114.8 (d), 124.8 (s), 128.0 (2×d), 128.1 (2×d), 130.2 (s), 131.1 (s), 131.8 (s), 138.6 (s), 149.3 (d), 160.2 (s), 178.5 (s). Anal calcd for C$_{21}$H$_{23}$ClN$_2$O$_3$: C, 65.20; H, 5.99; N, 7.24. Found: C, 65.06; H, 5.85; N, 7.41.

Methyl 6-[(dimethylamino)methylidene]-1-(2-methylbenzyl)-7-oxo-4,5,6,7-tetrahydro-1H-indole-2-carboxylate.

This compound was obtained by reaction of ethyl 1-(2-methylbenzyl)-7-oxo-4,5,6,7-tetrahydro-1H-indole-2-carboxylate 7a (R$^1$=COOEt) with METHOD C. Dark brown solid; yield: 72%; m.p.: 130-131° C.; IR: 1709 (CO), 1637 (CO) cm$^{-1}$; $^1$H nmr (DMSO-d$_6$) (ppm): 2.33 (3H, s, CH$_3$), 2.64 (2H, t, J=6.2 Hz, CH$_2$), 2.87 (2H, t, J=6.2 Hz, CH$_2$), 3.05 (6H, s, 2×CH$_3$), 3.67 (3H, s, CH$_3$), 5.98 (1H, d, J=7.4 Hz, Ar), 6.10 (2H, s, CH$_2$), 6.84 (1H, s, H-3), 6.94-7.17 (3H, m, Ar), 7.31 (1H, s, CH); $^{13}$C nmr (DMSO-d$_6$) (ppm): 18.6 (q), 22.4 (t), 24.0 (t), 43.2 (2×q), 46.7 (t), 51.3 (q), 103.4 (s), 114.6 (d), 123.1 (d), 124.8 (s), 125.9 (2×d), 129.4 (d), 130.1 (s), 132.3 (s), 133.8 (s), 138.3 (s), 149.1 (d), 160.5 (s), 178.4

(s). Anal calcd for $C_{21}H_{24}N_2O_3$: C, 71.57; H, 6.86; N, 7.95. Found: C, 71.74; H, 6.98; N, 7.78.

Methyl 6-[(dimethylamino)methylidene]-1-(4-methylbenzyl)-7-oxo-4,5,6,7-tetrahydro-1H-indole-2-carboxylate. This compound was obtained by reaction of ethyl 1-(4-methylbenzyl)-7-oxo-4,5,6,7-tetrahydro-1H-indole-2-carboxylate 7a ($R^1$=COOEt) with METHOD C and used in the next step without further purification.

Ethyl 6-[(dimethylamino)methylidene]-1-[(2,4-dimethylphenyl)methyl]-7-oxo-4,5,6,7-tetrahydro-1H-indole-2-carboxylate. This compound was obtained by reaction of ethyl 1-(2,4-dimethylbenzyl)-7-oxo-4,5,6,7-tetrahydro-1H-indole-2-carboxylate 7a ($R^1$=COOEt) with METHOD A and used in the next step without further purification.

Ethyl 6-[(dimethylamino)methylidene]-1-[(3,4-dimethylphenyl)methyl]-7-oxo-4,5,6,7-tetrahydro-1H-indole-2-carboxylate. This compound was obtained by reaction of ethyl 1-(3,4-dimethylbenzyl)-7-oxo-4,5,6,7-tetrahydro-1H-indole-2-carboxylate 7a ($R^1$=COOEt) with METHOD A and used in the next step without further purification.

Propan-2-yl 6-[(dimethylamino)methylidene]-1-[(4-methylphenyl)methyl]-7-oxo-4,5,6,7-tetrahydro-1H-indole-2-carboxylate. This compound was obtained by reaction of propan-2-yl 1-(4-methylbenzyl)-7-oxo-4,5,6,7-tetrahydro-1H-indole-2-carboxylate 7a ($R^1$=COOiPr) with METHOD A and used in the next step without further purification.

Ethyl 7-[(dimethylamino)methylidene]-1-[(4-methylphenyl)methyl]-8-oxo-1,4,5,6,7,8-hexahydrocyclohepta[b]pyrrole-2-carboxylate. This compound was obtained by reaction of ethyl 1-[(4-methylphenyl)methyl]-8-oxo-1,4,5,6,7,8-hexahydrocyclohepta[b]pyrrole-2-carboxylate 7b ($R^1$=COOEt) with METHOD B and used in the next step without further purification.

Ethyl 1-[(4-bromophenyl)methyl]-6-[(dimethylamino)methylidene]-7-oxo-4,5,6,7-tetrahydro-1H-indole-2-carboxylate. This compound was obtained by reaction of ethyl 1-[(4-bromophenyl)methyl]-7-oxo-4,5,6,7-tetrahydro-1H-indole-2-carboxylate 7a ($R^1$=COOEt) with METHOD D after 16 h: light brown solid; yield: 93%; m.p.: 142-143° C.; IR: 1710 (CO), 1635 (CO) cm$^{-1}$; $^1$H nmr (DMSO-$d_6$) (ppm): 1.20 (3H, t, J=7.1 Hz, CH$_3$), 2.60 (2H, t, J=6.7 Hz, CH$_2$), 2.84 (2H, t, J=6.7 Hz, CH$_2$), 3.06 (6H, s, 2×CH$_3$), 4.16 (2H, q, J=7.1 Hz, CH$_2$), 6.07 (2H, s, CH$_2$), 6.78 (1H, s, H-3), 6.91 (2H, d, J=8.3 Hz, H-2' and H-6'), 7.38 (1H, s, CH), 7.45 (2H, d, J=8.3 Hz, H-3' and H-5'); $^{13}$C nmr (DMSO-$d_6$) (ppm): 14.1 (q), 22.3 (t), 24.0 (t), 43.3 (2×q), 47.8 (t), 60.0 (t), 103.4 (s), 114.9 (d), 119.6 (s), 124.8 (s), 128.4 (2×d), 130.2 (s), 131.1 (2×d), 131.9 (s), 139.1 (s), 149.3 (d), 160.3 (s), 178.5 (s). Anal calcd for $C_{21}H_{23}BrN_2O_3$: C, 58.48; H, 5.37; N, 6.49. Found: C, 58.61; H, 5.29; N, 6.33.

Ethyl 6-[(dimethylamino)methylidene]-1-[(4-iodophenyl)methyl]-7-oxo-4,5,6,7-tetrahydro-1H-indole-2-carboxylate. This compound was obtained by reaction of ethyl 1-[(4-iodophenyl)methyl]-7-oxo-4,5,6,7-tetrahydro-1H-indole-2-carboxylate 7a ($R^1$=COOEt) with METHOD D after 3 h: yellow solid; yield: 86%; m.p.: 140-141° C.; IR: 1697 (CO), 1641 (CO) cm$^{-1}$; $^1$H nmr (DMSO-$d_6$) (ppm): 1.20 (3H, t, J=7.1 Hz, CH$_3$), 2.60 (2H, t, J=6.7 Hz, CH$_2$), 2.84 (2H, t, J=5.6.7 Hz, CH$_2$), 3.06 (6H, s, 2×CH$_3$), 4.16 (2H, q, J=7.1 Hz, CH$_2$), 6.06 (2H, s, CH$_2$), 6.76 (3H, d, J=9.3 Hz, H-3, H-2' and H-6'), 7.37 (1H, s, CH), 7.62 (2H, d, J=8.2 Hz, H-3' and H-5'); $^{13}$C nmr (DMSO-$d_6$) (ppm): 14.1 (q), 22.3 (t), 23.9 (t), 43.3 (2×q), 47.9 (t), 60.0 (t), 92.4 (s), 103.4 (s), 114.8 (d), 124.8 (s), 128.5 (2×d), 130.2 (s), 131.8 (s), 136.9 (2×d), 139.5 (s), 149.2 (d), 160.2 (s), 178.5 (s). Anal calcd for $C_{21}H_{23}IN_2O_3$: C, 52.73; H, 4.85; N, 5.86. Found: C, 52.88; H, 4.99; N, 5.72.

Ethyl 1-(cyclopropylmethyl)-6-[(dimethylamino)methylidene]-7-oxo-4,5,6,7-tetrahydro-1H-indole-2-carboxylate. This compound was obtained by reaction of 1-(cyclopropylmethyl)-7-oxo-4,5,6,7-tetrahydro-1H-indole-2-carboxylate 7a ($R^1$=COOEt) with METHOD D after 2 h and used in the next step without further purification.

Ethyl 6-[(dimethylamino)methylidene]-1-[(6-methylpyridin-3-yl)methyl]-7-oxo-4,5,6,7-tetrahydro-1H-indole-2-carboxylate. This compound was obtained by reaction of ethyl 1-[(6-methylpyridin-3-yl)methyl]-7-oxo-4,5,6,7-tetrahydro-1H-indole-2-carboxylate 7a ($R^1$=COOEt) with METHOD D after 1 h: brown oil; yield: 78%; IR: 1703 (CO), 1658 (CO) cm$^{-1}$; $^1$H nmr (DMSO-$d_6$) (ppm): 1.22 (3H, t, J=7.1 Hz, CH$_3$), 2.39 (3H, s, CH$_3$), 2.59 (2H, t, J=6.3 Hz, CH$_2$), 2.84 (2H, t, J=6.3 Hz, CH$_2$), 3.07 (6H, s, 2×CH$_3$), 4.18 (2H, q, J=7.1 Hz, CH$_2$), 6.08 (2H, s, CH$_2$), 6.78 (1H, s, H-3), 7.13 (1H, d, J=8.0 Hz, H-5'), 7.25 (1H, dd, J=8.0, 2.2 Hz, H-4'), 7.40 (1H, s, CH), 8.15 (1H, d, J=2.2 Hz, H-2'); $^{13}$C nmr (DMSO-$d_6$) (ppm): 14.1 (q), 22.3 (t), 23.6 (q), 24.0 (t), 43.3 (2×q), 45.9 (t), 60.0 (t), 103.4 (s), 114.8 (d), 122.6 (d), 124.7 (s), 130.3 (s), 131.8 (s), 131.9 (s), 134.4 (d), 147.3 (d), 149.3 (d), 156.2 (s), 160.3 (s), 178.5 (s). Anal calcd for $C_{21}H_{25}N_3O_3$: C, 68.64; H, 6.86; N, 11.44. Found: C, 68.79; H, 7.05; N, 11.31.

Ethyl 6-[(dimethylamino)methylidene]-7-oxo-1-[(2,4,6-trimethylphenyl)methyl]-4,5,6,7-tetrahydro-1H-indole-2-carboxylate. This compound was obtained by reaction of ethyl 7-oxo-1-[(2,4,6-trimethylphenyl)methyl]-4,5,6,7-tetrahydro-1H-indole-2-carboxylate 7a ($R^1$=COOEt) with METHOD D after 3 h: brown solid; yield: 93%; m.p.: 163-164° C.; IR: 1703 (CO), 1641 (CO) cm$^{-1}$; $^1$H nmr (DMSO-$d_6$) (ppm): 1.09 (3H, t, J=7.0 Hz, CH$_3$), 1.89 (6H, s, 2×CH$_3$), 2.14 (3H, s, CH$_3$), 2.57 (2H, t, J=6.4 Hz, CH$_2$), 2.81 (2H, t, J=6.4 Hz, CH$_2$), 3.05 (6H, s, 2×CH$_3$), 4.05 (2H, q, J=7.0 Hz, CH$_2$), 6.05 (2H, s, CH$_2$), 6.68-6.72 (3H, m, H-3, H-3' and H-5'), 7.34 (1H, s, CH); $^{13}$C nmr (DMSO-$d_6$) (ppm): 13.9 (q), 19.1 (2×q), 20.2 (q), 22.5 (t), 24.1 (t), 43.3 (2×q), 45.5 (t), 59.9 (t), 114.0 (d), 103.5 (s), 126.3 (s), 129.2 (2×d), 129.9 (s), 132.2 (s), 132.8 (s), 134.6 (s), 135.5 (2×s), 148.9 (d), 160.5 (s), 178.8 (s). Anal calcd for $C_{24}H_{30}N_2O_3$: C, 73.07; H, 7.66; N, 7.10. Found: C, 72.91; H, 7.79; N, 6.97.

Ethyl 6-[(dimethylamino)methylidene]-7-oxo-1-{[4-(trifluoromethyl)phenyl]methyl}-4,5,6,7-tetrahydro-1H-indole-2-carboxylate. This compound was obtained by reaction of ethyl 7-oxo-1-{[4-(trifluoromethyl)phenyl]methyl}-4,5,6,7-tetrahydro-1H-indole-2-carboxylate 7a ($R^1$=COOEt) with METHOD D after 16 h: brown oil; yield: 85%; IR: 1703 (CO), 1635 (CO) cm$^{-1}$; $^1$H nmr (DMSO-$d_6$) (ppm): 1.24 (3H, t, J=7.1 Hz, CH$_3$), 2.68 (2H, t, J=6.7 Hz, CH$_2$), 2.91 (2H, t, J=6.7 Hz, CH$_2$), 3.11 (6H, s, 2×CH$_3$), 4.21 (2H, q, J=7.1 Hz, CH$_2$), 6.24 (2H, s, CH$_2$), 6.87 (1H, s, H-3), 7.18 (2H, d, J=8.0 Hz, H-2' and H-6'), 7.42 (1H, s, CH), 7.69 (2H, d, J=8.0 Hz, H-3' and H-5'); $^{13}$C nmr (DMSO-$d_6$) (ppm): 14.0 (q), 22.3 (t), 24.0 (t), 43.2 (2×q), 48.3 (t), 60.0 (t), 103.3 (s), 114.8 (d), 124.9 (s), 125.2 (2×d), 126.6 (2×d), 129.6 (s), 130.3 (s), 131.9 (s), 144.5 (s), 146.9 (d, $J_{C-F}$=237.0 Hz), 149.2 (d), 160.2 (s), 178.5 (s). Anal calcd for $C_{22}H_{23}F_3N_2O_3$: C, 62.85; H, 5.51; N, 6.66. Found: C, 62.99; H, 5.34; N, 6.49.

Ethyl 6-[(dimethylamino)methylidene]-1-[(4-fluorophenyl)methyl]-7-oxo-4,5,6,7-tetrahydro-1H-indole-2-carboxylate. This compound was obtained by reaction of ethyl 1-[(4-fluorophenyl)methyl]-7-oxo-4,5,6,7-tetrahydro-1H-indole-2-carboxylate 7a ($R^1$=COOEt) with METHOD D after 5 h and used in the next step without further purification.

Ethyl 6-[(dimethylamino)methylidene]-1-[3-(dimethylamino)propyl]-7-oxo-4,5,6,7-tetrahydro-1H-indole-2-carboxylate. This compound was obtained by reaction of ethyl 1-[3-(dimethylamino)propyl]-7-oxo-4,5,6,7-tetrahydro-1H-indole-2-carboxylate 7a ($R^1$=COOEt) with METHOD D after 16 h: brown oil; yield: 98%; IR: 1703 (CO), 1658 (CO) cm$^{-1}$; $^1$H nmr (DMSO-d$_6$) (ppm): 1.27 (3H, t, J=7.1 Hz, CH$_3$), 1.72-1.83 (2H, m, CH$_2$), 2.11-2.33 (8H, m, 2×CH$_3$ and CH$_2$), 2.50-2.58 (2H, m, CH$_2$), 2.73-2.82 (2H, m, CH$_2$), 3.07 (6H, s, 2×CH$_3$), 2.33-3.46 (2H, m, CH$_2$), 4.23 (2H, q, J=7.1 Hz, CH$_2$), 4.68-4.76 (2H, m, CH$_2$), 6.66 (1H, s, H-3), 7.40 (1H, s, CH); $^{13}$C nmr (DMSO-d$_6$) (ppm): 14.2 (q), 22.4 (t), 24.0 (t), 29.5 (t), 43.2 (2×q), 44.3 (t), 45.1 (2×q), 56.5 (t), 59.9 (t), 103.7 (s), 113.9 (d), 124.8 (s), 129.7 (s), 131.8 (s), 148.9 (d), 160.3 (s), 178.5 (s). Anal calcd for C$_{19}$H$_{29}$N$_3$O$_3$: C, 65.68; H, 8.41; N, 12.09. Found: C, 65.49; H, 8.56; N, 11.97.

Propan-2-yl 6-[(dimethylamino)methylidene]-1-[(3-methylphenyl)methyl]-7-oxo-4,5,6,7-tetrahydro-1H-indole-2-carboxylate. This compound was obtained by reaction of propan-2-yl 1-[(3-methylphenyl)methyl]-7-oxo-4,5,6,7-tetrahydro-1H-indole-2-carboxylate 7d ($R^1$=COOiPr) with METHOD A and used in the next step without further purification.

Propan-2-yl 1-(cyclopropylmethyl)-6-[(dimethylamino)methylidene]-7-oxo-4,5,6,7-tetrahydro-1H-indole-2-carboxylate. This compound was obtained by reaction of propan-2-yl 1-(cyclopropylmethyl)-7-oxo-4,5,6,7-tetrahydro-1H-indole-2-carboxylate 7d ($R^1$=COOiPr) with METHOD A and used in the next step without further purification.

Propan-2-yl 6-[(dimethylamino)methylidene]-1-[(4-fluorophenyl)methyl]-7-oxo-4,5,6,7-tetrahydro-1H-indole-2-carboxylate. This compound was obtained by reaction of propan-2-yl 1-[(4-fluorophenyl)methyl]-7-oxo-4,5,6,7-tetrahydro-1H-indole-2-carboxylate 7d ($R^1$=COOiPr) with METHOD A and used in the next step without further purification.

6-[(Dimethylamino)methylidene]-1-[(3-methylphenyl)methyl]-7-oxo-N-(propan-2-yl)-4,5,6,7-tetrahydro-1H-indole-2-carboxamide. This compound was obtained by reaction of 1-[(3-methylphenyl)methyl]-7-oxo-N-(propan-2-yl)-4,5,6,7-tetrahydro-1H-indole-2-carboxamide 7e ($R^1$=CONHR$^4$) with METHOD D after 6 h and used in the next step without further purification.

N-cyclopropyl-6-[(dimethylamino)methylidene]-1-[(3-methylphenyl)methyl]-7-oxo-4,5,6,7-tetrahydro-1H-indole-2-carboxamide. This compound was obtained by reaction of N-cyclopropyl-1-[(3-methylphenyl)methyl]-7-oxo-4,5,6,7-tetrahydro-1H-indole-2-carboxamide 7e ($R^1$=CONHR$^4$) with METHOD D after 4 h: brown solid; yield: 99%; m.p.: 156-157° C.; IR: 3433 (NH), 1664 (CO), 1635 (CO) cm$^{-1}$; $^1$H nmr (DMSO-d$_6$) (ppm): 0.47-0.64 (4H, m, 2×CH$_2$), 2.21 (3H, s, CH$_3$), 2.68-2.82 (4H, m, 2×CH$_2$), 3.38 (1H, s, CH), 3.04 (6H, s, 2×CH$_3$), 6.09 (2H, s, CH$_2$), 6.54 (1H, s, H-3), 6.74-7.10 (4H, m, H-2', H-4', H-5' and H-6'), 7.31 (1H, s, CH), 8.28 (1H, s, NH); $^{13}$C nmr (DMSO-d$_6$) (ppm): 5.7 (2×t), 21.1 (q), 22.5 (d), 22.6 (t), 24.2 (t), 43.2 (2×q), 47.5 (t), 103.4 (s), 110.1 (d), 123.6 (d), 127.1 (2×d), 128.0 (d), 129.6 (s), 129.9 (s), 130.2 (s), 136.9 (s), 140.1 (s), 148.2 (d), 162.5 (s), 178.6 (s). Anal calcd for C$_{23}$H$_{27}$N$_3$O$_2$: C, 73.18; H, 7.21; N, 11.13. Found: C, 73.07; H, 7.36; N, 11.27.

6-[(Dimethylamino)methylidene]-1-[(4-methylphenyl)methyl]-7-oxo-N-(propan-2-yl)-4,5,6,7-tetrahydro-1H-indole-2-carboxamide. This compound was obtained by reaction of 1-[(4-methylphenyl)methyl]-7-oxo-N-(propan-2-yl)-4,5,6,7-tetrahydro-1H-indole-2-carboxamide 7e ($R^1$=CONHR$^4$) with METHOD D after 16 h: brown solid; yield: 99%; m.p.: 176-177° C.; IR: 3428 (NH), 1658 (CO), 1635 (CO) cm$^{-1}$; $^1$H nmr (DMSO-d$_6$) (ppm): 1.08 (6H, d, J=6.5 Hz, 2×CH$_3$), 2.21 (3H, s, CH$_3$), 2.55 (2H, t, J=6.7 Hz, CH$_2$), 2.82 (2H, t, J=6.7 Hz, CH$_2$), 3.04 (6H, s, 2×CH$_3$), 3.93-4.06 (1H, m, CH), 6.06 (2H, s, CH$_2$), 6.53 (1H, s, H-3), 6.93 (2H, d, J=7.8 Hz, H-3' and H-5'), 7.02 (2H, d, J=7.8 Hz, H-2' and H-6'), 7.33 (1H, s, CH), 8.06 (1H, d, J=7.7 Hz, NH); $^{13}$C nmr (DMSO-d$_6$) (ppm): 20.6 (q), 22.2 (2×q), 22.6 (t), 24.2 (t), 40.3 (d), 43.2 (2×q), 47.1 (t), 103.4 (s), 110.0 (d), 126.8 (2×d), 128.6 (2×d), 129.3 (s), 130.3 (s), 130.5 (s), 135.6 (s), 137.1 (s), 148.2 (d), 160.5 (s), 178.6 (s). Anal calcd for C$_{23}$H$_{29}$N$_3$O$_2$: C, 72.79; H, 7.70; N, 11.07. Found: C, 72.87; H, 7.59; N, 10.94.

N-cyclopropyl-6-[(dimethylamino)methylidene]-1-[(4-methylphenyl)methyl]-7-oxo-4,5,6,7-tetrahydro-1H-indole-2-carboxamide. This compound was obtained by reaction of N-cyclopropyl-1-[(4-methylphenyl)methyl]-7-oxo-4,5,6,7-tetrahydro-1H-indole-2-carboxamide 7e ($R^1$=CONHR$^4$) with METHOD D after 8 h: brown solid; yield: 78%; p.f.: 97-98° C.; IR: 3428 (NH), 1758 (CO), 1635 (CO) cm$^{-1}$; $^1$H nmr (DMSO-d$_6$) (ppm): 0.40-0.48 (2H, m, CH$_2$), 0.62-0.70 (2H, m, CH$_2$), 2.22 (3H, s, CH$_3$), 2.55 (2H, t, J=6.7 Hz, CH$_2$), 2.70-2.89 (3H, m, CH$_2$ e CH), 3.04 (6H, s, 2×CH$_3$), 5.77 (2H, s, CH$_2$), 6.52 (1H, s, H-3), 6.91 (2H, d, J=7.9 Hz, H-3' e H-5'), 7.03 (2H, d, J=7.9 Hz, H-2' e H-6'), 7.33 (1H, s, CH), 8.24 (1H, d, J=4.0 Hz, NH); $^{13}$C nmr (DMSO-d$_6$) (ppm): 5.7 (2×t), 20.6 (q), 22.5 (d), 22.6 (t), 24.2 (t), 43.2 (2×q), 47.2 (t), 103.4 (s), 110.1 (d), 126.7 (2×d), 128.6 (2×d), 129.6 (s), 129.9 (s), 130.3 (s), 135.6 (s), 137.2 (s), 148.2 (d), 162.5 (s), 178.6 (s). Anal calcd for C$_{23}$H$_{27}$N$_3$O$_2$: C, 73.18; H, 7.21; N, 11.13. Found: C, 73.22; H, 7.09; N, 11.02.

1-[(4-Bromophenyl)methyl]-6-[(dimethylamino)methylidene]-7-oxo-N-(propan-2-yl)-4,5,6,7-tetrahydro-1H-indole-2-carboxamide. This compound was obtained by reaction of 1-[(4-bromophenyl)methyl]-7-oxo-N-(propan-2-yl)-4,5,6,7-tetrahydro-1H-indole-2-carboxamide 7e ($R^1$=CONHR$^4$) with METHOD D after 8 h: light brown solid; yield: 99%; m.p.: 212-213° C.; IR: 3433 (NH), 1658 (CO), 1635 (CO) cm$^{-1}$; $^1$H nmr (DMSO-d$_6$) (ppm): 1.07 (6H, d, J=6.4 Hz, 2×CH$_3$), 2.57 (2H, t, J=5.8 Hz, CH$_2$), 2.83 (2H, t, J=5.8 Hz, CH$_2$), 3.04 (6H, s, 2×CH$_3$), 3.87-4.09 (1H, m, CH), 6.06 (2H, s, CH$_2$), 6.60 (1H, s, H-3), 6.98 (2H, d, J=8.0 Hz, H-2' and H-6'), 7.32 (1H, s, CH), 7.43 (2H, d, J=8.0 Hz, H-3' and H-5'), 8.07 (1H, d, J=7.7 Hz, NH); $^{13}$C nmr (DMSO-d$_6$) (ppm): 22.2 (2×q), 22.6 (t), 24.1 (t), 40.4 (d), 43.2 (2×q), 47.2 (t), 103.3 (s), 110.1 (d), 119.6 (s), 129.0 (2×d), 129.4 (s), 130.1 (s), 130.4 (s), 130.9 (2×d), 139.6 (s), 148.3 (d), 160.3 (s), 178.5 (s). Anal calcd for C$_{22}$H$_{26}$BrN$_3$O$_2$: C, 59.46; H, 5.90; N, 9.46. Found: C, C, 59.59; H, 6.11; N, 9.32.

1-[(4-Bromophenyl)methyl]-N-cyclopropyl-6-[(dimethylamino)methylidene]-7-oxo-4,5,6,7-tetrahydro-1H-indole-2-carboxamide. This compound was obtained by reaction of 1-[(4-bromophenyl)methyl]-N-cyclopropyl-7-oxo-4,5,6,7-tetrahydro-1H-indole-2-carboxamide 7e ($R^1$=CONHR$^4$) with METHOD D after 8 h: light brown solid; yield: 99%; m.p.: 191-192° C.; IR: 3433 (NH), 1653 (CO), 1635 (CO) cm$^{-1}$; $^1$H nmr (DMSO-d$_6$) (ppm): 0.50-0.65 (4H, m, 2×CH$_2$), 2.57 (2H, t, J=6.3 Hz, CH$_2$), 2.73-2.83 (3H, m, CH$_2$ and CH), 3.04 (6H, s, 2×CH$_3$), 6.08 (2H, s, CH$_2$), 6.62 (1H, s, H-3), 6.97 (2H, d, J=7.3 Hz, H-2' and H-6'), 7.32 (1H, s, CH), 7.45 (2H, d, J=8.3 Hz, H-3' and H-5'), 8.29 (1H, s, NH); $^{13}$C nmr (DMSO-d$_6$) (ppm): 6.2 (2×t), 23.0 (d), 23.1 (t), 24.6 (t), 43.7 (2×q), 47.8 (t), 103.9 (s), 110.8 (d), 120.0 (s), 129.4 (2×d), 130.0 (s), 130.1 (s), 130.9 (s), 131.4 (2×d), 140.1 (s), 148.8 (d), 162.8 (s), 179.0 (s). Anal calcd for $C_{22}H_{24}BrN_3O_2$: C, 59.73; H, 5.47; N, 9.50. Found: C, 59.87; H, 5.65; N, 9.39.

Ethyl 3-chloro-6-[(dimethylamino)methylidene]-1-[(4-methylphenyl)methyl]-7-oxo-4,5,6,7-tetrahydro-1H-indole-2-carboxylate. This compound was obtained by reaction of ethyl 3-chloro-1-[(4-methylphenyl)methyl]-7-oxo-4,5,6,7-tetrahydro-1H-indole-2-carboxylate 7f ($R^1$=COOEt) with METHOD D after 4 h: brown oil; yield: 80%; IR: 3377 (NH), 1702 (CO), 1666 (CO) cm$^{-1}$; $^1$H nmr (DMSO-d$_6$) (ppm): 1.21 (3H, t, J=7.1 Hz, CH$_3$), 2.23 (3H, s, CH$_3$), 2.54 (2H, t, J=6.9 Hz, CH$_2$), 2.88 (2H, t, J=6.9 Hz, CH$_2$), 3.09 (6H, s, 2×CH$_3$), 4.20 (2H, q, J=7.1 Hz, CH$_2$), 6.09 (2H, s, CH$_2$), 6.84 (2H, d, J=7.9 Hz, H-3' and H-5'), 7.06 (2H, d, J=7.9 Hz, H-2' and H-6'), 7.43 (1H, s, CH); $^{13}$C nmr (DMSO-d$_6$) (ppm): 13.9 (q), 20.1 (t), 20.6 (q), 23.2 (t), 43.4 (2×q), 48.3 (t), 60.5 (t), 102.8 (s), 115.7 (s), 121.4 (s), 126.1 (2×d), 128.2 (s), 128.8 (2×d), 130.1 (s), 135.9 (s), 136.1 (s), 150.0 (d), 159.5 (s), 177.8 (s). Anal calcd for $C_{22}H_{25}ClN_2O_3$: C, 65.91; H, 6.29; N, 6.99. Found: C, 65.79; H, 6.44; N, 7.08.

Ethyl 6-[(dimethylamino)methylidene]-3-iodo-1-[(4-methylphenyl)methyl]-7-oxo-4,5,6,7-tetrahydro-1H-indole-2-carboxylate. This compound was obtained by reaction of ethyl 3-iodo-1-[(4-methylphenyl)methyl]-7-oxo-4,5,6,7-tetrahydro-1H-indole-2-carboxylate 7f ($R^1$=COOEt) with METHOD D after 16 h: brown solid; resa: 66%; m.p.: 131-132° C.; IR: 3416 (NH), 1703 (CO), 1641 (CO) cm$^{-1}$; $^1$H nmr (DMSO-d$_6$) (ppm): 1.25 (3H, t, J=7.1 Hz, CH$_3$), 2.22 (3H, s, CH$_3$), 2.47 (2H, t, J=6.7 Hz, CH$_2$), 2.87 (2H, t, J=6.7 Hz, CH$_2$), 3.08 (6H, s, 2×CH$_3$), 4.20 (2H, q, J=7.1 Hz, CH$_2$), 6.10 (2H, s, CH$_2$), 6.83 (2H, d, J=8.0 Hz, H-3' and H-5'), 7.05 (2H, d, J=8.0 Hz, H-2' and H-6'), 7.42 (1H, s, CH); $^{13}$C nmr (DMSO-d$_6$) (ppm): 13.9 (q), 20.6 (q), 23.3 (t), 24.3 (t), 43.3 (2×q), 48.7 (t), 60.6 (t), 77.7 (s), 102.7 (s), 126.0 (s), 126.1 (2×d), 128.8 (2×d), 131.6 (s), 134.8 (s), 135.9 (s), 136.3 (s), 149.8 (d), 159.9 (s), 178.0 (s). Anal calcd for $C_{22}H_{25}IN_2O_3$: C, 53.67; H, 5.12; N, 5.69. Found: C, 53.80; H, 5.01; N, 5.55.

General Procedure for the Synthesis of 4,5,8,9-tetrahydro-1H-pyrrolo[3,2-h]quinolinones and 1,4,5,6,9,10-hexahydropyrrolo[3',2':6,7]cyclohepta[1,2-b]pyridinones of Type 9

To a suspension of 8 (4 mmol) in anhydrous ethanol (50 mL), a solution of the proper cyanomethylene compound of type $R^3SO_2CH_2CN$ (6 mmol) in anhydrous ethanol (60 mL) was added dropwise under nitrogen atmosphere. Then the reaction mixture was heated at reflux for 24 h. After cooling, the solvent was removed under reduced pressure and the crude was added of a mixture of anhydrous toluene/acetic acid (1:1) and the reaction mixture was heated at reflux for 24 h with the Dean-Stark apparatus to remove water azeotropically and to facilitate the cyclization of the pyridine ring. After cooling, the solid was filtered off and recrystallized from ethanol or purified by chromatography SEPA-CORE BÜCHI (DCM/AcOEt 9:1).

Ethyl 1-(2-methylbenzyl)-8-oxo-7-(phenylsulfonyl)-4,5,8,9-tetrahydro-1H-pyrrolo[3,2-h]quinoline-2-carboxylate (PP015). This product was obtained by reaction of ethyl 6-[(dimethylamino)methylidene]-1-(2-methylbenzyl)-7-oxo-4,5,6,7-tetrahydro-1H-indole-2-carboxylate with phenylsulfonylacetonitrile after 24 h at reflux. The crude was purified by chromatography. Dark yellow solid; yield: 62%; m.p.: 97-98° C.; IR: 3399 (NH), 1703 (CO), 1663 (CO) cm$^{-1}$; $^1$H nmr (DMSO-d$_6$) (ppm): 1.22 (3H, t, J=7.1 Hz, CH$_3$), 2.17 (3H, s, CH$_3$), 2.70 (2H, t, J=6.5 Hz, CH$_2$), 2.86 (2H, t, J=6.5 Hz, CH$_2$), 4.17 (2H, q, J=7.1 Hz, CH$_2$), 6.37 (2H, s, CH$_2$), 6.77-7.08 (5H, m, H-3', H-4', H-5', H-6' and H-7), 7.56-7.69 (3H, m, H-3", H-4" and H-5"), 7.93 (2H, d, J=7.3 Hz, H-2" e H-6"), 8.13 (1H, s, H-4), 11.91 (1H, s, NH); $^{13}$C nmr (DMSO-d$_6$) (ppm): 14.1 (q), 20.5 (q), 20.8 (t), 27.2 (t), 48.1 (t), 59.9 (t), 115.8 (d), 117.2 (s), 125.9 (2×d), 127.5 (2×d), 127.9 (s), 128.8 (2×d), 129.0 (2×d), 129.5 (d), 133.4 (d), 135.8 (s), 136.4 (s), 137.5 (s), 138.2 (s), 140.6 (s), 149.8 (s), 151.1 (s), 157.9 (s), 160.3 (s). Anal calcd for $C_{28}H_{26}N_2O_5S$: C, 66.91; H, 5.21; N, 5.57. Found: C, 66.84; H, 5.09; N, 5.76.

Ethyl 1-(3-methylbenzyl)-8-oxo-7-(phenylsulfonyl)-4,5,8,9-tetrahydro-1H-pyrrolo[3,2-h]quinoline-2-carboxylate (PP016). This product was obtained by reaction of ethyl 6-[(dimethylamino)methylidene]-1-(3-methylbenzyl)-7-oxo-4,5,6,7-tetrahydro-1H-indole-2-carboxylate with phenylsulfonylacetonitrile after 24 h at reflux. The crude was purified by chromatography. Dark yellow solid; yield: 64%; m.p.: 160-161° C.; IR: 3405 (NH), 1721 (CO), 1652 (CO) cm$^{-1}$; $^1$H nmr (DMSO-d$_6$) (ppm): 1.21 (3H, t, J=7.1 Hz, CH$_3$), 2.14 (3H, s, CH$_3$), 2.71 (2H, t, J=7.1 Hz, CH$_2$), 2.86 (2H, t, J=7.1 Hz, CH$_2$), 4.17 (2H, q, J=7.1 Hz, CH$_2$), 6.38 (2H, s, CH$_2$), 6.59 (1H, d, J=7.1 Hz, Ar), 6.77 (1H, s, H-7), 6.88-6.94 (2H, m, Ar), 7.05 (1H, t, J=7.5 Hz, Ar), 7.56-7.72 (3H, m, H-3", H-4" and H-5"), 7.93 (2H, d, J=7.5 Hz, H-2" and H-6"), 8.13 (1H, s, H-4), 11.94 (1H, s, NH); $^{13}$C nmr (DMSO-d$_6$) (ppm): 14.1 (q), 20.8 (q), 21.0 (t), 27.2 (t), 48.3 (t), 59.9 (t), 115.9 (d), 117.2 (s), 118.4 (s), 122.8 (d), 124.1 (s), 125.5 (s), 126.6 (d), 127.3 (d), 127.5 (s), 127.8 (2×d), 128.2 (d), 129.0 (2×d), 130.9 (s), 133.4 (d), 137.2 (s), 138.1 (d), 139.4 (s), 140.6 (s), 157.9 (s), 160.1 (s). Anal calcd for $C_{28}H_{26}N_2O_5S$: C, 66.91; H, 5.21; N, 5.57. Found: C, 67.09; H, 5.07; N, 5.69.

Ethyl 1-(4-chlorobenzyl)-8-oxo-7-(phenylsulfonyl)-4,5,8,9-tetrahydro-1H-pyrrolo[3,2-h]quinoline-2-carboxylate (PP017). This product was obtained by reaction of ethyl 6-[(dimethylamino)methylidene]-1-(4-chlorobenzyl)-7-oxo-4,5,6,7-tetrahydro-1H-indole-2-carboxylate with phenylsulfonylacetonitrile after 24 h at reflux. The crude was purified by chromatography. Dark yellow solid; yield: 65%; m.p.: 101-102° C.; IR: 3342 (NH), 1701 (CO), 1663 (CO) cm$^{-1}$; $^1$H nmr (CDCl$_3$) (ppm): 1.30 (3H, t, J=7.1 Hz, CH$_3$), 2.34 (3H, s, CH$_3$), 2.75-3.04 (4H, m, 2×CH$_2$), 4.25 (2H, q, J=7.1 Hz, CH$_2$), 6.15 (2H, s, CH$_2$), 6.89-7.01 (3H, m, Ar), 7.21-7.37 (2H, m, Ar), 7.48-7.64 (3H, m, H-3", H-4" and H-5"), 7.98-8.09 (4H, m, H-2", H-6", H-4 and NH); $^{13}$C nmr (CDCl$_3$) (ppm): 14.2 (q), 21.5 (t), 27.8 (t), 49.1 (t), 53.4 (t), 116.0 (d), 118.5 (s), 127.0 (s), 127.1 (s), 127.7 (2×d), 127.8 (2×d), 128.6 (s), 128.9 (2×d), 129.2 (2×d), 129.7 (d), 133.1 (s), 133.7 (d), 136.8 (s), 140.7 (s), 148.3 (s), 152.3 (s), 157.3 (s), 160.6 (s). Anal calcd for $C_{27}H_{23}ClN_2O_5S$: C, 62.01; H, 4.43; N, 5.36. Found: C, 61.92; H, 4.66; N, 5.19.

Ethyl 7-[(4-chlorophenyl)sulfonyl]-1-(4-methylbenzyl)-8-oxo-4,5,8,9-tetrahydro-1H-pyrrolo[3,2-h]quinoline-2-carboxylate (PP018). This product was obtained by reaction of ethyl 6-[(dimethylamino)methylidene]-1-(4-methylbenzyl)-7-oxo-4,5,6,7-tetrahydro-1H-indole-2-carboxylate with 4-chlorophenylsulfonyl acetonitrile after 24 h at reflux. The crude was purified by chromatography. Dark yellow solid; yield: 58%; m.p.: 196-197° C.; IR: 3285 (NH), 1712 (CO), 1671 (CO) cm$^{-1}$; $^1$H nmr (DMSO-d$_6$) (ppm): 1.14 (3H, t, J=7.0 Hz, CH$_3$), 2.34 (3H, s, CH$_3$), 2.55 (2H, t, J=6.9 Hz, CH$_2$), 2.92 (2H, t, J=6.9 Hz, CH$_2$), 4.08 (2H, q, J=7.0 Hz, CH$_2$), 6.37 (2H, s, CH$_2$), 6.87-7.13 (4H, m, H-2', H-3', H-4' and H-5'), 7.66 (2H, d, J=8.4 Hz, H-3" and H-4"), 7.91 (2H, d, J=8.4 Hz, H-2" and H-6"), 8.07 (1H, s, H-7), 8.15 (1H, s, H-4), 12.02 (1H, s, NH); $^{13}$C nmr (DMSO-d$_6$) (ppm): 14.0 (q), 18.7 (q), 20.8 (t), 27.3 (t), 47.1 (t), 59.8 (t), 103.6 (s), 115.9 (s), 116.0 (d), 122.5 (d), 125.6 (s), 126.0 (2×d), 127.5 (s), 129.1 (s), 129.5 (2×d), 129.9 (2×d), 131.1 (s), 131.2 (s), 134.2 (s), 138.3 (s), 138.4 (s), 139.3 (s), 157.8 (s), 159.8 (s). Anal calcd for $C_{28}H_{25}ClN_2O_5S$: C, 62.62; H, 4.33; N, 5.22. Found: C, 62.77; H, 4.25; N, 5.08.

Ethyl 7-(benzenesulfonyl)-1-[(2,4-dimethylphenyl)methyl]-8-oxo-4,5,8,9-tetrahydro-1H-pyrrolo[3,2-h]quinoline-2-carboxylate (PP021). This product was obtained by reaction of ethyl 6-[(dimethylamino)methylidene]-1-[(2,4-dimethylphenyl)methyl]-7-oxo-4,5,6,7-tetrahydro-1H-indole-2-carboxylate con phenylsulfonylacetonitrile after 24 h at reflux. The crude was purified by chromatography. Dark yellow solid; yield: 64%; m.p.: 182-183° C.; IR: 3319 (NH), 1699 (CO), 1640 (CO) cm$^{-1}$; $^1$H nmr (DMSO-d$_6$) (ppm): 1.20 (3H, t, J=7.1 Hz, CH$_3$), 1.97 (3H, s, CH$_3$), 2.18 (3H, s, CH$_3$), 2.79 (2H, t, J=7.1 Hz, CH$_2$), 2.99 (2H, t, J=7.1 Hz, CH$_2$), 4.14 (2H, q, J=7.1 Hz, CH$_2$), 5.80 (1H, d, J=7.7 Hz, Ar), 6.38 (2H, s, CH$_2$), 6.75 (1H, d, J=7.7 Hz, Ar), 6.96-6.98 (2H, m, Ar and H-7), 7.59-7.76 (3H, m, H-3", H-4" and H-5"), 7.97 (2H, d, J=6.7 Hz, H-2" and H-6"), 8.20 (1H, s, H-4), 11.94 (1H, s, NH); $^{13}$C nmr (DMSO-d$_6$) (ppm): 14.0 (q), 18.5 (q), 20.4 (q), 20.8 (t), 27.3 (t), 47.0 (t), 59.8 (t), 115.9 (s), 117.4 (s), 122.6 (d), 124.2 (s), 125.5 (s), 126.5 (d), 127.3 (s), 127.9 (2×d), 129.0 (2×d), 130.3 (d), 131.3 (s), 133.4 (d), 133.9 (s), 134.9 (s), 135.3 (s), 138.0 (d), 140.6 (s), 156.1 (s), 157.8 (s), 159.8 (s). Anal calcd for $C_{29}H_{28}N_2O_5S$: C, 67.42; H, 5.46; N, 5.42. Found: C, 67.31; H, 5.60; N, 5.33.

Ethyl 7-(benzenesulfonyl)-1-[(3,4-dimethylphenyl)methyl]-8-oxo-4,5,8,9-tetrahydro-1H-pyrrolo[3,2-h]quinoline-2-carboxylate (PP025). This product was obtained by reaction of ethyl 6-[(dimethylamino)methylidene]-1-[(3,4-dimethylphenyl)methyl]-7-oxo-4,5,6,7-tetrahydro-1H-indole-2-carboxylate con phenylsulfonylacetonitrile after 24 h at reflux. The crude was purified by chromatography. Dark yellow solid; yield: 65%; m.p.: 90-91° C.; IR: 3296 (NH), 1703 (CO), 1639 (CO) cm$^{-1}$; $^1$H nmr (DMSO-d$_6$) (ppm): 1.22 (3H, t, J=7.1 Hz, CH$_3$), 2.04 (3H, s, CH$_3$), 2.07 (3H, s, CH$_3$), 2.69 (2H, t, J=7.1 Hz, CH$_2$), 2.85 (2H, t, J=7.1 Hz, CH$_2$), 4.18 (2H, q, J=7.1 Hz, CH$_2$), 6.34 (2H, s, CH$_2$), 6.52 (1H, d, J=7.8 Hz, Ar), 6.73 (1H, s, Ar), 6.87-6.93 (2H, m, Ar and H-7), 7.56-7.70 (3H, m, H-3", H-4" and H-5"), 7.93 (2H, d, J=6.8 Hz, H-2" and H-6"), 8.13 (1H, s, H-4), 11.90 (1H, s, NH); $^{13}$C nmr (DMSO-d$_6$) (ppm): 14.1 (q), 18.9 (q), 19.5 (q), 20.8 (t), 27.2 (t), 48.0 (t), 59.9 (t), 115.9 (s), 123.2 (d), 125.4 (s), 127.3 (d), 127.5 (s), 127.8 (2×d), 129.0 (2×d), 129.4 (d), 130.8 (s), 133.4 (d), 134.5 (s), 135.8 (s), 137.9 (d), 140.6 (s), 142.0 (s), 150.7 (s), 151.2 (s), 157.0 (s), 157.8 (s), 160.1 (s). Anal calcd for $C_{29}H_{28}N_2O_5S$: C, 67.42; H, 5.46; N, 5.42. Found: C, 67.59; H, 5.57; N, 5.29.

Propan-2-yl 7-(benzenesulfonyl)-1-[(4-methylphenyl)methyl]-8-oxo-4,5,8,9-tetrahydro-1H-pyrrolo[3,2-h]quinoline-2-carboxylate (PP022). This product was obtained by reaction of propan-2-yl 6-[(dimethylamino)methylidene]-1-[(4-methylphenyl)methyl]-7-oxo-4,5,6,7-tetrahydro-1H-indole-2-carboxylate con phenylsulfonylacetonitrile after 24 h at reflux. The crude was purified by chromatography. Dark yellow solid; yield: 58%; m.p.: 97-98° C.; IR: 3399 (NH), 1700 (CO), 1664 (CO) cm$^{-1}$; $^1$H nmr (DMSO-d$_6$) (ppm): 1.19 (3H, s, CH$_3$), 1.22 (3H, s, CH$_3$), 2.16 (3H, s, CH$_3$), 2.69 (2H, t, J=7.2 Hz, CH$_2$), 2.85 (2H, t, J=7.2 Hz, CH$_2$), 4.93-5.05 (1H, m, CH), 6.36 (2H, s, CH$_2$), 6.76-6.84 (3H, m, H-2', H-6' and H-7), 6.98 (2H, d, J=7.8 Hz, H-3' and H-5'), 7.55-7.72 (3H, m, H-3", H-4" and H-5"), 7.93 (2H, d, J=7.8 Hz, H-2" and H-6"), 8.11 (1H, s, H-4), 11.95 (1H, s, NH); $^{13}$C nmr (DMSO-d$_6$) (ppm): 20.5 (q), 20.8 (t), 21.6 (2×q), 27.2 (t), 48.1 (t), 67.3 (d), 116.0 (d), 117.2 (s), 124.1 (s), 125.9 (2×d), 127.8 (2×d), 127.5 (s), 128.8 (2×d), 129.0 (2×d), 130.7 (s), 133.4 (d), 135.7 (s), 136.4 (s), 138.0 (d), 140.6 (s), 146.2 (s), 150.6 (s), 157.9 (s), 159.7 (s). Anal calcd for $C_{29}H_{28}N_2O_5S$: C, 67.42; H, 5.46; N, 5.42. Found: C, 67.29; H, 5.58; N, 5.55.

Ethyl 7-(4-methylbenzene-1-sulfonyl)-1-[(4-methylphenyl)methyl]-8-oxo-4,5,8,9-tetrahydro-1H-pyrrolo[3,2-h]quinoline-2-carboxylate (PP023). This product was obtained by reaction of ethyl 6-[(dimethylamino)methylidene]-1-(4-methylbenzyl)-7-oxo-4,5,6,7-tetrahydro-1H-indole-2-carboxylate con 4-toluensulfonylacetonitrile after 24 h at reflux. The crude was purified by chromatography. Dark yellow solid; yield: 65%; m.p.: 289-290° C.; IR: 3329 (NH), 1723 (CO), 1654 (CO) cm$^{-1}$; $^1$H nmr (DMSO-d$_6$) (ppm): 1.22 (3H, t, J=7.1 Hz, CH$_3$), 2.17 (3H, s, CH$_3$), 2.37 (3H, s, CH$_3$), 2.69 (2H, t, J=7.6 Hz, CH$_2$), 2.89 (2H, t, J=7.6 Hz, CH$_2$), 4.17 (2H, q, J=7.1 Hz, CH$_2$), 6.38 (2H, s, CH$_2$), 6.78 (2H, d, J=7.8 Hz, Ar), 6.87 (1H, s, H-7), 6.98 (2H, d, J=7.8 Hz, Ar), 7.39 (2H, d, J=8.0 Hz, Ar), 7.80 (2H, d, J=8.0 Hz, Ar), 8.07 (1H, s, H-4), 11.86 (1H, s, NH); $^{13}$C nmr (DMSO-d$_6$) (ppm): 14.1 (q), 20.5 (q), 20.8 (q), 21.0 (q), 27.2 (t), 48.0 (t), 59.9 (t), 115.9 (d), 117.5 (s), 125.4 (s), 125.9 (2×d), 127.4 (s), 127.9 (2×d), 128.8 (2×d), 129.6 (2×d), 130.7 (s), 133.5 (s), 135.7 (s), 136.4 (s), 137.8 (d), 144.0 (s), 150.4 (s), 157.8 (s), 160.1 (s), 164.7 (s). Anal calcd for $C_{29}H_{28}N_2O_5S$: C, 67.42; H, 5.46; N, 5.42. Found: C, 67.55; H, 5.39; N, 5.60.

Ethyl 7-(metansulfonyl)-1-[(4-methylphenyl)methyl]-8-oxo-4,5,8,9-tetrahydro-1H-pyrrolo[3,2-h]quinoline-2-carboxylate (PP024). This product was obtained by reaction of ethyl 6-[(dimethylamino)methylidene]-1-(4-methylbenzyl)-7-oxo-4,5,6,7-tetrahydro-1H-indole-2-carboxylate con methylsulfonylacetonitrile after 24 h at reflux. The crude was purified by chromatography. Dark yellow solid; yield: 60%; m.p.: 189-190° C.; IR: 3307 (NH), 1703 (CO), 1660 (CO) cm$^{-1}$; $^1$H nmr (DMSO-d$_6$) (ppm): 1.24 (3H, t, J=7.1 Hz, CH$_3$), 2.19 (3H, s, CH$_3$), 2.69 (2H, t, J=7.2 Hz, CH$_2$), 2.86 (2H, t, J=7.2 Hz, CH$_2$), 3.24 (3H, s, CH$_3$), 4.19 (2H, q, J=7.1 Hz, CH$_2$), 6.46 (2H, s, CH$_2$), 6.83-7.05 (5H, m, Ar and H-7), 7.92 (1H, s, H-4), 12.20 (1H, s, NH); $^{13}$C nmr (DMSO-d$_6$) (ppm): 14.6 (q), 21.0 (q), 21.4 (t), 27.7 (t), 42.4 (q), 49.4 (t), 59.9 (t), 116.4 (d), 117.3 (s), 125.4 (s), 126.6 (2×d), 127.8 (s), 128.8 (s), 129.4 (2×d), 136.3 (s), 136.9 (d), 155.1 (s), 156.9 (s), 158.5 (s), 160.7 (s), 161.1 (s). Anal calcd for $C_{23}H_{24}N_2O_5S$: C, 62.71; H, 5.49; N, 6.36. Found: C, 62.62; H, 5.31; N, 6.58.

Methyl 1-(4-methylbenzyl)-8-oxo-7-(phenylsulfonyl)-4,5,8,9-tetrahydro-1H-pyrrolo[3,2-h]quinoline-2-carboxylate (PP019). This product was obtained by reaction of methyl 6-[(dimethylamino)methylidene]-1-(4-methylbenzyl)-7-oxo-4,5,6,7-tetrahydro-1H-indole-2-carboxylate con phenylsulfonylacetonitrile after 24 h at reflux. The crude was purified by chromatography. Dark yellow solid; yield: 50%; m.p.: >400° C.; IR: 3390 (NH), 1703 (CO), 1680 (CO) cm$^{-1}$; $^1$H nmr (DMSO-d$_6$) (ppm): 1.27 (3H, t, J=7.1 Hz, CH$_3$), 2.17 (3H, s, CH$_3$), 2.66-2.73 (2H, m, CH$_2$), 2.85-2.92 (2H, m, CH$_2$), 3.71 (3H, s, CH$_3$), 6.38 (2H, s, CH$_2$), 6.79 (2H, d, J=7.9 Hz, H-3' and H-5'), 6.87 (1H, m, H-7), 6.98 (2H, d, J=8.5 Hz, H-2' and H-6'), 7.55-7.75 (3H, m, H-3", H-4" and H-5"), 7.93 (2H, d, J=6.8 Hz, H-2" and H-6"), 8.07 (1H, s, H-4), 11.95 (1H, s, NH); $^{13}$C nmr (DMSO-d$_6$) (ppm): 20.6 (q), 22.0 (t), 25.0 (t), 48.1 (t), 57.8 (q), 102.8 (s), 108.7 (s), 117.4 (d), 125.9 (s), 127.8 (2×d), 128.7 (2×d), 128.8 (2×d), 129.0 (2×d), 130.0 (s), 131.5 (s), 131.7 (s), 133.9 (d), 136.3 (d), 136.4 (s), 155.1 (s), 157.1 (s), 161.1 (s), 163.3 (s).

Anal calcd for $C_{27}H_{24}N_2O_5S$: C, 66.38; H, 4.95; N, 5.73. Found: C, 66.25; H, 5.08; N, 5.61.

Methyl 1-(2-methylbenzyl)-8-oxo-7-(phenylsulfonyl)-4,5,8,9-tetrahydro-1H-pyrrolo[3,2-h]quinoline-2-carboxylate (PP020). This product was obtained by reaction of methyl 6-[(dimethylamino)methylidene]-1-(2-methylbenzyl)-7-oxo-4,5,6,7-tetrahydro-1H-indole-2-carboxylate con phenylsulfonylacetonitrile after 24 h at reflux. The crude was purified by chromatography. Dark yellow solid; yield: 66%; m.p.: 158-159° C.; IR: 3502 (NH), 1711 (CO), 1669 (CO) cm$^{-1}$; $^1$H nmr (DMSO-d$_6$) (ppm): 2.35 (3H, s, CH$_3$), 2.75 (2H, t, J=6.7 Hz, CH$_2$), 2.96 (2H, t, J=6.7 Hz, CH$_2$), 3.64 (3H, s, CH$_3$), 6.38 (2H, s, CH$_2$), 6.90-7.12 (4H, m, Ar), 7.54-7.72 (3H, m, H-3", H-4" and H-5"), 7.91 (2H, d, J=7.0 Hz, H-2" and H-6"), 8.07 (1H, s, H-7), 8.15 (1H, s, H-4), 11.92 (1H, s, NH); $^{13}$C nmr (DMSO-d$_6$) (ppm): 18.8 (q), 20.9 (t), 27.3 (t), 47.1 (t), 51.3 (q), 116.0 (d), 117.6 (s), 122.6 (d), 125.1 (s), 126.0 (s), 127.4 (s), 127.9 (2×d), 128.7 (d), 129.0 (2×d), 129.5 (d), 131.4 (s), 131.7 (s), 133.5 (d), 134.2 (s), 138.3 (s), 140.5 (s), 150.6 (s), 157.8 (s), 160.2 (s). Anal calcd for $C_{27}H_{24}N_2O_5S$: C, 66.38; H, 4.95; N, 5.73. Found: C, 66.26; H, 5.07; N, 5.63.

Ethyl 8-(benzenesulfonyl)-1-[(4-methylphenyl)methyl]-9-oxo-1,4,5,6,9,10-hexahydropyrrolo[3',2':6,7]cyclohepta[1,2-b]pyridine-2-carboxylate (PP048). This product was obtained by reaction of ethyl 7-[(dimethylamino)methylidene]-1-[(4-methylphenyl)methyl]-8-oxo-1,4,5,6,7,8-hexahydrocyclohepta[b]pyrrolo-2-carboxylate con phenylsulfonylacetonitrile after 24 h at reflux. The crude was purified by chromatography. Dark yellow solid; yield: 50%; m.p.: 101-102° C.; IR: 3416 (NH), 1714 (CO), 1667 (CO) cm$^{-1}$; $^1$H nmr (CDCl$_3$) (ppm): 1.25 (3H, t, J=7.1 Hz, CH$_3$), 2.05-2.46 (7H, m, 2×CH$_2$ and CH$_3$), 2.89-2.66 (2H, m, CH$_2$), 4.21 (2H, q, J=7.1 Hz, CH$_2$), 5.75 (2H, s, CH$_2$), 6.69-7.56 (6H, m, Ar), 8.02-8.28 (4H, m, Ar and H-7), 11.13 (1H, s, NH); $^{13}$C nmr (CDCl$_3$) (ppm): 14.2 (q), 21.1 (q), 29.7 (t), 31.5 (t), 36.6 (t), 53.4 (t), 60.4 (t), 125.6 (d), 125.9 (s), 126.5 (s), 128.6 (2×d), 128.9 (2×d), 129.1 (s), 129.5 (2×d), 129.8 (2×d), 133.8 (s), 134.9 (s), 136.2 (s), 137.4 (s), 145.9 (d), 160.6 (s), 162.7 (s), 165.1 (s), 171.5 (s). Anal calcd for $C_{29}H_{28}N_2O_5S$: C, 67.42; H, 5.46; N, 5.42. Found: C, 67.68; H, 5.33; N, 5.58.

Ethyl 7-(benzenesulfonyl)-1-[(4-bromophenyl)methyl]-8-oxo-4,5,8,9-tetrahydro-1H-pyrrolo[3,2-h]quinoline-2-carboxylate (PP060). This compound was obtained by reaction of ethyl 1-[(4-bromophenyl)methyl]-6-[(dimethylamino)methylidene]-7-oxo-4,5,6,7-tetrahydro-1H-indole-2-carboxylate with phenylsulfonyl acetonitrile after 24 h at reflux. The crude product was purified by chromatography. Brown solid; yield: 65%; m.p.: 226-227° C.; IR: 3405 (NH), 1732 (CO), 1720 (CO) cm$^{-1}$; $^1$H nmr (DMSO-d$_6$) (ppm): 1.21 (3H, t, J=7.1 Hz, CH$_3$), 2.71 (2H, t, J=7.2 Hz, CH$_2$), 2.91 (2H, t, J=7.2 Hz, CH$_2$), 4.16 (2H, q, J=7.1 Hz, CH$_2$), 6.37 (2H, s, CH$_2$), 6.84-6.89 (3H, m, H-3, H-2' and H-6'), 7.39 (2H, d, J=8.3 Hz, H-3' and H-5'), 7.56-7.72 (3H, m, H-3", H-4" and H-5"), 7.93 (2H, d, J=7.2 Hz, H-2" and H-6"), 8.14 (1H, s, H-6), 11.93 (1H, s, NH); $^{13}$C nmr (DMSO-d$_6$) (ppm): 14.1 (q), 20.8 (t), 27.1 (t), 48.0 (t), 60.0 (t), 116.0 (d), 117.2 (s), 119.7 (s), 124.1 (s), 125.3 (s), 127.5 (s), 127.9 (2×d), 128.2 (2×d), 129.0 (2×d), 130.6 (s), 131.1 (2×d), 133.4 (d), 138.0 (d), 138.8 (s), 140.6 (s), 150.4 (s), 157.9 (s), 160.0 (s). Anal calcd for $C_{27}H_{23}BrN_2O_5S$: C, 57.15; H, 4.09; N, 4.94. Found: C, 57.12; H, 3.94; N, 5.08.

Ethyl 7-(benzenesulfonyl)-1-[(4-iodophenyl)methyl]-8-oxo-4,5,8,9-tetrahydro-1H-pyrrolo[3,2-h]quinoline-2-carboxylate (PP062). This compound was obtained by reaction of ethyl 6-[(dimethylamino)methylidene]-1-[(4-iodophenyl)methyl]-7-oxo-4,5,6,7-tetrahydro-1H-indole-2-carboxylate with phenylsulfonyl acetonitrile after 24 h at reflux. The crude product was purified by chromatography. Yellow solid; yield: 55%; m.p.: 189-190° C.; IR: 3324 (NH), 3399 (NH), 1700 (CO), 1696 (CO) cm$^{-1}$; $^1$H nmr (DMSO-d$_6$) (ppm): 1.21 (3H, t, J=6.7 Hz, CH$_3$), 2.71 (2H, t, J=6.8 Hz, CH$_2$), 2.91 (2H, t, J=6.8 Hz, CH$_2$), 4.16 (2H, q, J=6.7 Hz, CH$_2$), 6.35 (2H, s, CH$_2$), 6.71 (2H, d, J=7.5 Hz, H-2' and H-6'), 6.89 (1H, s, H-3), 7.54-7.64 (3H, m, H-3', H-5', H-3", H-4" and H-5"), 7.93 (2H, d, J=6.8 Hz, H-2" and H-6"), 8.14 (1H, s, H-6), 11.92 (1H, s, NH); $^{13}$C nmr (DMSO-d$_6$) (ppm): 14.1 (q), 20.8 (t), 27.1 (t), 48.1 (t), 60.0 (t), 92.5 (s), 111.1 (s), 116.0 (d), 117.3 (s), 119.1 (s), 124.2 (s), 125.3 (s), 127.5 (s), 127.9 (2×d), 128.4 (2×d), 129.0 (2×d), 130.6 (s), 133.4 (d), 137.0 (2×d), 139.2 (d), 140.6 (s), 157.9 (s), 160.0 (s). Anal calcd for $C_{27}H_{23}IN_2O_5S$: C, 52.78; H, 3.77; N, 4.56. Found: C, 52.90; H, 3.65; N, 4.69.

Ethyl 7-(benzenesulfonyl)-1-(cyclopropylmethyl)-8-oxo-4,5,8,9-tetrahydro-1H-pyrrolo[3,2-h]quinoline-2-carboxylate (PP064). This compound was obtained by reaction of (1-(cyclopropylmethyl)-6-[(dimethylamino)methylidene]-7-oxo-4,5,6,7-tetrahydro-1H-indole-2-carboxylate with phenylsulfonyl acetonitrile after 24 h at reflux. The crude product was purified by chromatography. Yellow solid; yield: 55%; m.p.: 195-196° C.; IR: 3416 (NH), 1751 (CO), 1716 (CO) cm$^{-1}$; $^1$H nmr (DMSO-d$_6$) (ppm): 0.24-0.28 (4H, m, 2×CH$_2$), 1.13-1.30 (4H, m, CH$_3$ and CH), 2.66 (2H, t, J=7.2 Hz, CH$_2$), 2.90 (2H, t, J=7.2 Hz, CH$_2$), 4.22 (2H, q, J=7.0 Hz, CH$_2$), 5.04 (2H, d, J=6.3 Hz, CH$_2$), 6.80 (1H, s, H-3), 7.57-7.70 (3H, m, H-3", H-4" and H-5"), 7.95 (2H, d, J=7.0 Hz, H-2" and H-6"), 8.15 (1H, s, H-6), 11.87 (1H, s, NH); $^{13}$C nmr (DMSO-d$_6$) (ppm): 3.1 (2×t), 13.3 (d), 14.2 (q), 20.8 (t), 27.3 (t), 48.6 (t), 59.9 (t), 115.5 (d), 117.1 (s), 124.0 (s), 125.0 (s), 127.2 (s), 127.9 (2×d), 129.0 (2×d), 130.3 (s), 133.4 (d), 138.0 (d), 140.7 (s), 150.8 (s), 157.8 (s), 160.4 (s). Anal calcd for $C_{24}H_{24}N_2O_5S$: C, 63.70; H, 5.35; N, 6.19. Found: C, 63.59; H, 5.23; N, 6.32.

Ethyl 7-(benzenesulfonyl)-1-[(6-methylpyridin-3-yl)methyl]-8-oxo-4,5,8,9-tetrahydro-1H-pyrrolo[3,2-h]quinoline-2-carboxylate (PP066). This compound was obtained by reaction of ethyl 6-[(dimethylamino)methylidene]-1-[(6-methylpyridin-3-yl)methyl]-7-oxo-4,5,6,7-tetrahydro-1H-indole-2-carboxylate with phenylsulfonyl acetonitrile after 24 h at reflux. The crude product was purified by chromatography. Light yellow solid; yield: 57%; m.p.: 290-291° C.; IR: 3393 (NH), 1700 (CO), 1692 (CO) cm$^{-1}$; $^1$H nmr (DMSO-d$_6$) (ppm): 1.23 (3H, t, J=7.1 Hz, CH$_3$), 2.34 (3H, s, CH$_3$), 2.71 (2H, t, J=7.4 Hz, CH$_2$), 2.91 (2H, t, J=7.4 Hz, CH$_2$), 4.19 (2H, q, J=7.1 Hz, CH$_2$), 6.37 (2H, s, CH$_2$), 6.89 (1H, s, H-3), 7.05-7.18 (2H, m, H-4' and H-5'), 7.57-7.74 (3H, m, H-3", H-4" and H-5"), 7.94 (2H, d, J=6.8 Hz, H-2" and H-6"), 8.12-8.15 (2H, m, H-6 and H-2'), 11.96 (1H, s, NH); $^{13}$C nmr (DMSO-d$_6$) (ppm): 14.1 (q), 20.8 (t), 23.5 (q), 27.1 (t), 46.1 (t), 60.0 (t), 116.0 (d), 122.5 (s), 122.7 (d), 125.5 (s), 126.3 (s), 127.9 (2×d), 128.4 (s), 129.0 (2×d), 131.9 (s), 133.4 (d), 134.2 (d), 138.1 (d), 139.5 (s), 140.2 (s), 143.1 (s), 147.1 (d), 156.4 (s), 159.1 (s), 162.7 (s). Anal calcd for $C_{27}H_{25}N_3O_5S$: C, 64.40; H, 5.00; N, 8.34. Found: C, 64.28; H, 5.19; N, 8.47.

Ethyl 7-(benzenesulfonyl)-8-oxo-1-[(2,4,6-trimethylphenyl)methyl]-4,5,8,9-tetrahydro-1H-pyrrolo[3,2-h]quinoline-2-carboxylate (PP068). This compound was obtained by reaction of ethyl 6-[(dimethylamino)methylidene]-7-oxo-1-[(2,4,6-trimethylphenyl)methyl]-4,5,6,7-tetrahydro-1H-indole-2-carboxylate with phenylsulfonyl acetonitrile after 24 h at reflux. The crude product was purified by chromatography. Brown solid; yield: 66%; m.p.: 156-157° C.; IR: 3405 (NH), 1703 (CO), 1641 (CO) cm$^{-1}$; $^1$H nmr (DMSO-d$_6$)

(ppm): 1.02 (3H, t, J=7.1 Hz, CH$_3$), 1.87 (6H, s, 2×CH$_3$), 2.12 (3H, s, CH$_3$), 2.72 (2H, t, J=5.7 Hz, CH$_2$), 2.86 (2H, t, J=5.7 Hz, CH$_2$), 3.96 (2H, q, J=7.1 Hz, CH$_2$), 6.27 (2H, s, CH$_2$), 6.66 (2H, s, H-3' and H-5'), 6.74 (1H, s, H-3), 7.57-7.69 (3H, m, H-3", H-4" and H-5"), 7.95 (2H, d, J=6.7 Hz, H-2" and H-6"), 8.18 (1H, s, H-6), 11.93 (1H, s, NH); $^{13}$C nmr (DMSO-d$_6$) (ppm): 13.9 (q), 19.2 (2×q), 20.2 (q), 20.9 (t), 27.3 (t), 46.2 (t), 60.6 (t), 115.0 (d), 121.5 (s), 126.7 (s), 126.1 (2×d), 128.0 (2×d), 129.6 (2×d), 133.8 (d), 134.6 (d), 134.8 (s), 135.8 (s), 137.7 (2×s), 140.6 (s), 140.9 (s), 141.6 (s), 145.1 (s), 155.6 (s), 157.7 (s), 160.0 (s). Anal calcd for C$_{30}$H$_{30}$N$_2$O$_5$S: C, 67.90; H, 5.70; N, 5.28. Found: C, 68.05; H, 5.59; N, 5.41.

Ethyl 7-(benzenesulfonyl)-8-oxo-1-{[4-(trifluoromethyl)phenyl]methyl}-4,5,8,9-tetrahydro-1H-pyrrolo[3,2-h]quinoline-2-carboxylate (PP070). This compound was obtained by reaction of ethyl 6-[(dimethylamino)methylidene]-7-oxo-1-{[4-(trifluoromethyl)phenyl]methyl}-4,5,6,7-tetrahydro-1H-indole-2-carboxylate with phenylsulfonyl acetonitrile after 24 h at reflux. The crude product was purified by chromatography. Brown solid; yield: 74%; m.p.: 109-110° C.; IR: 3377 (NH), 1701 (CO), 1685 (CO) cm$^{-1}$; $^1$H nmr (DMSO-d$_6$) (ppm): 1.19 (3H, t, J=7.0 Hz, CH$_3$), 2.74 (2H, t, J=6.9 Hz, CH$_2$), 2.93 (2H, t, J=6.9 Hz, CH$_2$), 4.15 (2H, q, J=7.0 Hz, CH$_2$), 6.49 (2H, s, CH$_2$), 6.92 (1H, s, H-3), 7.10 (2H, d, J=8.1 Hz, H-2' and H-6'), 7.57-7.70 (5H, m, H-3', H-5', H-3", H-4" and H-5"), 7.92 (2H, d, J=7.4 Hz, H-2" and H-6"), 8.14 (1H, s, H-6), 11.90 (1H, s, NH); $^{13}$C nmr (DMSO-d$_6$) (ppm): 14.5 (q), 21.3 (t), 27.6 (t), 48.9 (t), 60.5 (t), 116.6 (s), 117.9 (d), 122.9 (s), 125.6 (s), 125.7 (s), 125.8 (s), 126.5 (s), 127.0 (2×d), 127.1 (2×d), 127.6 (s), 128.0 (s), 128.4 (2×d), 129.5 (2×d), 131.1 (s), 133.8 (d), 138.6 (d), 142.9 (d, J$_{C-F}$=272.4 Hz), 158.4 (s), 160.5 (s). Anal calcd for C$_{28}$H$_{23}$F3N$_2$O$_5$S: C, 60.43; H, 4.17; N, 5.03. Found: C, 60.31; H, 4.25; N, 4.89.

Ethyl 7-(benzenesulfonyl)-1-[(4-fluorophenyl)methyl]-8-oxo-4,5,8,9-tetrahydro-1H-pyrrolo[3,2-h]quinoline-2-carboxylate (PP072). This compound was obtained by reaction of ethyl 6-[(dimethylamino)methylidene]-1-[(4-fluorophenyl)methyl]-7-oxo-4,5,6,7-tetrahydro-1H-indole-2-carboxylate with phenylsulfonyl acetonitrile after 24 h at reflux. The crude product was purified by chromatography. Dark yellow solid; yield: 54%; m.p.: 133-134° C.; IR: 3324 (NH), 1703 (CO), 1641 (CO) cm$^{-1}$; $^1$H nmr (DMSO-d$_6$) (ppm): 1.21 (3H, t, J=7.0 Hz, CH$_3$), 2.71 (2H, t, J=6.9 Hz, CH$_2$), 2.90 (2H, t, J=6.9 Hz, CH$_2$), 4.17 (2H, q, J=7.0 Hz, CH$_2$), 6.38 (2H, s, CH$_2$), 6.88 (1H, s, H-3), 6.96-7.05 (4H, m, H-2', H-3', H-5', and H-6'), 7.57-7.69 (3H, m, H-3", H-4" and H-5"), 7.93 (2H, d, J=7.3 Hz, H-2" and H-6"), 8.14 (1H, s, H-6), 11.92 (1H, s, NH); $^{13}$C nmr (DMSO-d$_6$) (ppm): 14.6 (q), 21.3 (t), 27.7 (t), 48.2 (t), 60.5 (t), 105.4 (s), 115.5 (2×d, J$_{C3'-F}$=21.4 Hz), 116.5 (d), 116.6 (s), 117.8 (s), 125.8 (s), 128.1 (s), 128.4 (2×d), 128.6 (2×d, J$_{C2'F}$=8.3 Hz), 128.7 (s), 129.5 (2×d), 133.9 (d), 136.0 (s), 138.5 (d), 141.2 (s), 158.4 (s), 159.9 (s), 161.8 (d, J$_{C4'-F}$=187.6 Hz). Anal calcd for C$_{27}$H$_{23}$FN$_2$O$_5$S: C, 64.02; H, 4.58; N, 5.53. Found: C, 63.91; H, 4.44; N, 5.67.

Ethyl 7-(benzenesulfonyl)-1-[3-(dimethylamino)propyl]-8-oxo-4,5,8,9-tetrahydro-1H-pyrrolo[3,2-h]quinoline-2-carboxylate (PP074). This compound was obtained by reaction of ethyl 6-[(dimethylamino)methylidene]-1-[3-(dimethylamino)propyl]-7-oxo-4,5,6,7-tetrahydro-1H-indole-2-carboxylate with phenylsulfonyl acetonitrile after 24 h at reflux. The crude product was purified by chromatography. Brown solid; yield: 51%; m.p.: 120-121° C.; IR: 3433 (NH), 1700 (CO), 1696 (CO) cm$^{-1}$; $^1$H nmr (DMSO-d$_6$) (ppm): 1.28 (3H, t, J=7.0 Hz, CH$_3$), 1.80-1.92 (2H, m, CH$_2$), 2.68-2.72 (10H, m, 2×CH$_3$ and 2×CH$_2$), 2.89-2.94 (2H, m, CH$_2$), 4.24 (2H, q, J=7.0 Hz, CH$_2$), 4.91-5.02 (2H, m, CH$_2$), 6.22 (1H, s, H-3), 7.57-7.72 (3H, m, H-3", H-4" and H-5"), 7.87 (2H, d, J=7.6 Hz, H-2" and H-6"), 8.21 (1H, s, H-6), 11.88 (1H, s, NH); $^{13}$C nmr (DMSO-d$_6$) (ppm): 14.7 (q), 21.3 (t), 28.0 (t), 43.4 (2×q), 44.5 (t), 56.0 (t), 60.4 (t), 63.2 (t), 115.9 (d), 123.3 (s), 125.4 (s), 126.8 (s), 127.4 (s), 127.7 (2×d), 129.4 (2×d), 131.2 (s), 133.8 (d), 139.3 (d), 141.8 (s), 150.5 (s), 159.0 (s), 160.7 (s). Anal calcd for C$_{25}$H$_{29}$N$_3$O$_5$S: C, 62.09; H, 6.04; N, 8.69. Found: C, 61.87; H, 6.21; N, 8.84.

Propan-2-yl 7-(benzenesulfonyl)-1-[(3-methylphenyl)methyl]-8-oxo-4,5,8,9-tetrahydro-1H-pyrrolo[3,2-h]quinoline-2-carboxylate (PP103). This compound was obtained by reaction of propan-2-yl 6-[(dimethylamino)methylidene]-1-[(3-methylphenyl)methyl]-7-oxo-4,5,6,7-tetrahydro-1H-indole-2-carboxylate with phenylsulfonyl acetonitrile after 24 h at reflux. The crude product was purified by chromatography. Dark yellow solid; yield: 57%; m.p.: 185-186° C.; IR: 3610 (NH), 1700 (CO), 1664 (CO) cm$^{-1}$; $^1$H nmr (DMSO-d$_6$) (ppm): 1.20 (6H, d, J=6.2 Hz, 2×CH$_3$), 2.14 (3H, s, CH$_3$), 2.70 (2H, t, J=7.3 Hz, CH$_2$), 2.89 (2H, t, J=7.3 Hz, CH$_2$), 4.95-5.06 (1H, m, CH), 6.38 (2H, s, CH$_2$), 6.59 (1H, d, J=7.0 Hz, Ar), 6.77 (1H, s, H-3), 6.85 (1H, s, H-2'), 6.92 (1H, d, J=7.2 Hz, Ar), 7.05 (1H, t, J=7.5 Hz, H-5'), 7.56-7.78 (3H, m, H-3", H-4" and H-5"), 7.93 (2H, d, J=7.4 Hz, H-2" and H-6"), 8.13 (1H, s, H-6), 11.90 (1H, s, NH); $^{13}$C nmr (DMSO-d$_6$) (ppm): 21.3 (t), 21.5 (q), 22.0 (2×q), 27.7 (t), 48.8 (t), 65.4 (d), 116.4 (d), 123.3 (s), 126.3 (d), 126.5 (s), 127.2 (d), 127.8 (d), 128.0 (d), 128.3 (2×d), 128.7 (s), 129.1 (s), 129.2 (s), 129.4 (s), 129.5 (2×d), 130.1 (s), 133.9 (d), 137.6 (d), 139.9 (s), 141.2 (s), 158.4 (s), 160.2 (s). Anal calcd for C$_{29}$H$_{28}$N$_2$O$_5$S: C, 67.42; H, 5.46; N, 5.42. Found: C, 67.60; H, 5.34; N, 5.53.

Propan-2-yl 7-(benzenesulfonyl)-1-(cyclopropylmethyl)-8-oxo-4,5,8,9-tetrahydro-1H-pyrrolo[3,2-h]quinoline-2-carboxylate (PP105). This compound was obtained by reaction of propan-2-yl 1-(cyclopropylmethyl)-6-[(dimethylamino)methylidene]-7-oxo-4,5,6,7-tetrahydro-1H-indole-2-carboxylate with phenylsulfonyl acetonitrile after 24 h at reflux. The crude product was purified by chromatography. Yellow solid; yield: 710%; m.p.: 204-205° C.; IR: 3359 (NH), 1709 (CO), 1635 (CO) cm$^{-1}$; $^1$H nmr (DMSO-d$_6$) (ppm): 0.23-0.28 (4H, m, 2×CH$_2$), 1.06-1.17 (1H, m, CH), 1.28 (6H, d, J=6.2 Hz, 2×CH$_3$), 2.67 (2H, t, J=7.4 Hz, CH$_2$), 2.90 (2H, t, J=7.4 Hz, CH$_2$), 5.02-5.11 (3H, m, CH$_2$ and CH), 6.77 (1H, s, H-3), 7.59-7.72 (3H, m, H-3", H-4" and H-5"), 7.96 (2H, d, J=7.6 Hz, H-2" and H-6"), 8.15 (1H, s, H-6), 11.85 (1H, s, NH); $^{13}$C nmr (DMSO-d$_6$) (ppm): 3.5 (2×t), 13.4 (d), 21.3 (t), 22.1 (2×q), 27.8 (t), 49.1 (t), 67.7 (d), 110.8 (s), 116.0 (d), 125.9 (s), 127.7 (s), 128.4 (2×d), 129.5 (2×d), 130.7 (s), 130.8 (s), 133.9 (d), 138.4 (d), 141.3 (s), 157.8 (s), 158.4 (s), 160.4 (s). Anal calcd for C$_{25}$H$_{26}$N$_2$O$_5$S: C, 64.36; H, 5.62; N, 6.00. Found: C, 64.23; H, 5.77; N, 5.93.

Propan-2-yl 7-(benzenesulfonyl)-1-[(4-fluorophenyl)methyl]-8-oxo-4,5,8,9-tetrahydro-1H-pyrrolo[3,2-h]quinoline-2-carboxylate (PP107). This compound was obtained by reaction of propan-2-yl 6-[(dimethylamino)methylidene]-1-[(4-fluorophenyl)methyl]-7-oxo-4,5,6,7-tetrahydro-1H-indole-2-carboxylate with phenylsulfonyl acetonitrile after 24 h at reflux. The crude product was purified by chromatography. Dark yellow solid; yield: 65%; m.p.: 121-122° C.; IR: 3319 (NH), 1705 (CO), 1697 (CO) cm$^{-1}$; $^1$H nmr (DMSO-d$_6$) (ppm): 1.20 (6H, d, J=6.1 Hz, 2×CH$_3$), 2.70 (2H, t, J=7.1 Hz, CH$_2$), 2.90 (2H, t, J=7.1 Hz, CH$_2$), 4.94-5.06 (1H, m, CH), 6.39 (2H, s, CH$_2$), 6.85 (1H, s, H-3), 6.95-7.06 (4H, m, H-2', H-3', H-5', and H-6'), 7.57-7.70 (3H, m, H-3", H-4" and H-5"), 7.95 (2H, d, J=7.6

Hz, H-2" and H-6"), 8.14 (1H, s, H-6), 11.92 (1H, s, NH); $^{13}$C nmr (DMSO-d$_6$) (ppm): 21.3 (t), 22.0 (2×q), 27.7 (t), 48.2 (t), 67.9 (d), 115.5 (2×d, $J_{C3'-F}$=21.4 Hz), 116.5 (d), 117.8 (s), 124.5 (s), 126.3 (s), 128.0 (s), 128.4 (2×d), 128.5 (2×d, $J_{C2'-F}$=8.1 Hz), 129.5 (2×d), 130.9 (s), 133.9 (d), 136.1 (s), 138.5 (d), 141.2 (s), 158.4 (s), 160.0 (s), 161.0 (s), 161.6 (d, $J_{C4-F}$=220.0 Hz). Anal calcd for $C_{28}H_{25}FN_2O_5S$: C, 64.60; H, 4.84; N, 5.38. Found: C, 64.77; H, 4.69; N, 5.24.

7-(Benzenesulfonyl)-1-[(3-methylphenyl)methyl]-8-oxo-N-(propan-2-yl)-4,5,8,9-tetrahydro-1H-pyrrolo[3,2-h]quinoline-2-carboxamide (PP083). This compound was obtained by reaction of 6-[(dimethylamino)methylidene]-1-[(3-methylphenyl)methyl]-7-oxo-N-(propan-2-yl)-4,5,6,7-tetrahydro-1H-indole-2-carboxamide with phenylsulfonyl acetonitrile after 24 h at reflux. The crude product was purified by chromatography. Dark yellow solid; yield: 53%; m.p.: 214-215° C.; IR: 3399 (NH), 3233 (NH), 1697 (CO), 1664 (CO) cm$^{-1}$; $^1$H nmr (DMSO-d$_6$) (ppm): 1.08 (6H, d, J=6.5 Hz, 2×CH$_3$), 2.13 (3H, s, CH$_3$), 2.50-2.52 (2H, m, CH$_2$), 2.64-2.69 (2H, m, CH$_2$), 3.89-4.06 (1H, m, CH), 6.34 (2H, s, CH$_2$), 6.64-7.07 (4H, m, H-2', H-4', H-5' and H-6'), 7.57-7.69 (3H, m, H-3", H-4" and H-5"), 7.93 (2H, d, J=6.7 Hz H-2" and H-6"), 8.11 (1H, s, H-6), 11.80 (1H, s, NH); $^{13}$C nmr (DMSO-d$_6$) (ppm): 21.2 (q), 22.6 (2×q), 24.6 (t), 27.0 (t), 42.9 (d), 48.9 (t), 111.0 (d), 122.9 (s), 125.4 (d), 127.5 (s), 127.9 (d), 128.1 (d), 128.2 (d), 128.6 (2×d), 129.0 (2×d), 131.8 (s), 133.6 (d), 134.1 (s), 137.9 (d), 138.4 (s), 138.9 (s), 140.2 (s), 142.9 (s), 149.2 (s), 158.4 (s), 160.7 (s). Anal calcd for $C_{29}H_{29}N_3O_4S$: C, 67.55; H, 5.67; N, 8.15. Found: C, 67.77; H, 5.81; N, 8.02.

7-(Benzenesulfonyl)-N-cyclopropyl-1-[(3-methylphenyl)methyl]-8-oxo-4,5,8,9-tetrahydro-1H-pyrrolo[3,2-h]quinoline-2-carboxamide (PP084). This compound was obtained by reaction of N-cyclopropyl-6-[(dimethylamino)methylidene]-1-[(3-methylphenyl)methyl]-7-oxo-4,5,6,7-tetrahydro-1H-indole-2-carboxamide with phenylsulfonyl acetonitrile after 24 h at reflux. The crude product was purified by chromatography. Brown solid; yield: 50%; m.p.: 104-105° C.; IR: 3374 (NH), 3251 (NH), 1695 (CO), 1667 (CO) cm$^{-1}$; $^1$H nmr (DMSO-d$_6$) (ppm): 0.47-0.66 (4H, m, 2×CH$_2$), 2.13 (3H, s, CH$_3$), 2.51-2.58 (2H, m, CH$_2$), 2.66-2.85 (3H, m, CH and CH$_2$), 6.36 (2H, s, CH$_2$), 6.64 (1H, s, H-3), 6.68-7.08 (4H, m, H-2', H-4', H-5' and H-6'), 7.61-7.79 (3H, m, H-3", H-4" and H-5"), 7.86-7.94 (2H, m, H-2" and H-6"), 8.07 (1H, s, H-6), 8.44 (1H, d, J=4.2 Hz, NH), 11.81 (1H, s, NH); $^{13}$C nmr (DMSO-d$_6$) (ppm): 6.2 (2×t), 21.5 (q), 21.6 (t), 23.0 (t), 27.8 (t), 48.2 (t), 113.5 (s), 119.5 (s), 111.8 (d), 123.8 (d), 124.6 (s), 127.6 (d), 127.7 (d), 128.0 (s), 128.2 (2×d), 128.4 (d), 129.4 (2×d), 131.2 (s), 133.8 (d), 134.3 (d), 137.5 (s), 140.3 (s), 141.3 (s), 146.6 (s), 158.4 (s), 162.9 (s). Anal calcd for $C_{29}H_{27}N_3O_4S$: C, 67.82; H, 5.30; N, 8.18. Found: 67.98; H, 5.17; N, 8.05.

7-(Benzenesulfonyl)-1-[(4-methylphenyl)methyl]-8-oxo-N-(propan-2-yl)-4,5,8,9-tetrahydro-1H-pyrrolo[3,2-h]quinoline-2-carboxamide (PP085). This compound was obtained by reaction of 6-[(dimethylamino)methylidene]-1-[(4-methylphenyl)methyl]-7-oxo-N-(propan-2-yl)-4,5,6,7-tetrahydro-1H-indole-2-carboxamide with phenylsulfonyl acetonitrile after 24 h at reflux. The crude product was purified by chromatography. Dark yellow solid; yield: 61%; m.p.: 152-153° C.; IR: 3417 (NH), 3359 (NH), 1663 (CO), 1641 (CO) cm$^{-1}$; $^1$H nmr (DMSO-d$_6$) (ppm): 1.08 (6H, d, J=6.5 Hz, 2×CH$_3$), 2.65 (2H, t, J=6.8 Hz, CH$_2$), 2.81 (2H, t, J=6.8 Hz, CH$_2$), 3.89-4.05 (1H, m, CH), 6.32 (2H, s, CH$_2$), 6.65 (1H, s, H-3), 6.85 (2H, d, J=8.0 Hz, H-3' and H-5'), 6.96 (2H, d, J=8.0 Hz, H-2' and H-6'), 7.57-7.69 (3H, m, H-3", H-4" and H-5"), 7.93 (2H, d, J=6.8 Hz, H-2" and H-6"), 8.05-8.08 (2H, m, H-6 and NH), 11.79 (1H, s, NH); $^{13}$C nmr (DMSO-d$_6$) (ppm): 21.1 (q), 22.8 (2×q), 23.9 (t), 26.2 (t), 42.8 (d), 48.6 (t), 111.2 (d), 122.4 (s), 127.5 (s), 128.5 (2×d), 128.8 (2×d), 129.2 (2×d), 129.6 (2×d), 131.8 (s), 133.4 (s), 133.9 (d), 134.3 (s), 136.5 (s), 138.2 (d), 139.6 (s), 142.9 (s), 148.7 (s), 158.3 (s), 162.4 (s). Anal calcd for $C_{29}H_{29}N_3O_4S$: C, 67.55; H, 5.67; N, 8.15. Found: C, 67.76; H, 5.43; N, 8.01.

7-(Benzenesulfonyl)-N-cyclopropyl-1-[(4-methylphenyl)methyl]-8-oxo-4,5,8,9-tetrahydro-1H-pyrrolo[3,2-h]quinoline-2-carboxamide (PP087). This compound was obtained by reaction of N-cyclopropyl-6-[(dimethylamino)methylidene]-1-[(4-methylphenyl)methyl]-7-oxo-4,5,6,7-tetrahydro-1H-indole-2-carboxamide with phenylsulfonyl acetonitrile after 24 h at reflux. The crude product was purified by chromatography. Light yellow solid; yield: 64%; m.p.: 241-242° C.; IR: 3426 (NH), 3336 (NH), 1653 (CO), 1635 (CO) cm$^{-1}$; $^1$H nmr (DMSO-d$_6$) (ppm): 0.48-0.69 (4H, m, 2×CH$_2$), 2.16 (3H, s, CH$_3$), 2.65-2.89 (4H, m, 2×CH$_2$), 3.33-3.45 (1H, m, CH), 6.34 (2H, s, CH$_2$), 6.64 (1H, s, H-3), 6.83 (2H, d, J=7.9 Hz, H-3' and H-5'), 6.97 (2H, d, J=7.9 Hz, H-2' and H-6'), 7.60-7.69 (3H, m, H-3", H-4" and H-5"), 7.93 (2H, d, J=7.4 Hz, H-2" and H-6"), 8.06 (1H, s, H-6), 8.26 (1H, d, J=3.8 Hz, NH), 11.79 (1H, s, NH); $^{13}$C nmr (DMSO-d$_6$) (ppm): 6.22 (2×t), 21.0 (q), 21.6 (t), 23.1 (d), 27.8 (t), 48.0 (t), 111.8 (d), 116.5 (s), 123.5 (s), 126.9 (2×d), 128.0 (s), 128.3 (2×d), 128.8 (s), 129.2 (2×d), 129.5 (2×d), 131.2 (s), 133.8 (d), 136.2 (s), 137.4 (s), 138.0 (d), 141.4 (s), 151.6 (s), 158.4 (s), 162.9 (s). Anal calcd for $C_{29}H_{27}N_3O_4S$: C, 67.82; H, 5.30; N, 8.18. Found: C, 67.69; H, 5.47; N, 7.92.

7-(Benzenesulfonyl)-1-[(4-bromophenyl)methyl]-8-oxo-N-(propan-2-yl)-4,5,8,9-tetrahydro-1H-pyrrolo[3,2-h]quinoline-2-carboxamide (PP096). This compound was obtained by reaction of 1-[(4-bromophenyl)methyl]-6-[(dimethylamino)methylidene]-7-oxo-N-(propan-2-yl)-4,5,6,7-tetrahydro-1H-indole-2-carboxamide with phenylsulfonyl acetonitrile after 24 h at reflux. The crude product was purified by chromatography. Light yellow solid; yield: 75%; m.p.: 296-297° C.; IR: 3353 (NH), 3250 (NH), 1652 (CO), 1635 (CO) cm$^{-1}$; $^1$H nmr (DMSO-d$_6$) (ppm): 1.07 (6H, d, J=6.5 Hz, 2×CH$_3$), 2.68 (2H, t, J=7.0 Hz, CH$_2$), 2.87 (2H, t, J=7.0 Hz, CH$_2$), 3.92-4.04 (1H, m, CH), 6.34 (2H, s, CH$_2$), 6.71 (1H, s, H-3), 6.92 (2H, d, J=8.3 Hz, H-2' and H-6'), 7.38 (2H, d, J=8.3 Hz, H-3' and H-5'), 7.56-7.69 (3H, m, H-3", H-4" and H-5'), 7.93 (2H, d, J=6.7 Hz, H-2" and H-6"), 8.05-8.08 (2H, m, H-6 and NH), 11.80 (1H, s, NH); $^{13}$C nmr (DMSO-d$_6$) (ppm): 21.1 (t), 22.2 (2×q), 27.3 (t), 40.4 (d), 47.4 (t), 111.3 (d), 116.1 (s), 119.7 (s), 123.1 (s), 127.5 (s), 127.8 (2×d), 127.9 (s), 128.8 (2×d), 129.0 (2×d), 130.8 (2×d), 131.0 (s), 133.3 (d), 137.6 (d), 139.3 (s), 140.8 (s), 151.0 (s), 157.9 (s), 160.2 (s). Anal calcd for $C_{28}H_{26}BrN_3O_4S$: C, 57.93; H, 4.51; N, 7.24. Found: C, 58.05; H, 4.77; N, 7.09.

7-(Benzenesulfonyl)-1-[(4-bromophenyl)methyl]-N-cyclopropyl-8-oxo-4,5,8,9-tetrahydro-1H-pyrrolo[3,2-h]quinoline-2-carboxamide (PP098). This compound was obtained by reaction of 1-[(4-bromophenyl)methyl]-N-cyclopropyl-6-[(dimethylamino)methylidene]-7-oxo-4,5,6,7-tetrahydro-1H-indole-2-carboxamide with phenylsulfonyl acetonitrile after 24 h at reflux. The crude product was purified by chromatography. Light yellow solid; yield: 73%; m.p.: 281-282° C.; IR: 3342 (NH), 3096 (NH), 1641 (CO), 1633 (CO) cm$^{-1}$; $^1$H nmr (DMSO-d$_6$) (ppm): 0.47-0.68 (4H, m, 2×CH$_2$), 2.67-2.72 (3H, m, CH$_2$ e CH), 2.83 (2H, t, J=7.0 Hz, CH$_2$), 6.35 (2H, s, CH$_2$), 6.69 (1H, s, H-3), 6.90 (2H, d, J=8.2 Hz, H-2' and H-6'), 7.38 (2H, d, J=8.2 Hz, H-3' and H-5'), 7.56-7.72 (3H, m, H-3", H-4" and H-5"), 7.93 (2H, d, J=7.1 Hz, H-2" and H-6"), 8.07 (1H, s, H-6), 8.27 (1H, d, J=3.9 Hz, NH), 11.81 (1H, s, NH); $^{13}$C nmr (DMSO-d$_6$) (ppm): 5.73 (2xt), 21.1 (t), 22.5 (d), 27.3 (t), 47.5 (t), 111.9 (d), 120.2 (s), 121.6 (s), 127.8 (2xd), 128.2 (s), 128.7 (2xd), 129.5 (s), 129.9 (2xd), 131.0 (2xd), 131.7 (s), 133.3 (d), 137.6 (d), 139.8 (s), 139.9 (s), 141.3 (s), 153.2 (s), 158.4 (s), 162.6 (s). Anal calcd for $C_{28}H_{24}BrN_3O_4S$: C, 58.14; H, 4.18; N, 7.26. Found: C, 57.95; H, 4.03; N, 7.41.

Ethyl 7-(benzenesulfonyl)-3-chloro-1-[(4-methylphenyl)methyl]-8-oxo-4,5,8,9-tetrahydro-1H-pyrrolo[3,2-h]quinoline-2-carboxylate (PP076). This compound was obtained by reaction of ethyl 3-chloro-6-[(dimethylamino)methylidene]-1-[(4-methylphenyl)methyl]-7-oxo-4,5,6,7-tetrahydro-1H-indole-2-carboxylate with phenylsulfonyl acetonitrile after 24 h at reflux. The crude product was purified by chromatography. Dark yellow solid; yield: 50%; m.p.: 127-128° C.; IR: 3377 (NH), 1699 (CO), 1696 (CO) cm$^{-1}$; $^1$H nmr (DMSO-d$_6$) (ppm): 1.22 (3H, t, J=7.0 Hz, CH$_3$), 2.18 (3H, s, CH$_3$), 2.68 (2H, t, J=7.5 Hz, CH$_2$), 2.96 (2H, t, J=7.5 Hz, CH$_2$), 4.22 (2H, q, J=7.0 Hz, CH$_2$), 6.36 (2H, s, CH$_2$), 6.79 (2H, d, J=7.8 Hz, H-3' and H-5'), 7.02 (2H, d, J=7.8 Hz, H-2' and H-6'), 7.57-7.70 (5H, m, H-3", H-4" and H-5"), 7.94 (2H, d, J=7.4 Hz, H-2" and H-6"), 8.20 (1H, s, H-6), 12.06 (1H, s, NH); $^{13}$C nmr (DMSO-d$_6$) (ppm): 14.7 (q), 21.1 (q), 25.5 (t), 27.0 (t), 54.3 (t), 61.5 (t), 119.2 (s), 122.4 (s), 123.6 (s), 128.6 (s), 128.6 (2xd), 129.1 (2xd), 127.6 (s), 128.0 (s), 129.2 (2xd), 129.6 (2xd), 133.3 (s), 133.8 (d), 136.7 (s), 139.8 (s), 143.2 (d), 143.5 (s), 158.2 (s), 160.2 (s). Anal calcd for $C_{28}H_{25}ClN_2O_5S$: C, 62.62; H, 4.69; N, 5.22. Found: C, 62.79; H, 4.53; N, 5.09.

Ethyl 7-(benzenesulfonyl)-3-iodo-1-[(4-methylphenyl)methyl]-8-oxo-4,5,8,9-tetrahydro-1H-pyrrolo[3,2-h]quinoline-2-carboxylate (PP077). This compound was obtained by reaction of ethyl 6-[(dimethylamino)methylidene]-3-iodo-1-[(4-methylphenyl)methyl]-7-oxo-4,5,6,7-tetrahydro-1H-indole-2-carboxylate with phenylsulfonyl acetonitrile after 24 h at reflux. The crude product was purified by chromatography. Yellow solid; yield: 61%; m.p.: 121-122° C.; IR: 3302 (NH), 1703 (CO), 1641 (CO) cm$^{-1}$; $^1$H nmr (DMSO-d$_6$) (ppm): 1.25 (3H, t, J=7.1 Hz, CH$_3$), 2.17 (3H, s, CH$_3$), 2.60 (2H, t, J=6.7 Hz, CH$_2$), 2.93 (2H, t, J=6.7 Hz, CH$_2$), 4.21 (2H, q, J=7.1 Hz, CH$_2$), 6.36 (2H, s, CH$_2$), 6.77 (2H, d, J=6.0 Hz, H-3' and H-5'), 6.99 (2H, d, J=6.0 Hz, H-2' and H-6'), 7.60-7.76 (3H, m, H-3", H-4" and H-5"), 7.92-8.17 (3H, m, H-6, H-2" and H-6"), 12.01 (1H, s, NH); $^{13}$C nmr (DMSO-d$_6$) (ppm): 13.9 (q), 20.5 (q), 22.9 (t), 26.7 (t), 49.2 (t), 60.6 (t), 75.1 (s), 104.3 (s), 117.5 (s), 125.9 (2xd), 127.9 (2xd), 128.9 (2xd), 129.0 (2xd), 130.5 (s), 132.5 (s), 136.0 (s), 136.1 (s), 133.5 (d), 137.2 (s), 137.8 (s), 138.3 (s), 140.5 (s), 157.9 (s), 159.8 (s). Anal calcd for $C_{28}H_{25}IN_2O_5S$: C, 53.51; H, 4.01; N, 4.46. Found: C, 53.69; H, 3.85; N, 4.61.

General Procedure for the Synthesis of Compounds of Type 10.

To a solution of the suitable tricyclic derivatives of type 9 (15 mmol) in anhydrous DMF (20 mL), NaH (0.64 g, 16 mmol) was added at 0° C., and the reaction mixture was stirred at room temperature for 3 h. Then iodomethane (16 mmol) was added at 0° C. and the reaction mixture was stirred at room temperature for 24 h. Then the reaction mixture was poured onto crushed ice and the precipitate was filtered off and dried, in absence the solution was extracted with DCM (3×30 mL). The organic layer was dried over Na$_2$SO$_4$ and the solvent was removed under reduced pressure. The crude product, containing N-methyl (10) and O-methyl derivatives (11), was purified by chromatography (DCM) allowing the isolation of N-methyl derivatives and O-methyl derivatives as pure products.

Ethyl 7-(benzenesulfonyl)-8-methoxy-1-[(4-methylphenyl)methyl]-4,5-dihydro-1H-pyrrolo[3,2-h]quinoline-2-carboxylate (PP014). This product was obtained by reaction of PP007. Yellow solid; yield: 56%; m.p.: 114-115° C.; IR: 1704 (CO)cm$^{-1}$; $^1$H nmr (CDCl$_3$) (ppm): 1.26 (3H, t, J=7.1 Hz, CH$_3$), 2.25 (3H, s, CH$_3$), 2.76-2.83 (2H, m, CH$_2$), 2.92-2.99 (2H, m, CH$_2$), 3.52 (3H, s, CH$_3$), 4.20 (2H, q, J=7.1 Hz, CH$_2$), 6.29 (2H, s, CH$_2$), 6.81 (2H, d, J=7.9 Hz, H-3" and H-5"), 6.90 (1H, s, H-3), 6.99 (2H, d, J=7.9 Hz, H-2" and H-6"), 7.48-7.58 (3H, m, H-3', H-4' and H-5'), 7.95-8.00 (2H, m, H-2' and H-6'), 8.16 (1H, s, H-6); $^{13}$C nmr (CDCl$_3$) (ppm): 14.3 (q), 21.0 (q), 21.6 (t), 28.2 (t), 49.5 (t), 54.1 (q), 60.2 (t), 115.8 (d), 119.2 (s), 124.9 (s), 125.5 (2xd), 126.1 (s), 127.2 (s), 128.5 (2xd), 128.6 (2xd), 129.0 (2xd), 131.6 (s), 133.1 (d), 136.1 (s), 136.4 (s), 138.1 (d), 140.8 (s), 150.6 (s), 158.2 (s), 160.6 (s). Anal calcd for $C_{29}H_{28}N_2O_5S$: C, 67.42; H, 5.46; N, 5.42. Found: C, 67.27; H, 5.31; N, 5.65.

Ethyl 8-(benzenesulfonyl)-9-methoxy-1-[(4-methylphenyl)methyl]-1,4,5,6-tetrahydropyrrolo[3',2':6,7]cyclohepta[1,2-b]pyridine-2-carboxylate (PP055). This product was obtained by reaction of PP048. Yellow solid; yield: 50%; m.p.: 121-122° C.; IR: 1703 (CO)cm$^{-1}$; $^1$H nmr (CDCl$_3$) (ppm): 1.27 (3H, t, J=7.1 Hz, CH$_3$), 2.18-2.28 (5H, m, CH$_2$ and CH$_3$), 2.44-2.56 (4H, m, 2×CH$_2$), 3.58 (3H, s, CH$_3$), 4.20 (2H, q, J=7.1 Hz, CH$_2$), 5.95 (2H, s, CH$_2$), 6.69 (2H, d, J=8.0 Hz, H-3" and H-5"), 6.92-6.96 (3H, m, H-2", H-6" and H-3), 7.45-7.60 (3H, m, H-3', H-4' and H-5'), 7.97-8.11 (2H, m, H-2' and H-6'), 8.25 (1H, s, H-7); $^{13}$C nmr (CDCl$_3$) (ppm): 14.3 (q), 21.0 (q), 23.1 (t), 30.9 (t), 32.7 (t), 47.9 (t), 54.4 (q), 60.4 (t), 117.6 (d), 125.3 (2xd), 125.7 (s), 127.8 (s), 128.2 (s), 128.5 (2xd), 129.0 (2xd), 129.4 (2xd), 132.1 (s), 134.0 (d), 135.3 (s), 136.6 (s), 138.1 (s), 141.1 (s), 142.1 (d), 145.5 (s), 153.9 (s), 160.7 (s). Anal calcd for $C_{30}H_{30}N_2O_5S$: C, 67.90; H, 5.70; N, 5.28. Found: C, 68.03; H, 5.58; N, 5.11.

General Procedure for the Synthesis of Compounds of Type 12 (R$^2$=Br)

To a solution of suitable tricyclic compounds of type 9 (0.22 mmol) in anhydrous DCM (20 mL), Br$_2$ (0.44 mmol, 0.02 mL) was added at 0° C. and the reaction mixture was stirred at room temperature for 24 h. Then the reaction mixture was evaporated under reduced pressure. The crude was purified by chromatography (DCM).

Ethyl 7-(benzenesulfonyl)-3-bromo-1-[(4-methylphenyl)methyl]-8-oxo-4,5,8,9-tetrahydro-1H-pyrrolo[3,2-h]quinoline-2-carboxylate (PP008). This product was obtained by reaction of PP007. Yellow solid; yield: 65%; m.p.: 126-127° C.; IR: 3318 (NH), 1709 (CO), 1692 (CO) cm$^{-1}$; $^1$H nmr (DMSO-d$_6$) (ppm): 1.23 (3H, t, J=6.8 Hz, CH$_3$), 2.17 (3H, s, CH$_3$), 2.65 (2H, t, J=6.4 Hz, CH$_2$), 2.96 (2H, t, J=6.4 Hz, CH$_2$), 4.21 (2H, q, J=6.8 Hz, CH$_2$), 6.37 (2H, s, CH$_2$), 6.79 (2H, d, J=7.4 Hz, H-3' and H-5'), 7.00 (2H, d, J=7.4 Hz, H-2' and H-6'), 7.60-7.69 (3H, m, H-3", H-4" and H-5"), 7.94 (2H, d, J=6.7 Hz, H-2" and H-6"), 8.19 (1H, s, H-4), 12.05 (1H, s, NH); $^{13}$C nmr (DMSO-d$_6$) (ppm): 13.9 (q), 18.5 (q), 20.5 (t), 26.5 (t), 49.0 (t), 60.6 (t), 103.8 (s), 118.0 (s), 123.4 (s), 124.3 (s), 126.0 (2xd), 127.9 (2xd), 128.9 (2xd), 129.0 (2xd), 130.0 (s), 133.5 (d), 135.9 (s), 136.0 (s), 138.5 (d), 140.4 (s), 149.8 (s), 157.8 (s), 159.5 (s), 159.9 (s). Anal calcd for $C_{28}H_{25}BrN_2O_5S$: C, 57.84; H, 4.33; N, 4.82. Found: C, 58.05; H, 4.24; N, 4.99.

Ethyl 8-(benzenesulfonyl)-3-bromo-1-[(4-methylphenyl)methyl]-9-oxo-1,4,5,6,9,10-hexahydropyrrolo[3',2':6,7]cyclohepta[1,2-b]pyridine-2-carboxylate (PP056). This product was obtained by reaction of PP048. Light brown solid; yield: 52%; m.p.: 124-125° C.; IR: 3377 (NH), 1708 (CO), 1701 (CO) cm$^{-1}$; $^1$H nmr (CDCl$_3$) (ppm): 1.27 (3H, t, J=8.0 Hz, CH$_3$), 2.23 (3H, s, CH$_3$), 2.24-2.52 (6H, m, 3×CH$_2$), 4.30 (2H, q, J=8.0 Hz, CH$_2$), 5.79 (2H, s, CH$_2$), 6.63 (2H, d, J=8.0 Hz, H-3" and H-5"), 6.93 (2H, d, J=8.0 Hz, H-2' and H-6'), 7.26-7.34 (3H, m, Ar), 7.95 (2H, d, J=8.0 Hz, H-2" and H-6") 8.32 (1H, s, H-6), 13.13 (1H, s, NH); $^{13}$C nmr (CDCl$_3$) (ppm): 14.1 (q), 21.1 (q), 29.1 (t), 32.8 (t), 51.1 (t), 61.4 (t), 106.7 (s), 120.6 (s), 124.7 (s), 125.8 (2×d), 127.3 (s), 127.9 (s), 128.4 (2×d), 129.1 (2×d), 129.3 (2×d), 133.5 (d), 134.8 (s), 137.3 (s), 139.4 (s), 142.9 (s), 145.8 (d), 159.4 (s), 159.8 (s), 160.2 (s). Anal calcd for C$_{29}$H$_{27}$BrN$_2$O$_5$S: C, 58.49; H, 4.57; N, 4.70. Found: 58.57; H, 4.69; N, 4.45.

Ethyl 3-bromo 1-(2-methylbenzyl)-8-oxo-7-(phenylsulfonyl)-4,5,8,9-tetrahydro-1H-pyrrolo[3,2-h]quinoline-2-carboxylate (PP027). This product was obtained by reaction of PP015. Yellow solid; yield: 52%; m.p.: 122-123° C.; IR: 3399 (NH), 1700 (CO), 1641 (CO) cm$^{-1}$; $^1$H nmr (DMSO-d$_6$) (ppm): 1.23 (3H, t, J=7.0 Hz, CH$_3$), 2.17 (3H, s, CH$_3$), 2.65 (2H, t, J=7.1 Hz, CH$_2$), 2.96 (2H, t, J=7.1 Hz, CH$_2$), 4.21 (2H, q, J=7.0 Hz, CH$_2$), 6.37 (2H, s, CH$_2$), 6.78 (2H, d, J=7.9 Hz, Ar), 7.00 (2H, d, J=7.9 Hz, Ar), 7.57-7.70 (3H, m, H-3", H-4" and H-5"), 7.94 (2H, d, J=6.9 Hz, H-2" and H-6"), 8.19 (1H, s, H-4), 12.04 (1H, s, NH); $^{13}$C nmr (DMSO-d$_6$) (ppm): 13.9 (q), 20.1 (q), 20.5 (t), 26.5 (t), 49.0 (t), 54.9 (t), 103.7 (s), 118.0 (s), 123.6 (s), 126.0 (2×d), 127.9 (2×d), 128.9 (2×d), 129.0 (2×d), 129.6 (d), 129.8 (s), 133.5 (d), 135.9 (s), 136.0 (s), 138.5 (s), 140.5 (s), 157.8 (s), 159.5 (s), 163.6 (s), 164.7 (s). Anal calcd for C$_{28}$H$_{25}$BrN$_2$O$_5$S: C, 57.84; H, 4.33; N, 4.82. Found: C, 57.98; H, 4.24; N, 4.68.

Ethyl 3-bromo 1-(3-methylbenzyl)-8-oxo-7-(phenylsulfonyl)-4,5,8,9-tetrahydro-1H-pyrrolo[3,2-h]quinoline-2-carboxylate (PP028). This product was obtained by reaction of PP016. Yellow solid; yield: 55%; m.p.: 150-151° C.; IR: 3313 (NH), 1704 (CO), 1669 (CO) cm$^{-1}$; $^1$H nmr (CDCl$_3$) (ppm): 1.31 (3H, t, J=7.1 Hz, CH$_3$), 2.27 (3H, s, CH$_3$), 2.70-2.86 (4H, m, 2×CH$_2$), 4.29 (2H, q, J=7.1 Hz, CH$_2$), 6.08 (2H, s, CH$_2$), 6.77-6.86 (2H, m, Ar), 7.03 (1H, d, J=7.6 Hz, Ar), 7.13-7.22 (1H, m, Ar), 7.46-7.64 (3H, m, H-4" and H-5"), 7.98-8.11 (3H, m, H-2", H-6" and H-4), 8.82 (1H, s, NH); $^{13}$C nmr (CDCl$_3$) (ppm): 14.1 (q), 20.7 (q), 21.5 (t), 27.2 (t), 50.6 (t), 61.2 (t), 104.6 (s), 118.0 (s), 120.2 (s), 121.4 (s), 122.9 (d), 125.1 (s), 126.7 (d), 128.1 (2×d), 128.5 (d), 128.7 (s), 128.9 (d), 129.1 (2×d), 129.4 (s), 133.6 (d), 135.7 (s), 137.5 (s), 138.7 (s), 140.5 (d), 157.2 (s), 160.0 (s). Anal calcd for C$_{27}$H$_{23}$BrN$_2$O$_5$S: C, 57.15; H, 4.09; N, 4.94. Found: C, 57.01; H, 4.27; N, 5.06.

Ethyl 3-bromo 1-(4-chlorobenzyl)-8-oxo-7-(phenylsulfonyl)-4,5,8,9-tetrahydro-1H-pyrrolo[3,2-h]quinoline-2-carboxylate (PP029). This product was obtained by reaction of PP017. Yellow solid; yield: 58%; m.p.: 106-107° C.; IR: 3342 (NH), 1701 (CO), 1694 (CO) cm$^{-1}$; $^1$H nmr (DMSO-d$_6$) (ppm): 1.22 (3H, t, J=7.1 Hz, CH$_3$), 2.67 (2H, t, J=7.5 Hz, CH$_2$), 2.97 (2H, t, J=7.5 Hz, CH$_2$), 4.20 (2H, q, J=7.1 Hz, CH$_2$), 6.38 (2H, s, CH$_2$), 6.92 (2H, d, J=8.3 Hz, H-2' and H-6'), 7.28 (2H, d, J=8.3 Hz, H-3' and H-5'), 7.57-7.70 (3H, m, H-3", H-4" and H-5"), 7.94 (2H, d, J=7.0 Hz, H-2" and H-6"), 8.19 (1H, s, H-4), 12.05 (1H, s, NH); $^{13}$C nmr (DMSO-d$_6$) (ppm): 13.9 (q), 20.1 (t), 26.4 (t), 48.9 (t), 60.6 (t), 102.6 (s), 104.0 (s), 123.3 (s), 127.9 (2×d), 128.3 (2×d), 129.0 (2×d), 129.7 (2×d), 131.4 (s), 133.5 (d), 134.5 (s), 137.9 (s), 138.7 (d), 140.4 (s), 141.2 (s), 142.6 (s), 157.8 (s), 159.4 (s), 164.8 (s). Anal calcd for C$_{27}$H$_{22}$BrClN$_2$O$_5$S: C, 53.88; H, 3.68; N, 4.65. Found: C, 54.02; H, 3.81; N, 4.47.

Methyl 3-bromo-1-(4-methylbenzyl)-8-oxo-7-(phenylsulfonyl)-4,5,8,9-tetrahydro-1H-pyrrolo[3,2-h]quinoline-2-carboxylate (PP031). This product was obtained by reaction of PP019. Yellow solid; yield: 54%; m.p.: 88-89° C.; IR: 3381 (NH), 1717 (CO), 1699 (CO) cm$^{-1}$; $^1$H nmr (DMSO-d$_6$) (ppm): 2.17 (3H, s, CH$_3$), 2.65-2.95 (4H, m, 2×CH$_2$), 3.74 (3H, s, CH$_3$), 6.36 (2H, s, CH$_2$), 6.78 (2H, d, J=7.0 Hz, H-2' and H-6'), 6.99 (2H, d, J=7.0 Hz, H-3' and H-5'), 7.60-7.69 (3H, m, H-3", H-4" and H-5"), 7.93 (2H, d, J=6.6 Hz, H-2" and H-6"), 8.18 (1H, s, H-4), 12.06 (1H, s, NH); $^{13}$C nmr (DMSO-d$_6$) (ppm): 20.1 (t), 20.5 (q), 26.4 (t), 49.0 (t), 51.6 (q), 103.8 (s), 118.0 (s), 123.4 (s), 124.3 (s), 126.0 (2×d), 127.9 (2×d), 128.5 (s), 128.9 (2×d), 129.0 (2×d), 130.0 (s), 130.7 (s), 133.5 (d), 135.9 (s), 136.0 (s), 138.5 (d), 140.4 (s), 157.8 (s), 159.9 (s). Anal calcd for C$_{27}$H$_{23}$BrN$_2$O$_5$S: C, 57.15; H, 4.09; N, 4.94. Found: C, 57.01; H, 4.27; N, 5.06.

Methyl 3-bromo-1-(2-methylbenzyl)-8-oxo-7-(phenylsulfonyl)-4,5,8,9-tetrahydro-1H-pyrrolo[3,2-h]quinoline-2-carboxylate (PP032). This product was obtained by reaction of PP020. Yellow solid; yield: 60%; m.p.: 101-102° C.; IR: 3307 (NH), 1704 (CO), 1667 (CO) cm$^{-1}$; $^1$H nmr (DMSO-d$_6$) (ppm): 2.32 (3H, s, CH$_3$), 2.71 (2H, t, J=8.1 Hz, CH$_2$), 3.02 (2H, t, J=8.1 Hz, CH$_2$), 3.64 (3H, s, CH$_3$), 6.41 (2H, s, CH$_2$), 6.94-7.3 (4H, m, H-3', H-4', H-5' and H-6'), 7.55-7.71 (3H, m, H-3", H-4" and H-5"), 7.92 (2H, d, J=6.6 Hz, H-2" and H-6"), 8.21 (1H, s, H-4), 12.04 (1H, s, NH); $^{13}$C nmr (DMSO-d$_6$) (ppm): 18.7 (q), 20.2 (t), 26.5 (t), 47.9 (t), 51.5 (q), 104.0 (s), 117.7 (s), 118.4 (s), 122.8 (d), 123.2 (s), 126.1 (d), 126.3 (d), 127.8 (d), 128.0 (2×d), 129.0 (2×d), 129.1 (s), 129.7 (d), 129.8 (d), 130.7 (d), 133.5 (d), 134.2 (s), 137.8 (s), 140.4 (s), 157.8 (s), 159.7 (s). Anal calcd for C$_{27}$H$_{23}$BrN$_2$O$_5$S: C, 57.15; H, 4.09; N, 4.94. Found: C, 57.02; H, 3.95; N, 5.08.

Ethyl 3-bromo-7-[(4-chlorophenyl)sulfonyl]-1-(3-methylbenzyl)-8-oxo-4,5,8,9-tetrahydro-1H-pyrrolo[3,2-h]quinoline-2-carboxylate (PP030). This product was obtained by reaction of PP018. Yellow solid; yield: 55%; m.p.: 89-90° C.; IR: 3399 (NH), 1713 (CO), 1684 (CO) cm$^{-1}$; $^1$H nmr (CDCl$_3$) (ppm): 1.27 (3H, t, J=7.1 Hz, CH$_3$), 2.36 (3H, s, CH$_3$), 2.75-2.88 (4H, m, 2×CH$_2$), 4.26 (2H, q, J=7.1 Hz, CH$_2$), 5.95 (2H, s, CH$_2$), 7.01-7.24 (4H, m, Ar), 7.54 (2H, d, J=8.5 Hz, Ar), 7.94 (2H, d, J=8.5 Hz, Ar), 8.07 (1H, s, H-4), 8.90 (1H, s, NH); $^{13}$C nmr (CDCl$_3$) (ppm): 14.0 (q), 19.1 (q), 20.8 (t), 27.0 (t), 49.1 (t), 61.2 (t), 104.6 (s), 120.2 (s), 120.9 (s), 125.4 (s), 126.8 (2×d), 128.3 (s), 129.3 (2×d), 129.7 (s), 129.8 (2×d), 130.7 (2×d), 134.4 (s), 135.4 (s), 138.7 (s), 140.3 (s), 141.1 (d), 145.4 (s), 156.9 (s), 159.8 (s). Anal calcd for C$_{28}$H$_{24}$BrClN$_2$O$_5$S: C, 54.60; H, 3.93; N, 4.55. Found: C, 54.47; H, 4.05; N, 4.39.

Ethyl 7-(benzenesulfonyl)-3-bromo-1-[(2,4-dimethylphenyl)methyl]-8-oxo-4,5,8,9-tetrahydro-1H-pyrrolo[3,2-h]quinoline-2-carboxylate (PP033). This product was obtained by reaction of PP021. Dark yellow solid; yield: 60%; m.p.: 301-302° C.; IR: 3273 (NH), 1709 (CO), 1664 (CO) cm$^{-1}$; $^1$H nmr (DMSO-d$_6$) (ppm): 1.12 (3H, t, J=7.1 Hz, CH$_3$), 2.12 (3H, s, CH$_3$), 2.17 (3H, s, CH$_3$), 2.69 (2H, t, J=7.1 Hz, CH$_2$), 2.98 (2H, t, J=7.1 Hz, CH$_2$), 4.11 (2H, q, J=7.1 Hz, CH$_2$), 5.83 (1H, d, J=7.3 Hz, Ar), 6.11 (2H, s, CH$_2$), 6.72 (1H, d, J=7.3 Hz, Ar), 6.90 (1H, s, Ar), 7.41-7.72 (3H, m, H-3", H-4" and H-5"), 7.90-8.00 (2H, m, H-2" and H-6"), 8.19 (1H, s, H-4), 12.03 (1H, s, NH); $^{13}$C nmr (DMSO-d$_6$) (ppm): 13.8 (q), 20.2 (t), 20.4 (q), 21.8 (q), 26.6 (t), 47.6 (t), 60.7 (t), 108.3 (s), 118.3 (s), 122.3 (d), 122.8 (s), 123.2 (s), 123.5 (s), 124.5 (s), 126.6 (d), 127.8 (d), 128.0 (2×d), 129.0

(2×d), 130.4 (s), 133.5 (d), 135.0 (s), 138.6 (d), 140.4 (s), 148.1 (s), 149.5 (s), 157.8 (s), 159.2 (s). Anal calcd for $C_{29}H_{25}BrN_2O_5S$: C, 58.69; H, 4.25; N, 4.72. Found: C, 58.78; H, 4.13; N, 4.59.

Ethyl 7-(benzenesulfonyl)-3-bromo-1-[(3,4-dimethylphenyl)methyl]-8-oxo-4,5,8,9-tetrahydro-1H-pyrrolo[3,2-h]quinoline-2-carboxylate (PP037). This product was obtained by reaction of PP025. Dark yellow solid; yield: 58%; m.p.: 156-157° C.; IR: 3027 (NH), 1709 (CO), 1641 (CO) cm$^{-1}$; $^1$H nmr (DMSO-d$_6$) (ppm): 1.24 (3H, t, J=7.2 Hz, CH$_3$), 2.06 (3H, s, CH$_3$), 2.08 (3H, s, CH$_3$), 2.65 (2H, t, J=7.0 Hz, CH$_2$), 2.95 (2H, t, J=7.0 Hz, CH$_2$), 4.22 (2H, q, J=7.2 Hz, CH$_2$), 6.33 (2H, s, CH$_2$), 6.52 (1H, d, J=7.7 Hz, Ar), 6.75 (1H, s, Ar), 6.93 (1H, d, J=7.7 Hz, Ar), 7.57-7.73 (3H, m, H-3", H-4" and H-5"), 7.94 (2H, d, J=7.4 Hz, H-2" and H-6"), 8.19 (1H, s, H-4), 12.03 (1H, s, NH); $^{13}$C nmr (DMSO-d$_6$) (ppm): 13.9 (q), 18.9 (q), 19.4 (q), 20.1 (t), 26.5 (t), 48.9 (t), 60.6 (t), 103.6 (s), 117.9 (s), 123.2 (d), 123.6 (s), 127.4 (d), 127.9 (2×d), 128.6 (s), 128.8 (s), 129.0 (2×d), 129.1 (s), 129.5 (d), 129.8 (s), 130.7 (s), 133.5 (d), 134.8 (s), 135.9 (s), 136.2 (s), 138.5 (d), 140.5 (s), 157.8 (s), 159.5 (s). Anal calcd for $C_{29}H_{27}BrN_2O_5S$: C, 58.49; H, 4.57; N, 4.70. Found: C, 58.56; H, 4.68; N, 4.59.

Propan-2-yl 7-(benzenesulfonyl)-3-bromo-1-[(4-methylphenyl)methyl]-8-oxo-4,5,8,9-tetrahydro-1H-pyrrolo[3,2-h]quinoline-2-carboxylate (PP034). This product was obtained by reaction of PP022. Dark yellow solid; yield: 55%; m.p.: 98-99° C.; IR: 3302 (NH), 1703 (CO), 1641 (CO) cm$^{-1}$; $^1$H nmr (DMSO-d$_6$) (ppm): 1.20 (3H, s, CH$_3$), 1.23 (3H, s, CH$_3$), 2.17 (3H, s, CH$_3$), 2.64 (2H, t, J=7.1 Hz, CH$_2$), 2.95 (2H, t, J=7.1 Hz, CH$_2$), 4.97-5.13 (1H, m, CH), 6.35 (2H, s, CH$_2$), 6.79 (2H, d, J=7.9 Hz, H-2' and H-6'), 7.00 (2H, d, J=7.9 Hz, H-3' and H-5'), 7.57-7.73 (3H, m, H-3", H-4" and H-5"), 7.94 (2H, d, J=7.1 Hz, H-2" and H-6"), 8.18 (1H, s, H-4), 12.03 (1H, s, NH); $^{13}$C nmr (DMSO-d$_6$) (ppm): 20.1 (t), 20.5 (q), 21.5 (2×q), 26.5 (t), 48.8 (t), 68.5 (d), 103.5 (s), 117.9 (s), 124.0 (s), 124.2 (s), 126.0 (2×d), 127.9 (2×d), 128.8 (s), 128.9 (2×d), 129.0 (2×d), 129.1 (s), 129.6 (s), 133.5 (d), 135.9 (s), 136.0 (s), 138.5 (d), 140.5 (s), 157.8 (s), 159.1 (s). Anal calcd for $C_{29}H_{27}BrN_2O_5S$: C, 58.49; H, 4.57; N, 4.70. Found: C, 58.59; H, 4.37; N, 4.99.

Ethyl 3-bromo-7-(4-methylbenzene-1-sulfonyl)-1-[(4-methylphenyl)methyl]-8-oxo-4,5,8,9-tetrahydro-1H-pyrrolo[3,2-h]quinoline-2-carboxylate (PP035). This product was obtained by reaction of PP023. Dark yellow solid; yield: 65%; m.p.: 95-96° C.; IR: 3371 (NH), 1712 (CO), 1664 (CO) cm$^{-1}$; $^1$H nmr (DMSO-d$_6$) (ppm): 1.23 (3H, t, J=7.0 Hz, CH$_3$), 2.17 (3H, s, CH$_3$), 2.37 (3H, s, CH$_3$), 2.65 (2H, t, J=7.0 Hz, CH$_2$), 2.95 (2H, t, J=7.0 Hz, CH$_2$), 4.21 (2H, q, J=7.0 Hz, CH$_2$), 6.37 (2H, s, CH$_2$), 6.78 (2H, d, J=7.8 Hz, H-2' and H-6'), 7.00 (2H, d, J=7.8 Hz, H-3' and H-5'), 7.40 (2H, d, J=8.0 Hz, H-2" and H-6"), 7.81 (2H, d, J=8.0 Hz, H-3" and H-5"), 8.17 (1H, s, H-4), 11.98 (1H, s, NH); $^{13}$C nmr (DMSO-d$_6$) (ppm): 13.9 (q), 20.1 (t), 20.5 (q), 21.0 (q), 26.5 (t), 48.9 (t), 60.6 (t), 103.8 (s), 118.3 (s), 123.5 (s), 124.2 (s), 125.9 (2×d), 127.9 (s), 128.0 (2×d), 128.9 (2×d), 129.5 (2×d), 132.3 (s), 135.9 (s), 136.0 (s), 137.6 (s), 138.3 (d), 144.1 (s), 145.7 (s), 157.8 (s), 159.5 (s), 162.1 (s). Anal calcd for $C_{29}H_{27}BrN_2O_5S$: C, 58.49; H, 4.57; N, 4.70. Found: C, 58.33; H, 4.65; N, 4.84.

Ethyl 3-bromo-7-(metansulfonyl)-1-[(4-methylphenyl)methyl]-8-oxo-4,5,8,9-tetrahydro-1H-pyrrolo[3,2-h]quinoline-2-carboxylate (PP036). This product was obtained by reaction of PP024. Dark yellow solid; yield: 57%; m.p.: 242-243° C.; IR: 3307 (NH), 1700 (CO), 1667 (CO) cm$^{-1}$; $^1$H nmr (DMSO-d$_6$) (ppm): 1.31 (3H, t, J=7.1 Hz, CH$_3$), 2.05 (3H, s, CH$_3$), 2.71 (2H, t, J=7.2 Hz, CH$_2$), 2.99 (2H, t, J=7.2 Hz, CH$_2$), 3.32 (3H, s, CH$_3$), 4.29 (2H, q, J=7.1 Hz, CH$_2$), 6.52 (2H, s, CH$_2$), 6.91 (2H, d, J=7.8 Hz, H-2' and H-6'), 7.11 (2H, d, J=7.8 Hz, H-3' and H-5'), 8.04 (1H, s, H-4), 12.36 (1H, s, NH); $^{13}$C nmr (DMSO-d$_6$) (ppm): 14.1 (q), 20.6 (t), 20.7 (q), 26.4 (t), 41.9 (q), 49.0 (t), 59.7 (t), 103.9 (s), 118.4 (s), 123.3 (s), 124.2 (s), 126.1 (2×d), 127.8 (s), 129.0 (2×d), 130.1 (s), 131.7 (s), 136.0 (s), 136.1 (s), 138.0 (d), 158.0 (s), 160.0 (s), 162.3 (s). Anal calcd for $C_{23}H_{23}BrN_2O_5S$: C, 53.18; H, 4.46; N, 5.39. Found: C, 53.05; H, 4.58; N, 5.27.

Ethyl 7-(benzenesulfonyl)-3-bromo-1-[(4-methylphenyl)methyl]-8-oxo-8,9-dihydro-1H-pyrrolo[3,2-h]quinoline-2-carboxylate (14, PP057). This product was obtained by reaction of PP058 (13). Dark yellow solid; yield: 54%; m.p.: 105-106° C.; IR: 3381 (NH), 1708 (CO), 1664 (CO) cm$^{-1}$; $^1$H nmr (DMSO-d$_6$) (ppm): 1.25 (2H, t, J=6.8 Hz, CH$_3$), 2.18 (3H, s, CH$_3$), 4.25 (2H, q, J=6.8 Hz, CH$_2$), 6.35 (2H, s, CH$_2$), 6.79 (2H, d, J=7.7 Hz, H-2' and H-6'), 7.01 (2H, d, J=7.7 Hz, H-3' and H-5'), 7.60-7.74 (5H, m, Ar), 7.94 (2H, d, J=7.3 Hz, Ar), 8.19 (1H, s, H-4), 12.09 (1H, s, NH); $^{13}$C nmr (DMSO-d$_6$) (ppm): 14.0 (q), 20.6 (q), 52.9 (t), 60.7 (t), 103.7 (s), 106.5 (s), 111.4 (s), 119.6 (s), 123.1 (s), 126.0 (2×d), 126.1 (d), 128.1 (2×d), 128.3 (d), 128.5 (d), 128.9 (2×d), 129.0 (2×d), 129.5 (s), 129.6 (s), 133.5 (d), 141.1 (s), 145.1 (s), 152.1 (s), 157.9 (s), 159.7 (s). Anal calcd for $C_{28}H_{23}BrN_2O_5S$: C, 58.04; H, 4.00; N, 4.83. Found: C, 57.94; H, 4.11; N, 4.99.

Ethyl 7-(benzenesulfonyl)-3-bromo-1-[(4-bromophenyl)methyl]-8-oxo-4,5,8,9-tetrahydro-1H-pyrrolo[3,2-h]quinoline-2-carboxylate (PP061). This compound was obtained by reaction of PP060. Yellow solid; yield: 66%; m.p.: 135-136° C.; IR: 3324 (NH), 1709 (CO), 1685 (CO) cm$^{-1}$; $^1$H nmr (DMSO-d$_6$) (ppm): 1.21 (3H, t, J=7.1 Hz, CH$_3$), 2.66 (2H, t, J=7.3 Hz, CH$_2$), 2.96 (2H, t, J=7.3 Hz, CH$_2$), 4.19 (2H, q, J=7.1 Hz, CH$_2$), 6.35 (2H, s, CH$_2$), 6.84 (2H, d, J=8.2 Hz, H-2' and H-6'), 7.39 (2H, d, J=8.2 Hz, H-3' and H-5'), 7.56-7.72 (3H, m, H-3", H-4" and H-5"), 7.94 (2H, d, J=7.6 Hz, H-2" and H-6"), 8.18 (1H, s, H-6), 12.12 (1H, s, NH); $^{13}$C nmr (DMSO-d$_6$) (ppm): 13.9 (q), 20.1 (t), 26.4 (t), 48.9 (t), 60.6 (t), 96.5 (s), 104.0 (s), 118.1 (s), 119.9 (s), 121.6 (s), 123.2 (s), 124.3 (s), 128.0 (2×d), 128.2 (2×d), 129.0 (2×d), 129.7 (s), 131.2 (2×d), 133.5 (d), 138.4 (d), 140.4 (s), 149.5 (s), 157.9 (s), 159.3 (s). Anal calcd for $C_{27}H_{22}Br_2N_2O_5S$: C, 50.17; H, 3.43; N, 4.33. Found: C, 50.31; H, 3.18; N, 4.49.

Ethyl 7-(benzenesulfonyl)-3-bromo-1-[(4-iodophenyl)methyl]-8-oxo-4,5,8,9-tetrahydro-JH-pyrrolo[3,2-h]quinoline-2-carboxylate (PP063). This compound was obtained by reaction of PP062. Light yellow solid; yield: 67%; m.p.: 129-130° C.; IR: 3330 (NH), 1703 (CO), 1658 (CO) cm$^{-1}$; $^1$H nmr (DMSO-d$_6$) (ppm): 1.28 (3H, t, J=7.2 Hz, CH$_3$), 2.72 (2H, t, J=7.1 Hz, CH$_2$), 3.03 (2H, t, J=7.1 Hz, CH$_2$), 4.26 (2H, q, J=7.2 Hz, CH$_2$), 6.41 (2H, s, CH$_2$), 6.77 (2H, d, J=8.2 Hz, H-2' and H-6'), 7.62-7.76 (5H, m, H-3', H-5', H-3", H-4" and H-5"), 8.00 (2H, d, J=7.1 Hz, H-2" and H-6"), 8.25 (1H, s, H-6), 12.11 (1H, s, NH); $^{13}$C nmr (DMSO-d$_6$) (ppm): 13.9 (q), 20.2 (t), 26.3 (t), 48.9 (t), 60.6 (t), 92.7 (s), 104.0 (s), 112.1 (s), 118.0 (s), 123.3 (s), 124.3 (s), 127.9 (2×d), 128.3 (2×d), 129.0 (2×d), 129.6 (s), 129.7 (s), 133.5 (d), 137.0 (2×d), 138.8 (d), 140.4 (s), 157.9 (s), 159.3 (s), 164.7 (s). Anal calcd for $C_{27}H_{22}BrIN_2O_5S$: C, 46.77; H, 3.20; N, 4.04. Found: C, 46.64; H, 3.11; N, 4.23.

Ethyl 7-(benzenesulfonyl)-3-bromo-1-(cyclopropylmethyl)-8-oxo-4,5,8,9-tetrahydro-1H-pyrrolo[3,2-h]quinoline-2-carboxylate (PP065). This compound was obtained by reaction of PP064. White solid; yield: 69%; m.p.: 192-

193° C.; IR: 3553 (NH), 1703 (CO), 1637 (CO) cm$^{-1}$; $^1$H nmr (DMSO-d$_6$) (ppm): 0.21-0.30 (4H, m, 2×CH$_2$), 1.03-1.12 (1H, m, CH), 1.32 (3H, t, J=6.7 Hz, CH$_3$), 2.58-2.65 (2H, m, CH$_2$), 2.91-2.95 (2H, m, CH$_2$), 4.30 (2H, q, J=6.7 Hz, CH$_2$), 5.04 (2H, d, J=6.6 Hz, CH$_2$), 7.62-7.71 (3H, m, H-3', H-4' and H-5'), 7.95 (2H, d, J=7.3 Hz H-2' and H-6'), 8.20 (1H, s, H-6), 12.00 (1H, s, NH); $^{13}$C nmr (DMSO-d$_6$) (ppm): 3.6 (2×t), 13.8 (d), 14.5 (q), 20.7 (t), 27.0 (t), 50.1 (t), 61.1 (t), 103.7 (s), 118.3 (s), 118.6 (s), 123.7 (s), 124.7 (s), 128.3 (s), 128.4 (2×d), 129.5 (2×d), 129.9 (s), 134.0 (d), 138.9 (d), 141.0 (s), 158.3 (s), 160.3 (s). Anal calcd for C$_{24}$H$_{23}$BrN$_2$O$_5$S: C, 54.24; H, 4.36; N, 5.27. Found: C, 54.05; H, 4.18; N, 5.39.

Ethyl 7-(benzenesulfonyl)-3-bromo-1-[(6-methylpyridin-3-yl)methyl]-8-oxo-4,5,8,9-tetrahydro-1H-pyrrolo[3,2-h]quinoline-2-carboxylate (PP067). This compound was obtained by reaction of PP066. White solid; yield: 67%; m.p.: 301-302° C.; IR: 3439 (NH), 1703 (CO), 1614 (CO) cm$^{-1}$; $^1$H nmr (DMSO-d$_6$) (ppm): 1.29 (3H, t, J=7.1 Hz, CH$_3$), 2.32 (3H, s, CH$_3$), 3.18-3.46 (4H, m, 2×CH$_2$), 4.32 (2H, q, J=7.1 Hz, CH$_2$), 6.67 (2H, s, CH$_2$), 7.00-7.12 (2H, m, Ar), 7.60-7.75 (3H, m, Ar), 7.88-7.92 (1H, m, Ar), 7.98-8.06 (2H, s, Ar), 8.15-8.22 (1H, m, Ar), 9.14 (1H, s, NH); $^{13}$C nmr (DMSO-d$_6$) (ppm): 14.4 (q), 21.3 (t), 23.9 (q), 28.7 (t), 48.1 (t), 62.0 (t), 109.8 (s), 122.4 (s), 123.2 (s), 123.4 (d), 128.7 (s), 128.8 (2×d), 129.0 (d), 129.5 (s), 129.6 (2×d), 131.7 (s), 132.0 (s), 134.9 (d), 140.4 (s), 141.0 (s), 142.5 (d), 147.5 (d), 156.0 (s), 157.1 (s), 160.4 (s). Anal calcd for C$_{27}$H$_{24}$BrN$_3$O$_5$S: C, 55.68; H, 4.15; N, 7.21. Found: C, 55.79; H, 3.97; N, 7.35.

Ethyl 7-(benzenesulfonyl)-3-bromo-8-oxo-1-[(2,4,6-trimethylphenyl)methyl]-4,5,8,9-tetrahydro-1H-pyrrolo[3,2-h]quinoline-2-carboxylate (PP069). This compound was obtained by reaction of PP068. Dark yellow solid; yield: 62%; m.p.: 110-111° C.; IR: 3342 (NH), 1660 (CO), 1642 (CO) cm$^{-1}$; $^1$H nmr (DMSO-d$_6$) (ppm): 1.28 (3H, t, J=7.1 Hz, CH$_3$), 1.94 (6H, s, 2×CH$_3$), 2.19 (3H, s, CH$_3$), 2.68 (2H, t, J=7.4 Hz, CH$_2$), 3.00 (2H, t, J=7.4 Hz, CH$_2$), 3.92 (2H, q, J=7.1 Hz, CH$_2$), 5.81 (2H, s, CH$_2$), 6.77 (2H, s, H-3' and H-5'), 7.50-8.02 (3H, m, H-2", H-3", H-4", H-5", and H-6"), 8.27 (1H, s, H-6), 12.08 (1H, s, NH); $^{13}$C nmr (DMSO-d$_6$) (ppm): 14.2 (q), 19.7 (2×q), 20.5 (t), 20.8 (q), 27.2 (t), 46.9 (t), 61.1 (t), 101.0 (s), 115.7 (s), 126.6 (2×d), 127.0 (s), 128.4 (2×d), 129.5 (2×d), 132.0 (s), 134.0 (d), 135.1 (d), 136.2 (s), 137.0 (2×s), 137.4 (s), 138.2 (s), 141.1 (s), 142.1 (s), 156.1 (s), 158.3 (s), 160.3 (s). Anal calcd for C$_{30}$H$_{29}$BrN$_2$O$_5$S: C, 59.11; H, 4.80; N, 4.60. Found: C, 58.94; H, 4.69; N, 4.75.

Ethyl 7-(benzenesulfonyl)-3-bromo-8-oxo-1-{[4-(trifluoromethyl)phenyl]methyl}-4,5,8,9-tetrahydro-1H-pyrrolo[3,2-h]quinoline-2-carboxylate (PP071). This compound was obtained by reaction of PP070. Dark yellow solid; yield: 75%; m.p.: 185-186° C.; IR: 3439 (NH), 1703 (CO), 1658 (CO) cm$^{-1}$; $^1$H nmr (DMSO-d$_6$) (ppm): 1.18 (3H, t, J=7.0 Hz, CH$_3$), 2.69 (2H, t, J=7.4 Hz, CH$_2$), 2.99 (2H, t, J=7.4 Hz, CH$_2$), 4.18 (2H, q, J=7.0 Hz, CH$_2$), 6.49 (2H, s, CH$_2$), 7.11 (2H, d, J=7.9 Hz, H-2' and H-6'), 7.59-7.71 (5H, m, H-3', H-5', H-3", H-4" and H-5"), 7.93 (2H, d, J=7.3 Hz, H-2" and H-6"), 8.19 (1H, s, H-6), 12.01 (1H, s, NH); $^{13}$C nmr (DMSO-d$_6$) (ppm): 14.3 (q), 20.6 (t), 26.9 (t), 49.8 (t), 61.1 (t), 104.6 (s), 118.7 (s), 123.7 (s), 124.9 (s), 125.7 (s), 125.8 (s), 127.0 (2×d), 127.1 (2×d), 127.7 (s), 128.1 (s), 128.4 (2×d), 128.5 (s), 129.5 (2×d), 130.2 (s), 134.0 (d), 139.0 (d), 142.6 (d, J$_{C-F}$=251.8 Hz), 158.3 (s), 159.8 (s). Anal calcd for C$_{28}$H$_{22}$BrF$_3$N$_2$O$_5$S: C, 52.92; H, 3.49; N, 4.41. Found: C, 53.07; H, 3.61; N, 4.28.

Ethyl 7-(benzenesulfonyl)-3-bromo-1-[(4-fluorophenyl)methyl]-8-oxo-4,5,8,9-tetrahydro-1H-pyrrolo[3,2-h]quinoline-2-carboxylate (PP073). This compound was obtained by reaction of PP072. Yellow solid; yield: 64%; m.p.: 136-137° C.; IR: 3313 (NH), 1703 (CO), 1641 (CO) cm$^{-1}$; $^1$H nmr (DMSO-d$_6$) (ppm): 1.21 (3H, t, J=7.1 Hz, CH$_3$), 2.66 (2H, t, J=7.6 Hz, CH$_2$), 2.96 (2H, t, J=7.6 Hz, CH$_2$), 4.21 (2H, q, J=7.1 Hz, CH$_2$), 6.38 (2H, s, CH$_2$), 6.93-7.07 (4H, m, H-2', H-3', H-5', and H-6'), 7.58-7.71 (3H, m, H-3", H-4" and H-5"), 7.94 (2H, d, J=7.4 Hz, H-2" and H-6"), 8.19 (1H, s, H-6), 12.03 (1H, s, NH); $^{13}$C nmr (DMSO-d$_6$) (ppm): 14.4 (q), 20.6 (t), 26.9 (t), 49.1 (t), 61.1 (t), 104.4 (s), 115.6 (2×d, J$_{C3'-F}$=21.4 Hz), 118.6 (s), 123.9 (s), 124.8 (s), 128.4 (2×d), 128.5 (s), 128.6 (2×d, J$_{C2'-F}$=8.3 Hz), 128.7 (s), 129.5 (2×d), 130.2 (s), 134.0 (d), 135.5 (s), 139.0 (d), 141.0 (s), 150.1 (s), 158.4 (s), 161.5 (d, J$_{C4'-F}$=243.7 Hz). Anal calcd for C$_{27}$H$_{22}$BrFN$_2$O$_5$S: C, 55.39; H, 3.79; N, 4.79. Found: C, 55.22; H, 3.87; N, 4.65.

Ethyl 7-(benzenesulfonyl)-1-[3-(dimethylamino)propyl]-8-oxo-4,5,8,9-tetrahydro-1H-pyrrolo[3,2-h]quinoline-2-carboxylate (PP075). This compound was obtained by reaction of PP074. Dark yellow solid; yield: 56%; m.p.: 255-256° C.; IR: 3410 (NH), 1664 (CO), 1606 (CO) cm$^{-1}$; $^1$H nmr (DMSO-d$_6$) (ppm): 1.26 (3H, t, J=7.0 Hz, CH$_3$), 1.82-1.96 (2H, m, CH$_2$), 2.67-2.72 (10H, m, 2×CH$_3$ and 2×CH$_2$), 2.93-2.98 (2H, m, CH$_2$), 4.24 (2H, q, J=7.0 Hz, CH$_2$), 4.90-5.02 (2H, m, CH$_2$), 7.57-7.72 (3H, m, H-3", H-4" and H-5"), 7.88 (2H, d, J=7.6 Hz, H-2" and H-6"), 8.23 (1H, s, H-6), 11.91 (1H, s, NH); $^{13}$C nmr (DMSO-d$_6$) (ppm): 14.6 (q), 21.5 (t), 27.8 (t), 43.4 (2×q), 44.7 (t), 56.5 (t), 60.1 (t), 63.6 (t), 105.9 (s), 123.0 (s), 124.7 (s), 126.4 (s), 127.0 (s), 127.5 (2×d), 129.4 (2×d), 132.6 (s), 133.5 (d), 139.7 (d), 141.5 (s), 151.5 (s), 158.7 (s), 160.9 (s). Anal calcd for C$_{25}$H$_{29}$N$_3$O$_5$S: C, 62.09; H, 6.04; N, 8.69. Found: C, 61.87; H, 6.21; N, 8.84.

Propan-2-yl 7-(benzenesulfonyl)-3-bromo-1-[(3-methylphenyl)methyl]-8-oxo-4,5,8,9-tetrahydro-1H-pyrrolo[3,2-h]quinoline-2-carboxylate (PP104). This compound was obtained by reaction of PP103. Light brown solid; yield: 68%; m.p.: 187-188° C.; IR: 3302 (NH), 1683 (CO), 1680 (CO) cm$^{-1}$; $^1$H nmr (DMSO-d$_6$) (ppm): 1.20 (6H, d, J=6.2 Hz, 2×CH$_3$), 2.15 (3H, s, CH$_3$), 2.64 (2H, t, J=7.4 Hz, CH$_2$), 2.95 (2H, t, J=7.4 Hz, CH$_2$), 4.99-5.07 (1H, m, CH), 6.36 (2H, s, CH$_2$), 6.60 (1H, d, J=7.5 Hz, Ar), 6.79 (1H, s, H-2'), 6.95 (1H, d, J=7.3 Hz, Ar), 7.07 (1H, t, J=7.5 Hz, H-5'), 7.57-7.71 (3H, m, H-3", H-4" and H-5"), 7.94 (2H, d, J=7.3 Hz, H-2" and H-6"), 8.19 (1H, s, H-6), 12.03 (1H, s, NH); $^{13}$C nmr (DMSO-d$_6$) (ppm): 20.6 (t), 21.5 (q), 21.9 (2×q), 27.0 (t), 49.6 (t), 68.9 (d), 103.9 (s), 118.5 (s), 123.5 (s), 124.5 (s), 127.1 (s), 127.4 (d), 128.1 (d), 128.4 (2×d), 128.8 (d), 129.5 (2×d), 130.0 (d), 130.1 (s), 134.0 (d), 137.8 (d), 138.9 (s), 139.0 (s), 139.3 (s), 141.0 (s), 158.4 (s), 159.6 (s). Anal calcd for C$_{29}$H$_{27}$BrN$_2$O$_5$S: C, 58.49; H, 4.57; N, 4.70. Found: C, 58.61; H, 4.39; N, 4.88.

Propan-2-yl 7-(benzenesulfonyl)-3-bromo-1-(cyclopropylmethyl)-8-oxo-4,5,8,9-tetrahydro-1H-pyrrolo[3,2-h]quinoline-2-carboxylate (PP106). This compound was obtained by reaction of PP105. Yellow solid; yield: 72%; m.p.: 196-197° C.; IR: 3319 (NH), 1701 (CO), 1685 (CO) cm$^{-1}$; $^1$H nmr (DMSO-d$_6$) (ppm): 0.22-0.31 (4H, m, 2×CH$_2$), 1.10-1.34 (7H, m, 2×CH$_3$ e CH), 2.63 (2H, t, J=7.4 Hz, CH$_2$), 2.95 (2H, t, J=7.4 Hz, CH$_2$), 5.06-5.14 (3H, m, CH$_2$ and CH), 7.63-7.71 (3H, m, H-3", H-4" and H-5"), 7.97-8.07 (2H, m, H-2" and H-6"), 8.21 (1H, s, H-6), 11.99 (1H, s, NH); $^{13}$C nmr (DMSO-d$_6$) (ppm): 3.6 (2×t), 13.8 (d), 20.7 (t), 22.1 (2×q), 27.1 (t), 50.0 (t), 69.0 (d), 103.5 (s), 118.4 (s), 124.1 (s), 124.7 (s), 128.2 (s), 128.5 (2×d), 129.5 (2×d), 129.8 (s), 134.0 (d), 138.9 (d), 141.1 (s), 150.4 (s), 158.3 (s), 159.9 (s). Anal calcd for $C_{25}H_{25}BrN_2O_5S$: C, 55.05; H, 4.62; N, 5.14. Found: C, 55.16; H, 4.43; N, 5.02.

Propan-2-yl 7-(benzenesulfonyl)-3-bromo-1-[(4-fluorophenyl)methyl]-8-oxo-4,5,8,9-tetrahydro-1H-pyrrolo[3,2-h]quinoline-2-carboxylate (PP108). This compound was obtained by reaction of PP107. Yellow solid; yield: 85%; m.p.: 135-136° C.; IR: 3307 (NH), 1703 (CO), 1646 (CO) cm$^{-1}$; $^1$H nmr (DMSO-d$_6$) (ppm): 1.20 (6H, d, J=6.1 Hz, 2×CH$_3$), 2.65 (2H, t, J=7.4 Hz, CH$_2$), 2.96 (2H, t, J=7.4 Hz, CH$_2$), 4.97-5.09 (1H, m, CH), 6.38 (2H, s, CH$_2$), 6.94-7.08 (4H, m, H-2', H-3', H-5' and H-6'), 7.58-7.71 (3H, m, H-3", H-4" and H-5"), 7.95 (2H, d, J=7.5 Hz, H-2" and H-6"), 8.19 (1H, s, H-6), 12.03 (1H, s, NH); $^{13}$C nmr (DMSO-d$_6$) (ppm): 20.6 (t), 21.9 (2×q), 26.9 (t), 49.0 (t), 69.0 (d), 104.1 (s), 115.6 (2×d, $J_{C3'-F}$=21.4 Hz), 118.5 (s), 124.2 (s), 124.7 (s), 128.4 (2×d), 128.6 (2×d, $J_{C2'-F}$=8.1 Hz), 129.5 (2×d), 129.9 (s), 134.0 (d), 135.5 (s), 138.9 (d), 141.0 (s), 150.1 (s), 158.4 (s), 159.5 (s), 161.6 (d, $J_{C4'-F}$=242.9 Hz). Anal calcd for $C_{28}H_{24}BrFN_2O_5S$: C, 56.10; H, 4.04; N, 4.67. Found: C, 55.98; H, 3.89; N, 4.74.

7-(Benzenesulfonyl)-3-bromo-1-[(3-methylphenyl)methyl]-8-oxo-N-(propan-2-yl)-4,5,8,9-tetrahydro-1H-pyrrolo[3,2-h]quinoline-2-carboxamide (PP091). This compound was obtained by reaction of PP083. White solid; yield: 57%; m.p.: 206-207° C.; IR: 3419 (NH), 3406 (NH), 1629 (CO), 1622 (CO) cm$^{-1}$; $^1$H nmr (DMSO-d$_6$) (ppm): 1.15 (6H, s, 2×CH$_3$), 1.24 (3H, s, CH$_3$), 2.59-2.67 (2H, m, CH$_2$), 2.91-2.98 (2H, m, CH$_2$), 3.96-4.17 (1H, m, CH), 6.13 (2H, s, CH$_2$), 6.86-7.23 (4H, m, H-2', H-4', H-5' and H-6'), 7.62-7.89 (3H, m, H-3", H-4" and H-5"), 7.88-7.94 (2H, m, H-2" and H-6"), 8.24 (1H, s, H-6), 12.01 (1H, s, NH); $^{13}$C nmr (DMSO-d$_6$) (ppm): 20.1 (t), 20.9 (q), 21.8 (2×q), 40.9 (d), 96.8 (s), 116.6 (s), 122.7 (s), 124.3 (d), 126.0 (s), 127.0 (s), 127.8 (2×d), 127.9 (d), 128.0 (s), 128.1 (d), 128.9 (2×d), 131.5 (s), 133.3 (d), 133.4 (d), 137.2 (s), 137.8 (d), 138.3 (s), 140.7 (s), 158.0 (s), 158.9 (s). Anal calcd for $C_{29}H_{28}BrN_3O_4S$: C, 58.59; H, 4.75; N, 7.07. Found: C, 58.44; H, 4.63; N, 7.22.

7-(Benzenesulfonyl)-N-cyclopropyl-1-[(3-methylphenyl)methyl]-8-oxo-4,5,8,9-tetrahydro-1H-pyrrolo[3,2-h]quinoline-2-carboxamide (PP092). This compound was obtained by reaction of PP084. Light brown solid; yield: 50%; m.p.: 142-143° C.; IR: 3474 (NH), 3331 (NH), 1697 (CO), 1645 (CO) cm$^{-1}$; $^1$H nmr (DMSO-d$_6$) (ppm): 0.38-0.61 (4H, m, 2×CH$_2$), 2.30 (3H, s, CH$_3$), 2.55 (2H, t, J=6.9 Hz, CH$_2$), 2.93 (2H, t, J=6.9 Hz, CH$_2$), 3.33-3.40 (1H, m, CH), 6.20 (2H, s, CH$_2$), 6.99-7.21 (4H, m, H-2', H-4', H-5' and H-6'), 7.55-7.71 (5H, m, H-3", H-4" and H-5"), 7.94 (2H, d, J=7.2 Hz, H-2" and H-6"), 8.28 (1H, s, H-6), 9.12 (1H, s, NH), 11.96 (1H, s, NH); $^{13}$C nmr (DMSO-d$_6$) (ppm): 6.7 (2×t), 21.3 (q), 22.8 (t), 23.8 (d), 27.2 (t), 48.9 (t), 102.3 (s), 122.5 (s), 124.8 (d), 125.0 (s), 127.8 (d), 128.1 (d), 128.4 (d), 128.8 (2×d), 129.4 (2×d), 132.9 (s), 133.6 (d), 134.1 (d), 137.3 (s), 138.5 (d), 139.4 (s), 141.3 (s), 143.4 (s), 146, 1 (s), 158.3 (s), 163.4 (s). Anal calcd for $C_{29}H_{26}BrN_3O_4S$: C, 58.79; H, 4.42; N, 7.09. Found: 58.91; H, 4.29; N, 7.22.

7-(Benzenesulfonyl)-3-bromo-1-[(4-methylphenyl)methyl]-8-oxo-N-(propan-2-yl)-4,5,8,9-tetrahydro-1H-pyrrolo[3,2-h]quinoline-2-carboxamide (PP086). This compound was obtained by reaction of PP085. Dark green solid; yield: 59%; m.p.: 102-103° C.; IR: 3422 (NH), 3324 (NH), 1661 (CO), 1652 (CO) cm$^{-1}$; $^1$H nmr (DMSO-d$_6$) (ppm): 1.07 (6H, d, J=6.5 Hz, 2×CH$_3$), 2.18 (3H, s, CH$_3$), 2.62-2.69 (2H, m, CH$_2$), 2.85-2.90 (2H, m, CH$_2$), 3.91-4.08 (1H, m, CH), 6.02 (2H, s, CH$_2$), 6.90-7.10 (4H, m, H-2', H-3', H-5' and H-6'), 7.61-7.77 (3H, m, H-3", H-4" and H-5"), 7.92-8.10 (4H, m, H-2", H-6", H-6 and NH), 11.91 (1H, s, NH); $^{13}$C nmr (DMSO-d$_6$) (ppm): 20.1 (t), 22.8 (2×q), 24.6 (t), 42.9 (d), 48.9 (t), 101.8 (s), 122.7 (s), 124.5 (s), 128.8 (2×d), 129.0 (2×d), 129.3 (2×d), 129.7 (2×d), 133.2 (s), 133.6 (d), 133.8 (s), 137.0 (s), 138.7 (d), 140.1 (s), 141.3 (s), 143.5 (s), 145.8 (s), 158.4 (s), 161.2 (s). Anal calcd for $C_{29}H_{28}BrN_3O_4S$: C, 58.59; H, 4.75; N, 7.07. Found: C, 58.43; H, 4.88; N, 7.33.

7-(Benzenesulfonyl)-3-bromo-N-cyclopropyl-1-[(4-methylphenyl)methyl]-8-oxo-4,5,8,9-tetrahydro-1H-pyrrolo[3,2-h]quinoline-2-carboxamide (PP088). This compound was obtained by reaction of PP087. Orange solid; yield: 69%; m.p.: 102-103° C.; IR: 3461 (NH), 3387 (NH), 1665 (CO), 1653 (CO) cm$^{-1}$; $^1$H nmr (DMSO-d$_6$) (ppm): 0.99-1.27 (4H, m, 2×CH$_2$), 2.17 (3H, s, CH$_3$), 2.64-2.94 (4H, m, 2×CH$_2$), 3.28-3.45 (1H, m, CH), 6.18 (2H, s, CH$_2$), 6.86-7.08 (4H, m, H-2', H-3', H-5' and H-6'), 7.54-7.72 (3H, m, H-3", H-4" and H-5"), 7.78-8.06 (2H, m, H-2" and H-6"), 8.08 (1H, s, H-6), 9.08 (1H, s, NH), 12.52 (1H, s, NH); $^{13}$C nmr (DMSO-d$_6$) (ppm): 8.22 (2×t), 21.2 (q), 23.6 (t), 24.9 (d), 27.1 (t), 48.3 (t), 102.4 (s), 122.5 (s), 124.6 (s), 128.4 (2×d), 129.1 (2×d), 129.2 (2×d), 129.6 (2×d), 132.9 (s), 133.7 (d), 133.9 (s), 136.5 (s), 138.4 (d), 139.6 (s), 141.2 (s), 142.9 (s), 146.4 (s), 158.4 (s), 166.2 (s). Anal calcd for $C_{29}H_{26}BrN_3O_4S$: C, 58.79; H, 4.42; N, 7.09. Found: C, 58.65; H, 4.33; N, 7.25.

7-(Benzenesulfonyl)-3-bromo-1-[(4-bromophenyl)methyl]-8-oxo-N-(propan-2-yl)-4,5,8,9-tetrahydro-1H-pyrrolo[3,2-h]quinoline-2-carboxamide (PP097). This compound was obtained by reaction of PP096. White solid; yield: 67%; m.p.: 161-162° C.; IR: 3416 (NH), 3348 (NH), 1669 (CO), 1658 (CO) cm$^{-1}$; $^1$H nmr (DMSO-d$_6$) (ppm): 1.04 (6H, d, J=6.4 Hz, 2×CH$_3$), 2.61 (2H, t, J=7.3 Hz, CH$_2$), 2.89 (2H, t, J=7.3 Hz, CH$_2$), 3.91-4.01 (1H, m, CH), 6.03 (2H, s, CH$_2$), 7.03 (2H, d, J=8.1 Hz, H-2' and H-6'), 7.39 (2H, d, J=8.1 Hz, H-3' and H-5'), 7.57-7.70 (3H, m, H-3", H-4" and H-5"), 7.94 (2H, d, J=7.1 Hz, H-2" and H-6"), 8.11 (1H, s, H-6), 8.26 (2H, d, J=7.9 Hz, NH), 11.97 (1H, s, NH); $^{13}$C nmr (DMSO-d$_6$) (ppm): 20.1 (t), 21.8 (2×q), 26.6 (t), 40.9 (d), 47.9 (t), 97.0 (s), 114.1 (s), 116.6 (s), 120.2 (s), 121.4 (s), 122.7 (s), 125.9 (s), 127.0 (s), 127.9 (2×d), 129.0 (2×d), 129.4 (2×d), 131.1 (2×d), 131.4 (s), 133.4 (d), 137.9 (d), 140.7 (s), 158.1 (s), 158.7 (s). Anal calcd for $C_{28}H_{25}Br_2N_3O_4S$: C, 51.00; H, 3.82; N, 6.37. Found: C, 51.15; H, 3.74; N, 6.45.

7-(Benzenesulfonyl)-3-bromo-1-[(4-bromophenyl)methyl]-N-cyclopropyl-8-oxo-4,5,8,9-tetrahydro-1H-pyrrolo[3,2-h]quinoline-2-carboxamide PP099). This compound was obtained by reaction of PP098. Yellow solid; yield: 70%; m.p.: 165-166° C.; IR: 3381 (NH), 3319 (NH), 1669 (CO), 1633 (CO) cm$^{-1}$; $^1$H nmr (DMSO-d$_6$) (ppm): 1.05-12 (4H, m, 2×CH$_2$), 2.53-2.56 (2H, m, CH$_2$), 3.36-3.43 (2H, m, CH$_2$), 4.28-4.48 (1H, m, CH), 6.38 (2H, s, CH$_2$), 7.05 (2H, d, J=7.9 Hz, H-2' and H-6'), 7.36 (2H, d, J=7.9 Hz, H-3' and H-5'), 7.50-7.72 (3H, m, H-3", H-4" and H-5"), 8.01 (2H, d, J=7.1 Hz, H-2" and H-6"), 9.11 (2H, s, H-6 and NH), 12.42 (1H, s, NH); $^{13}$C nmr (DMSO-d$_6$) (ppm): 5.70 (2×t), 22.3 (d), 23.1 (t), 26.3 (t), 93.2 (s), 117.4 (s), 120.1 (s), 121.1 (s), 121.3 (s), 123.2 (s), 128.2 (2×d), 129.0 (2×d), 129.1 (2×d), 129.4 (s), 131.1 (2×d), 133.7 (d), 138.0 (d), 141.1 (s), 141.8 (s), 156.2 (s), 159.7 (s), 160.0 (s). Anal calcd for $C_{28}H_{23}Br_2N_3O_4S$: C, 51.16; H, 3.53; N, 6.39. Found: 51.02; H, 3.39; N, 6.51.

General Procedure for the Synthesis of Compounds of Type 9 ($R^1$=COOH) and 12 ($R^1$=COOH)

To a solution of the suitable derivatives of type 9,12 ($R^1$=COOEt) (0.5 mmol) in EtOH (10 mL), KOH (0.42 g, 7.5 mmol) was added and the reaction mixture was heated at reflux for 24 h. After cooling, the solvent was removed under reduced pressure. The residue was added of water and the solution was acidified with HCl 6M. The solid formed was filtered off, dried and recrystallized from ethanol.

7-(Benzenesulfonyl)-1-[(3-methylphenyl)methyl]-8-oxo-4,5,8,9-tetrahydro-1H-pyrrolo[3,2-h]quinoline-2-carboxylic acid (PP090). This compound was obtained by reaction of PP016. Yellow solid; yield: 80%; m.p.: 189-190° C.; IR: 3384 (NH), 3323 (NH), 1702 (CO), 1667 (CO) cm$^{-1}$; $^1$H nmr (DMSO-d$_6$) (ppm): 2.20 (3H, s, CH$_3$), 2.71-2.94 (4H, m, 2×CH$_2$), 6.46 (2H, s, CH$_2$), 6.66 (1H, d, J=7.2 Hz, Ar), 6.82-7.15 (4H, m, H-3 and Ar), 7.62-7.75 (3H, m, H-3", H-4" and H-5"), 7.98 (2H, d, J=6.8 Hz, H-2" and H-6"), 8.17 (1H, s, H-6), 11.98 (1H, s, NH), 12.69 (1H, s, OH); $^{13}$C nmr (DMSO-d$_6$) (ppm): 21.4 (t), 21.5 (q), 27.8 (t), 48.6 (t), 101.5 (s), 116.0 (s), 116.3 (d), 123.1 (s), 123.4 (d), 127.1 (s), 127.2 (d), 127.8 (d), 128.3 (d), 128.7 (2×d), 129.5 (2×d), 130.1 (d), 133.9 (d), 137.6 (s), 137.7 (s), 140.1 (s), 141.2 (s), 141.8 (s), 158.4 (s), 158.8 (s), 162.3 (s). Anal calcd for C$_{26}$H$_{22}$N$_2$O$_5$S: C, 65.81; H, 4.67; N, 5.90. Found: C, 65.66; H, 4.84; N, 6.12.

7-(Benzenesulfonyl)-3-bromo-1-[(3-methylphenyl)methyl]-8-oxo-4,5,8,9-tetrahydro-1H-pyrrolo[3,2-h]quinoline-2-carboxylic acid (PP081). This compound was obtained by reaction of PP028. Yellow solid; yield: 87%; m.p.: 177-178° C.; IR: 3502 (NH), 3302 (OH), 1675 (CO), 1641 (CO) cm$^{-1}$; $^1$H nmr (DMSO-d$_6$) (ppm): 2.15 (3H, s, CH$_3$), 2.65 (2H, t, J=7.5 Hz, CH$_2$), 2.95 (2H, t, J=7.5 Hz, CH$_2$), 6.42 (2H, s, CH$_2$), 6.60 (1H, d, J=7.5 Hz, Ar), 6.79 (1H, s, H-2'), 6.95 (1H, d, J=7.5 Hz, Ar), 7.07 (1H, t, J=7.5 Hz, H-5'), 7.56-7.73 (3H, m, H-3", H-4" and H-5"), 7.94 (2H, d, J=7.6 Hz, H-2" and H-6"), 8.17 (1H, s, H-6), 12.05 (1H, s, NH), 13.23 (1H, s, OH); $^{13}$C nmr (DMSO-d$_6$) (ppm): 20.2 (t), 21.0 (q), 26.5 (t), 48.9 (t), 103.4 (s), 117.8 (s), 122.9 (d), 124.7 (s), 124.8 (s), 126.9 (d), 127.5 (d), 127.9 (2×d), 128.3 (d), 129.0 (2×d), 129.5 (s), 133.5 (d), 137.3 (s), 138.4 (d), 139.1 (s), 140.5 (s), 146.4 (s), 149.8 (s), 157.9 (s), 161.1 (s). Anal calcd for C$_{26}$H$_{21}$BrN$_2$O$_5$S: C, 56.43; H, 3.82; N, 5.06. Found: C, 56.56; H, 3.99; N, 4.87.

7-(Benzenesulfonyl)-1-[(4-methylphenyl)methyl]-8-oxo-4,5,8,9-tetrahydro-1H-pyrrolo[3,2-h]quinoline-2-carboxylic acid (PP078). This compound was obtained by reaction of PP007. Yellow solid; yield: 75%; m.p.: 246-147° C.; IR: 3421 (NH), 3342 (OH), 1709 (CO), 1646 (CO) cm$^{-1}$; $^1$H nmr (DMSO-d$_6$) (ppm): 2.17 (3H, s, CH$_3$), 2.69-2.72 (2H, m, CH$_2$), 2.85-2.88 (2H, m, CH$_2$), 6.39 (2H, s, CH$_2$), 6.67-6.83 (3H, m, H-3, H-3' and H-5'), 6.98 (2H, d, J=7.9 Hz, H-2' and H-6'), 7.56-7.73 (3H, m, H-3", H-4" and H-5"), 7.93 (2H, d, J=7.5 Hz, H-2" and H-6"), 8.11 (1H, s, H-6), 11.89 (1H, s, OH), 12.01 (1H, s, NH); $^{13}$C nmr (DMSO-d$_6$) (ppm): 20.5 (q), 20.9 (t), 27.2 (t), 47.8 (t), 115.8 (d), 122.5 (s), 126.0 (2×d), 127.8 (2×d), 128.8 (2×d), 129.0 (2×d), 131.8 (s), 132.1 (s), 133.4 (d), 133.8 (s), 134.2 (s), 136.9 (s), 137.9 (d), 140.2 (s), 143.4 (s), 148.0 (s), 158.7 (s), 162.6 (s). Anal calcd for C$_{26}$H$_{22}$N$_2$O$_5$S: C, 65.81; H, 4.67; N, 5.90. Found: C, 65.97; H, 4.75; N, 5.71.

7-(Benzenesulfonyl)-3-bromo-1-[(4-methylphenyl)methyl]-8-oxo-4,5,8,9-tetrahydro-1H-pyrrolo[3,2-h]quinoline-2-carboxylic acid (PP079). This compound was obtained by reaction of PP008. Yellow solid; yield: 75%; m.p.: 164-165° C.; IR: 3450 (NH), 3336 (OH), 1662 (CO), 1657 (CO) cm$^{-1}$; $^1$H nmr (DMSO-d$_6$) (ppm): 2.14 (3H, s, CH$_3$), 2.51-2.63 (2H, m, CH$_2$), 2.73-2.76 (2H, m, CH$_2$), 6.46 (2H, s, CH$_2$), 6.85-6.99 (4H, m, H-2', H-3', H-5' and H-6'), 7.50-7.63 (3H, m, H-3", H-4" and H-5"), 7.93-7.96 (3H, m, H-6, H-2" and H-6"), 11.87 (1H, s, OH), 12.09 (1H, s, NH); $^{13}$C nmr (DMSO-d$_6$) (ppm): 20.6 (q), 20.7 (t), 26.9 (t), 48.1 (t), 103.6 (s), 122.6 (s), 126.6 (2×d), 127.6 (2×d), 128.5 (2×d), 128.6 (2×d), 132.8 (d), 133.3 (s), 133.8 (s), 134.1 (s), 137.3 (d), 138.9 (s), 140.1 (s), 141.3 (s), 143.7 (s), 146.1 (s), 158.5 (s), 160.5 (s). Anal calcd per C$_{26}$H$_{21}$BrN$_2$O$_5$S: C, 56.43; H, 3.82; N, 5.06. Found: C, 56.29; H, 3.71; N, 5.14.

7-(Benzenesulfonyl)-1-[(3,4-dimethylphenyl)methyl]-8-oxo-4,5,8,9-tetrahydro-1H-pyrrolo[3,2-h]quinoline-2-carboxylic acid (PP094). This compound was obtained by reaction of PP025. Yellow solid; yield: 72%; m.p.: 260-261° C.; IR: 3318 (NH), 3193 (OH), 1709 (CO), 1645 (CO) cm$^{-1}$; $^1$H nmr (DMSO-d$_6$) (ppm): 2.03 (3H, s, CH$_3$), 2.06 (3H, s, CH$_3$), 2.68 (2H, t, J=6.5 Hz, CH$_2$), 2.87 (2H, t, J=6.5 Hz, CH$_2$), 6.36 (2H, s, CH$_2$), 6.54 (1H, d, J=7.6 Hz, H-6'), 6.74 (1H, s, H-3), 6.83 (1H, s, H-2'), 6.90 (1H, d, J=7.6 Hz, H-5'), 7.56-7.68 (3H, m, H-3", H-4" and H-5"), 7.93 (2H, d, J=7.3 Hz, H-2" and H-6"), 8.12 (1H, s, H-6), 11.94 (1H, s, NH), 12.51 (1H, s, OH); $^{13}$C nmr (DMSO-d$_6$) (ppm): 18.9 (q), 19.5 (q), 20.9 (t), 27.3 (t), 47.8 (t), 115.8 (d), 117.0 (s), 123.2 (d), 123.6 (s), 126.5 (s), 127.3 (d), 127.4 (s), 127.8 (2×d), 129.0 (2×d), 129.3 (d), 130.4 (s), 133.4 (d), 134.4 (s), 135.7 (s), 137.0 (s), 138.0 (d), 140.7 (s), 150.5 (s), 157.8 (s), 161.8 (s). Anal calcd for C$_{27}$H$_{24}$N$_2$O$_5$S: C, 66.38; H, 4.95; N, 5.73. Found: C, 66.22; H, 5.07; N, 5.88.

7-(Benzenesulfonyl)-3-bromo-1-[(3,4-dimethylphenyl)methyl]-8-oxo-4,5,8,9-tetrahydro-1H-pyrrolo[3,2-h]quinoline-2-carboxylic acid (PP095). This compound was obtained by reaction of PP037. Dark yellow solid; yield: 77%; m.p.: 249-150° C.; IR: 3485 (NH), 3365 (OH), 11653 (CO), 1648 (CO) cm$^{-1}$; $^1$H nmr (DMSO-d$_6$) (ppm): 1.99 (3H, s, CH$_3$), 2.03 (3H, s, CH$_3$), 2.42-2.51 (2H, m, CH$_2$), 2.68-71 (2H, m, CH$_2$), 6.32 (2H, s, CH$_2$), 6.63 (1H, d, J=7.6 Hz, H-6'), 6.79-6.84 (2H, m, H-2' and H-5'), 7.51-7.63 (3H, m, H-3", H-4" and H-5"), 7.81 (1H, s, H-6), 7.92 (2H, d, J=7.3 Hz, H-2" and H-6"), 11.91 (1H, s, NH), 12.54 (1H, s, OH); $^{13}$C nmr (DMSO-d$_6$) (ppm): 19.3 (q), 19.9 (q), 21.3 (t), 27.5 (t), 48.4 (t), 97.6 (s), 110.8 (s), 115.2 (d), 124.5 (d), 125.9 (s), 127.6 (s), 127.9 (2×d), 128.5 (d), 129.1 (2×d), 129.5 (d), 133.2 (d), 134.5 (s), 135.6 (s), 135.8 (s), 137.6 (d), 138.3 (s), 142.2 (s), 152.0 (s), 163.4 (s), 163.8 (s). Anal calcd for C$_{27}$H$_{23}$BrN$_2$O$_5$S: C, 57.15; H, 4.09; N, 4.94. Found: C, 57.00; H, 4.26; N, 5.09.

General Procedure for the Synthesis of Compounds of Type 9 (R$^1$=CONHR$^4$) and 12 (R$^1$=CONHR$^4$)

To a suspension of the suitable acid derivatives 9,12 (R$^1$=COOH) (0.19 mmol) in anhydrous DMF (3 mL) N,N-diisopropylethylamine (0.19 mL, 1.09 mmol), 1-hydroxybenzotriazole hydrate (0.04 g, 0.30 mmol), and EDC (0.05 g, 0.28 mmol) were added. The reaction mixture was stirred at room temperature for 10 min. Then the proper amine (0.76 mmol) was added in one portion, and the resulting suspension was stirred at room temperature for 16 h. Then the reaction mixture was poured onto crushed ice and the solid formed was filtered off, dried and recrystallized from ethanol.

7-(Benzenesulfonyl)-1-[(3-methylphenyl)methyl]-8-oxo-4,5,8,9-tetrahydro-1H-pyrrolo[3,2-h]quinoline-2-carboxamide (PP093). This compound was obtained by reaction of PP090 with ammonium carbonate. Yellow solid; yield: 54%; m.p.: 269-270° C.; IR: 3421 (NH), 3342-3313 (NH$_2$), 1657 (CO), 1637 (CO) cm$^{-1}$; $^1$H nmr (DMSO-d$_6$) (ppm): 2.13 (3H, s, CH$_3$), 2.66 (2H, t, J=6.5 Hz, CH$_2$), 2.85 (2H, t, J=6.5 Hz, CH$_2$), 6.42 (2H, s, CH$_2$), 6.64 (1H, d, J=7.4 Hz, Ar), 6.77 (2H, s, H-3 and H-2'), 6.90 (1H, d, J=7.4 Hz, Ar), 7.03 (1H, t, J=7.4 Hz, H-5'), 7.56-7.74 (5H, m, H-3", H-4", H-5" and NH$_2$), 7.92 (2H, d, J=6.9 Hz, H-2" and H-6"), 8.07 (1H, s, H-6), 11.79 (1H, s, NH); $^{13}$C nmr (DMSO-d$_6$) (ppm): 21.5 (q), 21.6 (t), 27.9 (t), 48.3 (t), 110.0 (s), 116.7 (s), 112.4 (d), 123.7 (d), 127.5 (d), 127.7 (d), 128.0 (s), 128.3 (2×d), 128.5 (d), 129.2 (s), 129.4 (2×d), 130.7 (s), 132.0 (d), 133.8 (d), 137.5 (s), 140.5 (s), 141.4 (s), 151.5 (s), 158.4 (s), 163.4 (s). Anal calcd for C$_{26}$H$_{23}$N$_3$O$_4$S: C, 65.94; H, 4.90; N, 8.87. Found: C, 65.81; H, 5.04; N, 9.03.

7-(Benzenesulfonyl)-1-[(3-methylphenyl)methyl]-8-oxo-4,5,8,9-tetrahydro-1H-pyrrolo[3,2-h]quinoline-2-carboxamide (PP082). This compound was obtained by reaction of PP081 with ammonium carbonate. White solid; yield: 51%; m.p.: 253-254° C.; IR: 3502 (NH), 3387-3365 (NH$_2$), 1658 (CO), 1649 (CO) cm$^{-1}$; $^1$H nmr (DMSO-d$_6$) (ppm): 2.15 (3H, s, CH$_3$), 2.56-2.64 (2H, m, CH$_2$), 2.86-2.93 (2H, m, CH$_2$), 6.11 (2H, s, CH$_2$), 6.74-7.11 (4H, m, H-2', H-4', H-5' and H-6'), 7.56-7.78 (7H, m, H-3", H-4", H-5" and NH$_2$), 7.94 (2H, d, J=6.8 Hz, H-2" and H-6"), 8.06 (1H, s, H-6), 11.93 (1H, s, NH); $^{13}$C nmr (DMSO-d$_6$) (ppm): 21.3 (q), 24.1 (t), 26.7 (t), 48.6 (t), 108.8 (s), 122.7 (s), 125.2 (d), 127.9 (d), 128.0 (d), 128.8 (2×d), 128.4 (d), 128.6 (s), 129.4 (2×d), 133.6 (d), 134.2 (s), 137.5 (d), 137.9 (s), 138.8 (s), 140.0 (s), 141.1 (s), 143.5 (s), 146.7 (s), 158.4 (s), 163.0 (s). Anal calcd per C$_{26}$H$_{22}$BrN$_3$O$_4$S: C, 56.53; H, 4.01; N, 7.61. Trovato: C, 56.41; H, 4.14; N, 7.50.

7-(Benzenesulfonyl)-3-bromo-1-[(4-methylphenyl) methyl]-8-oxo-4,5,8,9-tetrahydro-1H-pyrrolo[3,2-h]quinoline-2-carboxamide (PP080). This compound was obtained by reaction of PP078 with ammonium carbonate. Dark yellow solid; yield: 50%; m.p.: 138-139° C.; IR: 3393 (NH), 3345-3307 (NH$_2$), 1667 (CO), 1655 (CO) cm$^{-1}$; $^1$H nmr (DMSO-d$_6$) (ppm): 2.16 (3H, s, CH$_3$), 2.67-2.72 (2H, m, CH$_2$), 2.82-3.06 (2H, m, CH$_2$), 6.40 (2H, s, CH$_2$), 6.77-6.83 (3H, m, H-3, H-3' and H-5'), 6.96 (2H, d, J=7.9 Hz, H-2' and H-6'), 7.20 (2H, s, NH$_2$), 7.56-7.73 (3H, m, H-3", H-4" and H-5"), 7.92 (2H, d, J=7.0 Hz, H-2" and H-6"), 8.06 (1H, s, H-6), 11.81 (1H, s, NH); $^{13}$C nmr (DMSO-d$_6$) (ppm): 21.0 (t), 21.6 (q), 27.8 (t), 48.0 (t), 102.7 (s), 109.3 (s), 112.4 (d), 126.7 (2×d), 128.1 (s), 128.2 (2×d), 129.2 (2×d), 129.5 (2×d), 130.6 (s), 130.7 (s), 133.8 (d), 138.3 (d), 136.1 (s), 137.5 (s), 141.3 (s), 156.3 (s), 158.3 (s), 163.4 (s). Anal calcd for C$_{26}$H$_{23}$N$_3$O$_4$S: C, 65.94; H, 4.90; N, 8.87. Found: C, 65.82; H, 5.01; N, 8.74.

7-(Benzenesulfonyl)-3-bromo-1-[(4-methylphenyl) methyl]-8-oxo-4,5,8,9-tetrahydro-1H-pyrrolo[3,2-h]quinoline-2-carboxamide (PP089). This compound was obtained by reaction of PP079 with ammonium carbonate. Green solid; yield: 52%; m.p.: 218-219° C.; IR: 3609 (NH), 3583-3567 (NH$_2$), 1709 (CO), 1651 (CO) cm$^{-1}$; $^1$H nmr (DMSO-d$_6$) (ppm): 2.11 (3H, s, CH$_3$), 2.44-2.56 (2H, m, CH$_2$), 2.77-2.82 (2H, m, CH$_2$), 6.02 (2H, s, CH$_2$), 6.84 (2H, d, J=8.0 Hz, H-3' e H-5'), 6.92 (2H, d, J=8.0 Hz, H-2' e H-6'), 7.53-7.73 (5H, m, H-3", H-4", H-5" e NH$_2$), 7.87 (2H, d, J=6.1 Hz, H-2" e H-6"), 8.03 (1H, s, H-6), 11.84 (1H, s, NH); $^{13}$C nmr (DMSO-d$_6$) (ppm): 20.6 (q), 26.8 (t), 29.3 (t), 40.4 (d), 48.2 (t), 97.3 (s), 117.3 (s), 122.9 (s), 125.0 (s), 126.7 (2×d), 127.8 (2×d), 128.8 (2×d), 129.0 (2×d), 131.2 (s), 133.7 (d), 135.8 (s), 136.4 (d), 140.7 (s), 141.1 (s), 145.9 (s), 158.5 (s), 159.7 (s), 162.0 (s). Anal calcd per C$_{26}$H$_{22}$BrN$_3$O$_4$S: C, 56.53; H, 4.01; N, 7.61. Found: C, 56.38; H, 4.31; N, 7.46.

N,7-di(benzenesulfonyl)-3-bromo-1-[(3-methylphenyl) methyl]-8-oxo-4,5,8,9-tetrahydro-JH-pyrrolo[3,2-h]quinoline-2-carboxamide (PP100). This compound was obtained by reaction of PP081 with benzenesulfonamide. Yellow solid; yield: 56%; m.p.: 122-123° C.; IR: 3610 (NH), 3588 (NH), 1680 (CO), 1652 (CO) cm$^{-1}$; $^1$H nmr (DMSO-d$_6$) (ppm): 2.08 (3H, s, CH$_3$), 2.61 (2H, t, J=6.5 Hz, CH$_2$), 2.91 (2H, t, J=6.5 Hz, CH$_2$), 6.97 (2H, s, CH$_2$), 6.51 (1H, d, J=6.8 Hz, Ar), 6.65 (1H, s, Ar), 6.93 (2H, d, J=6.1 Hz, Ar), 7.53-7.70 (6H, m, Ar), 7.86-7.94 (5H, m, Ar and NH), 8.15 (1H, s, H-6), 12.01 (1H, s, NH); $^{13}$C nmr (DMSO-d$_6$) (ppm): 20.5 (q), 21.4 (t), 27.00 (t), 48.6 (t), 105.3 (s), 124.1 (s), 124.0 (d), 126.0 (s), 126.5 (s), 127.6 (s), 127.7 (s), 127.8 (2×d), 127.9 (d), 128.3 (d), 128.4 (2×d), 128.5 (s), 128.6 (d), 128.7 (d), 129.4 (2×d), 129.5 (2×d), 133.8 (s), 133.9 (s), 134.0 (d), 137.9 (d), 138.4 (s), 138.8 (s), 141.1 (s), 158.4 (s). Anal calcd for C$_{32}$H$_{26}$BrN$_3$O$_6$S$_2$: C, 55.49; H, 3.78; N, 6.07. Found: C, 55.61; H, 3.63; N, 6.19.

7-(Benzenesulfonyl)-3-bromo-N-tert-butyl-1-[(3-methylphenyl)methyl]-8-oxo-4,5,8,9-tetrahydro-1H-pyrrolo[3,2-h]quinoline-2-carboxamide (PP101). This compound was obtained by reaction of PP081 with t-butylamine. White solid; yield: 59%; m.p.: 216-217° C.; IR: 3381 (NH), 3315 (NH), 1700 (CO), 1684 (CO) cm$^{-1}$; $^1$H nmr (DMSO-d$_6$) (ppm): 1.28 (9H, s, 3×CH$_3$), 2.16 (3H, s, CH$_3$), 2.59 (2H, t, J=6.3 Hz, CH$_2$), 2.88 (2H, t, J=6.3 Hz, CH$_2$), 6.04 (2H, s, CH$_2$), 6.89-7.09 (4H, m, H-2', H-4', H-5' and H-6'), 7.53-7.69 (3H, m, H-3", H-4" and H-5"), 7.93-7.99 (3H, m, H-2", H-6" and NH), 8.10 (1H, s, H-6), 11.91 (1H, s, NH); $^{13}$C nmr (DMSO-d$_6$) (ppm): 20.7 (q), 21.4 (t), 27.2 (t), 28.7 (3×q), 48.7 (t), 55.4 (s), 97.4 (s), 111.0 (s), 117.0 (s), 123.3 (s), 125.0 (d), 127.5 (d), 128.2 (d), 128.3 (2×d), 128.6 (d), 128.7 (s), 129.5 (2×d), 132.6 (s), 133.8 (d), 137.7 (d), 138.3 (s), 138.8 (s), 141.3 (s), 151.0 (s), 158.5 (s), 159.9 (s). Anal calcd for C$_{30}$H$_{30}$BrN$_3$O$_4$S: C, 59.21; H, 4.97; N, 6.91. Found: C, 65.81; H, 5.04; N, 9.03.

7-(Benzenesulfonyl)-3-bromo-N-(5-tert-butyl-1,2-oxazol-3-yl)-1-[(3-methylphenyl)methyl]-8-oxo-4,5,8,9-tetrahydro-1H-pyrrolo[3,2-h]quinoline-2-carboxamide (PP102). This compound was obtained by reaction of PP081 with 5-tert-butylisoxazol-3-amine. White solid; yield: 50%; m.p.: 202-203° C.; IR: 3353 (NH), 3289 (NH), 1695 (CO), 1677 (CO) cm$^{-1}$; $^1$H nmr (DMSO-d$_6$) (ppm): 1.23 (9H, s, 3×CH$_3$), 2.20 (3H, s, CH$_3$), 2.62 (2H, t, J=6.5 Hz, CH$_2$), 2.94 (2H, t, J=6.5 Hz, CH$_2$), 6.14 (2H, s, CH$_2$), 6.80-6.86 (2H, m, Ar), 7.00-7.15 (2H, m, Ar), 7.58-7.69 (4H, m, H-3", H-4", H-5" and CH-isoxazole), 7.93-7.95 (3H, m, H-2", H-6" and NH), 8.14 (1H, s, H-6), 11.88 (1H, s, NH); $^{13}$C nmr (DMSO-d$_6$) (ppm): 20.4 (q), 21.4 (t), 27.1 (t), 29.5 (3×q), 36.3 (s), 49.3 (t), 96.2 (s), 101.6 (d), 117.0 (s), 123.1 (s), 125.0 (d), 126.6 (s), 126.9 (s), 128.3 (2×d), 128.4 (d), 128.5 (d), 128.8 (d), 129.5 (2×d), 131.1 (s), 133.8 (d), 137.7 (s), 137.9 (d), 138.3 (s), 138.6 (s), 141.3 (s), 151.0 (s), 158.5 (s), 161.8 (s), 162.8 (s). Anal calcd for C$_{33}$H$_{31}$BrN$_4$O$_5$S: C, 58.67; H, 4.63; N, 8.29. Found: C, 58.81; H, 4.49; N, 8.41.

General Procedure for the Synthesis of Compound of Type 13

To a solution of the suitable tricyclic derivatives of type 9 (0.22 mmol) in anhydrous DMF (20 mL), potassium hydroxide was added and the reaction mixture was stirred at room temperature. After 15 min. iodine (0.056 g, 0.22 mmol) was added and the reaction mixture was heated at 40° C. for 24 h. After cooling, the reaction mixture was poured onto crushed ice. The precipitate was filtered off, dried and purified by chromatography (DCM).

Ethyl 1-(4-methylbenzyl)-8-oxo-7-(phenylsulfonyl)-8,9-dihydro-1H-pyrrolo[3,2-h]quinoline-2-carboxylate (13, PP058). This product was obtained by reaction of PP007. Dark yellow solid; yield: 50%; m.p.: 197-198° C.; IR: 3348 (NH), 1713 (CO), 1669 (CO) cm$^{-1}$; $^1$H nmr (CDCl$_3$) (ppm): 1.39 (2H, t, J=7.1 Hz, CH$_3$), 2.31 (3H, s, CH$_3$), 4.38 (2H, q, J=7.1 Hz, CH$_2$), 6.10 (2H, s, CH$_2$), 7.04 (2H, d, J=7.9 Hz, H-2' and H-6'), 7.19 (2H, d, J=7.9 Hz, H-3' and H-5'), 7.28 (1H, s, H-7), 7.39-7.59 (6H, m, Ar), 8.10-8.13 (2H, m, Ar), 9.10 (1H, s, NH); $^{13}$C nmr (CDCl$_3$) (ppm): 14.2 (q), 21.2 (q), 49.8 (t), 61.5 (t), 111.9 (d), 115.2 (s), 118.5 (d), 122.9 (d), 125.4 (s), 125.6 (2×d), 128.4 (s), 128.8 (2×d), 129.1 (2×d), 130.0 (s), 130.8 (2×d), 131.0 (s), 131.8 (s), 132.5 (s), 133.6 (d), 138.7 (s), 139.5 (s), 145.5 (d), 156.3 (s), 161.1 (s). Anal calcd for C$_{28}$H$_{24}$N$_2$O$_5$S: C, 67.18; H, 4.83; N, 5.60. Found: C, 67.30; H, 4.71; N, 5.49.

The following additional compounds were prepared according to synthetic schemes 1 and 2 (PP001-7, 9-13, 26, 38-47, 49-54), as reported in Barraja P, et al. Bioorg Med Chem 2010, 18, 4830-4843; Spanò V, et al. Eur J Med Chem 2017, 128, 300-318.

| CPD | R | R$^1$ | R$^2$ | R$^3$ | n |
|---|---|---|---|---|---|
| PP001(#) | SO$_2$Ph | H | — | SO$_2$Ph | 1 |
| PP002(#) | H | H | — | SO$_2$Ph | 1 |
| PP003(#) | SO$_2$Ph | H | — | CN | 1 |
| PP004(#) | Me | H | — | SO$_2$Ph | 1 |
| PP005(#) | Bn | H | — | SO$_2$Ph | 1 |
| PP006(#) | Ph | H | — | SO$_2$Ph | 1 |
| PP007(#) | 4-MeBn | COOEt | — | SO$_2$Ph | 1 |
| PP009(#) | H | COOEt | — | SO$_2$Ph | 1 |
| PP010(#) | Me | COOEt | — | SO$_2$Ph | 1 |
| PP011(#) | Bn | COOEt | — | SO$_2$Ph | 1 |
| PP012(#) | 4-MeBn | H | — | SO$_2$Ph | 1 |
| PP013(#) | 4-MeOBn | COOEt | — | SO$_2$Ph | 1 |
| PP026(#) | 4-MeOBn | H | — | SO$_2$Ph | 1 |
| PP038(#) | Me | H | — | SO$_2$Ph | 2 |
| PP039(#) | Bn | H | — | SO$_2$Ph | 2 |
| PP040(#) | 2-OMeBn | H | — | SO$_2$Ph | 2 |
| PP041(#) | 3-OMeBn | H | — | SO$_2$Ph | 2 |
| PP042(#) | 4-OMeBn | H | — | SO$_2$Ph | 2 |
| PP043(#) | Me | COOEt | — | SO$_2$Ph | 2 |
| PP044(#) | Bn | COOEt | — | SO$_2$Ph | 2 |
| PP045(#) | 2-OMeBn | COOEt | — | SO$_2$Ph | 2 |
| PP046(#) | 3-OMeBn | COOEt | — | SO$_2$Ph | 2 |
| PP047(#) | 4-OMeBn | COOEt | — | SO$_2$Ph | 2 |
| PP049(§) | Me | H | — | SO$_2$Ph | 2 |
| PP050(§) | Me | COOEt | — | SO$_2$Ph | 2 |
| PP051(*) | Me | H | — | SO$_2$Ph | 2 |
| PP052(*) | 4-OMeBn | H | — | SO$_2$Ph | 2 |
| PP053(*) | Me | COOEt | — | SO$_2$Ph | 2 |
| PP054(*) | 4-OMeBn | COOEt | — | SO$_2$Ph | 2 |

(#)Compounds of formula 9 in Scheme 2;
(§)Compounds of formula 10 in Scheme 2;
(*)Compounds of formula 11 in Scheme 2;
(ˆ) Compounds of formula 12 in Scheme 2

Scheme 3 describes the general synthesis of pyrrolo[3,2-h]quinazolines of formulas 15-18, as reported in Table 3. The synthetic procedure of Scheme 3 is particularly preferred for compounds where R$^1$ is an ester such as COOEt and R$^2$ is a halogen atom such as Br. Annelation of the pyrimidine ring to the cyclohexapyrrole scaffold bearing the decoration of the best candidates of type 9 was achieved by reacting the enaminoketones 8 with guanidine nitrate in the presence of sodium methoxide (MeONa) as the base, to obtain the 2-amino substituted pyrrolo[3,2-h]quinazolines 15 (Scheme 3). The latter were sulphonylated at the amino group generating compounds 16. Both 15 and 16 were then brominated at the pyrrole ring furnishing the corresponding bromo derivatives 17 and 18 (Scheme 3).

Scheme 3. Synthesis of pyrrolo[3,2-h]quinazolines.

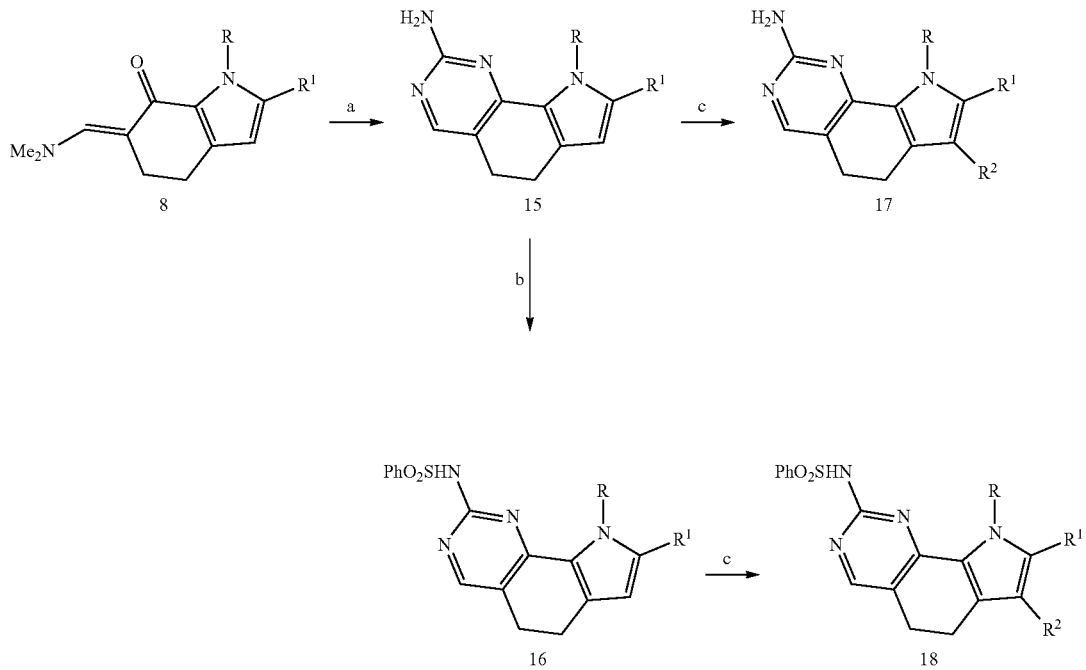

(a) guanidine nitrate, MeONa, ethanol, reflux; (b) benzenesulfonyl chloride, pyridine, r.t., 24 h; (c) Br$_2$ (1:2), DMF, r.t., 16 h.

The derivatives reported in Table 3 below are exemplary compounds that may be prepared according to the synthetic procedure of Scheme 3. Relative additivity indeces (AI %), which were measured as described in the Materials and Methods section, are also reported.

TABLE 3

Pyrrolo[3,2-h]quinazolines of formula:

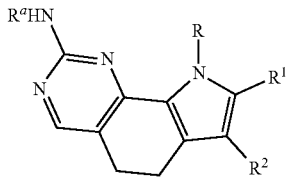

| CPD | R | $R^1$ | $R^2$ | $R^a$ | $AI^a$ |
|---|---|---|---|---|---|
| SVQ4 | 3-MeBn | COOEt | Br | H | 4% |
| SVQ9 | 4-MeBn | COOEt | H | $SO_2Ph$ | 98% |
| SVQ10 | 4-MeBn | COOEt | Br | $SO_2Ph$ | 134% |
| SVQ11 | 3-MeBn | COOEt | H | $SO_2Ph$ | 151% |
| SVQ12 | 3-MeBn | COOEt | Br | $SO_2Ph$ | 152% |
| SVQ13 | 3,4-$(Me)_2$Bn | COOEt | H | $SO_2Ph$ | 86% |
| SVQ14 | 3,4-$(Me)_2$Bn | COOEt | Br | $SO_2Ph$ | 128% |
| SVQ15 | 4-BrBn | COOEt | H | $SO_2Ph$ | 100% |
| SVQ16 | 4-BrBn | COOEt | Br | $SO_2Ph$ | 98% |

$^a$Activity of compounds (at 10 μM) was expressed as additivity index (AI %) which is calculated as $(QR_{TOT}\text{-}QR_{VX})/QR_{VX}$ where $QR_{TOT}$ is the quenching rate (HS-YFP assay) in the presence of test compound plus VX-809 and $QR_{VX}$ is the quenching rate with VX-809 alone).

A detailed description of the synthesis of exemplary compounds produced according to Scheme 3 is provided hereinbelow.

General Procedure for the Synthesis of Compounds of Type 15

To a suspension of MeONa (1.08 g, 20 mmol) in anhydrous ethanol (15 mL), guanidine nitrate (1.22 g, 10 mmol) and a solution of the suitable enaminoketons of type 8 (2 mmol) in anhydrous ethanol (20 mL) were added. The reaction mixture was heated at reflux up to completeness. Then the reaction mixture was poured onto crushed ice and the precipitate was filtered off, dried and purified by chromatography (DCM/AcOEt 9:1).

Ethyl 2-amino-9-[(4-methylphenyl)methyl]-6,9-dihydro-5H-pyrrolo[3,2-h]quinazoline-8-carboxylate (SVQ1). This compound was obtained by reaction of ethyl 6-[(dimethylamino)methylidene]-1-(4-methylbenzyl)-7-oxo-4,5,6,7-tetrahydro-1H-indole-2-carboxylate after 6 h. White solid; yield: 85%; m.p.: 171-172° C.; IR: 3416-3313 ($NH_2$), 1699 (CO) $cm^{-1}$; $^1H$ nmr (DMSO-$d_6$) (ppm): 1.23 (3H, t, J=7.1 Hz, $CH_3$), 2.20 (3H, s, $CH_3$), 2.64 (4H, s, 2×$CH_2$), 4.18 (2H, q, J=7.1 Hz, $CH_2$), 6.37-6.43 (4H, m, $CH_2$ and $NH_2$), 6.84 (1H, s, H-3), 6.90 (2H, d, J=8.0 Hz, H-3' and H-5'), 7.03 (2H, d, J=8.0 Hz, H-2' and H-6'), 8.05 (1H, s, H-6); $^{13}C$ nmr (DMSO-$d_6$) (ppm): 14.1 (q), 20.5 (q), 21.1 (t), 24.3 (t), 48.1 (t), 59.8 (t), 115.8 (d), 116.5 (s), 125.0 (s), 126.3 (2×d), 127.3 (s), 128.8 (2×d), 130.5 (s), 135.8 (s), 136.5 (s), 154.7 (s), 156.0 (d), 160.2 (s), 161.9 (s). Anal calcd for $C_{21}H_{22}N_4O_2$: C, 69.59; H, 6.12; N, 15.46. Found: C, 69.78; H, 6.01; N, 15.32.

Ethyl 2-amino-9-[(3-methylphenyl)methyl]-6,9-dihydro-5H-pyrrolo[3,2-h]quinazoline-8-carboxylate (SVQ3). This compound was obtained by reaction of ethyl 6-[(dimethylamino)methylidene]-1-(3-methylbenzyl)-7-oxo-4,5,6,7-tetrahydro-1H-indole-2-carboxylate after 3 h. Brown solid; yield: 92%; m.p.: 149-150° C.; IR: 3461-3416 ($NH_2$), 1697 (CO) $cm^{-1}$; $^1H$ nmr (DMSO-$d_6$) (ppm): 1.23 (3H, t, J=7.0 Hz, $CH_3$), 2.20 (3H, s, $CH_3$), 2.65 (4H, s, 2×$CH_2$), 4.18 (2H, q, J=7.0 Hz, $CH_2$), 6.42 (4H, s, $CH_2$ and $NH_2$), 6.69-7.14 (5H, m, H-3, H-2', H-4', H-5' and H-6'), 8.05 (1H, s, H-6); $^{13}C$ nmr (DMSO-$d_6$) (ppm): 14.1 (q), 21.0 (q), 21.1 (t), 24.3 (t), 48.4 (t), 59.8 (t), 115.9 (d), 123.2 (d), 125.0 (s), 126.9 (d), 127.2 (s), 127.3 (d), 128.2 (d), 130.7 (s), 137.1 (s), 139.5 (s), 154.7 (s), 156.2 (d), 160.4 (s), 162.1 (s). Anal calcd for $C_{21}H_{22}N_4O_2$: C, 69.59; H, 6.12; N, 15.46. Found: C, 69.46; H, 6.24; N, 15.32.

Ethyl 2-amino-9-[(3,4-dimethylphenyl)methyl]-6,9-dihydro-5H-pyrrolo[3,2-h]quinazoline-8-carboxylate (SVQ5). This compound was obtained by reaction of ethyl 6-[(dimethylamino)methylidene]-1-[(3,4-dimethylphenyl)methyl]-7-oxo-4,5,6,7-tetrahydro-1H-indole-2-carboxylate after 2 h. White solid; yield: 82%; m.p.: 157-158° C.; IR: 3513-3410 ($NH_2$), 1703 (CO) $cm^{-1}$; $^1H$ nmr (DMSO-$d_6$) (ppm): 1.24 (3H, t, J=7.0 Hz, $CH_3$), 2.10 (6H, s, 2×$CH_3$), 2.64 (4H, s, 2×$CH_2$), 4.19 (2H, q, J=7.0 Hz, $CH_2$), 6.38-6.42 (4H, m, $CH_2$ e $NH_2$), 6.65 (1H, d, J=7.6 Hz, H-6'), 6.79 (1H, s, H-2'), 6.83 (1H, s, H-3), 6.96 (1H, d, J=6.5 Hz, H-5'), 8.05 (1H, s, H-6); $^{13}C$ nmr (DMSO-$d_6$) (ppm): 14.1 (q), 18.9 (q), 19.5 (q), 20.1 (t), 24.3 (t), 48.1 (t), 59.8 (t), 115.8 (d), 116.4 (s), 123.6 (d), 124.9 (s), 127.1 (d), 127.6 (s), 129.3 (d), 130.6 (s), 134.5 (s), 135.7 (s), 136.8 (s), 154.6 (s), 156.1 (d), 160.2 (s), 161.9 (s). Anal calcd for $C_{22}H_{24}N_4O_2$: C, 70.19; H, 6.43; N, 14.88. Found: C, 70.07; H, 6.56; N, 15.01.

Ethyl 2-amino-9-[(4-bromophenyl)methyl]-6,9-dihydro-5H-pyrrolo[3,2-h]quinazoline-8-carboxylate (SVQ7). This compound was obtained by reaction of ethyl 1-[(4-bromophenyl)methyl]-6-[(dimethylamino)methylidene]-7-oxo-4,5,6,7-tetrahydro-1H-indole-2-carboxylate after 5 h. White solid; yield: 74%; m.p.: 168-169° C.; IR: 3513-3410 ($NH_2$), 1697 (CO) $cm^{-1}$; $^1H$ nmr (DMSO-$d_6$) (ppm): 1.23 (3H, t, J=7.0 Hz, $CH_3$), 2.66 (4H, s, 2×$CH_2$), 4.18 (2H, q, J=7.0 Hz, $CH_2$), 6.35-6.42 (4H, m, $CH_2$ and $NH_2$), 6.87 (1H, s, H-3), 6.98 (2H, d, J=8.3 Hz, H-2' and H-6'), 7.44 (2H, d, J=8.3 Hz, H-3' and H-5'), 8.06 (1H, s, H-6); $^{13}C$ nmr (DMSO-$d_6$) (ppm): 14.1 (q), 21.1 (t), 24.3 (t), 48.1 (t), 59.9 (t), 115.9 (d), 116.5 (s), 119.8 (s), 124.8 (s), 127.4 (s), 128.6 (2×d), 130.4 (s), 131.1 (2×d), 138.9 (s), 154.4 (s), 156.2 (d), 160.1 (s), 161.9 (s). Anal calcd for $C_{20}H_{19}BrN_4O_2$: C, 56.22; H, 4.48; N, 13.11. Found: C, 56.10; H, 4.51; N, 12.98.

General Procedure for the Synthesis of Compounds of Type 16

To a solution of suitable tricyclic compounds of type 15 (0.67 mmol) in anhydrous pyridine (1.8 mL), benzensulfonyl chloride (0.17 mL, 1.3 mmol) was added and the reaction mixture was stirred at room temperature for 24 h. Then the reaction mixture was poured onto crushed ice and the precipitate was filtered off, dried and purified by chromatography (DCM/AcOEt 95:5).

Ethyl 2-[(benzenesulfonyl)amino]-9-[(4-methylphenyl)methyl]-6,9-dihydro-5H-pyrrolo[3,2-h]quinazoline-8-carboxylate (SVQ9). This compound was obtained by reaction of SVQ1. White solid; yield: 82%; m.p.: 218-219° C.; IR: 3422 (NH), 1709 (CO) $cm^{-1}$; $^1H$ nmr (DMSO-$d_6$) (ppm): 1.22 (3H, t, J=7.1 Hz, $CH_3$), 2.20 (3H, s, $CH_3$), 2.69 (4H, s, 2×$CH_2$), 4.18 (2H, q, J=7.1 Hz, $CH_2$), 6.31 (2H, s, $CH_2$), 6.77-6.84 (3H, m, H-3, H-3' and H-5'), 7.01 (2H, d, J=7.9 Hz, H-2' and H-6'), 7.48-7.56 (3H, m, H-3", H-4" and H-5"), 7.86 (2H, d, J=7.1 Hz, H-2" and H-6"), 8.26 (1H, s, H-6), 11.82 (1H, s, NH); $^{13}C$ nmr (DMSO-$d_6$) (ppm): 14.6 (q), 20.0 (t), 21.5 (q), 24.8 (t), 48.7 (t), 60.5 (t), 116.4 (d), 117.3 (s), 124.0 (s), 125.7 (2×d) 128.0 (2×d), 128.1 (2×d), 129.9 (2×d), 131.0 (d), 135.2 (s), 136.4 (s), 136.5 (s), 137.3 (s), 155.3 (d), 156.4 (s), 160.0 (s), 161.1 (s), 162.2 (s). Anal calcd for $C_{27}H_{26}N_4O_4S$: C, 64.52; H, 5.21; N, 11.15. Found: C, 64.65; H, 5.09; N, 11.02.

Ethyl 2-[(benzenesulfonyl)amino]-9-[(3-methylphenyl)methyl]-6,9-dihydro-5H-pyrrolo[3,2-h]quinazoline-8-carboxylate (SVQ11). This compound was obtained by reaction of SVQ3. Yellow solid; yield: 92%; m.p.: 201-202° C.; IR: 3399 (NH), 1709 (CO) cm$^{-1}$; $^1$H nmr (DMSO-d$_6$) (ppm): 1.21 (3H, t, J=7.0 Hz, CH$_3$), 2.19 (3H, s, CH$_3$), 2.69 (4H, s, 2×CH$_2$), 4.17 (2H, q, J=7.0 Hz, CH$_2$), 6.33 (2H, s, CH$_2$), 6.62 (1H, d, J=7.5 Hz, Ar), 6.78-6.85 (2H, m, H-3 and Ar), 6.94-7.12 (2H, m, Ar), 7.44-7.56 (3H, m, H-3", H-4" and H-5"), 7.81 (2H, d, J=6.5 Hz, H-2" and H-6"), 8.26 (1H, s, H-6), 11.81 (1H, s, NH); $^{13}$C nmr (DMSO-d$_6$) (ppm): 13.0 (q), 20.4 (t), 20.0 (q), 24.2 (t), 48.4 (t), 60.1 (t), 115.9 (d), 122.0 (s), 122.8 (d), 122.9 (s), 126.6 (2×d), 126.7 (d), 127.3 (d), 128.2 (d), 128.9 (2×d), 129.6 (s), 132.6 (d), 137.1 (s), 139.4 (s), 140.2 (s), 140.8 (s), 154.5 (d), 155.1 (s), 155.3 (s), 160.0 (s). Anal calcd for $C_{27}H_{26}N_4O_4S$: C, 64.52; H, 5.21; N, 11.15. Found: C, 64.40; H, 5.33; N, 11.02.

Ethyl 2-[(benzenesulfonyl)amino]-9-[(3,4-dimethylphenyl)methyl]-6,9-dihydro-5H-pyrrolo[3,2-h]quinazoline-8-carboxylate (SVQ13). This compound was obtained by reaction of SVQ5. Pale yellow solid; yield: 73%; m.p.: 239-240° C.; IR: 3371 (NH), 1703 (CO) cm$^{-1}$; $^1$H nmr (DMSO-d$_6$) (ppm): 1.22 (3H, t, J=7.1 Hz, CH$_3$), 2.09 (3H, s, CH$_3$), 2.11 (3H, s, CH$_3$), 2.68 (4H, s, 2×CH$_2$), 4.18 (2H, q, J=7.1 Hz, CH$_2$), 6.29 (2H, s, CH$_2$), 6.53 (1H, d, J=7.5 Hz, H-6'), 6.75 (1H, s, H-3), 6.84 (1H, s, H-2'), 6.94 (1H, d, J=7.5 Hz, H-5'), 7.44-7.56 (3H, m, H-3", H-4" and H-5"), 7.86 (2H, d, J=6.8 Hz, H-2" and H-6"), 8.26 (1H, s, H-6), 11.81 (1H, s, NH); $^{13}$C nmr (DMSO-d$_6$) (ppm): 14.1 (q), 18.9 (q), 19.5 (q), 20.4 (t), 24.3 (t), 48.0 (t), 60.1 (t), 115.9 (d), 121.9 (s), 122.0 (s), 123.2 (d), 126.7 (2×d), 127.4 (d), 128.9 (2×d), 129.3 (d), 129.6 (s), 132.6 (s), 134.5 (s), 135.7 (s), 136.8 (s), 140.8 (s), 153.1 (s), 154.5 (d), 155.1 (s), 155.3 (s), 160.0 (s). Anal calcd for $C_{28}H_{28}N_4O_4S$: C, 65.10; H, 5.46; N, 10.85. Found: C, 65.23; H, 5.32; N, 10.80.

Ethyl 2-[(benzenesulfonyl)amino]-9-[(4-bromophenyl)methyl]-6,9-dihydro-5H-pyrrolo[3,2-h]quinazoline-8-carboxylate (SVQ15). This compound was obtained by reaction of SVQ7. White solid; yield: 79%; m.p.: 208-209° C.; IR: 3399 (NH), 1709 (CO) cm$^{-1}$; $^1$H nmr (DMSO-d$_6$) (ppm): 1.21 (3H, t, J=7.0 Hz, CH$_3$), 2.70 (4H, s, 2×CH$_2$), 4.18 (2H, q, J=7.0 Hz, CH$_2$), 6.31 (2H, s, CH$_2$), 6.77-6.89 (3H, m, H-3 and Ar), 7.41-7.52 (5H, m, Ar), 7.83 (2H, d, J=6.0 Hz, Ar), 8.27 (1H, s, H-6), 11.82 (1H, s, NH); $^{13}$C nmr (DMSO-d$_6$) (ppm): 14.0 (q), 20.4 (t), 24.2 (t), 47.9 (t), 60.2 (t), 116.1 (d), 119.8 (s), 122.0 (s), 122.1 (s), 126.4 (d), 128.6 (2×d), 128.2 (2×d), 128.9 (2×d), 129.4 (s), 131.1 (2×d), 132.6 (d), 138.8 (s), 140.7 (s), 149.0 (s), 155.0 (d), 155.1 (s), 159.8 (s). Anal calcd for $C_{26}H_{23}BrN_4O_4S$: C, 55.03; H, 4.09; N, 9.87. Found: C, 55.26; H, 3.98; N, 9.76.

General Procedure for the Synthesis of Compounds of Type 17 and 18

To a solution of suitable tricyclic compounds of type 15 or 16 (0.22 mmol) in anhydrous DCM (20 ml), Br$_2$ (0.44 mmol, 0.02 mL) was added at 0° C. and the reaction mixture was stirred at room temperature for 24 h. Then the reaction mixture was evaporated under reduced pressure. The crude was purified by chromatography (DCM/AcOEt 95:5).

Ethyl 2-amino-7-bromo-9-[(4-methylphenyl)methyl]-6,9-dihydro-5H-pyrrolo[3,2-h]quinazoline-8-carboxylate (SVQ2). This compound was obtained by reaction of SVQ1. White solid; yield: 87%; m.p.: 140-141° C.; IR: 3608-3586 (NH$_2$), 1664 (CO) cm$^{-1}$; $^1$H nmr (DMSO-d$_6$) (ppm): 1.25 (3H, t, J=7.1 Hz, CH$_3$), 2.21 (3H, s, CH$_3$), 2.60-2.70 (4H, m, 2×CH$_2$), 4.26 (2H, q, J=7.1 Hz, CH$_2$), 6.41 (2H, s, CH$_2$) 6.51 (2H, s, NH$_2$), 6.89 (2H, d, J=8.0 Hz, H-3' and H-5'), 7.05 (2H, d, J=8.0 Hz, H-2' and H-6'), 8.11 (1H, s, H-6); $^{13}$C nmr (DMSO-d$_6$) (ppm): 13.9 (q), 20.4 (t), 20.6 (q), 23.6 (t), 49.0 (t), 60.6 (t), 103.7 (s), 116.5 (s), 123.2 (s), 126.3 (2×d), 126.5 (s), 127.8 (s), 128.9 (2×d), 129.7 (s), 136.0 (s), 153.9 (s), 156.8 (d), 159.5 (s), 161.9 (s). Anal calcd for $C_{21}H_{21}BrN_4O_2$: C, 57.15; H, 4.80; N, 12.70. Found: C, 57.02; H, 4.92; N, 12.57.

Ethyl 2-amino-7-bromo-9-[(3-methylphenyl)methyl]-6,9-dihydro-5H-pyrrolo[3,2-h]quinazoline-8-carboxylate (SVQ4). This compound was obtained by reaction of SVQ3. Yellow solid; yield: 60%; m.p.: 119-120° C.; IR: 3307-3193 (NH$_2$), 1697 (CO)cm$^{-1}$; $^1$H nmr (DMSO-d$_6$) (ppm): 1.23 (3H, t, J=7.0 Hz, CH$_3$), 2.58-2.72 (4H, m, 2×CH$_2$), 4.22 (2H, q, J=7.0 Hz, CH$_2$), 6.43 (2H, s, CH$_2$), 6.49 (2H, s, NH$_2$), 6.71 (1H, d, J=7.6 Hz, Ar), 6.88 (1H, s, H-2'), 7.01 (1H, d, J=7.6 Hz, Ar), 7.12 (1H, t, J=7.6 Hz, H-5'), 8.11 (1H, s, H-6); $^{13}$C nmr (DMSO-d$_6$) (ppm): 14.4 (q), 20.8 (t), 21.5 (q), 24.1 (t), 49.8 (t), 61.0 (t), 104.2 (s), 107.0 (s), 123.7 (d), 123.8 (s), 127.5 (d), 128.1 (d), 128.3 (s), 128.8 (d), 130.2 (s), 137.8 (s), 139.4 (s), 154.5 (d), 157.1 (d), 160.0 (s), 162.4 (s). Anal calcd for $C_{21}H_{21}BrN_4O_2$: C, 57.15; H, 4.80; N, 12.70. Found: C, 57.02; H, 4.93; N, 12.62.

Ethyl 2-amino-7-bromo-9-[(3,4-dimethylphenyl)methyl]-6,9-dihydro-5H-pyrrolo[3,2-h]quinazoline-8-carboxylate (SVQ6). This compound was obtained by reaction of SVQ5. Yellow solid; yield: 78%; m.p.: 244-245° C.; IR: 3296-3188 (NH$_2$), 1703 (CO) cm$^{-1}$; $^1$H nmr (DMSO-d$_6$) (ppm): 1.25 (3H, t, J=7.0 Hz, CH$_3$), 2.12 (6H, s, 2×CH$_3$), 2.69-2.77 (4H, m, 2×CH$_2$), 4.27 (2H, q, J=7.0 Hz, CH$_2$), 6.26 (2H, s, CH$_2$), 6.68 (1H, d, J=6.5 Hz, H-6'), 6.88 (1H, s, H-2'), 6.99 (1H, d, J=6.5 Hz, H-5'), 8.04 (2H, s, NH$_2$), 8.19 (1H, s, H-6); $^{13}$C nmr (DMSO-d$_6$) (ppm): 13.8 (q), 18.9 (q), 19.4 (q), 20.1 (t), 23.2 (t), 49.3 (t), 61.8 (t), 103.2 (s), 117.0 (s), 123.7 (d), 126.9 (s), 127.4 (s), 127.7 (d), 129.5 (d), 132.6 (s), 135.1 (s), 135.6 (s), 136.1 (s), 144.4 (d), 155.4 (s), 159.0 (s), 159.3 (s). Anal calcd for $C_{22}H_{23}BrN_4O_2$: C, 58.03; H, 5.09; N, 12.30. Found: C, 58.26; H, 4.97; N, 12.17.

Ethyl 2-amino-7-bromo-9-[(4-bromophenyl)methyl]-6,9-dihydro-5H-pyrrolo[3,2-h]quinazoline-8-carboxylate (SVQ8). This compound was obtained by reaction of SVQ7. Brown solid; yield: 69%; m.p.: 174-175° C.; IR: 3519-3416 (NH$_2$), 1703 (CO) cm$^{-1}$; $^1$H nmr (DMSO-d$_6$) (ppm): 1.24 (3H, t, J=7.0 Hz, CH$_3$), 2.58-2.73 (4H, m, 2×CH$_2$), 4.24 (2H, q, J=7.0 Hz, CH$_2$), 6.39 (2H, s, CH$_2$), 6.66 (2H, s, NH$_2$), 6.97 (2H, d, J=8.3 Hz, H-2' and H-6'), 7.47 (2H, d, J=8.3 Hz, H-3' and H-5'), 8.12 (1H, s, H-6); $^{13}$C nmr (DMSO-d$_6$) (ppm): 13.9 (q), 23.7 (t), 27.6 (t), 49.6 (t), 61.3 (t), 99.1 (s), 112.5 (s), 122.8 (s), 127.4 (s), 128.7 (2×d), 129.8 (s), 131.2 (2×d), 132.5 (s), 134.4 (s), 144.9 (d), 156.8 (s), 159.9 (s), 162.9 (s). Anal calcd for $C_{20}H_{18}Br_2N_4O_2$: C, 47.46; H, 3.58; N, 11.07. Found: C, 47.62; H, 3.41; N, 10.94.

Ethyl 2-[(benzenesulfonyl)amino]-7-bromo-9-[(4-methylphenyl)methyl]-6,9-dihydro-5H-pyrrolo[3,2-h]quinazoline-8-carboxylate (SVQ10). This compound was obtained by reaction of SVQ9. Pale yellow solid; yield: 80%; m.p.: 221-222° C.; IR: 3604 (NH), 1703 (CO) cm$^{-1}$; $^1$H nmr (DMSO-d$_6$) (ppm): 1.23 (3H, t, J=7.1 Hz, CH$_3$), 2.21 (3H, s, CH$_3$), 2.51 (2H, t, J=7.0 Hz, CH$_2$), 2.78 (2H, t, J=7.0 Hz, CH$_2$), 4.21 (2H, q, J=7.1 Hz, CH$_2$), 6.30 (2H, s, CH$_2$), 6.76

(2H, d, J=7.8 Hz, H-3' and H-5'), 7.03 (2H, d, J=7.8 Hz, H-2' and H-6'), 7.47-7.56 (3H, m, H-3", H-4" and H-5"), 7.85 (1H, d, J=7.1 Hz, H-2" and H-6"), 8.33 (1H, s, H-6), 11.86 (1H, s, NH); $^{13}$C nmr (DMSO-d$_6$) (ppm): 13.9 (q), 19.8 (t), 20.6 (q), 23.6 (t), 49.0 (t), 60.8 (t), 103.7 (s), 122.3 (s), 124.7 (s), 126.0 (d), 126.7 (d), 128.7 (s), 128.9 (d), 129.0 (d), 129.3 (s), 132.7 (d), 135.9 (s), 136.1 (s), 140.5 (s), 154.4 (s). 155.2 (s), 156.1 (d), 159.3 (s). Anal calcd for C$_{27}$H$_{25}$BrN$_4$O$_4$S: C, 55.77; H, 4.33; N, 9.64. Found: C, 55.64; H, 4.43; N, 9.77.

Ethyl 2-[(benzenesulfonyl)amino]-7-bromo-9-[(3-methylphenyl)methyl]-6,9-dihydro-5H-pyrrolo[3,2-h]quinazoline-8-carboxylate (SVQ12). This compound was obtained by reaction of SVQ11. White solid; yield: 78%; m.p.: 237-238° C.; IR: 3387 (NH), 1703 (CO) cm$^1$; $^1$H nmr (DMSO-d$_6$) (ppm): 1.21 (3H, t, J=7.0 Hz, CH$_3$), 2.20 (3H, s, CH$_3$), 2.60-2.63 (2H, m, CH$_2$), 2.75-2.78 (2H, m, CH$_2$), 4.20 (2H, q, J=7.0 Hz, CH$_2$), 6.32 (2H, s, CH$_2$), 6.60 (1H, d, J=7.3 Hz, Ar), 6.79 (1H, s, H-2'), 6.97-7.14 (2H, m, Ar), 7.43-7.55 (3H, m, H-3", H-4" and H-5"), 7.85 (2H, d, J=7.1 Hz, H-2" and H-6"), 8.33 (1H, s, H-6), 11.87 (1H, s, NH); $^{13}$C nmr (DMSO-d$_6$) (ppm): 13.9 (q), 19.8 (t), 21.0 (q), 23.6 (t), 49.3 (t), 60.8 (t), 103.6 (s), 122.3 (s), 122.9 (d), 124.7 (s), 126.7 (2×d), 126.8 (d), 127.6 (d), 128.3 (d), 128.7 (s), 128.9 (d), 129.2 (2×d), 132.7 (d), 137.3 (s), 138.8 (s), 140.5 (s), 154.4 (s), 155.1 (s), 159.3 (s), 160.6 (s). Anal calcd for C$_{27}$H$_{25}$BrN$_4$O$_4$S: C, 55.77; H, 4.33; N, 9.64. Found: C, 55.91; H, 4.21; N, 9.53.

Ethyl 2-[(benzenesulfonyl)amino]-7-bromo-9-[(3,4-dimethylphenyl)methyl]-6,9-dihydro-5H-pyrrolo[3,2-h]quinazoline-8-carboxylate (SVQ14). This compound was obtained by reaction of SVQ13. Orange solid; yield: 68%; m.p.: 224-225° C.; IR: 3399 (NH), 1700 (CO) cm$^1$; $^1$H nmr (DMSO-d$_6$) (ppm): 1.24 (3H, t, J=7.0 Hz, CH$_3$), 2.11 (3H, s, CH$_3$), 2.13 (3H, s, CH$_3$), 2.72-2.83 (4H, m, 2×CH$_2$), 4.23 (2H, q, J=7.0 Hz, CH$_2$), 6.25 (2H, s, CH$_2$), 6.53 (1H, d, J=6.4 Hz, H-6'), 6.75 (1H, s, H-2'), 6.97 (1H, d, J=6.4 Hz, H-5'), 7.43-7.57 (3H, m, H-3", H-4" and H-5"), 7.85 (2H, d, J=6.6 Hz, H-2" and H-6"), 8.35 (1H, s, H-6); $^{13}$C nmr (DMSO-d$_6$) (ppm): 14.3 (q), 19.4 (q), 19.9 (q), 20.3 (t), 24.1 (t), 49.5 (t), 61.3 (t), 104.0 (s), 123.9 (d), 127.2 (2×d), 128.0 (d), 129.5 (2×d), 130.0 (d), 120.7 (s), 129.0 (s), 129.2 (s), 133.4 (d), 135.4 (s), 135.5 (s), 136.4 (s), 136.7 (s), 140.6 (s), 152.7 (d), 153.9 (s), 155.6 (s), 159.9 (s). Anal calcd for C$_{28}$H$_{27}$BrN$_4$O$_4$S: C, 56.47; H, 4.57; N, 9.41. Found: C, 56.59; H, 4.36; N, 9.29.

Ethyl 2-[(benzenesulfonyl)amino]-7-bromo-9-[(4-bromophenyl)methyl]-6,9-dihydro-5H-pyrrolo[3,2-h]quinazoline-8-carboxylate (SVQ16). This compound was obtained by reaction of SVQ15. White solid; yield: 76%; m.p.: 204-205° C.; IR: 3393 (NH), 1700 (CO) cm$^1$; $^1$H nmr (DMSO-d$_6$) (ppm): 1.21 (3H, t, J=7.1 Hz, CH$_3$), 2.62 (2H, t, J=6.7 Hz, CH$_2$), 2.80 (2H, t, J=6.7 Hz, CH$_2$), 4.21 (2H, q, J=7.1 Hz, CH$_2$), 6.31 (2H, s, CH$_2$), 6.85 (2H, d, J=8.3 Hz, Ar), 7.42-7.57 (5H, m, Ar), 7.81 (2H, d, J=8.3 Hz, Ar), 8.35 (1H, s, H-6), 11.86 (1H, s, NH); $^{13}$C nmr (DMSO-d$_6$) (ppm): 13.9 (q), 19.8 (t), 23.5 (t), 60.8 (t), 103.9 (s), 120.0 (s), 124.3 (s), 126.6 (2×d), 128.3 (2×d), 128.6 (s), 129.0 (2×d), 129.4 (s), 131.2 (2×d), 132.9 (d), 138.3 (s), 139.2 (s), 140.5 (s), 149.7 (s), 155.1 (s), 156.1 (d), 159.2 (s). Anal calcd for C$_{26}$H$_{22}$Br$_2$N$_4$O$_4$S: C, 48.31; H, 3.43; N, 8.67. Found: C, 48.19; H, 3.55; N, 8.54.

Ethyl and isopropyl pyrrole-2-carboxyesters 20a and 20b respectively can be synthesized by reaction of trichloroacetyl pyrrole 19 in the presence of potassium ethoxide in ethanol or potassium carbonate in isopropanol (Scheme 4). Alkylation at the pyrrole nitrogen carried out in the presence of NaH, KI and ethyl 4-bromobutyrate or ethyl 5-bromovalerate gave compounds of formula 21 which were hydrolyzed in basic media to give the corresponding acids of formula 22. The latter were cyclized into ketones of formula 23 in polyphosphoric acid (R$^2$=COOEt) or trifluoroacetic anhydride (R$^2$=COOiPr) and subsequently converted into the key enaminoketones 24.

Scheme 4. Synthesis of 5,6,7,8-tetrahydroindolizines 23 a,c and 6,7,8,9-tetrahydro-5H-pyrrolo[1,2-a]azepines 23 b,d and their corresponding enaminoketones 24a-d.

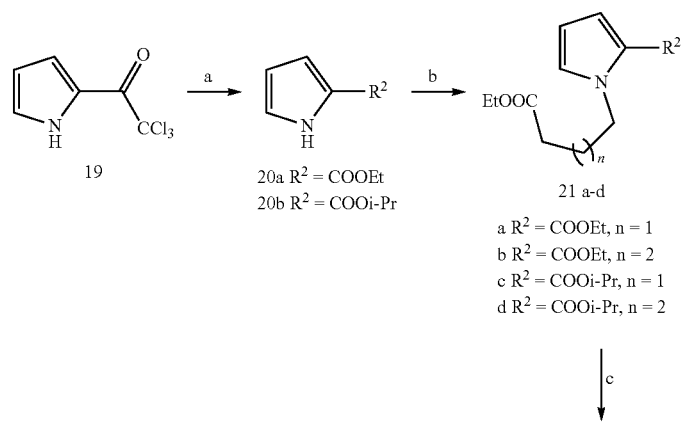

a R$^2$ = COOEt, n = 1
b R$^2$ = COOEt, n = 2
c R$^2$ = COOi-Pr, n = 1
d R$^2$ = COOi-Pr, n = 2

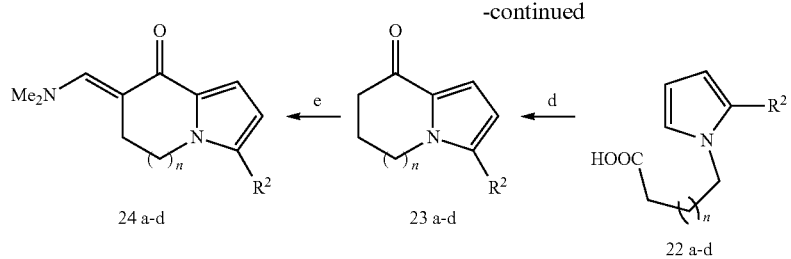

(a) EtOK, ethanol (R¹ = Et), r.t.; 30 min or K₂CO₃, 2-propanol (R¹ = iPr), r.t., 24 h then 19, 60° C., 2 h; (b) for 21a,b: NaH, DMF, 40° C., 3 h then KI, ethyl 4-bromobutyrrate (n = 1) or ethyl 5-bromovalerate (n = 2), reflux, 16 h, for 21 c,d: NaH, DMF, r.t., 16 h then KI, ethyl 4-bromobutyrrate (n = 1) or ethyl 5-bromovalerate (n = 2), r.t., 3 h; (c) for 22 a,b: NaOH, ethanol, r.t., 24-72 h, for 22 c,d: NaOH, ethanol, 70° C., 12-24 h; (d) polyphosphoric acid (R¹ = Et), 35° C., 16 h or trifluoroacetic anhydride (R¹ = iPr), DCM, r.t., 24 h; (e) DMFDMA (1:10), DMF, reflux, 2-24 h.

Scheme 5 describes the general synthesis of pyrrolo[1,2-h][1,7]naphthyridinones (n=1), pyrido[2,3-c]pyrrolo[1,2-a]azepinones (n=2), pyrimido[5,4-g]indolizines (n=1) and pyrimido[4,5-c]pyrrolo[1,2-a]azepines (n=2) as reported in Tables 4 and 5.

To obtain the new tricyclic systems of type 25, enaminoketones 24 were reacted with phenylsulfonylacetonitrile as dinucleophile in refluxing ethanol (Scheme 5). Similarly to the previous class of pyridine compounds 9, the new derivatives 25 were subjected to methylation in DMF in the presence of NaH and iodomethane as methylating agent (Scheme 5). A mixture of the O-methyl derivatives 26 and the N-methyl derivatives 27 was isolated. Moreover, bromination of the pyrrole ring was achieved in DCM and Br₂ as brominating agent, leading to the bromo derivatives of formula 28 (Table 4). Enaminones 24 were also reacted with guanidine nitrate or 1-substituted guanidines in the presence of sodium methoxide to annelate the pyrimidine ring into the basic scaffold leading to the tryciclic derivatives 29. The 2-amino derivatives were subsequently acetylated with acetyl chloride and trimethylamine to give compounds 30.

Scheme 5. Synthesis of pyrrolo[1,2-h][1,7]naphthyridinones (n = 1), pyrido[2,3-c]pyrrolo[1,2-a]azepinones (n = 2), pyrimido[5,4-g]indolizines (n = 1) and pyrimido[4,5-c]pyrrolo[1,2-a]azepines (n = 2).

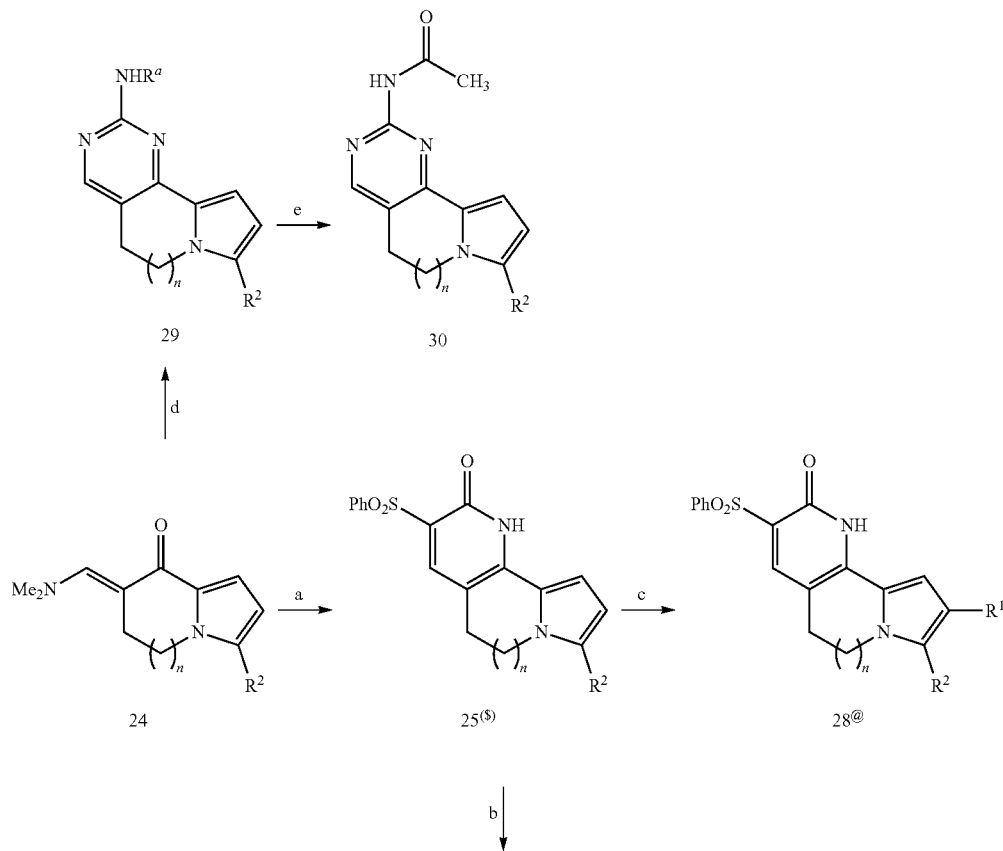

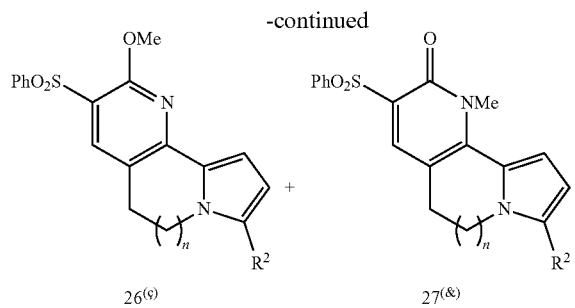

(a) PhSO$_2$CH$_2$CN, ethanol, reflux, 24 h; (b) NaH, DMF, 0° C. to r.t., 3 h then iodomethane, 0° C. to r.t., 16 h; (c) Br$_2$ (1:2), DCM, r.t., 16 h; (d) guanidine nitrate, MeONa, ethanol, reflux, or 1-substituted guanidine, DMF, 100° C.; (e) for R$^2$ = H: acetyl chloride, triethylamine, 1,4-dioxane, reflux.

The derivatives reported in Tables 4 and 5 below are exemplary compounds that may be prepared according to the synthetic procedure of Schemes 4 and 5. Relative additivity indeces (AI %), which were measured as described in the Materials and Methods section, are also reported.

TABLE 4

Pyrrolo[1,2-h][1,7]naphthyridinones (n = 1) and pyrido[2,3-c]pyrrolo[1,2-a]azepinones (n = 2)

| CPD | R$^2$ | R$^1$ | n | AI (%)$^a$ |
|---|---|---|---|---|
| QZN2(@) | COOEt | Br | 1 | 19% |
| QZN5($) | COOEt | — | 2 | 19% |
| QZN6(@) | COOEt | Br | 2 | 136% |
| QZN10(@) | COOiPr | Br | 1 | 101% |
| QZN13($) | COOiPr | — | 2 | 8% |
| QZN14(@) | COOiPr | Br | 2 | 141% |

($)Compounds of formula 25 in Scheme 4;
(@)Compounds of formula 28 in Scheme 4
$^a$Activity of compounds (at 10 μM) was expressed as additivity index (AI %) which is calculated as (QR$_{TOT}$ - QR$_{VX}$)/QR$_{VX}$ where QR$_{TOT}$ is the quenching rate (HS-YFP assay) in the presence of test compound plus VX-809 and QR$_{VX}$ is the quenching rate with VX-809 alone.

TABLE 5

Pyrimido[5,4-g]indolizines (n = 1) and pyrimido[4,5-c]pyrrolo[1,2-a]azepines (n = 2) of formula:

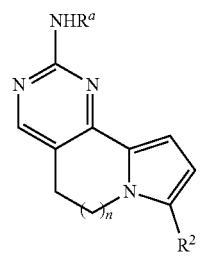

| CPD | R$^2$ | R$^a$ | n | AI (%)$^a$ |
|---|---|---|---|---|
| QZQ14 | COOEt | cyclopentyl | 1 | 18% |
| QZQ20 | COOiPr | cyclopentyl | 1 | 5% |
| QZQ21 | COOiPr | H | 2 | 6% |
| QZQ26 | COOiPr | COMe | 2 | 2% |

$^a$ Activity of compounds (at 10 μM) was expressed as additivity index (AI %) which is calculated as (QR$_{TOT}$-QR$_{VX}$)/QR$_{VX}$ where QR$_{TOT}$ is the quenching rate (HS-YFP assay) in the presence of test compound plus VX-809 and QR$_{VX}$ is the quenching rate with VX-809 alone.

A detailed description of the synthesis of exemplary compounds produced according to Schemes 4 and 5 is provided hereinbelow.

Synthesis of propan-2-yl 1H-pyrrole-2-carboxylate 20

A suspension of K$_2$CO$_3$ (3.96 g) in 2-propanol (12 mL) was stirred at room temperature for 16 h. Then a solution of 2,2,2-trichloro-1-(1H-pyrrol-2-yl)ethanone 19 (1.5 g, 7.2 mmol) in 2-propanol was added dropwise and the reaction mixture was heated at 60° C. for 1 h and 30 min. After cooling, the solvent was removed under reduced pressure. The residue was added with water and the solution was acidified with HCl 6M and then extracted with ethyl acetate (1×40 mL). The organic phase was dried on Na$_2$SO$_4$ and the solvent was removed under reduced pressure to give the desired compound 20. Colorless oil; yield 65%; IR: 1699 (CO) cm$^{-1}$; $^1$H nmr (DMSO-d$_6$) (ppm): 1.27 (6H, d, J=6.2 Hz, 2×CH$_3$), 1.28 (3H, s, CH$_3$), 4.97-5.15 (1H, m, CH), 6.12-6.18 (1H, m, Ar), 6.72-6.79 (1H, m, Ar), 6.97-7.02 (1H, m, Ar); $^{13}$C nmr (DMSO-d$_6$) (ppm): 21.8 (2×q), 66.6 (d), 109.3 (d), 114.7 (d), 121.1 (s), 123.7 (d), 159.9 (s), 171.9 (s). Anal calcd for C$_8$H$_{11}$NO$_2$: C, 62.73; H, 7.24; N, 9.14. Found: C, 62.87; H, 7.08; N, 8.99.

Synthesis of 1-Substituted pyrrole-2-carboxylate 21a,b

To a solution of ethyl 1H-pyrrole-2-carboxylate 20a (3.6 mmol) in anhydrous DMF (15 mL), NaH (7.2 mmol) was added at 0° C. and the reaction mixture was stirred at 40° C. for 3 h. After cooling, KI (0.64 g, 4.0 mmol), ethyl 4-bromobutyrate or ethyl 5-bromovalerate (7.2 mmol) were added and the reaction mixture was heated at reflux for 16 h. After cooling, the reaction mixture was poured onto crushed ice and the aqueous solution was extracted with ethyl acetate (3×50 mL). The organic layers were dried over Na$_2$SO$_4$ and the solvent removed under reduced pressure. The crude product was purified by chromatography column (Petroleum ether/AcOEt 9:1).

Ethyl 1-(4-ethoxy-4-oxobutyl)-1H-pyrrole-2-carboxylate (21a). This compound was obtained by reaction of 20a with ethyl 4-bromobutyrate. Yellow oil; yield: 85%; IR: 1718 (CO), 1684 (CO) cm$^{-1}$; $^1$H nmr (DMSO-d$_6$) (ppm): 1.22-1.38 (6H, m, 2×CH$_3$), 2.02-2.16 (2H, m, CH$_2$), 2.28 (2H, t, J=6.8 Hz, CH$_2$), 4.07-4.41 (6H, m, 3×CH$_2$), 6.10-6.13 (1H, m, Ar), 6.80-6.85 (1H, m, Ar), 6.94-6.96 (1H, m, Ar; $^{13}$C nmr (DMSO-d$_6$) (ppm): 14.2 (q), 14.4 (q), 26.7 (t), 31.0 (t), 48.1 (t), 59.8 (t), 60.6 (t), 108.0 (d), 118.2 (d), 121.9 (s), 128.8 (d), 161.1 (s), 172.9 (s). Anal calcd for $C_{13}H_{19}NO_4$: C, 61.64; H, 7.56; N, 5.53. Found: C, 61.51; H, 7.69; N, 5.75.

Ethyl 1-(5-ethoxy-5-oxopentyl)-1H-pyrrole-2-carboxylate (21b). This compound was obtained by reaction of 20a with ethyl 5-bromovalerate. Yellow oil; yield: 75%; IR: 1715 (CO), 1698 (CO) cm$^{-1}$; $^1$H nmr (CDCl$_3$) (ppm): 1.21-1.38 (6H, m, 2×CH$_3$), 1.54-1.69 (2H, m, CH$_2$), 1.73-1.87 (2H, m CH$_2$), 2.31 (2H, t, J=7.3 Hz, CH$_2$), 4.06-4.35 (6H, m, 3×CH$_2$), 6.09-6.13 (1H, m, Ar), 6.82-6.84 (1H, m, Ar), 6.94-6.97 (1H, m, Ar); $^{13}$C nmr (CDCl$_3$) (ppm): 14.2 (q), 14.4 (q), 22.0 (t), 31.0 (t), 33.8 (t), 48.8 (t), 59.7 (t), 60.3 (t), 107.9 (d), 118.1 (d), 121.8 (s), 128.6 (d), 161.1 (s), 173.3 (s). Anal calcd for $C_{14}H_{21}NO_4$: C, 62.90; H, 7.92; N, 5.24. Found: C, 63.09; H, 7.84; N, 5.43.

Synthesis of 1-Substituted pyrrole-2-carboxylate 21c,d

To a solution of propan-2-yl 1H-pyrrole-2-carboxylate 20b (3.6 mmol) in anhydrous DMF (15 mL), NaH (7.2 mmol) was added at 0° C. and the reaction mixture was stirred at room temperature for 16 h. Then KI (0.64 g, 4.0 mmol), ethyl 4-bromobutyrate or ethyl 5-bromovalerate (7.2 mmol) were added at 0° C. and the reaction mixture was stirred at room temperature for 3 h. After cooling, the reaction mixture was poured onto crushed ice and the aqueous solution was extracted with ethyl acetate (3×50 mL). The organic layers were dried over Na$_2$SO$_4$ and the solvent removed under reduced pressure. The crude product was purified by chromatography column (Petroleum ether/AcOEt 9:1).

Propan-2-yl 1-(4-ethoxy-4-oxobutyl)-1H-pyrrole-2-carboxylate (21c). This compound was obtained by reaction of 20b with ethyl 4-bromobutyrate. Colorless oil; yield: 90%; IR: 1729 (CO), 1696 (CO) cm$^{-1}$; $^1$H nmr (DMSO-d$_6$) (ppm): 1.13-1.31 (9H, m, 3×CH$_3$), 1.89-99 (2H, m, CH$_2$), 2.21 (2H, t, J=7.3 Hz, CH$_2$), 4.03 (2H, q, J=7.1 Hz, CH$_2$), 4.29 (2H, t, J=7.3 Hz, CH$_2$), 4.95-5.12 (1H, m, CH), 6.08-6.11 (1H, m, Ar), 6.81-6.84 (1H, m, Ar), 7.09-7.15 (1H, m, Ar); $^{13}$C nmr (DMSO-d$_6$) (ppm): 14.0 (q), 21.7 (2×q), 26.4 (t), 30.5 (t), 47.4 (t), 59.9 (t), 66.6 (d), 107.7 (d), 117.8 (d), 121.3 (s), 129.5 (d), 159.7 (s), 172.1 (s). Anal calcd for $C_{14}H_{21}NO_4$: C, 62.90; H, 7.92; N, 5.24. Found: C, 63.02; H, 8.06; N, 5.13.

Propan-2-yl 1-(5-ethoxy-5-oxopentyl)-1H-pyrrole-2-carboxylate (21d). This compound was obtained by reaction of 20b with ethyl 5-bromovalerate. Colorless oil; yield: 84%; IR: 1724 (CO), 1695 (CO) cm$^{-1}$; $^1$H nmr (DMSO-d$_6$) (ppm): 1.12-1.27 (9H, m, 3×CH$_3$), 1.40-1.51 (2H, m, CH$_2$), 1.59-1.73 (2H, m, CH$_2$), 2.28 (2H, t, J=7.2 Hz, CH$_2$), 4.03 (2H, q, J=7.1 Hz, CH$_2$), 4.26 (2H, t, J=7.2 Hz, CH$_2$), 4.97-5.10 (1H, m, CH), 6.06-6.09 (1H, m, Ar), 6.80-6.85 (1H, m, Ar), 7.11-7.13 (1H, m, Ar); $^{13}$C nmr (DMSO-d$_6$) (ppm): 14.0 (q), 21.4 (t), 21.7 (2×q), 30.5 (t), 32.9 (t), 47.9 (t), 59.6 (t), 66.5 (d), 107.6 (d), 117.7 (d), 121.3 (s), 129.5 (d), 159.7 (s), 172.6 (s). Anal calcd for $C_{15}H_{23}NO_4$: C, 64.03; H, 8.24; N, 4.98. Found: C, 64.19; H, 8.02; N, 5.12.

General Procedure for the Synthesis of 4-[2-(substituted)-1H-pyrrol-1-yl]butanoic acid and 5-[2-(Substituted)-1H-pyrrol-1-yl]pentanoic acid 22

To a solution of 21 (0.440 g, 1.65 mmol) in EtOH (14 mL) was added a solution of 5% NaOH (1.42 mL, 1.65 mmol). The mixture was stirred at room temperature or at 70° C. up to completeness (TLC). Then the solvent was removed under reduced pressure and water and crushed ice were added. The solution was acidified with 6 M HCl and the aqueous solution was extracted with ethyl acetate (3×50 mL). The organic layers were dried over Na$_2$SO$_4$ and the solvent removed under reduced pressure. The crude product was purified by chromatography column (DCM/AcOEt 8:2).

4-[2-(Ethoxycarbonyl)-1H-pyrrol-1-yl]butanoic acid (22a). This compound was obtained by reaction of ethyl 1-(4-ethoxy-4-oxobutyl)-1H-pyrrole-2-carboxylate (21a) after 24 h at room temperature. Yellow oil; yield: 75%; IR: 3123 (OH), 1716 (CO); 1675 (CO)cm$^{-1}$; $^1$H nmr (CDCl$_3$) (ppm): 1.34 (3H, t, J=7.2 Hz, CH$_3$), 1.90-2.20 (2H, m, CH$_2$), 2.31 (2H, t, J=6.5 Hz, CH$_2$), 4.21-4.41 (2H, m, 2×CH$_2$), 6.11 (1H, s, Ar), 6.84 (1H, s, Ar), 6.96 (1H, s, Ar), 9.30 (1H, s, OH); $^{13}$C nmr (CDCl$_3$) (ppm): 14.4 (q), 26.5 (t), 30.7 (t), 47.9 (t), 59.9 (t), 108.1 (d), 118.4 (d), 121.8 (s), 128.9 (d), 161.2 (s), 178.2 (s). Anal calcd for $C_{11}H_{15}NO_4$: C, 58.66; H, 6.71; N, 6.22. Found: C, 58.48; H, 6.91; N, 6.10.

5-[2-(Ethoxycarbonyl)-1H-pyrrol-1-yl]pentanoic acid (22b). This compound was obtained by reaction of ethyl 1-(5-ethoxy-5-oxopentyl)-1H-pyrrole-2-carboxylate (21b) after 72 h at room temperature. Yellow oil; yield: 65%; IR: 3123 (OH), 1702 (CO); 1681 (CO) cm$^{-1}$; $^1$H nmr (DMSO-d$_6$) (ppm): 1.26 (3H, t, J=7.0 Hz, CH$_3$), 1.35-1.49 (2H, m, CH$_2$), 1.60-1.74 (2H, m, CH$_2$), 2.21 (2H, t, J=7.3 Hz, CH$_2$), 4.15-4.31 (4H, m, 2×CH$_2$), 5.96-6.20 (1H, m, Ar), 6.69-6.93 (1H, m, Ar), 7.12-7.17 (1H, m, Ar), 12.04 (1H, s, OH); $^{13}$C nmr (DMSO-d$_6$) (ppm): 14.2 (q), 21.4 (t), 30.6 (t), 33.1 (t), 47.9 (t), 59.3 (t), 107.6 (d), 117.7 (d), 120.9 (s), 129.6 (d), 160.2 (s), 174.3 (s). Anal calcd for $C_{12}H_{17}NO_4$: C, 60.24; H, 7.16; N, 5.85. Found: C, 60.37; H, 7.02; N, 5.99.

4-{2-[(Propan-2-yloxy)carbonyl]-1H-pyrrol-1-yl}butanoic acid (22c). This compound was obtained by reaction of propan-2-yl 1-(4-ethoxy-4-oxobutyl)-1H-pyrrole-2-carboxylate (21c) after 12 h at 70° C. colorless oil; yield: 81%; IR: 3113 (OH), 1706 (CO); 1685 (CO) cm$^{-1}$; $^1$H nmr (DMSO-d$_6$) (ppm): 1.26 (6H, d, J=6.2 Hz, 2×CH$_3$), 1.82-1.92 (2H, m, CH$_2$), 2.14 (2H, t, J=7.3 Hz, CH$_2$), 4.28 (2H, t, J=7.3 Hz, CH$_2$), 4.95-5.13 (1H, m, CH), 6.008-6.11 (1H, m, Ar), 6.81-6.84 (1H, m, Ar), 7.09-7.11 (1H, m, Ar), 12.15 (1H, s, OH); $^{13}$C nmr (DMSO-d$_6$) (ppm): 21.7 (2×q), 26.6 (t), 30.5 (t), 47.5 (t), 66.6 (d), 107.7 (d), 117.8 (d), 121.3 (s), 129.5 (d), 159.7 (s), 173.8 (s). Anal calcd for $C_{12}H_{17}NO_4$: C, 60.24; H, 7.16; N, 5.85. Found: C, 60.12; H, 7.29; N, 6.05.

5-{2-[(Propan-2-yloxy)carbonyl]-1H-pyrrol-1-yl}pentanoic acid (22d). This compound was obtained by reaction of propan-2-yl 1-(5-ethoxy-5-oxopentyl)-1H-pyrrole-2-carboxylate (21d) after 24 h at 70° C. Colorless oil; yield: 74%, IR: 3131 (OH), 1704 (CO), 1696 (CO) cm$^{-1}$; $^1$H nmr (DMSO-d$_6$) (ppm): 1.27 (6H, d, J=6.4 Hz, 2×CH$_3$), 1.59-1.67 (2H, m, CH$_2$), 1.71-1.76 (2H, m, CH$_2$), 2.21 (2H, t, J=7.4 Hz, CH$_2$), 4.26 (2H, t, J=7.4 Hz, CH$_2$), 5.01-5.10 (1H, m, CH), 6.06-6.12 (1H, m, Ar), 6.80-6.85 (1H, m, Ar), 7.12-7.16 (1H, m, Ar), 12.05 (1H, s, OH); $^{13}$C nmr (DMSO-d$_6$) (ppm): 21.4 (t), 21.7 (2×q), 30.7 (t), 33.1 (t), 47.9 (t), 59.6 (t), 66.5 (d), 107.6 (d), 117.7 (d), 121.3 (s), 129.5 (d), 159.8 (s), 174.2 (s). Anal calcd for $C_{13}H_{19}NO_4$: C, 61.64; H, 7.56; N, 5.53. Found: C, 61.52; H, 7.39; N, 5.71.

General Procedure for the Synthesis of ethyl 8-oxo-5,6,7,8-tetrahydroindolizine-3-carboxylate 23a and ethyl 9-oxo-6,7,8,9-tetrahydro-5H-pyrrolo[1,2-a]azepine-3-carboxylate 23b The suitable acid derivative 22a,b (8.37 mmol) was stirred in polyphosphoric acid (13 g) at 35° C. for 16 h. The reaction mixture was quenched with water and crushed ice and the resulting solution was extracted with ethyl acetate (3×50 mL). The organic layer were dried over $Na_2SO_4$, and the solvent removed under reduced pressure. The crude product was purified by chromatography column (DCM).

Ethyl 8-oxo-5,6,7,8-tetrahydroindolizine-3-carboxylate (23a). This compound was obtained by reaction of 4-[2-(ethoxycarbonyl)-1H-pyrrol-1-yl]butanoic acid (22a). Yellow oil; yield: 70%; IR: 1704 (CO), 1687 (CO) $cm^{-1}$; $^1$H nmr ($CDCl_3$) (ppm): 1.37 (3H, t, J=6.7 Hz, $CH_3$), 2.16.2.41 (2H, m, $CH_2$), 2.61 (2H, t, J=6.6 Hz, $CH_2$), 4.31 (2H, q, J=6.7 Hz, $CH_2$), 4.55 (2H, t, J=6.6 Hz, $CH_2$), 5.32 (1H, s, Ar), 6.90 (1H, s, Ar); $^{13}$C nmr ($CDCl_3$) (ppm): 14.2 (q), 23.3 (t), 36.0 (t), 44.5 (t), 60.5 (t), 112.4 (d), 116.8 (d), 126.0 (s), 135.5 (s), 160.6 (s), 188.3 (s). Anal calcd for $C_{11}H_{13}NO_3$: C, 63.76; H, 6.32; N, 6.76. Found: C, 63.89; H, 6.13; N, 6.61.

Ethyl 9-oxo-6,7,8,9-tetrahydro-5H-pyrrolo[1,2-a]azepine-3-carboxylate (23b). This compound was obtained by reaction of 5-[2-(ethoxycarbonyl)-1H-pyrrol-1-yl]pentanoic acid (22b). Yellow oil; yield: 65%; IR: 1708 (CO), 1679 (CO) $cm^{-1}$; $^1$H nmr (DMSO-$d_6$) (ppm): 1.37 (3H, t, J=7.1 Hz, $CH_3$), 1.82-1.94 (2H, m, $CH_2$), 2.00-2.13 (2H, m, $CH_2$), 2.77 (2H, t, J=6.0 Hz, $CH_2$), 4.32 (2H, q, J=7.1 Hz, $CH_2$), 4.79 (2H, t, J=6.0 Hz, $CH_2$), 6.85-6.92 (2H, m, Ar); $^{13}$C nmr (DMSO-$d_6$) (ppm): 14.3 (q), 19.4 (t), 26.1 (t), 39.6 (t), 44.0 (t), 60.7 (t), 114.6 (d), 116.9 (d), 139.8 (s), 161.2 (s), 193.8 (s). Anal calcd for $C_{12}H_{15}NO_3$: C, 65.14; H, 6.83; N, 6.33. Found: C, 64.98; H, 6.72; N, 6.57.

General Procedure for the Synthesis of propan-2-yl 8-oxo-5,6,7,8-tetrahydroindolizine-3-carboxylate 23c and propan-2-yl 9-oxo-6,7,8,9-tetrahydro-5H-pyrrolo[1,2-a]azepine-3-carboxylate 23d To a solution of 22c,d (4.32 g, 18 mmol) in anhydrous DCM (52 mL) trifluoroacetic anhydride (16.6 mL, 217 mmol) was added and the reaction mixture was stirred at room temperature for 24 h. The solvent was removed under reduced pressure and water and crushed ice were added. The solution was neutralized with a saturated solution of $NaHCO_3$. Then the aqueous phase was extracted with dichloromethane (3×50 mL). The organic layers were dried over $Na_2SO_4$, and the solvent removed under reduced pressure. The crude product was purified by chromatography column (Cyclohexane/AcOEt 8:2).

Propan-2-yl 8-oxo-5,6,7,8-tetrahydroindolizine-3-carboxylate (23c). This compound was obtained by reaction of 4-{2-[(propan-2-yloxy)carbonyl]-1H-pyrrol-1-yl}butanoic acid (22c). Pale yellow solid; yield 65%; m.p.: 66-67° C.; IR: 1703 (CO), 1669 (CO) $cm^{-1}$; $^1$H nmr (DMSO-$d_6$) (ppm): 1.30 (6H, d, J=6.2 Hz, 2×$CH_3$), 2.15-2.27 (2H, m, $CH_2$), 2.57 (2H, t, J=6.0 Hz, $CH_2$), 4.48 (2H, t, J=6.0 Hz, $CH_2$), 5.04-5.17 (1H, m, CH), 6.80-6.88 (2H, m, Ar); $^{13}$C nmr (DMSO-$d_6$) (ppm): 21.6 (2×q), 22.8 (t), 35.5 (t), 44.4 (t), 67.9 (d), 111.5 (d), 116.3 (d), 125.7 (s), 134.3 (s), 159.6 (s), 188.4 (s). Anal calcd for $C_{12}H_{15}NO_3$: C, 65.14; H, 6.83; N, 6.33. Found: C, 65.27; H, 7.03; N, 6.21.

Propan-2-yl 9-oxo-6,7,8,9-tetrahydro-5H-pyrrolo[1,2-a]azepine-3-carboxylate (23d). This compound was obtained by reaction of 5-{2-[(propan-2-yloxy)carbonyl]-1H-pyrrol-1-yl}pentanoic acid (22d). Yellow oil; yield: 62%, IR: 1703 (CO), 1658 (CO) $cm^{-1}$; $^1$H nmr (DMSO-$d_6$) (ppm): 1.29 (6H, d, J=6.2 Hz, 2×$CH_3$), 1.68-1.80 (2H, m, $CH_2$), 1.88-1.99 (2H, m, $CH_2$), 2.71-2.77 (2H, m, $CH_2$), 4.72-4.78 (2H, m, $CH_2$), 5.06-5.16 (1H, m, CH), 6.71-6.86 (2H, m, Ar); $^{13}$C nmr (DMSO-$d_6$) (ppm): 18.8 (t), 21.6 (2×q), 25.5 (t), 39.0 (t), 43.5 (t), 67.8 (d), 113.5 (d), 116.1 (d), 126.0 (s), 139.3 (s), 159.8 (s), 193.1 (s). Anal calcd for $C_{13}H_{17}NO_3$: C, 66.36; H, 7.28; N, 5.95. Found: C, 66.18; H, 7.09; N, 6.07.

General Procedure for the Synthesis of 3-substituted-7-(dimethylamino)methylene)-8-oxo-5,6,7,8-tetrahydroindolizine 24a,c and 3-substituted-8-(dimethylamino)methylene)-9-oxo-6,7,8,9-tetrahydro-5H-pyrrolo[1,2-a]azepine 24b,d To a solution of 23 (0.44 g, 2 mmol) in anhydrous DMF (2.6 mL) was added DMFDMA (2.64 mL, 20 mmol). The reaction mixture was stirred at reflux up to completeness (TLC). The reaction mixtures was poured onto crushed ice. The precipitate was filtered off and dried, in absence the solution was extracted with ethyl acetate (3×30 mL). The organic layer was dried over $Na_2SO_4$ and the solvent was removed under reduced pressure.

Ethyl 7-[(dimethylamino)methylidene]-8-oxo-5,6,7,8-tetrahydroindolizine-3-carboxylate (24a). This compound was obtained by reaction of ethyl 8-oxo-5,6,7,8-tetrahydroindolizine-3-carboxylate (23a) after 2 h and used in the next step without further purification.

Ethyl 8-(dimethylamino)methylene)-9-oxo-6,7,8,9-tetrahydro-5H-pyrrolo[1,2-a]azepine-3-carboxylate (24b). This compound was obtained by reaction of ethyl 9-oxo-6,7,8,9-tetrahydro-5H-pyrrolo[1,2-a]azepine-3-carboxylate (23b) after 3 h: yellow solid; yield: 87%, mp: 115-116° C.; IR: 1697 (CO), 1641 (CO) $cm^{-1}$; $^1$H nmr (DMSO-$d_6$) (ppm): 1.28 (3H, t, J=7.1 Hz, $CH_3$), 1.86-199 (2H, m, $CH_2$), 2.32 (2H, t, J=6.3 Hz, $CH_2$), 3.11 (6H, s, 2×$CH_3$), 4.25 (2H, q, J=7.1 Hz, $CH_2$), 4.51 (2H, t, J=6.3 Hz, $CH_2$), 6.44 (1H, d, J=4.0 Hz, Ar), 6.82 (1H, d, J=4.0 Hz, Ar), 7.53 (1H, s, CH); $^{13}$C nmr (DMSO-$d_6$) (ppm): 14.2 (q), 21.7 (t), 30.6 (t), 42.9 (t), 43.1 (2×q), 59.8 (t), 102.4 (s), 110.6 (d), 116.1 (d), 122.3 (s), 142.1 (s), 150.1 (d), 160.4 (s), 184.9 (s). Anal calcd for $C_{15}H_{20}N_2O_3$: C, 65.20; H, 7.30; N, 10.14. Found: C, 65.08; H, 7.56; N, 10.27.

Propan-2-yl 7-[(dimethylamino)methylidene]-8-oxo-5,6,7,8-tetrahydroindolizine-3-carboxylate (24c). This compound was obtained by reaction of propan-2-yl 8-oxo-5,6,7,8-tetrahydroindolizine-3-carboxylate (23c) after 3 h: yellow solid; yield: 56%, mp: 126-127° C.; IR: 1691 (CO), 1603 (CO) $cm^{-1}$; $^1$H nmr (DMSO-$d_6$) (ppm): 1.28 (6H, d, J=6.2 Hz, 2×$CH_3$), 3.04-3.12 (8H, m, $CH_2$ and 2×$CH_3$), 4.41 (2H, t, J=6.6 Hz, $CH_2$), 5.01-5.14 (1H, m, CH), 6.61 (1H, d, J=4.1 Hz, Ar), 6.81 (1H, d, J=4.1 Hz, Ar), 7.49 (1H, s, CH); $^{13}$C nmr (DMSO-$d_6$) (ppm): 21.7 (2×q), 23.7 (t), 23.8 (t), 43.2 (2×q), 67.3 (d), 98.5 (s), 110.1 (d), 116.5 (d), 123.4 (s), 136.6 (s), 149.2 (d), 159.9 (s), 176.5 (s). Anal calcd for $C_{15}H_{20}N_2O_3$: C, 65.20; H, 7.30; N, 10.14. Found: C, 65.34; H, 7.19; N, 10.02.

Propan-2-yl 8-[(dimethylamino)methylidene]-9-oxo-6,7,8,9-tetrahydro-5H-pyrrolo[1,2-a]azepine-3-carboxylate (24d). This compound was obtained by reaction of propan-2-yl 9-oxo-6,7,8,9-tetrahydro-5H-pyrrolo[1,2-a]azepine-3-carboxylate (23d) after 2 h and used in the next step without further purification.

General Procedure for the Synthesis of Compounds Type 25

To a solution of the enamiketones 24 (2.76 mmol) in anhydrous ethanol (20 mL) under nitrogen atmosphere phenylsulfonylacetonitrile (0.75 g, 4.14 mmol) was added. The reaction mixture was heated under reflux for 24 h. The solvent was removed under reduced pressure. The crude product was recrystallized from diethyl ether.

Ethyl 3-(benzenesulfonyl)-2-oxo-1,2,5,6-tetrahydropyrrolo[1,2-h][1,7]naphthyridine-8-carboxylate (QZN1). This compound was obtained by reaction of ethyl 7-[(dimethylamino)methylidene]-8-oxo-5,6,7,8-tetrahydroindolizine-3-carboxylate (24a). Brown solid; yield: 68%; mp: 145-146° C.; IR: 3365 (NH), 1718 (CO), 1646 (CO) cm$^{-1}$; $^1$H nmr (DMSO-d$_6$) (ppm): 1.29 (3H, t, J=7.1 Hz, CH$_3$), 3.01 (2H, t, J=7.0 Hz, CH$_2$), 4.27 (2H, q, J=7.1 Hz, CH$_2$), 4.54 (2H, t, J=7.0 Hz, CH$_2$), 6.65 (1H, d, J=4.0 Hz, Ar), 7.16 (1H, d, J=4.0 Hz, Ar), 7.55-7.73 (3H, m, Ar), 7.96-8.01 (2H, m, Ar), 8.29 (1H, s, H-4), 12.58 (1H, s, NH); $^{13}$C nmr (DMSO-d$_6$) (ppm): 14.2 (q), 24.8 (t), 42.1 (t), 60.3 (t), 108.4 (s), 110.4 (d), 117.6 (d), 118.7 (s), 120.1 (s), 125.5 (s), 128.0 (2×d), 128.8 (2×d), 133.3 (d), 138.9 (d), 140.3 (s), 144.1 (s), 157.1 (s), 159.9 (s). Anal calcd for C$_{20}$H$_{18}$N$_2$O$_5$S: C, 60.29; H, 4.55; N, 7.03. Found: C, 60.54; H, 4.41; N, 6.92.

Ethyl 3-(benzenesulfonyl)-2-oxo-1,5,6,7-tetrahydro-2H-pyrido[2,3-c]pyrrolo[1,2-a]azepine-9-carboxylate (QZN5). This compound was obtained by reaction of ethyl 8-(dimethylamino)methylene)-9-oxo-6,7,8,9-tetrahydro-5H-pyrrolo[1,2-a]azepine-3-carboxylate (24b). Yellow solid; yield: 51%, mp: 340-341° C.; IR: 3131 (NH), 1703 (CO), 1652 (CO) cm$^{-1}$; $^1$H nmr (DMSO-d$_6$) (ppm): 1.29 (3H, t, J=7.1 Hz, CH$_3$), 2.23-2.26 (2H, m, CH$_2$), 2.32-2.59 (2H, s, CH$_2$), 4.27 (2H, q, J=7.1 Hz, CH$_3$), 4.38 (2H, t, J=6.1 Hz, CH$_2$), 6.64 (1H, d, J=4.2 Hz, Ar), 6.94 (1H, d, J=4.2 Hz, Ar), 7.57-7.70 (3H, m, Ar), 8.00 (2H, d, J=6.9 Hz, Ar), 8.33 (1H, s, H-4), 12.54 (1H, s, NH); $^{13}$C nmr (DMSO-d$_6$) (ppm): 14.7 (q), 27.2 (t), 31.8 (t), 44.0 (t), 60.6 (t), 112.7 (d), 117.0 (d), 117.7 (s), 125.7 (s), 126.5 (s), 128.7 (2×d), 129.3 (2×d), 133.3 (s), 133.8 (d), 140.7 (s), 145.2 (s), 146.0 (d), 157.6 (s), 160.5 (s). Anal calcd for C$_{21}$H$_{20}$N$_2$O$_5$S: C, 61.15; H, 4.89; N, 6.79. Found: C, 61.27; H, 5.02; N, 6.58.

Propan-2-yl 3-(benzenesulfonyl)-2-oxo-1,2,5,6-tetrahydropyrrolo[1,2-h][1,7]naphthyridine-8-carboxylate (QZN9). This compound was obtained by reaction of isopropyl propan-2-yl 7-[(dimethylamino)methylidene]-8-oxo-5,6,7,8-tetrahydroindolizine-3-carboxylate (24c). white solid; yield: 61%, mp: 332-333° C.; IR: 3125 (NH), 1703 (CO), 1652 (CO) cm$^{-1}$; $^1$H nmr (DMSO-d$_6$) (ppm): 1.29 (6H, d, J=6.2 Hz, 2×CH$_3$), 3.00 (2H, t, J=6.7 Hz, CH$_2$), 4.54 (2H, t, J=6.7 Hz, CH$_2$), 5.07-5.13 (1H, m, CH), 6.91 (2H, d, J=4.1 Hz, Ar), 7.14 (1H, d, J=4.1 Hz, Ar), 7.56-7.69 (3H, m, Ar), 7.99 (2H, d, J=7.5 Hz, Ar), 8.29 (1H, s, H-4), 12.57 (1H, s, NH); $^{13}$C nmr (DMSO-d$_6$) (ppm): 22.1 (2×q), 25.3 (t), 42.6 (t), 68.3 (d), 107.5 (s), 110.8 (d), 118.0 (d), 123.9 (s), 126.3 (s), 128.5 (2×d), 129.2 (2×d), 133.8 (d), 138.7 (d), 140.8 (s), 145.8 (s), 149.7 (s), 157.5 (s), 160.0 (s). Anal calcd for C$_{21}$H$_{20}$N$_2$O$_5$S: C, 61.15; H, 4.89; N, 6.79. Found: C, 61.07; H, 4.72; N, 6.88.

Propan-2-yl 3-(benzenesulfonyl)-2-oxo-1,5,6,7-tetrahydro-2H-pyrido[2,3-c]pyrrolo[1,2-a]azepine-9-carboxylate (QZN13). This compound was obtained by reaction of propan-2-yl 8-[(dimethylamino)methylidene]-9-oxo-6,7,8,9-tetrahydro-5H-pyrrolo[1,2-a]azepine-3-carboxylate (24d). White solid; yield: 54%, mp: 237-238° C.; IR: 3131 (NH), 1697 (CO), 1646 (CO) cm$^{-1}$; $^1$H nmr (DMSO-d$_6$) (ppm): 1.30 (6H, d, J=6.1 Hz, 2×CH$_3$), 2.12-2.34 (2H, m, CH$_2$), 2.42-2.51 (2H, m, CH$_2$), 4.29-4.43 (2H, m, CH$_2$), 5.04-5.16 (1H, m, CH), 6.63 (1H, d, J=4.1 Hz, Ar), 6.91 (1H, d, J=4.1 Hz, Ar), 7.57-7.73 (3H, m, Ar), 8.01 (2H, d, J=6.9 Hz, Ar), 8.33 (1H, s, H-4), 12.53 (1H, s, NH); $^{13}$C nmr (DMSO-d$_6$) (ppm): 21.7 (2×q), 26.7 (t), 31.3 (t), 43.6 (t), 67.6 (d), 102.8 (s), 112.1 (d), 116.4 (d), 121.4 (s), 125.6 (s), 128.2 (2×d), 128.8 (2×d), 133.4 (d), 137.0 (d), 140.1 (s), 145.5 (s), 155.7 (s), 157.2 (s), 159.7 (s). Anal calcd for C$_{22}$H$_{22}$N$_2$O$_5$S: C, 61.96; H, 5.20; N, 6.57. Found: C, 62.15; H, 5.37; N, 6.41.

General Procedure for the Synthesis of Compounds of Type 26 and 27

To a solution of the suitable derivatives of type 25 (15 mmol) in anhydrous DMF (20 mL), NaH (0.64 g, 16 mmol) was added at 0° C. and the reaction mixture was stirred at room temperature. After 6 h, iodomethane (16 mmol) was added at 0° C. and the reaction mixture was stirred at room temperature for 24 h. Then the reaction mixture was poured onto crushed ice. The precipitate was filtered off and dried, in absence the solution was extracted with ethyl acetate (3×30 mL). The organic layer was dried over Na$_2$SO$_4$ and the solvent was removed under reduced pressure. The crude product, containing O-methyl (26) and N-methyl substituted derivatives (27), was purified by chromatography column (DCM/AcOEt 95:5).

Ethyl 3-(benzenesulfonyl)-2-methoxy-5,6-dihydropyrrolo[1,2-h][1,7]naphthyridine-8-carboxylate (QZN3). This compound was obtained by reaction of QZN1. Light yellow solid; yield: 25%, mp: 157-158° C.; IR: 1697 (CO) cm$^{-1}$; $^1$H nmr (CDCl$_3$) (ppm): 1.37 (3H, t, J=7.1 Hz, CH$_3$), 3.13 (2H, t, J=6.9 Hz, CH$_2$), 3.96 (3H, s, CH$_3$), 4.32 (2H, q, J=7.1 Hz, CH$_2$), 4.67 (2H, t, J=6.9 Hz, CH$_2$), 6.88 (1H, d, J=4.1 Hz, Ar), 7.01 (1H, d, J=4.1 Hz, Ar), 7.46-7.64 (3H, m, 3H—Ar), 7.98-8.03 (2H, m, Ar), 8.23 (1H, s, H-4); $^{13}$C nmr (CDCl$_3$) (ppm): 14.4 (q), 26.9 (t), 42.2 (t), 54.0 (q), 60.4 (t), 109.5 (d), 118.4 (d), 119.2 (s), 121.0 (s), 124.9 (s), 128.5 (2×d), 128.7 (2×d), 133.3 (d), 134.61 (s), 138.5 (d), 140.6 (s), 149.2 (s), 159.11 (s), 161.1 (s). Anal calcd for C$_{21}$H$_{20}$N$_2$O$_5$S: C, 61.15; H, 4.89; N, 6.79. Found: C, 61.27; H, 4.65; N, 6.91.

Ethyl 3-(benzenesulfonyl)-1-methyl-2-oxo-1,2,5,6-tetrahydropyrrolo[1,2-h][1,7]naphthyridine-8-carboxylate (QZN4). This compound was obtained by reaction of QZN1. Yellow solid; yield: 53%, mp: 250-251° C.; IR: 1709 (CO), 1658 (CO) cm$^{-1}$; $^1$H nmr (CDCl$_3$) (ppm): 1.38 (3H, t, J=7.1 Hz, CH$_3$), 2.93 (2H, t, J=6.4 Hz, CH$_2$), 3.77 (3H, s, CH$_3$), 4.35 (2H, q, J=7.1 Hz, CH$_2$), 4.68 (2H, t, J=6.4 Hz, CH$_2$), 6.76 (1H, d, J=4.4 Hz, Ar), 7.03 (1H, d, J=4.4 Hz, Ar), 7.47-7.64 (3H, m, 3H—Ar), 8.12-8.18 (2H, m, 2H—Ar), 8.27 (1H, s, H-4); $^{13}$C nmr (CDCl$_3$) (ppm): 14.4 (q), 27.7 (t), 35.2 (q), 41.8 (t), 60.9 (t), 110.7 (s), 113.9 (d), 117.3 (d), 125.4 (s), 125.5 (s), 127.1 (s), 128.6 (2×d), 129.0 (2×d), 133.3 (d), 139.9 (s), 141.5 (d), 143.1 (s), 157.8 (s), 160.5 (s). Anal calcd for C$_{21}$H$_{20}$N$_2$O$_5$S: C, 61.15; H, 4.89; N, 6.79. Found: C, 60.98; H, 5.03; N, 6.53.

Ethyl 3-(benzenesulfonyl)-2-methoxy-6,7-dihydro-5H-pyrido[2,3-c]pyrrolo[1,2-a]azepine-9-carboxylate (QZN7). This compound was obtained by reaction of QZN5. White solid; yield: 23%, mp: 157-158° C.; IR: 1697 cm$^{-1}$; $^1$H nmr (CDCl$_3$) (ppm): 1.38 (3H, t, J=7.1 Hz, CH$_3$), 2.31-2.45 (2H, m, CH$_2$), 2.70 (2H, t, J=7.0 Hz, CH$_2$), 3.96 (3H, s, CH$_3$), 4.27-4.45 (4H, m, 2×CH$_2$), 6.62 (1H, d, J=4.1 Hz, Ar), 7.01 (1H, d, J=4.1 Hz, Ar), 7.49-7.65 (3H, m, Ar), 8.01-8.06 (2H, m, Ar), 8.27 (1H, s, H-4); $^{13}$C nmr (CDCl$_3$) (ppm): 14.4 (q), 28.7 (t), 31.5 (t), 43.8 (t), 51.1 (q), 60.3 (t), 111.0 (d), 117.4 (d), 121.6 (s), 125.0 (s), 126.5 (s), 128.6 (2×d), 128.7 (2×d), 133.4 (d), 140.0 (s), 140.5 (s), 140.6 (d), 153.4 (s), 158.4 (s), 161.1 (s). Anal calcd for C$_{22}$H$_{22}$N$_2$O$_5$S: C, 61.96; H, 5.20; N, 6.57. Found: C, 62.08; H, 5.45; N, 6.37.

Ethyl 3-(benzenesulfonyl)-1-methyl-2-oxo-1,5,6,7-tetrahydro-2H-pyrido[2,3-c]pyrrolo[1,2-a]azepine-9-carboxylate (QZN8). This compound was obtained by reaction of QZN5. Yellow solid; Yield: 45%, mp: 238-239° C.; IR: 1697 (CO), 1658 (CO) cm$^{-1}$; $^1$H nmr (CDCl$_3$) (ppm): 1.39 (3H, t, J=7.1 Hz, CH$_3$), 2.05-2.19 (2H, m, CH$_2$), 2.37-2.62 (2H, m, CH$_2$), 3.60 (3H, s, CH$_3$), 4.34 (2H, q, J=7.1 Hz, CH$_2$), 5.35-5.45 (2H, m, CH$_2$), 6.37 (1H, d, J=4.2 Hz, Ar), 7.04

(1H, d, J=4.2 Hz, Ar), 7.49-7.65 (3H, m, Ar), 8.11-8.18 (2H, m, Ar), 8.28 (1H, s, H-4); $^{13}$C nmr (CDCl$_3$) (ppm): 14.4 (q), 28.3 (t), 31.9 (t), 35.3 (q), 43.3 (t), 60.6 (t), 112.6 (d), 116.3 (s), 116.8 (s), 124.4 (s), 127.6 (s), 128.6 (2×d), 129.1 (2×d), 130.6 (s), 133.4 (d), 139.7 (s), 143.3 (d), 145.8 (s), 157.6 (s), 160.7 (s). Anal calcd for C$_{22}$H$_{22}$N$_2$O$_5$S: C, 61.96; H, 5.20; N, 6.57. Found: C, 61.83; H, 5.13; N, 6.65.

Propan-2-yl 3-(benzenesulfonyl)-2-methoxy-5,6-dihydropyrrolo[1,2-h][1,7]naphthyridine-8-carboxylate (QZN11). This compound was obtained by reaction of QZN9. Yellow solid; yield: 24%, mp: 168-169° C.; IR: 1692 (CO) cm$^{-1}$; $^1$H nmr (CDCl$_3$) (ppm): 1.35 (6H, d, J=6.2 Hz, 2×CH$_3$), 3.31 (2H, t, J=6.9 Hz, CH$_2$), 3.97 (3H, s, CH$_3$), 4.67 (2H, t, J=6.9 Hz, CH$_2$), 5.13-5.26 (1H, m, CH), 6.88 (1H, d, J=4.1 Hz Ar), 6.99 (1H, d, J=4.1 Hz, Ar), 7.47-7.63 (3H, m, Ar), 8.03 (2H, d, J=6.6 Hz Ar), 8.22 (1H, s, H-4); $^{13}$C nmr (CDCl$_3$) (ppm): 22.0 (2×q), 26.9 (t), 42.2 (t), 54.0 (q), 67.9 (d), 109.4 (d), 118.2 (d), 119.1 (s), 120.9 (s), 125.4 (s), 128.5 (2×d), 128.7 (2×d), 133.3 (d), 134.5 (s), 138.5 (d), 140.7 (s), 149.2 (s), 159.1 (s), 160.7 (s). Anal calcd for C$_{22}$H$_{22}$N$_2$O$_5$S: C, 61.96; H, 5.20; N, 6.57. Found: C, 61.76; H, 5.04; N, 6.75.

Propan-2-yl 3-(benzenesulfonyl)-1-methyl-2-oxo-1,2,5,6-tetrahydropyrrolo[1,2-h][1,7]naphthyridine-8-carboxylate (QZN12). This compound was obtained by reaction of QZN9. Yellow solid; yield: 45%, mp: 207-208° C.; IR: 1703 (CO), 1658 (CO) cm$^{-1}$; $^1$H nmr (CDCl$_3$) (ppm): 1.36 (6H, d, J=6.2 Hz, 2×CH$_3$), 2.92 (2H, t, J=7.2 Hz, CH$_2$), 3.77 (3H, s, CH$_3$), 4.68 (2H, t, J=7.2 Hz, CH$_2$), 5.18-5.24 (1H, m, CH), 6.75 (1H, d, J=4.4 Hz, Ar), 7.01 (1H, d, J=4.4 Hz, Ar), 7.47-7.63 (3H, m, Ar), 8.11-8.17 (2H, m, Ar), 8.27 (1H, s, H-4); $^{13}$C nmr (CDCl$_3$) (ppm): 21.9 (2×q), 27.7 (t), 35.1 (q), 41.8 (t), 68.5 (d), 110.7 (s), 113.8 (d), 117.2 (d), 125.4 (s), 125.8 (s), 126.9 (d), 128.6 (2×d), 129.1 (2×d), 133.3 (d), 139.9 (s), 141.5 (d), 143.2 (s), 157.8 (s), 160.1 (s). Anal calcd for C$_{22}$H$_{22}$N$_2$O$_5$S: C, 61.96; H, 5.20; N, 6.57. Found: C, 62.11; H, 5.34; N, 6.39.

Propan-2-yl 3-(benzenesulfonyl)-2-methoxy-6,7-dihydro-5H-pyrido[2,3-c]pyrrolo[1,2-a]azepine-9-carboxylate (QZN15). This compound was obtained by reaction of QZN13. White solid; yield: 28%, mp: 211-212° C.; IR: 1696 (CO) cm$^{-1}$; $^1$H nmr (CDCl$_3$) (ppm): 1.35 (6H, d, J=6.2 Hz, 2×CH$_3$), 2.35-2.44 (2H, m, CH$_2$), 2.64-2.73 (2H, m, CH$_2$), 3.95 (3H, s, CH$_3$), 4.41 (2H, t, J=6.5 Hz, CH$_2$), 5.16 (1H, m, CH), 6.62 (1H, d, J=4.1 Hz, Ar), 7.00 (1H, d, J=4.1 Hz, Ar), 7.49-7.65 (3H, m, Ar), 8.0 (2H, d, J=6.8 Hz, Ar), 8.27 (1H, s, H-4); $^{13}$C nmr (CDCl$_3$) (ppm): 22.1 (2×q), 28.7 (t), 31.5 (t), 43.7 (t), 51.1 (q), 67.7 (d), 109.9 (d), 117.3 (d), 121.6 (s), 125.5 (s), 126.5 (s), 128.6 (2×d), 128.7 (2×d), 133.4 (d), 139.9 (s), 140.5 (d), 153.4 (s), 158.4 (s), 159.8 (s), 160.7 (s). Anal calcd for C$_{23}$H$_{24}$N$_2$O$_5$S: C, 62.71; H, 5.49; N, 6.36. Found: C, 62.89; H, 5.64; N, 6.18.

Propan-2-yl 3-(benzenesulfonyl)-1-methyl-2-oxo-1,5,6,7-tetrahydro-2H-pyrido[2,3-c]pyrrolo[1,2-a]azepine-9-carboxylate (QZN16). This compound was obtained by reaction of QZN13. Yellow solid; Yield: 41%, mp: 253-254° C.; IR: 1697 (CO), 1658 (CO) cm$^{-1}$; $^1$H nmr (CDCl$_3$) (ppm): 1.37 (6H, d, J=6.2 Hz, 2×CH$_3$), 2.08-2.61 (4H, m, 2×CH$_2$), 3.60 (3H, s, CH$_3$), 5.15-5.44 (3H, m, CH$_2$ and CH), 6.35 (1H, d, J=4.1 Hz, Ar), 7.02 (1H, d, J=4.1 Hz, Ar), 7.54-7.62 (3H, m, Ar), 8.14-8.19 (2H, m, Ar), 8.29 (1H, s, H-4); $^{13}$C nmr (CDCl$_3$) (ppm): 22.0 (2×q), 28.4 (t), 31.8 (t), 35.3 (q), 43.3 (t), 68.2 (d), 112.5 (d), 116.3 (s), 117.8 (d), 124.9 (s), 127.7 (s), 128.6 (2×d), 129.2 (2×d), 130.5 (s), 133.4 (d), 139.7 (s), 143.3 (d), 145.9 (s), 157.6 (s), 160.2 (s). Anal calcd for C$_{23}$H$_{24}$N$_2$O$_5$S: C, 62.71; H, 5.49; N, 6.36. Found: C, 62.59; H, 5.36; N, 6.49.

General Procedure for the Synthesis of Compounds of Type 28

To a solution of suitable tricyclic compounds of type 25 (0.22 mmol) in anhydrous DCM (20 ml), Br$_2$ (0.44 mmol, 0.02 mL) was added at 0° C. and the reaction mixture was stirred at room temperature for 24 h. Then the reaction mixture was evaporated under reduced pressure. The crude product was recrystallized from diethyl ether.

Ethyl 3-(benzenesulfonyl)-9-bromo-2-oxo-1,2,5,6-tetrahydropyrrolo[1,2-h][1,7]naphthyridine-8-carboxylate (QZN2). This compound was obtained by reaction of QZN1. Yellow solid; yield: 63%; mp: 196-197° C.; IR: 3342 (NH), 1700 (CO), 1669 (CO) cm$^{-1}$; $^1$H nmr (DMSO-d$_6$) (ppm): 1.37 (3H, t, J=7.1 Hz, CH$_3$), 2.99 (2H, t, J=7.0 Hz, CH$_2$), 4.33 (2H, q, J=7.1 Hz, CH$_2$), 4.67 (2H, t, J=7.0 Hz, CH$_2$), 7.03 (1H, s, Ar), 7.49-7.65 (3H, m, Ar), 8.09-8.17 (2H, m, Ar), 8.31 (1H, s, H-4), 10.02 (1H, s, NH); $^{13}$C nmr (DMSO-d$_6$) (ppm): 14.3 (q), 23.8 (t), 42.8 (t), 61.3 (t), 97.5 (s), 108.2 (s), 120.8 (d), 122.3 (s), 126.2 (s), 127.9 (s), 128.7 (2×d), 129.0 (2×d), 133.6 (d), 138.8 (s), 139.6 (s), 143.8 (d), 156.0 (s), 159.6 (s). Anal calcd for C$_{20}$H$_{17}$BrN$_2$O$_5$S: C, 50.32; H, 3.59; N, 5.87. Found: C, 50.54; H, 3.70; N, 5.69.

Ethyl 3-(benzenesulfonyl)-10-bromo-2-oxo-1,5,6,7-tetrahydro-2H-pyrido[2,3-c]pyrrolo[1,2-a]azepine-9-carboxylate (QZN6). This compound was obtained by reaction of QZN5. White solid; yield: 90%, mp: 172-173° C.; IR: 3399 (NH), 1705 (CO), 1652 (CO) cm$^{-1}$; $^1$H nmr (CDCl$_3$) (ppm): 1.33 (3H, t, J=7.1 Hz, CH$_3$), 2.18-2.21 (2H, m, CH$_2$), 2.38-2.46 (2H, m, CH$_2$), 4.21-4.38 (4H, m, 2×CH$_2$), 7.05 (1H, s, Ar), 7.58-7.75 (3H, m, Ar), 8.02 (2H, d, J=6.9 Hz, Ar), 8.37 (1H, s, H-4), 12.48 (1H, s, NH); $^{13}$C nmr (CDCl$_3$) (ppm): 14.0 (q), 26.0 (t), 31.4 (t), 46.7 (t), 61.1 (t), 98.0 (s), 106.7 (s), 119.2 (d), 123.0 (s), 124.6 (s), 128.3 (2×d), 128.8 (2×d), 134.0 (d), 140.3 (s), 140.4 (s), 147.9 (d), 157.3 (s), 159.1 (s), 159.7 (s). Anal calcd for C$_{21}$H$_{19}$BrN$_2$O$_5$S: C, 51.33; H, 3.90; N, 5.70. Found: C, 51.45; H, 4.05; N, 5.59.

Propan-2-yl 3-(benzenesulfonyl)-9-bromo-2-oxo-1,2,5,6-tetrahydropyrrolo[1,2-h][1,7]naphthyridine-8-carboxylate (QZN10). This compound was obtained by reaction of QZN9. White solid; yield: 69%, mp: 174-175° C.; IR: 3336 (NH), 1705 (CO), 1669 (CO) cm$^{-1}$; $^1$H nmr (CDCl$_3$) (ppm): 1.40 (6H, d, J=6.1 Hz, 2×CH$_3$), 2.94-3.18 (2H, m, CH$_2$), 4.59-4.83 (2H, m, CH$_2$), 5.15-5.36 (1H, m, CH), 7.02 (1H, s, Ar), 7.45-7.69 (3H, m, Ar), 8.11-8.22 (2H, m, Ar), 8.37 (1H, s, H-4), 9.25 (1H, s, NH); $^{13}$C nmr (CDCl$_3$) (ppm): 22.1 (2×q), 26.3 (t), 43.7 (t), 69.2 (d), 98.0 (s), 102.7 (s), 109.3 (s), 120.9 (d), 122.4 (s), 124.9 (s), 126.8 (s), 129.1 (2×d), 129.5 (2×d), 133.7 (d), 144.6 (d), 156.3 (s), 158.7 (s), 159.1 (s). Anal calcd for C$_{21}$H$_{19}$BrN$_2$O$_5$S: C, 51.33; H, 3.90; N, 5.70. Found: C, 51.23; H, 4.11; N, 5.53.

Propan-2-yl 3-(benzenesulfonyl)-10-bromo-2-oxo-1,5,6,7-tetrahydro-2H-pyrido[2,3-c]pyrrolo[1,2-a]azepine-9-carboxylate (QZN14). This compound was obtained by reaction of QZN13. White solid; yield: 84%, mp: 167-168° C.; IR: 3422 (NH), 1702 (CO), 1646 (CO) cm$^{-1}$; $^1$H nmr (DMSO-d$_6$) (ppm): 1.28-1.35 (6H, m, 2×CH$_3$), 2.18-2.41 (2H, m, CH$_2$), 2.44 (2H, s, CH$_2$), 4.14-4.40 (2H, m, CH$_2$), 5.03-5.15 (1H, m, CH), 7.00 (1H, s, H—Ar), 7.58-7.72 (3H, m, 3×H-Ar), 8.01 (2H, d, 2H—Ar), 8.37 (1H, s, 1H—Ar), 12.11-12.81 (1H, m, NH); $^{13}$C nmr (DMSO-d$_6$) (ppm): 22.6 (2×q), 25.4 (t), 28.8 (t), 48.6 (t), 69.9 (d), 98.6 (s), 121.2 (d), 124.4 (s), 125.3 (s), 129.1 (2×d), 129.5 (2×d), 133.8 (d), 134.0 (s), 135.5 (s), 138.0 (s), 139.9 (s), 145.1 (d), 157.1 (s), 161.5 (s). Anal calcd for $C_{22}H_{21}BrN_2O_5S$: C, 52.28; H, 4.19; N, 5.54. Found: C, 52.14; H, 4.04; N, 5.77.

General Procedure for the Synthesis of Compound of Type 29 ($R^a$=H)

To a suspension of MeONa (0.81 g, 15 mmol) in anhydrous ethanol (20 mL), guanidine nitrate (0.92 g, 7.5 mmol) and a solution of the suitable enaminoketons of type 24 (2 mmol) in anhydrous ethanol (20 mL) were added. The reaction mixture was heated at reflux up to completeness (TLC). Then the reaction mixture was poured onto crushed ice and the precipitate was filtered off, dried and purified by chromatography (DCM/AcOEt 9:1).

Ethyl 2-amino-5,6-dihydropyrimido[5,4-g]indolizine-8-carboxylate (QZQ1) This compound was obtained by reaction of ethyl 7-[(dimethylamino)methylidene]-8-oxo-5,6,7,8-tetrahydroindolizine-3-carboxylate after 7 h. White solid; yield: 62%; mp: 222-223° C.; IR: 3270-3160 ($NH_2$), 1663 (CO) $cm^{-1}$; $^1H$ nmr (DMSO-$d_6$) (ppm): 1.29 (3H, t, J=7.1 Hz, $CH_3$), 2.91 (2H, t, J=6.8 Hz, $CH_2$), 4.26 (2H, q, J=7.1 Hz, $CH_2$), 4.54 (2H, t, J=6.8 Hz, $CH_2$), 6.53 (2H, s, $NH_2$), 6.76 (1H, d, J=4.1 Hz, Ar), 6.94 (1H, d, J=4.1 Hz, Ar), 8.17 (1H, s, H-4); $^{13}C$ nmr (DMSO-$d_6$) (ppm): 14.2 (q), 23.4 (t), 42.3 (t), 59.9 (t), 108.0 (d), 112.1 (s), 117.5 (d), 124.0 (s), 134.1 (s), 152.9 (s), 156.7 (d), 160.2 (s), 162.9 (s). Anal calcd for $C_{13}H_{14}N_4O_2$: C, 60.45; H, 5.46; N, 21.69. Found: C, 60.58; H, 5.39; N, 21.80.

Ethyl 2-amino-6,7-dihydro-5H-pyrimido[4,5-c]pyrrolo[1,2-a]azepine-9-carboxylate (QZQ5). This compound was obtained by reaction of ethyl 8-(dimethylamino)methylene)-9-oxo-6,7,8,9-tetrahydro-5H-pyrrolo[1,2-a]azepine-3-carboxylate after 3 h. White solid; yield: 41%; mp: 180-181° C.; 3411-3320 ($NH_2$), 1696 (CO) $cm^{-1}$; $^1H$ nmr (DMSO-$d_6$) (ppm): 1.30 (3H, t, J=7.1 Hz, $CH_3$), 2.14-2.20 (2H, m, $CH_2$), 2.42 (2H, t, J=6.3 Hz, $CH_2$), 4.20-4.36 (4H, m, 2×$CH_2$), 6.54 (1H, d, J=4.0 Hz, Ar), 6.59 (2H, s, $NH_2$) 6.93 (1H, d, J=4.0 Hz, Ar), 8.18 (1H, s, H-4); $^{13}C$ nmr (DMSO-$d_6$) (ppm): 14.2 (q), 24.8 (t), 30.5 (t), 43.6 (t), 59.8 (t), 109.7 (d), 116.8 (d), 118.3 (s), 123.8 (s), 139.8 (s), 157.6 (s), 158.5 (d), 160.2 (s), 162.9 (s). Anal calcd for $C_{14}H_{16}N_4O_2$: C, 61.75; H, 5.92; N, 20.58. Found: C, 61.62; H, 5.77; N, 20.72.

Propan-2-yl 2-amino-5,6-dihydropyrimido[5,4-g]indolizine-8-carboxylate (QZQ7). This compound was obtained by reaction of propan-2-yl 7-[(dimethylamino)methylidene]-8-oxo-5,6,7,8-tetrahydroindolizine-3-carboxylate after 1 h. White solid; yield: 71%; mp: 211-212° C.; IR: 3414-3332 ($NH_2$), 1695 (CO) $cm^{-1}$; $^1H$ nmr ($CDCl_3$) (ppm): 1.35 (6H, d, J=6.2 Hz, 2×$CH_3$), 2.96 (2H, t, J=6.8 Hz, $CH_2$), 5.14-4.65 (2H, t, J=6.8 Hz, $CH_2$), 5.12-5.25 (3H, m, CH and $NH_2$), 6.91-7.03 (2H, m, Ar), 8.15 (1H, s, H-4); $^{13}C$ nmr ($CDCl_3$) (ppm): 22.1 (2×q), 24.4 (t), 42.5 (t), 67.9 (d), 109.3 (d), 113.6 (s), 118.1 (d), 125.6 (s), 133.8 (s), 154.4 (s), 156.1 (d), 160.7 (s), 162.5 (s). Anal calcd for $C_{14}H_{16}N_4O_2$: C, 61.75; H, 5.92; N, 20.58. Found: C, 61.89; H, 6.11; N, 20.33.

Propan-2-yl 2-amino-6,7-dihydro-5H-pyrimido[4,5-c]pyrrolo[1,2-a]azepine-9-carboxylate (QZQ21). This compound was obtained by reaction of propan-2-yl 8-[(dimethylamino)methylidene]-9-oxo-6,7,8,9-tetrahydro-5H-pyrrolo[1,2-a]azepine-3-carboxylate after 1 h. White solid; yield: 86%; mp: 176-177° C.; IR: 3514-3411 ($NH_2$), 1692 (CO) $cm^{-1}$; $^1H$ nmr (DMSO-$d_6$) (ppm): 1.30 (6H, d, J=6.0 Hz, 2×$CH_3$), 2.09-2.24 (2H, m, $CH_2$), 2.41-2.51 (2H, m, $CH_2$), 4.24-4.32 (2H, m, $CH_2$), 5.06-5.12 (1H, m, CH), 6.51-6.61 (2H, m, Ar and $NH_2$), 6.92 (1H, s, Ar), 8.18 (1H, s, H-4); $^{13}C$ nmr (DMSO-$d_6$) (ppm): 22.16 (2×q), 27.9 (t), 31.1 (t), 47.3 (t), 68.9 (d), 108.7 (d), 117.7 (s), 126.9 (s), 121.5 (s), 128.5 (s), 148.2 (s), 154.6 (d), 161.1 (s), 162.2 (s). Anal calcd for $C_{15}H_{18}N_4O_2$: C, 62.92; H, 6.34; N, 19.57. Found: C, 63.09; H, 6.52; N, 19.38.

General Procedure for the Synthesis of Compounds of Type 29

A solution of the suitable enaminoketons 24 (1.5 mmol) and phenylguanidine ($R^a$=Ph), cyclohexylguanidine ($R^a$=cyclohexyl) or cyclopentylguanidine ($R^a$=cyclopentyl) (4.5 mmol) in anhydrous DMF (8 mL) was heated at 100° C. up to completeness (TLC). Then the reaction mixture was poured onto crushed ice and the precipitate was filtered off, dried and purified by chromatography (DCM).

Ethyl 2-anilino-5,6-dihydropyrimido[5,4-g]indolizine-8-carboxylate (QZQ2). This compound was obtained by reaction of ethyl 7-[(dimethylamino)methylidene]-8-oxo-5,6,7,8-tetrahydroindolizine-3-carboxylate with phenylguanidine after 1 h. Yellow solid; Yield: 55%; mp: 177-178° C.; IR: 3417 (NH), 1698 (CO) $cm^{-1}$; $^1H$ nmr (DMSO-$d_6$) (ppm): 1.31 (3H, t, J=7.1 Hz, $CH_3$), 3.02 (2H, t, J=6.8 Hz, $CH_2$), 4.28 (2H, q, J=7.1 Hz, $CH_2$), 4.60 (2H, t, J=6.8 Hz, $CH_2$), 6.89-7.01 (2H, m, Ar), 77.24-7.33 (3H, m, Ar), 7.83 (2H, d, J=7.7 Hz, Ar), 8.41 (1H, s, H-4), 9.58 (1H, s, NH); $^{13}C$ nmr (DMSO-$d_6$) (ppm): 14.2 (q), 23.4 (t), 42.2 (t), 60.0 (t), 108.6 (d), 114.3 (s), 117.7 (d), 118.4 (2×d), 121.0 (d), 128.4 (2×d), 133.8 (s), 140.8 (s), 152.7 (s), 156.5 (d), 159.2 (s), 159.8 (s), 160.1 (s). Anal calcd for $C_{19}H_{18}N_4O_2$: C, 68.25; H, 5.43; N, 16.76. Found: C, 68.13; H, 5.57; N, 16.89.

Ethyl 2-(cyclohexylamino)-5,6-dihydropyrimido[5,4-g]indolizine-8-carboxylate (QZQ3). This compound was obtained by reaction of ethyl 7-[(dimethylamino)methylidene]-8-oxo-5,6,7,8-tetrahydroindolizine-3-carboxylate with cyclohexylguanidine after 6 h. White solid; yield: 52%; mp: 130-131° C.; IR: 3433 (NH), 1697 (CO) $cm^{-1}$; $^1H$ nmr (DMSO-$d_6$) (ppm): 1.09-1.33 (13H, m, $CH_3$ and 5×$CH_2$), 2.92 (2H, t, J=6.6 Hz, $CH_2$), 3.70-3.73 (1H, m, CH), 4.25 (2, q, J=7.1 Hz, $CH_2$), 4.54 (2H, t, J=6.6 Hz, $CH_2$), 6.76 (1H, d, J=4.1 Hz, Ar), 6.89-6.96 (2H, m, Ar and NH), 8.19 (1H, s, H-4); $^{13}C$ nmr (DMSO-$d_6$) (ppm): 14.2 (q), 23.4 (t), 24.8 (2×t), 25.4 (t), 32.4 (2×t), 42.4 (t), 49.3 (d), 59.9 (t), 108.0 (d), 111.6 (s), 117.5 (d), 124.0 (s), 134.3 (s), 152.8 (s), 156.4 (d), 160.2 (s), 161.1 (s). Anal calcd for $C_{19}H_{24}N_4O_2$: C, 67.04; H, 7.11; N, 16.46. Found: C, 67.29; H, 6.98; N, 16.32.

Ethyl 2-anilino-6,7-dihydro-5H-pyrimido[4,5-c]pyrrolo[1,2-a]azepine-9-carboxylate (QZQ6). This compound was obtained by reaction of ethyl 8-(dimethylamino)methylene)-9-oxo-6,7,8,9-tetrahydro-5H-pyrrolo[1,2-a]azepine-3-carboxylate with phenylguanidine after 5 h. White solid; yield: 56%; mp: 134-135° C.; IR: 3443 (NH), 1697 (CO) $cm^{-1}$; $^1H$ nmr (DMSO-$d_6$) (ppm): 1.31 (3H, t, J=7.1 Hz, $CH_3$), 2.20-2.26 (2H, m, $CH_2$), 2.50-2.57 (2H, m, $CH_2$), 4.22-4.42 (4H, m, 2×$CH_2$), 6.71 (1H, d, J=4.1 Hz, Ar), 6.89-7.00 (2H, m, Ar), 7.28 (2H, t, J=8.3 Hz, Ar), 7.81 (2H, d, J=7.6 Hz, Ar), 8.43 (1H, s, H-4), 9.67 (1H, s, NH); $^{13}C$ nmr (DMSO-$d_6$) (ppm): 14.2 (q), 25.1 (t), 30.6 (t), 43.8 (t), 59.9 (t), 110.4 (d), 116.3 (d), 118.5 (2×d), 120.6 (s), 121.0 (d), 124.4 (s), 128.4 (2×d), 139.4 (s), 140.7 (s), 157.3 (s), 158.4 (d), 159.1 (s), 160.2 (s). Anal calcd for $C_{20}H_{20}N_4O_2$: C, 68.95; H, 5.79; N, 16.08. Found: C, 69.12; H, 5.64; N, 15.96.

Ethyl 2-(cyclohexylamino)-6,7-dihydro-5H-pyrimido[4,5-c]pyrrolo[1,2-a]azepine-9-carboxylate (QZQ7). This compound was obtained by reaction of ethyl 8-(dimethylamino)methylene)-9-oxo-6,7,8,9-tetrahydro-5H-pyrrolo[1,2-a]azepine-3-carboxylate with cyclohexylguanidine after 2 h. Yellow solid; yield: 61%; mp: 98-99° C.; IR: 3422 (NH), 1693 (CO) $cm^{-1}$; $^1H$ nmr (DMSO-$d_6$) (ppm): 1.09-1.90

(13H, m, CH₃ and 5×CH₂), 2.10-2.24 (2H, m, CH₂), 2.41 (2H, t, J=6.5 Hz, CH₂), 3.72-3.82 (1H, m, CH), 4.20-4.37 (2H, m, 2×CH₂), 6.39 (1H, d, J=4.0 Hz, Ar), 6.92-7.03 (2H, m, Ar and NH), 8.19 (1H, d, H-4); $^{13}$C nmr (DMSO-d₆) (ppm): 14.2 (q), 24.8 (3×t), 25.4 (t), 30.4 (t), 32.4 (2×t), 43.6 (t), 49.2 (d), 59.8 (t), 109.5 (d), 116.8 (d), 123.8 (s), 124.0 (s), 139.9 (s), 141.6 (s), 158.3 (d), 160.2 (s), 161.0 (s). Anal calcd for C₂₀H₂₆N₄O₂: C, 67.77; H, 7.39; N, 15.81. Found: C, 67.64; H, 7.27; N, 15.99.

Propan-2-yl 2-anilino-5,6-dihydropyrimido[5,4-g]indolizine-8-carboxylate (QZQ18). This compound was obtained by reaction of propan-2-yl 7-[(dimethylamino)methylidene]-8-oxo-5,6,7,8-tetrahydroindolizine-3-carboxylate with phenylguanidine after 3 h. White solid; yield: 79%; mp: 184-185° C.; IR: 3422 (NH), 1695 (CO) cm⁻¹; $^1$H nmr (CDCl₃) (ppm): 1.30 (6H, d, J=6.2 Hz, 2×CH₃), 3.01 (2H, t, J=6.8 Hz, CH₂), 4.68 (2H, t, J=6.8 Hz, CH₂), 5.14-5.26 (1H, m, CH), 6.98-7.07 (3H, m, Ar and NH), 7.21-7.39 (3H, m, Ar), 7.68 (1H, d, J=7.7 Hz, Ar), 8.26 (1H, s, H-4); $^{13}$C nmr (CDCl₃) (ppm): 22.1 (2×q), 24.4 (t), 42.5 (t), 67.9 (d), 109.3 (d), 114.4 (s), 118.1 (d), 118.9 (2×d), 122.2 (d), 125.6 (s), 128.9 (2×d), 134.0 (s), 139.8 (s), 154.0 (s), 156.1 (d), 159.5 (s), 160.1 (s). Anal calcd for C₂₀H₂₀N₄O₂: C, 68.95; H, 5.79; N, 16.08. Found: C, 68.79; H, 5.91; N, 16.21.

Propan-2-yl 2-(cyclohexylamino)-5,6-dihydropyrimido[5,4-g]indolizine-8-carboxylate (QZQ19). This compound was obtained by reaction of propan-2-yl 7-[(dimethylamino)methylidene]-8-oxo-5,6,7,8-tetrahydroindolizine-3-carboxylate with cyclohexylguanidine after 2 h. Yellow solid; yield: 86%; mp: 123-124° C.; IR: 3399 (NH), 1694 (CO) cm⁻¹; $^1$H nmr (DMSO-d₆) (ppm): 1.27-1.86 (16H, m, 2×CH₃ and 5×CH₂), 2.64-2.73 (2H, m, CH₂), 3.12-3.22 (1H, m, CH), 4.38-4.44 (2H, m, CH₂), 5.01-5.13 (1H, m, CH), 6.59 (1H, d, J=4.1 Hz, Ar), 6.82 (1H, d, J=4.1 Hz, Ar), 7.27 (1H, s, H-4), 10.04-10.14 (1H, m, NH); $^{13}$C nmr (DMSO-d₆) (ppm): 21.7 (2×q), 24.0 (2×t), 24.7 (t), 26.4 (t), 33.4 (2×t), 33.7 (t), 55.8 (d), 67.3 (d), 96.4 (s), 109.8 (d), 116.5 (d), 123.5 (s), 136.8 (s), 136.9 (s), 151.4 (d), 159.9 (s). Anal calcd for C₂₀H₂₆N₄O₂: C, 67.77; H, 7.39; N, 15.81. Found: C, 67.89; H, 7.51; N, 15.69.

Propan-2-yl 2-anilino-6,7-dihydro-5H-pyrimido[4,5-c]pyrrolo[1,2-a]azepine-9-carboxylate (QZQ22). This compound was obtained by reaction of propan-2-yl 8-[(dimethylamino)methylidene]-9-oxo-6,7,8,9-tetrahydro-5H-pyrrolo[1,2-a]azepine-3-carboxylate with phenylguanidine after 2 h. White solid; yield: 80%; mp: 101-102° C.; IR: 3421 (NH), 1691 (CO) cm⁻¹; $^1$H nmr (CDCl₃) (ppm): 1.36 (6H, d, J=6.1 Hz, 2×CH₃), 2.30-2.39 (2H, m, CH₂), 2.59 (2H, t, J=7.0 Hz, CH₂), 4.46 (2H, t, J=7.0 Hz, CH₂), 5.14-5.29 (1H, m, CH), 6.75 (1H, d, J=3.6 Hz, Ar), 6.69-7.06 (2H, m, Ar and NH), 7.26-7.37 (3H, m, Ar), 7.66 (1H, d, J=7.8 Hz, Ar), 8.28 (1H, s, H-4); $^{13}$C nmr (CDCl₃) (ppm): 22.3 (2×q), 27.8 (t), 31.0 (t), 46.9 (t), 68.9 (d), 108.7 (d), 121.0 (s), 122.0 (2×d), 123.9 (d), 122.1 (s), 126.9 (d), 128.5 (s), 129.9 (2×d), 139.9 (s), 147.7 (s), 156.1 (d), 159.7 (s), 161.4 (s). Anal calcd for C₂₁H₂₂N₄O₂: C, 69.59; H, 6.12; N, 15.46. Found: C, 69.71; H, 6.34; N, 15.32.

Propan-2-yl 2-(cyclohexylamino)-6,7-dihydro-5H-pyrimido[4,5-c]pyrrolo[1,2-a]azepine-9-carboxylate (QZQ23). This compound was obtained by reaction of propan-2-yl 8-[(dimethylamino)methylidene]-9-oxo-6,7,8,9-tetrahydro-5H-pyrrolo[1,2-a]azepine-3-carboxylate with cyclohexylguanidine after 4 h. White solid; yield: 98%; mp: 108-109° C.; IR: 3381 (NH), 1685 (CO) cm⁻¹; $^1$H nmr (CDCl₃) (ppm): 1.03-1.35 (10H, m, 2×CH₃ and 2×CH₂), 1.59-1.80 (4H, m, 2×CH₂), 1.93-2.10 (4H, m, 2×CH₂), 2.15-2.21 (2H, m, CH₂), 3.10-3.16 (1H, m, CH), 4.53 (2H, t, J=6.3 Hz, CH₂), 5.10-5.23 (1H, s, CH), 6.56 (1H, d, J=4.1 Hz, Ar), 6.86-6.92 (2H, m, Ar), 10.28-10.37 (1H, m, NH); $^{13}$C nmr (CDCl₃) (ppm): 22.0 (2×q), 24.5 (2×t), 25.2 (t), 26.9 (t), 31.1 (t), 34.1 (2×t), 43.5 (t), 57.4 (d), 67.5 (d), 102.4 (2×s), 110.2 (d), 116.7 (d), 123.9 (s), 142.6 (s), 152.3 (d), 160.9 (s), 185.1 (s). Anal calcd for C₂₁H₂₈N₄O₂: C, 68.45; H, 7.66; N, 15.21. Found: C, 68.32; H, 7.79; N, 15.08.

Ethyl 2-(cyclopentylamino)-5,6-dihydropyrimido[5,4-g]indolizine-8-carboxylate (QZQ14). This compound was obtained by reaction of ethyl 7-[(dimethylamino)methylidene]-8-oxo-5,6,7,8-tetrahydroindolizine-3-carboxylate with cyclopentylguanidine after 2 h. Pale yellow solid; yield: 52%; mp: 95-96° C.; IR: 3405 (NH), 1699 (CO) cm⁻¹; $^1$H nmr (DMSO-d₆) (ppm): 1.28 (3H, t, J=7.1 Hz, CH₃), 1.48-1.67 (6H, m, 3×CH₂), 1.87-1.99 (2H, m, CH₂), 2.64-274 (2H, m, CH₂), 3.72-3.85 (1H, m, CH), 4.24 (2H, q, J=7.1 Hz, CH₂), 4.33-4.51 (2H, m, CH₂), 6.59-6.62 (1H, m, Ar), 6.81-6.90 (1H, m, Ar), 7.31-7.35 (1H, m, Ar), 10.01-10.11 (1H, m, NH); $^{13}$C nmr (DMSO-d₆) (ppm): 14.2 (q), 23.0 (2×t), 26.4 (t), 33.5 (2×t), 43.9 (t), 59.1 (d), 59.9 (t), 96.5 (s), 109.4 (d), 116.8 (d), 123.2 (s), 136.8 (s), 137.0 (s), 151.9 (d), 160.3 (s), 176.7 (s). Anal calcd for C₁₈H₂₂N₄O₂: C, 66.24; H, 6.79; N, 17.17. Found: C, 66.12; H, 6.91; N, 17.08.

Ethyl 2-(cyclopentylamino)-6,7-dihydro-5H-pyrimido[4,5-c]pyrrolo[1,2-a]azepine-9-carboxylate (QZQ15). This compound was obtained by reaction of ethyl 8-(dimethylamino)methylene)-9-oxo-6,7,8,9-tetrahydro-5H-pyrrolo[1,2-a]azepine-3-carboxylate with cyclopentylguanidine after 3 h. Yellow solid; yield: 61%; mp: 98-99° C.; IR: 3405 (NH), 1696 (CO) cm⁻¹; $^1$H nmr (DMSO-d₆) (ppm): 1.31 (3H, t, J=7.1 Hz, CH₃), 1.49-1.68 (6H, m, 3×CH₂), 1.90-2.24 (4H, m, 2×CH₂), 3.72-3.82 (1H, m, CH), 4.23 (2H, q, J=7.1 Hz, CH₂), 4.38-4.47 (2H, m, CH₂), 6.39-6.41 (1H, m, Ar), 6.80.6.83 (1H, m, Ar), 7.454-7.61 (1H, m, Ar), 10.20-10.30 (1H, m, NH); $^{13}$C nmr (DMSO-d₆) (ppm): 14.2 (q), 23.0 (2×t), 25.8 (t), 30.4 (t), 33.5 (2×t), 43.1 (t), 59.2 (d), 59.8 (t), 101.4 (s), 109.5 (d), 116.1 (s), 116.2 (d), 122.4 (s), 142.5 (s), 147.6 (s), 153.6 (d), 160.3 (s). Anal calcd for C₁₉H₂₄N₄O₂: C, 67.04; H, 7.11; N, 16.46. Found: C, 67.22; H, 6.96; N, 16.31.

Propan-2-yl 2-(cyclopentylamino)-5,6-dihydropyrimido[5,4-g]indolizine-8-carboxylate (QZQ20). This compound was obtained by reaction of propan-2-yl 7-[(dimethylamino)methylidene]-8-oxo-5,6,7,8-tetrahydroindolizine-3-carboxylate with cyclopentylguanidine after 3 h. White solid; yield: 73%; mp: 124-125° C.; IR: 3406 (NH), 1692 (CO) cm⁻¹; $^1$H nmr (CDCl₃) (ppm): 1.33 (6H, d, J=6.3 Hz, 2×CH₃), 1.64-1.99 (8H, m, 4×CH₂), 2.70 (2H, t, J=6.4 Hz, CH₂), 3.64-3.73 (1H, m, CH), 4.52 (2H, t, J=6.4 Hz, CH₂), 5.11-5.23 (1H, m, J=6.2 Hz, CH), 6.79-6.93 (3H, m, Ar), 10.09-10.18 (1H, m, NH); $^{13}$C nmr (CDCl₃) (ppm): 22.0 (2×q), 23.5 (2×t), 27.4 (t), 34.1 (2×t), 44.2 (t), 60.2 (d), 67.7 (d), 97.1 (s), 110.1 (d), 117.4 (d), 124.5 (s), 132.5 (s), 137.0 (s), 151.1 (d), 160.9 (s), 178.2 (s). Anal calcd for C₁₉H₂₄N₄O₂: C, 67.04; H, 7.11; N, 16.46. Found: C, 66.91; H, 7.23; N, 16.58.

Propan-2-yl 2-(cyclopentylamino)-6,7-dihydro-5H-pyrimido[4,5-c]pyrrolo[1,2-a]azepine-9-carboxylate (QZQ24). This compound was obtained by reaction of propan-2-yl 8-[(dimethylamino)methylidene]-9-oxo-6,7,8,9-tetrahydro-5H-pyrrolo[1,2-a]azepine-3-carboxylate with cyclopentylguanidine after 2 h. Brown solid; yield: 82%; mp: 140-141° C.; IR: 3416 (NH), 1690 (CO) cm⁻¹; $^1$H nmr (CDCl₃) (ppm): 1.34 (6H, d, J=6.2 Hz, 2×CH₃), 1.60-1.78 (6H, m, 3×CH₂), 1.82-2.22 (6H, m, 3×CH₂), 3.65-3.77 (1H, m, CH), 4.53 (2H, t, J=6.2 Hz, CH$_2$), 5.10-5.23 (1H, m, CH), 6.55 (1H, d, J=4.0 Hz, Ar), 6.84-6.95 (2H, m, Ar), 10.32-10.36 (1H, m, NH); $^{13}$C nmr (CDCl$_3$) (ppm): 22.0 (2×q), 23.5 (2×t), 26.8 (t), 31.0 (t), 34.1 (2×t), 43.5 (t), 60.2 (d), 67.5 (d), 102.5 (2×s), 110.2 (d), 116.7 (d), 124.0 (s), 142.6 (s), 152.9 (d), 160.9 (s), 185.1 (s). Anal calcd for C$_{20}$H$_{26}$N$_4$O$_2$: C, 67.77; H, 7.39; N, 15.81. Found: C, 67.90; H, 7.54; N, 15.63.

General Procedure for the Synthesis of Compounds of Type 30

To a solution of compounds of type 29 (R$^a$=H) (0.15 g, 0.52 mmol) in anhydrous dioxane (20 mL) acetyl chloride (0.057 mL, 0.78 mmol) and triethylamine (0.08 mL, 0.57 mmol) were added and the reaction mixture was stirred at reflux up to completeness (TLC). Then the reaction mixture was poured onto crushed ice and the precipitate was filtered off, dried and purified by chromatography (DCM).

Ethyl 2-acetamido-5,6-dihydropyrimido[5,4-g]indolizine-8-carboxylate (QZQ4). This compound was obtained by reaction of QZQ1 after 4 h. White solid; yield: 77%, mp: 249-250° C.; IR: 3403 (NH), 1663 (CO), 1651 (CO) cm$^{-1}$; $^1$H nmr (DMSO-d$_6$) (ppm): 1.31 (3H, t, J=7.1 Hz, CH$_3$), 2.22 (3H, s, CH$_3$), 3.08 (2H, t, J=6.8 Hz, CH$_2$), 4.28 (2H, q, J=7.1 Hz, CH$_2$), 4.62 (2H, t, J=6.8 Hz, CH$_2$), 6.88 (1H, d, J=4.1 Hz, Ar), 6.99 (1H, d, J=4.1 Hz, Ar), 8.54 (1H, s, H-4), 10.46 (1H, s, NH); $^{13}$C nmr (DMSO-d$_6$) (ppm): 14.2 (q), 23.5 (t), 24.6 (q), 41.9 (t), 60.1 (t), 109.1 (d), 117.7 (d), 118.5 (s), 124.8 (s), 133.2 (s), 153.1 (s), 156.6 (d), 156.8 (s), 160.1 (s), 169.2 (s). Anal calcd for C$_{15}$H$_{16}$N$_4$O$_3$: C, 59.99; H, 5.37; N, 18.66. Found: C, 60.11; H, 5.56; N, 18.51.

Ethyl 2-acetamido-6,7-dihydro-5H-pyrimido[4,5-c]pyrrolo[1,2-a]azepine-9-carboxylate (QZQ8). This compound was obtained by reaction of QZQ5 after 2 h. White solid; yield: 79%, mp: 211-212° C.; IR: 3387 (NH), 1700 (CO), 1695 (CO) cm$^{-1}$; $^1$H nmr (DMSO-d$_6$) (ppm): 1.30 (3H, t, J=7.1 Hz, CH$_3$), 2.21-2.29 (5H, m, CH$_3$ and CH$_2$), 2.61 (2H, t, J=6.8 Hz, CH$_2$), 4.27 (2H, q, J=7.1 Hz, CH$_2$), 4.39 (2H, t, J=6.8 Hz, CH$_2$), 6.71 (1H, d, J=4.1 Hz, Ar), 6.98 (1H, d, J=4.1 Hz, Ar), 8.57 (1H, s, H-4), 10.54 (1H, s, NH); $^{13}$C nmr (DMSO-d$_6$) (ppm): 14.2 (q), 24.6 (q), 25.5 (t), 30.1 (t), 44.0 (t), 67.9 (d), 111.1 (d), 116.9 (d), 124.8 (s), 138.7 (s), 145.1 (s), 156.6 (s), 157.4 (s), 158.7 (d), 160.2 (s), 169.1 (s). Anal calcd for C$_{16}$H$_{18}$N$_4$O$_3$: C, 61.13; H, 5.77; N, 17.82. Found: C, 61.01; H, 5.98; N, 17.64.

Propan-2-yl 2-acetamido-5,6-dihydropyrimido[5,4-g]indolizine-8-carboxylate (QZQ25). This compound was obtained by reaction of QZQ17 after 4 h. White solid; yield: 63%; mp: 242-243° C.; IR: 3199 (NH), 1693 (CO), 1675 (CO) cm$^{-1}$; $^1$H nmr (CDCl$_3$) (ppm): 1.36 (6H, d, J=6.2 Hz, 2×CH$_3$), 2.59 (3H, s, CH$_3$), 3.08 (2H, t, J=6.8 Hz, CH$_2$), 4.71 (2H, t, J=6.8 Hz, CH$_2$), 5.17-5.27 (1H, m, CH), 6.95-7.05 (2H, m, Ar), 8.47 (1H, s, H-4), 8.92 (1H, s, NH); $^{13}$C nmr (CDCl$_3$) (ppm): 22.0 (2×q), 24.5 (t), 25.4 (q), 42.2 (t), 68.1 (d), 110.5 (d), 117.4 (d), 117.5 (s), 124.8 (s), 126.4 (s), 138.7 (s), 156.5 (d), 156.7 (s), 160.6 (s), 161.1 (s). Anal calcd for C$_{16}$H$_{18}$N$_4$O$_3$: C, 61.13; H, 5.77; N, 17.82. Found: C, 61.24; H, 5.49; N, 17.97.

Propan-2-yl 2-acetamido-6,7-dihydro-5H-pyrimido[4,5-c]pyrrolo[1,2-a]azepine-9-carboxylate (QZQ26). This compound was obtained by reaction of QZQ21 after 5 h. white solid; yield: 58%; mp: 211-212° C.; IR: 3388 (NH), 1689 (CO), 1673 (CO) cm$^{-1}$; $^1$H nmr (CDCl$_3$) (ppm): 1.36 (6H, d, J=6.2 Hz, 2×CH$_3$), 2.34-2.44 (2H, m, CH$_2$), 2.54 (3H, s, CH$_3$), 2.67 (2H, t, J=6.9 Hz, CH$_2$), 4.46 (2H, t, J=6.9 Hz, CH$_2$), 5.14-5.27 (1H, m, CH), 6.74 (1H, d, J=4.1 Hz, Ar), 7.02 (1H, d, J=4.1 Hz, Ar), 8.47 (1H, s, H-4), 8.62 (1H, s, NH); $^{13}$C nmr (CDCl$_3$) (ppm): 22.0 (2×q), 25.3 (q), 26.2 (t), 30.8 (t), 44.1 (t), 67.9 (t), 111.5 (d), 117.4 (d), 117.5 (s), 124.9 (s), 126.4 (s), 138.7 (s), 156.5 (s), 158.4 (d), 158.7 (s), 160.6 (s). Anal calcd for C$_{17}$H$_{20}$N$_4$O$_3$: C, 62.18; H, 6.14; N, 17.06. Found: C, 62.03; H, 6.29; N, 15.87.

Scheme 6 describes the general synthesis of pyrazolo[4,3-h]quinolines as reported in Table 6. In addition, the skilled person will recognise that compounds of formula 33 as shown in Scheme 6 can be reacted as described in Scheme 2 for compounds of formula 8 to obtain additional compounds of the present invention.

The synthesis of derivatives pyrazolo[4,3-h]quinolines of type 34 was achieved according to synthetic Scheme 6 starting from ketone 31 prepared according to the synthetic procedure by Beria et al J. Med. Chem. 2010, 53, 3532-3551. Functionalization of the pyrazole nitrogen was obtained with classical procedures in N,N-dimethylformamide (DMF) or tetrahydrofuran (THF) with sodium hydride (NaH) as the base, followed by nucleophilic substitution with aryl halides and alkyl halides giving the corresponding N-substituted derivatives 32. Direct introduction of the α-enamino functionality using Bredereck's reagent, t-butoxy-bis-(dimethylamino)methane (TBDMAM) gave compounds of formula 32 which were subjected to the final cyclization step to 34.

Scheme 6. Synthesis of pyrazolo[4,3-h]quinolines.

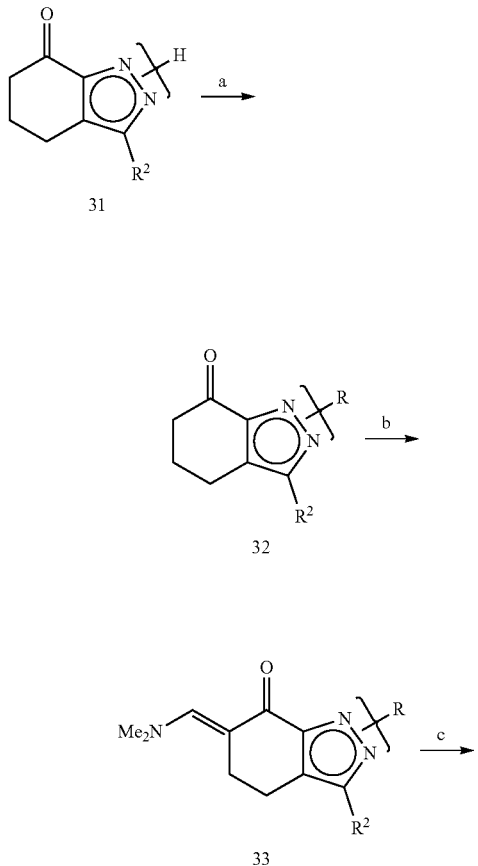

-continued

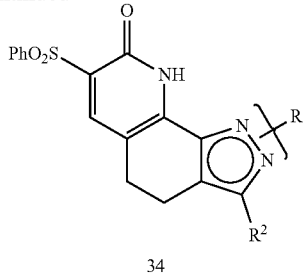

34

(a) NaH, THF or DMF, 0° C. to r.t., 90 min then substituted arylalkyl halides or alkyl halides, 0° C. to r.t.; (b) TBDMAM (1:3), toluene, reflux; (c) PhSO$_2$CH$_2$CN, ethanol, reflux, 24 h.

The derivatives reported in Tables 6 below are exemplary compounds that may be prepared according to the synthetic procedure of Scheme 6. Relative additivity indeces (AI %), which were measured as described in the Materials and Methods section, are also reported.

TABLE 6

Pyrazolo[4,3-h]quinolines of formula:

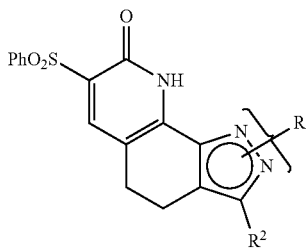

| CPD | R | R$^2$ | AI (%)$^a$ |
|---|---|---|---|
| PZ1 | 4-MeBn (N-1) | COOEt | 88% |
| PZ3 | 3-MeBn (N-1) | COOEt | 163% |
| PZ5 | 4-BrBn (N-1) | COOEt | 64% |
| PZ7 | 3,4-(Me)$_2$Bn (N-1) | COOEt | 104% |
| PZ8 | 3,4-(Me)$_2$Bn (N-2) | COOEt | 21% |

$^a$ Activity of compounds (at 10 µM) was expressed as additivity index (AI %) which is calculated as (QR$_{TOT}$-QR$_{VX}$)/QR$_{VX}$ where QR$_{TOT}$ is the quenching rate (HS-YFP assay) in the presence of test compound plus VX-809 and QR$_{VX}$ is the quenching rate with VX-809 alone.

A detailed description of the synthesis of exemplary compounds reported in Scheme 6 is provided hereinbelow.

General Procedure for the Synthesis of ethyl 1-substituted-7-oxo-4,5,6,7-tetrahydro-1H-indazole-3-carboxylate 32

To a solution of ethyl 7-oxo-4,5,6,7-tetrahydro-1H-indazole-3-carboxylate 31 (9 mmol) in anhydrous DMF (17 mL), NaH (0.24 g, 10 mmol) was added at 0° C. and the reaction was stirred at room temperature for 1 h. Then the suitable aralkyl halide (13.5 mmol) was added at 0° C. and the reaction mixture was stirred at room temperature up to completeness (TLC). Then the reaction mixture was poured onto crushed ice. The precipitate was filtered and dried, in absence the solution was extracted with DCM (3×50 mL). The organic layer was dried (Na$_2$SO$_4$) and the solvent was removed under reduced pressure. The crude product was purified by chromatography (DCM).

Ethyl 1-[(3-methylphenyl)methyl]-7-oxo-4,5,6,7-tetrahydro-1H-indazole-3-carboxylate. This compound was obtained from reaction of 31 with 3-methylbenzyl chloride: colorless oil; yield: 48%; IR: 1714 (CO), 1685 (CO) cm$^{-1}$; $^1$H nmr (CDCl$_3$) (ppm): 1.41 (3H, t, J=7.1 Hz, CH$_3$), 2.05-2.18 (2H, m, CH$_2$), 2.30 (3H, s, CH$_3$), 2.54 (2H, t, J=6.1 Hz, CH$_2$), 3.03 (2H, t, J=6.1 Hz, CH$_2$), 4.43 (2H, q, J=7.1 Hz, CH$_2$), 5.72 (2H, s, CH$_2$), 7.05-7.27 (4H, m, H-2', H-4', H-5' and H-6'); $^{13}$C nmr (CDCl$_3$) (ppm): 14.4 (q), 21.4 (q), 21.9 (t), 24.2 (t), 39.3 (t), 55.7 (t), 61.1 (t), 125.2 (d), 128.5 (d), 128.8 (d), 128.9 (d), 133.6 (s), 135.4 (s), 135.8 (s), 138.2 (s), 139.0 (s), 162.2 (s), 189.3 (s). Anal calcd for C$_{18}$H$_{20}$N$_2$O$_3$: C, 69.21; H, 6.45; N, 8.97. Found: C, 69.08; H, 6.58; N, 9.09.

Ethyl 2-[(3-methylphenyl)methyl]-7-oxo-4,5,6,7-tetrahydro-2H-indazole-3-carboxylate. This compound was obtained from reaction of 31 with 3-methylbenzyl chloride: colorless oil; yield: 39%; IR: 1718 (CO), 1695 (CO) cm$^{-1}$; $^1$H nmr (CDCl$_3$) (ppm): 1.36 (3H, t, J=7.1 Hz, CH$_3$), 2.08-2.21 (2H, m, CH$_2$), 2.30 (3H, s, CH$_3$), 2.64 (2H, t, J=6.1 Hz, CH$_2$), 2.97 (2H, t, J=6.1 Hz, CH$_2$), 4.34 (2H, q, J=7.1 Hz, CH$_2$), 5.80 (2H, s, CH$_2$), 7.05-7.28 (4H, m, H-2', H-4', H-5' and H-6'); $^{13}$C nmr (CDCl$_3$) (ppm): 14.2 (q), 21.4 (q), 22.3 (t), 23.9 (t), 39.4 (t), 56.3 (t), 61.3 (t), 125.1 (d), 128.4 (d), 128.6 (d), 128.8 (d), 129.1 (s), 132.6 (s), 135.9 (s), 138.2 (s), 145.4 (s), 159.5 (s), 193.1 (s). Anal calcd for C$_{18}$H$_{20}$N$_2$O$_3$: C, 69.21; H, 6.45; N, 8.97. Found: C, 69.33; H, 6.32; N, 9.08.

Ethyl 1-[(4-methylphenyl)methyl]-7-oxo-4,5,6,7-tetrahydro-1H-indazole-3-carboxylate. This compound was obtained from reaction of 31 with 4-methylbenzyl chloride: colorless oil; yield: 45%; IR: 1721 (CO), 1686 (CO) cm$^{-1}$; $^1$H nmr (CDCl$_3$) (ppm): 1.41 (3H, t, J=7.1 Hz, CH$_3$), 2.07-2.14 (2H, m, CH$_2$), 2.32 (3H, s, CH$_3$), 2.54 (2H, t, J=6.2 Hz, CH$_2$), 3.02 (2H, t, J=6.2 Hz, CH$_2$), 4.42 (2H, q, J=7.1 Hz, CH$_2$), 5.72 (2H, s, CH$_2$), 7.09 (2H, d, J=8.0 Hz, H-3' and H-5'), 7.26 (2H, d, J=8.0 Hz, H-2' and H-6'); $^{13}$C nmr (CDCl$_3$) (ppm): 14.4 (q), 21.1 (q), 21.9 (t), 24.2 (t), 39.3 (t), 55.5 (t), 61.0 (t), 128.2 (2×d), 129.3 (2×d), 133.0 (s), 133.7 (s), 135.3 (s), 137.8 (s), 138.9 (s), 162.1 (s), 189.3 (s). Anal calcd per C$_{18}$H$_{20}$N$_2$O$_3$: C, 69.21; H, 6.45; N, 8.97. Found: C, 69.10; H, 6.57; N, 8.84.

Ethyl 2-[(4-methylphenyl)methyl]-7-oxo-4,5,6,7-tetrahydro-2H-indazole-3-carboxylate. This compound was obtained from reaction of 31 with 4-methylbenzyl chloride: white solid; yield: 25%; m.p.: 107-108° C.; IR: 1718 (CO), 1694 (CO) cm$^{-1}$; $^1$H nmr (CDCl$_3$) (ppm): 1.36 (3H, t, J=7.1 Hz, CH$_3$), 2.07-2.16 (2H, m, CH$_2$), 2.30 (3H, s, CH$_3$), 2.63 (2H, t, J=6.2 Hz, CH$_2$), 2.96 (2H, t, J=6.2 Hz, CH$_2$), 4.34 (2H, q, J=7.1 Hz, CH$_2$), 5.80 (2H, s, CH$_2$), 7.10 (2H, d, J=7.9 Hz, H-3' and H-5'), 7.25 (2H, d, J=7.9 Hz, H-2' and H-6'); $^{13}$C nmr (CDCl$_3$) (ppm): 14.2 (q), 21.2 (q), 22.3 (t), 23.9 (t), 39.4 (t), 56.1 (t), 61.3 (t), 128.1 (2×d), 129.0 (s), 129.2 (2×d), 132.5 (s), 133.0 (s), 137.8 (s), 145.4 (s), 159.5 (s), 193.0 (s). Anal calcd for C$_{18}$H$_{20}$N$_2$O$_3$: C, 69.21; H, 6.45; N, 8.97. Found: C, 69.08; H, 6.56; N, 8.86.

Ethyl 1-[(3,4-dimethylphenyl)methyl]-7-oxo-4,5,6,7-tetrahydro-1H-indazole-3-carboxylate. This compound was obtained from reaction of 31 with 3,4-dimethylbenzyl chloride: white solid; yield: 45%; m.p.: 79-80° C.; IR: 1710 (CO), 1682 (CO) cm$^{-1}$; $^1$H nmr (DMSO-d$_6$) (ppm): 1.30 (3H, t, J=7.0 Hz, CH$_3$), 1.96-2.10 (2H, m, CH$_2$), 2.16 (6H, s, CH$_3$), 2.54 (2H, t, J=5.6 Hz, CH$_2$), 2.93 (2H, t, J=5.6 Hz, CH$_2$), 4.29 (2H, q, J=7.0 Hz, CH$_2$), 5.63 (2H, s, CH$_2$), 6.90 (1H, d, J=7.6 Hz, H-6'), 7.01 (1H, s, H-1'), 7.06 (1H, d, J=7.6 Hz, H-5'); $^{13}$C nmr (DMSO-d$_6$) (ppm): 14.6 (q), 19.4 (q), 19.8 (q), 21.8 (t), 24.2 (t), 39.2 (t), 55.0 (t), 60.8 (t), 125.4 (d), 129.2 (d), 130.1 (d), 133.4 (s), 134.2 (s), 135.6 (s), 136.3

(s), 136.8 (s), 138.8 (s), 161.8 (s), 189.7 (s). Anal calcd for $C_{19}H_{22}N_2O_3$: C, 69.92; H, 6.79; N, 8.58. Found: C, 70.11; H, 6.58; N, 8.77.

Ethyl 2-[(3,4-dimethylphenyl)methyl]-7-oxo-4,5,6,7-tetrahydro-2H-indazole-3-carboxylate. This compound was obtained from reaction of 31 with 3,4-dimethylbenzyl chloride: white solid; yield: 23%; m.p.: 96-97° C.; IR: 1717 (CO), 1689 (CO) cm$^{-1}$; $^1$H nmr (DMSO-d$_6$) (ppm): 1.30 (3H, t, J=7.1 Hz, CH$_3$), 1.99-2.07 (2H, m, CH$_2$), 2.16 (6H, s, 2×CH$_3$), 2.52 (2H, t, J=6.0 Hz, CH$_2$), 2.90 (2H, t, J=6.0 Hz, CH$_2$), 4.31 (2H, q, J=7.1 Hz, CH$_2$), 5.69 (2H, s, CH$_2$), 6.90 (1H, d, J=7.7 Hz, H-6'), 7.02 (1H, s, H-1'), 7.06 (1H, d, J=7.7 Hz, H-5'); $^{13}$C nmr (DMSO-d$_6$) (ppm): 14.4 (q), 19.4 (q), 19.8 (q), 22.1 (t), 23.9 (t), 39.7 (t), 55.6 (t), 61.6 (t), 125.4 (d), 129.1 (d), 129.2 (s), 130.0 (d), 132.7 (s), 134.3 (s), 136.3 (s), 136.7 (s), 145.5 (s), 159.5 (s), 192.4 (s). Anal calcd for $C_{19}H_{22}N_2O_3$: C, 69.92; H, 6.79; N, 8.58. Found: 69.79; H, 6.64; N, 8.71.

Ethyl 1-[(4-bromophenyl)methyl]-7-oxo-4,5,6,7-tetrahydro-1H-indazole-3-carboxylate. This compound was obtained from reaction of 31 with 4-bromobenzyl bromide: yellow oil; yield: 51%; IR: 1717 (CO), 1684 (CO) cm$^{-1}$; $^1$H nmr (DMSO-d$_6$) (ppm): 1.29 (3H, t, J=7.0 Hz, CH$_3$), 1.95-2.12 (2H, m, CH$_2$), 2.53 (2H, t, J=5.5 Hz, CH$_2$), 2.93 (2H, t, J=5.5 Hz, CH$_2$), 4.29 (2H, q, J=7.0 Hz, CH$_2$), 5.69 (2H, s, CH$_2$), 7.15 (2H, d, J=8.0 Hz, H-2' and H-6'), 7.51 (2H, d, J=8.0 Hz, H-3' and H-5'); $^{13}$C nmr (DMSO-d$_6$) (ppm): 14.6 (q), 21.8 (t), 24.2 (t), 39.1 (t), 55.6 (t), 60.9 (t), 121.5 (s), 130.2 (2×d), 132.0 (2×d), 133.5 (s), 135.7 (s), 136.2 (s), 139.1 (s), 145.6 (s), 161.7 (s), 189.8 (s). Anal calcd for $C_{17}H_{17}BrN_2O_3$: C, 54.13; H, 4.54; N, 7.43. Found: C, 54.01; H, 4.72; N, 7.56.

Ethyl 2-[(4-bromophenyl)methy]-7-oxo-4,5,6,7-tetrahydro-2H-indazole-3-carboxylate. This compound was obtained from reaction of 31 with 4-bromobenzyl bromide: yellow oil; yield: 21%; IR: 1718 (CO), 1700 (CO) cm$^{-1}$; $^1$H nmr (DMSO-d$_6$) (ppm): 1.27 (3H, t, J=7.1 Hz, CH$_3$), 1.98-2.14 (2H, m, CH$_2$), 2.53 (2H, t, J=5.9 Hz, CH$_2$), 2.90 (2H, t, J=5.9 Hz, CH$_2$), 4.29 (2H, q, J=7.0 Hz, CH$_2$), 5.75 (2H, s, CH$_2$), 7.15 (2H, d, J=8.2 Hz, H-2' and H-6'), 7.51 (2H, d, J=8.2 Hz, H-3' and H-5'); $^{13}$C nmr (DMSO-d$_6$) (ppm): 14.3 (q), 21.1 (t), 23.9 (t), 39.6 (t), 55.3 (t), 61.7 (t), 121.5 (s), 129.4 (s), 130.0 (2×d), 131.9 (2×d), 132.7 (s), 136.4 (s), 145.7 (s), 159.4 (s), 192.3 (s). Anal calcd for $C_{17}H_{17}BrN_2O_3$: C, 54.13; H, 4.54; N, 7.43. Found: C, 54.27; H, 4.68; N, 7.31.

General Procedure for the Synthesis of ethyl 6-[(dimethylamino)methylidene]-1-substituted-7-oxo-4,5,6,7-tetrahydro-1H-indazole-3-carboxylate and ethyl 6-[(dimethylamino)methylidene]-2-substituted-7-oxo-4,5,6,7-tetrahydro-2H-indazole-3-carboxylate 33

To a solution of 32 (2.6 mmol) in anhydrous toluene (3 mL) TBDMAM (1.61 mL, 7.8 mmol) was added and the reaction mixture was heated at reflux up to completeness (TLC). After cooling, the solvent was removed under reduced pressure.

6-[(dimethylamino)methylidene]-1-[(3-methylphenyl)methyl]-1,4,5,6-tetrahydro-7H-indazol-7-one. This compound was obtained by reaction of ethyl 1-[(3-methylphenyl)methyl]-7-oxo-4,5,6,7-tetrahydro-1H-indazole-3-carboxylate after 16 h and used in the next step without further purification.

6-[(dimethylamino)methylidene]-2-[(3-methylphenyl)methyl]-2,4,5,6-tetrahydro-7H-indazol-7-one. This compound was obtained by reaction of ethyl 2-[(3-methylphenyl)methyl]-7-oxo-4,5,6,7-tetrahydro-2H-indazole-3-carboxylate after 3 h and used in the next step without further purification.

6-[(dimethylamino)methylidene]-1-[(4-methylphenyl)methyl]-1,4,5,6-tetrahydro-7H-indazol-7-one. This compound was obtained by reaction of ethyl 1-[(4-methylphenyl)methyl]-7-oxo-4,5,6,7-tetrahydro-1H-indazole-3-carboxylate after 16 h and used in the next step without further purification.

6-[(dimethylamino)methylidene]-2-[(4-methylphenyl)methyl]-2,4,5,6-tetrahydro-7H-indazol-7-one. This compound was obtained by reaction of ethyl 2-[(4-methylphenyl)methyl]-7-oxo-4,5,6,7-tetrahydro-2H-indazole-3-carboxylate after 3 h and used in the next step without further purification.

6-[(dimethylamino)methylidene]-1-[(3,4-dimethylphenyl)methyl]-1,4,5,6-tetrahydro-7H-indazol-7-one. This compound was obtained by reaction of ethyl 1-[(3,4-dimethylphenyl)methyl]-7-oxo-4,5,6,7-tetrahydro-1H-indazole-3-carboxylate after 5 h and used in the next step without further purification.

6-[(dimethylamino)methylidene]-2-[(3,4-dimethylphenyl)methyl]-2,4,5,6-tetrahydro-7H-indazol-7-one. This compound was obtained by reaction of ethyl 2-[(3,4-dimethylphenyl)methyl]-7-oxo-4,5,6,7-tetrahydro-2H-indazole-3-carboxylate after 1 h and used in the next step without further purification.

1-[(4-bromophenyl)methyl]-6-[(dimethylamino)methylidene]-1,4,5,6-tetrahydro-7H-indazol-7-one. This compound was obtained by reaction of ethyl 1-[(4-bromophenyl)methyl]-7-oxo-4,5,6,7-tetrahydro-1H-indazole-3-carboxylate after 5 h and used in the next step without further purification.

2-[(4-bromophenyl)methyl]-6-[(dimethylamino)methylidene]-2,4,5,6-tetrahydro-7H-indazol-7-one. This compound was obtained by reaction of ethyl 2-[(4-bromophenyl)methyl]-7-oxo-4,5,6,7-tetrahydro-2H-indazole-3-carboxylate after 2 h and used in the next step without further purification.

General Procedure for the Synthesis of pyrazolo[4,3-h]quinolinones 34

To a solution of the enamiketones 33 (2.76 mmol) in anhydrous ethanol (20 mL) under nitrogen atmosphere phenylsulfonylacetonitrile was added (0.75 g, 4.14 mmol). The reaction mixture was heated under reflux for 24 h. The solvent was removed under reduced pressure. The crude product was purified by chromatography (DCM/AcOEt 9:1)

Ethyl 7-(benzenesulfonyl)-1-[(4-methylphenyl)methyl]-8-oxo-4,5,8,9-tetrahydro-1H-pyrazolo[4,3-h]quinoline-3-carboxylate (PZ1). This compound was obtained by reaction of 6-[(dimethylamino)methylidene]-1-[(4-methylphenyl)methyl]-1,4,5,6-tetrahydro-7H-indazol-7-one. Light yellow solid; yield: 79%; m.p.: 312-313° C.; IR: 3416 (NH), 1718 (CO), 1601 (CO) cm$^{-1}$; $^1$H nmr (DMSO-d$_6$) (ppm): 1.30 (3H, t, J=7.1 Hz, CH$_3$), 2.21 (3H, s, CH$_3$), 2.99 (4H, s, 2×CH$_2$), 4.28 (2H, q, J=7.1 Hz, CH$_2$), 6.01 (2H, s, CH$_2$), 7.08-7.10 (4H, m, H-2', H-4', H-5' and H-6'), 7.62-7.66 (3H, m, H-3", H-4" and H-5"), 7.97 (2H, d, J=6.5 Hz, H-2" and H-6"), 8.26 (1H, s, H-6), 12.20 (1H, s, NH); $^{13}$C nmr (DMSO-d$_6$) (ppm): 14.1 (q), 19.1 (t), 20.6 (q), 26.7 (t), 54.2 (t), 60.2 (t), 119.2 (s), 123.7 (s), 125.5 (s), 127.5 (2×d), 127.9 (2×d), 128.9 (2×d), 129.0 (2×d), 133.6 (s), 134.2 (d), 135.8 (s), 136.7 (d), 138.2 (s), 138.9 (s), 140.3 (s), 147.8 (s), 158.2

(s), 161.6 (s). Anal calcd for $C_{27}H_{25}N_3O_5S$: C, 64.40; H, 5.00; N, 8.34. Found: C, 64.51; H, 4.90; N, 8.45.

Ethyl 7-(benzenesulfonyl)-2-[(4-methylphenyl)methyl]-8-oxo-4,5,8,9-tetrahydro-2H-pyrazolo[4,3-h]quinoline-3-carboxylate (PZ2). This compound was obtained by reaction of 6-[(dimethylamino)methylidene]-2-[(4-methylphenyl)methyl]-2,4,5,6-tetrahydro-7H-indazol-7-one. Yellow solid; yield: 81%; m.p.: 201-202° C.; IR: 3233 (NH), 1718 (CO), 1664 (CO) cm$^{-1}$; $^1$H nmr (DMSO-d$_6$) (ppm): 1.29 (3H, t, J=7.0 Hz, CH$_3$), 2.24 (3H, s, CH$_3$), 2.88-2.96 (4H, m, 2×CH$_2$), 4.29 (2H, q, J=7.0 Hz, CH$_2$), 5.69 (2H, s, CH$_2$), 6.98-7.11 (4H, m, H-2', H-4', H-5' and H-6'), 7.55-7.69 (3H, m, H-3", H-4" and H-5"), 7.98 (2H, d, J=6.9 Hz, H-2" and H-6"), 8.29 (1H, s, H-6), 12.62 (1H, s, NH); $^{13}$C nmr (DMSO-d$_6$) (ppm): 13.9 (q), 19.4 (t), 20.6 (q), 25.1 (t), 54.9 (t), 61.3 (t), 114.2 (s), 125.9 (s), 127.2 (2×d), 128.1 (2×d), 128.7 (2×d), 128.8 (s), 128.9 (s), 129.0 (2×d), 129.0 (s), 133.3 (d), 133.7 (s), 133.8 (d), 136.9 (s), 140.2 (s), 141.9 (s), 157.1 (s), 158.9 (s). Anal calcd for $C_{27}H_{25}N_3O_5S$: C, 64.40; H, 5.00; N, 8.34. Found: C, 64.28; H, 5.13; N, 8.21.

Ethyl 7-(benzenesulfonyl)-1-[(3-methylphenyl)methyl]-8-oxo-4,5,8,9-tetrahydro-1H-pyrazolo[4,3-h]quinoline-3-carboxylate (PZ3). This compound was obtained by reaction of 6-[(dimethylamino)methylidene]-1-[(3-methylphenyl)methyl]-1,4,5,6-tetrahydro-7H-indazol-7-one. White solid; yield: 87%; m.p.: 269-270° C.; IR: 3176 (NH), 1700 (CO), 1697 (CO) cm$^{-1}$; $^1$H nmr (DMSO-d$_6$) (ppm): 1.30 (3H, t, J=7.1 Hz, CH$_3$), 2.20 (3H, s, CH$_3$), 3.00 (4H, s, 2×CH$_2$), 4.28 (2H, q, J=7.1 Hz, CH$_2$), 6.03 (2H, s, CH$_2$), 6.95-7.18 (4H, m, H-2', H-4', H-5' and H-6'), 7.59-7.75 (3H, m, H-3", H-4" and H-5"), 7.97 (2H, d, J=6.8 Hz, H-2" and H-6"), 8.27 (1H, s, H-6), 12.71 (1H, s, NH); $^{13}$C nmr (DMSO-d$_6$) (ppm): 14.1 (q), 19.1 (t), 20.9 (q), 26.6 (t), 54.3 (t), 60.2 (t), 119.3 (s), 123.8 (s), 124.5 (d), 125.4 (d), 128.0 (2×d), 128.1 (d), 128.2 (d), 128.4 (d), 129.0 (2×d), 135.6 (d), 135.9 (s), 137.2 (s), 137.5 (s), 138.3 (s), 138.9 (d), 140.3 (s), 147.8 (s), 158.1 (s), 161.6 (s). Anal calcd for $C_{27}H_{25}N_3O_5S$: C, 64.40; H, 5.00; N, 8.34. Found: C, 64.52; H, 4.87; N, 8.42.

Ethyl 7-(benzenesulfonyl)-2-[(3-methylphenyl)methyl]-8-oxo-4,5,8,9-tetrahydro-2H-pyrazolo[4,3-h]quinoline-3-carboxylate (PZ4). This compound was obtained by reaction of 6-[(dimethylamino)methylidene]-2-[(3-methylphenyl)methyl]-2,4,5,6-tetrahydro-7H-indazol-7-one. Light brown solid; yield: 83%; m.p.: 225-226° C.; IR: 3233 (NH), 1721 (CO), 1699 (CO) cm$^{-1}$; $^1$H nmr (DMSO-d$_6$) (ppm): 1.28 (3H, t, J=6.9 Hz, CH$_3$), 2.24 (3H, s, CH$_3$), 2.89-2.97 (4H, m, 2×CH$_2$), 4.30 (2H, q, J=6.9 Hz, CH$_2$), 5.70 (2H, s, CH$_2$), 6.97-7.21 (4H, m, H-2', H-4', H-5' and H-6'), 7.57-7.70 (3H, m, H-3", H-4" and H-5"), 7.98 (2H, d, J=7.4 Hz, H-2" and H-6"), 8.29 (1H, s, H-6), 12.61 (1H, s, NH); $^{13}$C nmr (DMSO-d$_6$) (ppm): 14.4 (q), 19.8 (t), 21.4 (q), 25.6 (t), 55.5 (t), 61.7 (t), 124.4 (s), 124.8 (d), 126.4 (s), 128.2 (d), 128.6 (2×d), 128.8 (d), 128.9 (d), 129.2 (2×d), 129.5 (d), 133.8 (d), 137.1 (s), 137.2 (s), 138.1 (s), 138.2 (s), 140.7 (s), 141.5 (s), 144.0 (d), 157.5 (s), 159.4 (s). Anal calcd for $C_{27}H_{25}N_3O_5S$: C, 64.40; H, 5.00; N, 8.34. Found: 64.56; H, 4.88; N, 8.23.

Ethyl 7-(benzenesulfonyl)-1-[(4-bromophenyl)methyl]-8-oxo-4,5,8,9-tetrahydro-1H-pyrazolo[4,3-h]quinoline-3-carboxylate (PZ5). This compound was obtained by reaction of 1-[(4-bromophenyl)methyl]-6-[(dimethylamino)methylidene]-1,4,5,6-tetrahydro-7H-indazol-7-one. White solid; yield: 85%; m.p.: 304-305° C.; IR: 3405 (NH), 1736 (CO), 1716 (CO) cm$^{-1}$; $^1$H nmr (DMSO-d$_6$) (ppm): 1.29 (3H, t, J=7.1 Hz, CH$_3$), 3.00 (4H, s, 2×CH$_2$), 4.28 (2H, q, J=7.1 Hz, CH$_2$), 6.03 (2H, s, CH$_2$), 7.19 (2H, d, J=8.2 Hz, H-2' and H-6'), 7.48 (2H, d, J=8.1 Hz, H-3' and H-5'), 7.60-7.74 (3H, m, H-3", H-4" and H-5"), 7.96 (2H, d, J=7.3 Hz, H-2" and H-6"), 8.26 (1H, s, H-6), 12.20 (1H, s, NH); $^{13}$C nmr (DMSO-d$_6$) (ppm): 14.6 (q), 19.6 (t), 27.1 (t), 54.2 (t), 60.8 (t), 119.9 (s), 121.3 (s), 124.4 (s), 125.9 (s), 128.5 (2×d), 129.5 (2×d), 130.3 (2×d), 131.9 (2×d), 134.1 (d), 136.4 (s), 137.1 (d), 139.0 (s), 139.4 (s), 140.8 (s), 148.2 (s), 158.7 (s), 162.0 (s). Anal calcd for $C_{26}H_{22}BrN_3O_5S$: C, 54.94; H, 3.90; N, 7.39. Found: 54.79; H, 4.08; N, 7.52.

Ethyl 7-(benzenesulfonyl)-2-[(4-bromophenyl)methyl]-8-oxo-4,5,8,9-tetrahydro-2H-pyrazolo[4,3-h]quinoline-3-carboxylate (PZ6). This compound was obtained by reaction of 1-[(4-bromophenyl)methyl]-6-[(dimethylamino)methylidene]-1,4,5,6-tetrahydro-7H-indazol-7-one. Yellow solid; yield: 77%; m.p.: 268-269° C.; IR: 3216 (NH), 1715 (CO), 1675 (CO) cm$^{-1}$; $^1$H nmr (DMSO-d$_6$) (ppm): 1.28 (3H, t, J=7.1 Hz, CH$_3$), 2.89-2.97 (4H, m, 2×CH$_2$), 4.28 (2H, q, J=7.1 Hz, CH$_2$), 5.71 (2H, s, CH$_2$), 7.17 (2H, d, J=8.1 Hz, H-2' and H-6'), 7.51 (2H, d, J=8.1 Hz, H-3' and H-5'), 7.56-7.70 (3H, m, H-3", H-4" and H-5"), 7.97 (2H, d, J=7.9 Hz, H-2" and H-6"), 8.29 (1H, s, H-6), 12.59 (1H, s, NH); $^{13}$C nmr (DMSO-d$_6$) (ppm): 14.3 (q), 19.8 (t), 25.5 (t), 55.0 (t), 61.8 (t), 109.4 (s), 107.9 (s), 121.3 (s), 124.2 (s), 126.4 (s), 128.6 (2×d), 129.2 (2×d), 129.5 (s), 129.9 (2×d), 131.7 (s), 131.9 (2×d), 133.8 (d), 136.7 (s), 140.7 (s), 157.4 (s), 159.4 (s). Anal calcd for $C_{26}H_{22}BrN_3O_5S$: C, 54.94; H, 3.90; N, 7.39. Found: 55.10; H, 3.75; N, 7.51.

Ethyl 7-(benzenesulfonyl)-1-[(3,4-dimethylphenyl)methyl]-8-oxo-4,5,8,9-tetrahydro-1H-pyrazolo[4,3-h]quinoline-3-carboxylate (PZ7). This compound was obtained by reaction of 6-[(dimethylamino)methylidene]-1-[(3,4-dimethylphenyl)methyl]-1,4,5,6-tetrahydro-7H-indazol-7-one. White solid; yield: 78%; m.p.: 260-261° C.; IR: 3405 (NH), 1738 (CO), 1592 (CO) cm$^{-1}$; $^1$H nmr (DMSO-d$_6$) (ppm): 1.29 (3H, t, J=7.1 Hz, CH$_3$), 2.09 (3H, s, CH$_3$), 2.11 (3H, s, CH$_3$), 2.98 (4H, s, 2×CH$_2$), 4.28 (2H, q, J=7.1 Hz, CH$_2$), 5.96 (2H, s, CH$_2$), 6.89 (1H, d, J=7.5 Hz, H-6'), 6.96 (2H, d, J=7.3 Hz, H-2' and H-5'), 7.59-7.73 (3H, m, H-3", H-4" and H-5"), 7.96 (2H, d, J=7.3 Hz, H-2" and H-6"), 8.25 (1H, s, H-6), 12.19 (1H, s, NH); $^{13}$C nmr (DMSO-d$_6$) (ppm): 14.6 (q), 19.4 (q), 19.6 (q), 19.8 (t), 27.2 (t), 54.7 (t), 60.7 (t), 119.7 (s), 124.3 (s), 125.4 (d), 126.0 (s), 128.5 (2×d), 129.2 (d), 129.5 (2×d), 129.9 (d), 134.1 (d), 135.0 (s), 136.0 (s), 136.3 (d), 136.5 (s), 138.6 (s), 139.4 (s), 140.9 (s), 148.4 (s), 158.6 (s), 162.1 (s). Anal calcd for $C_{28}H_{27}N_3O_5S$: C, 64.97; H, 5.26; N, 8.12. Found: 65.09; H, 5.14; N, 8.01.

Ethyl 7-(benzenesulfonyl)-2-[(3,4-dimethylphenyl)methyl]-8-oxo-4,5,8,9-tetrahydro-2H-pyrazolo[4,3-h]quinoline-3-carboxylate (PZ8). This compound was obtained by reaction of 6-[(dimethylamino)methylidene]-2-[(3,4-dimethylphenyl)methyl]-1,4,5,6-tetrahydro-7H-indazol-7-one. Yellow solid; yield: 87%; m.p.: 220-221° C.; IR: 3228 (NH), 1718 (CO), 1670 (CO) cm$^{-1}$; $^1$H nmr (DMSO-d$_6$) (ppm): 1.29 (3H, t, J=7.1 Hz, CH$_3$), 2.15 (6H, s, 2×CH$_3$), 2.80-3.04 (4H, m, 2×CH$_2$), 4.30 (2H, q, J=7.1 Hz, CH$_2$), 5.66 (2H, s, CH$_2$), 6.91 (1H, d, J=7.6 Hz, H-6'), 7.03-7.06 (2H, m, H-2' and H-5'), 7.57-7.60 (3H, m, H-3", H-4" and H-5"), 7.97 (2H, d, J=8.1 Hz, H-2" and H-6"), 8.28 (1H, s, H-6), 12.53 (1H, s, NH); $^{13}$C nmr (DMSO-d$_6$) (ppm): 14.4 (q), 19.4 (2×q), 19.9 (t), 25.5 (t), 55.4 (t), 61.7 (t), 103.7 (s), 109.8 (s), 112.8 (s), 125.2 (d), 126.4 (s), 128.1 (s), 128.6 (2×d), 128.9 (d), 129.2 (2×d), 129.3 (s), 130.0 (d), 133.8 (d), 134.6 (s), 136.2 (s), 136.7 (s), 140.7 (s), 149.6 (s), 157.5 (s), 159.4 (s). Anal calcd for $C_{28}H_{27}N_3O_5S$: C, 64.97; H, 5.26; N, 8.12. Found: 65.12; H, 5.08; N, 8.29.

Biological Data

The complete set of compounds including those reported in Tables 1-6 was subjected to functional assays in heterologous cells (CFBE41o−) with F508del-CFTR protein expression. The most active compounds were tested on primary airway epithelial cells obtained from patients homozygous for the F508del mutation, upon obtaining informed consent.

Materials and Methods

Evaluation of CFTR Function by Kinetic Fluorescence Assay

CFBE41o– cells, with expression of F508del-CFTR and halogen-sensitive fluorescent protein, were generated as previously described (Sondo E, et al. Am J Physiol. 2011, 301, C872-C885). For the test, the cells were seeded in 96-well microplates using a culture medium consisting of DMEM and Ham's F12 (1:1) supplemented with 10% foetal bovine serum. After 24 hours from seeding, the cells were treated for another 24 hours with the test compounds dissolved in the culture medium at the desired concentrations. As a negative control, the solvent of the compounds (dimethyl sulfoxide, DMSO) dissolved in the medium with the same dilution ratio (final percentage of DMSO:0.1-0.2%) was used. As a positive control, the corrector VX-809 (Selleck Chemicals, S1565) was used at a concentration of 1 µM. After treatment, the medium with the compounds was removed and the cells were stimulated with forskolin (Sigma-Aldrich, F6886) 20 µM plus genistein (Sigma-Aldrich, G6649) 50 µM (in 60 µl of PBS saline) to maximally activate the CFTR channels present in the membrane. In a microplate reader (FLUOstar-Omega, BMG) the fluorescence of the cells in each well was read for 14 seconds, with an injection of 165 µl of a iodide-enriched saline (modified PBS where NaCl, 137 mM, has been replaced with the same concentration of NaI). The iodide transport activity in each well was evaluated by subtraction of the background fluorescence (measured in a well without cells), subsequent normalization with respect to the initial fluorescence and finally by interpolation of the fluorescence quenching phase with an exponential function that allows the derivation of the maximum slope (quenching rate, QR).

To assess the function and pharmacological sensitivity of G542X-CFTR mutant, inventors used the null version of CFBE41o– cells, i.e. cells with negligible expression of endogenous CFTR and without HS-YFP. Such cells were transiently transfected with the plasmid coding for HS-YFP alone or in combination with: empty plasmid, plasmid coding for wild type CFTR, or plasmid coding for G542X-CFTR. For transfection, cells were seeded in 96-well microplates (30,000 cells/well) in 150 µl of antibiotic-free culture medium. After 24 hours, cells were transfected with the desired plasmids. For each well, 0.2 µg of total plasmid DNA and 0.5 µl of Lipofectamine 2000 (Invitrogen) were first pre-mixed in 50 µl of OPTIMEM (Invitrogen) to generate transfection complexes (60 minutes at room temperature), and then added to the cells. After 24 hour, the complexes were removed by replacement with fresh culture medium. The HS-YFP functional assay was performed after further 24 hours.

Evaluation of the Transepithelial Ionic Current

The culture and functional study of human primary nasal and bronchial epithelial cells have been described in detail above (Scudieri P, et al. J Physiol. 2012, 590, 6141-6155). Briefly, nasal epithelial cells were taken after informed consent using the "brushing" technique. Bronchial cells were instead obtained by proteolytic digestion of bronchi isolated from the lungs of patients (suffering from CF or other pulmonary pathology (idiopathic pulmonary fibrosis, pulmonary hypertension, emphysema) subjected to transplant operations. The informed consent of the patients was obtained also in this case. After isolation, epithelial cells were cultured in a liquid medium of defined serum-free composition. This medium consists of a mixture of LHC9/RPMI 1640 (1:1) enriched with various hormones and growth factors (Scudieri P, et al. J Physiol. 2012, 590, 6141-6155). After 3-5 passages, necessary for the expansion of the initial number, the cells were seeded at high density on Snapwell porous supports (Corning, 3801). After 24 hours, the culture medium was replaced by a mixture consisting of DMEM and Ham's F12 (1:1) enriched with 2% foetal bovine serum and other supplements. After 5-6 days from seeding, the cells were put in an "air-liquid interface" condition, i.e. by removing the culture medium from the apical side. In this way the mucociliary differentiation is promoted with the formation of an epithelium provided with high electrical resistance. For functional evaluations, carried out 12-14 days after seeding, the Snapwell supports were inserted into vertical diffusion chambers in which the two compartments, apical and basolateral, were filled with saline solution and connected by Ag/AgCl electrodes to an epithelial Voltage Clamp (EVC-4000, World Precision Instruments). Transepithelial ion transport recordings were performed in the short-circuit current configuration. With this mode, the transepithelial potential difference is locked to zero and the resulting current, supplied by the Voltage Clamp is recorded by an AD/DA converter (PowerLab, ADInstruments).

Analysis of F508del-CFTR Maturation by Immunoblot

CFBE41o– cells were grown to confluence on 60-mm diameter dishes and lysed in RIPA buffer containing a complete protease inhibitor (Roche; cat. n. 11697498001). Cell lysates were centrifuged at 12000 rpm at 4° C. for 10 min. Supernatant protein concentration was calculated using the BCA assay (Euroclone; cat. n. EMP014500) following the manufacturer's instructions. Equal amounts of total protein content (30 µg) were separated onto 10% Criterion TGX Precast gels (Bio-rad laboratories Inc.; cat. n. 4561033), transferred to nitrocellulose membrane with Trans-Blot Turbo system (Bio-rad Laboratories Inc.) and analyzed by Western blotting. Primary antibody for CFTR was anti-CFTR 596 (University of North Carolina at Chapel Hill, and Cystic Fibrosis Foundation Therapeutics, see Cui L, et al. J. Mol Biol 2007, 365, 981-994) at 1:5000 dilution. As secondary antibody, anti-mouse HRP-conjugated Ab 97023 (Abcam) was used at 1:10000 dilution. Results were subsequently visualized by chemiluminescence using the SuperSignal West Femto Substrate (Thermo Scientific) and the Molecular Imager ChemiDoc XRS System.

Analysis of F508del-CFTR Localization by Immunofluorescence

CFBE41o– cells were seeded in a 12-well µ-chamber (81201, Ibidi) at a density of 25.000 cells per well and treated with compounds for 24 hr. Cells were then rinsed with PBS and fixed by adding 100 µl per well of 10% neutral buffered formalin for 5 minutes at room temperature. After 3 washes with 300 µl of PBS, cells were permeabilized with PBS-Triton X-100 0.3% for 5 min, blocked with PBS-BSA 1% for 2 hr, and incubated overnight at 4° C. with 100 µl of primary antibody diluted in blocking solution. The CFTR antibody was ab570 mouse IgG1 (University of North Carolina at Chapel Hill, and Cystic Fibrosis Foundation Therapeutics, see Cui L, et al. J. Mol Biol 2007, 365, 981-994) diluted at 1:250. Following incubation with primary antibody, cells were rinsed three times with PBS and incubated with 100 µl of a solution of secondary goat anti-mouse Alexa Fluor-546 antibodies (Invitrogen A-11030) diluted in PBS-BSA 1% for 1 hour in the dark. After three further washes in PBS, cells were covered with mounting medium and coverslip, and then analysed using a laser-scanning confocal microscope SPE (Leica Microsystems).

Results

Structure-Activity Relationship

As reported in the above tables, the "additivity index" (AI) was used as a parameter to report the ability of the compounds of the invention to synergize with class 1 correctors such as VX-809. In the example of FIG. 1, the AI of PP007 at 10 µM is 74%.

It is noted that in the pyrrolo[3,2-h]quinolinone series 1, the potency order is: P007 (R=4-MeBn $R^2$=H)>PP011 (R=Bn $R^2$=H)>PP010 (R=Me $R^2$=H), indicating that the absence of the 4-methyl group in benzyl (PP011) or the substitution with a small alkyl group such as methyl (PP010) causes a reduction in activity. The introduction of a bromine atom in the tricyclic scaffold at position 7 determines an important increase in potency, leading to one of the most active derivatives of the series PP008 (R=4-MeBn $R^2$=Br).

In both classes of compounds (pyrrolo[3,2-h]quinolinone 1 and heterocyclic pyrrole[3',2':6,7]cyclohepta[1,2-b]pyridine 2), the bromo derivatives PP008 and PP056 are more potent than the non-halogenated analogues PP007 and PP048 respectively.

Focusing on the substituent R, the compounds PP015 (R=2-MeBn) and PP016 (R=3-MeBn) were synthesized. These compounds present a methyl displaced from the original 4-benzyl position at the new 2- and 3-benzyl positions respectively; PP017 (R=4-ClBn), in which the 4-MeBn substituent was replaced with a 4-Clbenzyl to evaluate the different electronic effect of the chlorine atom in the same position of the benzyl system on the activity. Furthermore, the dimethyl benzyl derivatives PP021 (R=2.4-diMeBn) and PP025 (R=3.4-diMeBn) in which, in addition to the methyl at position 4, there is an additional methyl at position 2 and 3 respectively, were prepared to evaluate the possible additive effect of the methyl group at ortho and meta benzyl positions. All the derivatives were then converted into their brominated analogues PP027, PP028, PP029 respectively, and PP033, PP037 for dimethyls. Methoxy esters PP019 (R=4-MeBn), PP020 (R=2-MeBn), and isopropyl PP022 (R=4-MeBn) and their bromo derivatives PP032, PP031, PP034 respectively, were considered.

Referring to the substituent R3, the effect of introducing a chlorine atom or a methyl group at position 4 of the phenylsulfonyl group PP018 ($R3$=4-Cl$SO_2$Ph) and PP023 ($R^3$=4-Me$SO_2$Ph) and 4-methyl sulfonyl PP024 (R3=4-Me$SO_2$) and their bromine analogues PP030, PP035 and PP036 ($R^2$=Br) respectively, was evaluated.

The 2-Me benzyl substituent produces a derivative (PP027) with potency comparable to that of PP008. Significant results were obtained for the PP028 derivative in which the methyl was moved to the benzyl position 3, with an important increase in efficiency in combination with the VX-809 and potency, even compared to PP008. The role of the 3-methyl substituent is also evident in the two N-dimethylbenzyl substituted pyrrole quinolinones. In fact, while for PP033 2,4 dimethyl benzyl there is a reduction in activity compared to PP008, for PP037, where the two methyls are simultaneously present at the positions 3,4, which had already proved to be the best, a marked activity is obtained with an increase in potency compared to PP008. Increased activity is also obtained switching to the isopropyl ester (R') keeping the 4-methyl benzyl substituent on the pyrrole nitrogen (compare PP034 with PP008) and for the aromatic analogue derivative PP057 of P008.

Evaluation of the Corrective Activity of the Compounds of the Invention in CFBE41o– Cells The activity of the synthesized compounds was initially evaluated on the CFBE41o– cell line with expression of the mutated F508del-CFTR protein described above (Sondo E, et al. Am J Physiol. 2011, 301, C872-C885). For this purpose, a functional assay based on the fluorescent YFP protein sensitive to halides, HS-YFP, was used (Galietta L J, et al. J Biol Chem. 2001, 276, 19723-19728). The fluorescence of the HS-YFP protein is turned off by iodide. Therefore, if exposed to a solution containing iodide, cells with HS-YFP expression show a quenching speed of the fluorescence which depends on the presence and activity of anionic channels. Under control conditions, the mutated CFTR protein presents a serious defect of stability and maturation, so it remains trapped in the endoplasmic reticulum not reaching the cell surface in enough quantity. In the HS-YFP-based assay, this defect results in a low anion transport capacity and therefore in a low quenching rate (QR). Treatment for a prolonged time (e.g. 24 hours) with a corrector determines an improvement in protein maturation with an increase in the number of CFTR channels present in the membrane and therefore an increase in the flux of iodide and QR.

In a first phase, the authors screened about 200 heterocyclic molecules with various nitrogenated tricyclic scaffolds. Conditions previously described have been used for screening (Sondo E, et al. Am J Physiol. 2011, 301, C872-C885) and reported herein in the Materials and Methods section. A threshold equal to the average value plus three times the standard deviation of the QR of wells without compounds (only DMSO in the culture medium) was used as a criterion for the selection of active compounds.

After the screening, only one compound was active, PP007. This compound was tested again on the same cells at different concentrations, either alone or in combination with the corrector VX-809 (1 µM). The plot in FIG. 1 shows the results. Compared to cells under control conditions (cells treated with DMSO alone in the culture medium), the compound causes a significant increase in F508del-CFTR activity. This effect is particularly evident in cells treated with the combination PP007/VX-809. In fact, the net result of the combination is greater than the sum of the single effects, thus demonstrating a synergistic mechanism of action.

Following the promising results obtained with PP007, compounds with a similar structure were analysed. The plots in FIG. 2 show the result obtained with PP007 and analogues thereof at the concentrations of 1 and 10 µM, in the presence and absence of the corrector VX-809. Various compounds exhibit significant corrective activity when administered to the cells alone and especially if combined with VX-809. The effect of the combination is particularly evident at 10 µM concentration, at which some compounds amplify the effect of VX-809 by 3-4 times.

Evaluation of the Corrective Activity of the Compounds of the Invention in Bronchial and Nasal Epithelial Cells To further confirm the corrective capacity of the compounds of the present invention, the compound PP008, one of the most active molecules, was tested on bronchial and nasal epithelial cells of CF patients with the F508del mutation in homozygosity (FIG. 3).

The cells were grown in such a way as to generate differentiated epithelia on porous supports (Snapwell). The epithelia were then studied in Ussing chamber experiments in short-circuit conditions for the evaluation of the F508del-CFTR protein function (Sondo E, et al. Am J Physiol 2011, 301, C872-C885). As a channel-protein able to mediate a chloride ion flux, CFTR activity is detected as a transepithelial ionic current. In such experiments, we proceed by first blocking the ENaC sodium channel with amiloride (10 μM; Sigma-Aldrich, A7410) and then maximally stimulating the CFTR protein with a cAMP analogue (CPT-cAMP; Sigma-Aldrich, C3912) and with the VX-770 potentiator (1 μM; Selleck Chemicals, S1144). The potentiator is given to the cells acutely during recording (see trace); the corrector is added to the culture medium, kept for 24 hours and then removed. After activation, the CFTR protein is blocked with a specific inhibitor (inh-172 10 μM; Selleck Chemicals, S7139). Precisely it was the amplitude of the current drop induced by inh-172 which is associated with the levels of F508del-CFTR protein in the plasma membrane (apical), and therefore reveal the possible activity of corrective compounds. After 24-hour incubation, compound PP008 (10 μM) produced a significant increase in current in bronchial cells blocked by inh-172 (FIG. 3A, B). This increase was even greater when the cells were treated with the PP008 combination plus VX-809 (1 μM). It should be noted that the effect of the combination is significantly greater than the sum of the effects of the individual correctors (FIG. 3A, B).

Furthermore, the activity value of F508del-CFTR obtained from the combination (about 12 μA/cm$^2$) is greater than 50% of the value measured in bronchial epithelial cells of control subjects (transplanted patients for non-CF pathology) with normal CFTR expression.

The synergistic effect obtained with the combination of PP008 with VX-809 was also confirmed in nasal epithelial cells obtained from FC patients homozygous for the mutation F508del (FIG. 3C).

Comparison of the Compounds of the Invention with Trimethylangelicin (TMA)

The activity of PP008 was compared with that of trimethylangelicin (TMA), a compound described as a very effective corrector of the mutated CFTR protein.

The results are shown in FIG. 4. TMA was tested at sub micromolar concentrations (50-500 nM), for which corrective activity was reported (Favia M, et al. Am J Physiol 2014, 307, L48-L61). Higher concentrations (1 and 10 μM) have also been tested to allow comparison with PP008.

The result shown in the plot, rather unexpectedly, reveals that the TMA is ineffective at all concentrations. The negative results obtained with TMA suggest that its activity is strongly influenced by the cellular context and/or experimental conditions. The present data indicate that the corrective effect of PP008 and its active analogues has a different mechanism of action than that reported for TMA, despite a certain structural similarity. In this regard it should be noted that according to other authors TMA does not increase the effect of VX-809 (Laselva O, et al. Biochem Pharmacol 2016, 119, 85-92) while in the present experiment there is a strong synergistic effect produced by the combination PP008/VX-809.

The compounds of the present invention offer various advantages in that they present a corrective activity of the mutant F508del-CFTR both in cell lines and primary cultures of bronchial and nasal epithelial cells of CF patients. Furthermore, the compounds exhibit a high synergistic action in combination with the compound VX-809 (lumacaftor).

The present invention has been illustrated and described in a preferred form of practical embodiment, but it is understood that exclusive variants can be basically applied thereto, yet without departing from the scope of industrial protection.

Evaluation of Compounds on F508del-CFTR Protein Maturation and Trafficking

To analyze the mechanism of action of the compounds of the invention, two types of experiments were carried out. In the first type of experiment, the electrophoretic mobility of F508del-CFTR protein was determined by immunoblot assay. This is a frequently used method to assess the effect of correctors at the protein level. In control conditions, F508del-CFTR migrates predominantly as a single band of 150 kDa called "band B". This is the immature form of the protein residing in the endoplasmic reticulum. When the protein folding and stability is improved by correctors, an additional band appears at higher molecular weight (170 kDa). This is the so-called band C, which represents the mature form of the CFTR protein that has reached the Golgi compartment and acquired full glycosylation.

As shown in FIG. 5, treatment of cells with VX-809 causes appearance of band C in cell lysates. In agreement with results from functional assays, treatment of cells with combinations of VX-809 plus compounds of the present invention (PP008, PP028, or PP034) resulted in a marked increase in band C expression with respect to cells treated with VX-809 alone.

As a second type of experiment, the localization of F508del-CFTR protein was evaluated by immunofluorescence. Cells were treated with compounds, then fixed and immunostained with antibodies against CFTR. Images were taken with a confocal microscope. FIG. 6 shows that, in untreated cells, F508del-CFTR protein is essentially intracellular. After treatment with VX-809, the protein is still largely expressed in intracellular compartments. However, combinations of VX-809 with active compounds of the present invention (PP028 in the example of FIG. 6) cause appearance of F508del-CFTR at the cell periphery, in agreement with improved trafficking to the plasma membrane.

In conclusion, results obtained by immunoblot (FIG. 6) and immunofluoresence (FIG. 6) indicate that the marked functional rescue of F508del-CFTR by compounds of the present invention (FIGS. 1-3) is due to improved maturation and trafficking of the protein.

Effect of Compounds on G542X-CFTR

To assess the ability of compounds of present invention to improve the rescue of premature stop codon (class I) mutations, we carried out experiments on G542X-CFTR (FIG. 7). Null CFBE41o– cells, devoid of endogenous CFTR expression, were transiently transfected with empty, wild type CFTR or G542X-CFTR plasmids. All cells also received the HS-YFP plasmid to allow functional determination of CFTR-dependent anion transport. FIG. 7 shows results obtained from such experiments. Where indicated, cells with G542X-CFTR were also treated with G418 (0.5 mg/ml) for 24 hr to induce readthrough of the stop codon mutation, with and without correctors (VX-809 and/or PP028, labeled as VX and PP). As expected, treatment with G418 caused a modest but significant increase in CFTR activity (QR) resulting from readthrough activity, i.e. synthesis of full length CFTR protein. Importantly, co-treatment of cells with G418 plus VX-809 or PP028 further increased activity with respected to G418 alone. In particular, PP028 appeared significantly more effective than VX-809. The activity resulting from wild type CFTR is also shown for comparison.

The invention claimed is:

1. A method for the treatment of a pathology associated with a defect in an ABC (ATP-binding cassette) transporter, the method comprising administering to a patient in need thereof a compound of general formula (I):

(I)

wherein:
A is a pentatomic aromatic heterocyclic ring, comprising one, two or three nitrogen atoms;
R is selected from the group consisting of: hydrogen, linear or branched $C_1$-$C_6$ alkyl, cycloalkyl, heterocycloalkyl, aryl, arylalkyl, heteroaryl, heteroarylalkyl, arylsulfonyl, halogen and alkylamine, wherein said linear or branched $C_1$-$C_6$ alkyl, cycloalkyl, heterocycloalkyl, aryl, arylalkyl, heteroaryl, arylsulfonyl or alkylamine is optionally substituted with one or more substituents independently selected from: linear or branched $C_1$-$C_6$ alkyl, nitro, amino, halogen, haloalkyl and alkoxy;
$R^1$ and $R^2$ are independently selected from the group consisting of: hydrogen, carboxylic acid, carboxylic ester, carboxamide from primary, secondary or tertiary amine, halogen, nitro, amine, azide, alkylamine, arylalkyl and trifluoroalkyl, wherein said carboxylic acid, carboxylic ester, carboxamide from primary, secondary or tertiary amine, halogen, nitro, amine, azide, alkylamine or trifluorolalkyl is optionally substituted with one or more substituents independently selected from: linear or branched $C_1$-$C_6$ alkyl, cycloalkyl, nitro, amino, halogen, arylsulfonyl, optionally substituted heteroaryl and haloalkyl;
$R^3$ is absent or present and is selected from the group consisting of: carbonitrile, carboxylic ester, carboxamide, alkylsulfonyl, arylsulfonyl, wherein said carboxylic ester, carboxamide, alkylsulfonyl or arylsulfonyl is optionally substituted with one or more substituents independently selected from: linear or branched C1-C6 alkyl, nitro, amino, halogen and haloalkyl;
B is a cycloalkyl, aryl, or heterocycloalkyl ring wherein said heterocycloalkyl ring comprises one nitrogen;
$R^4$ is selected from the group consisting of: hydrogen, alkyl, aryl, arylalkyl and heteroaryl;
X is selected from the group consisting of: C=O, C—O-alkyl, and C—$NR^aR^b$,
$R^a$ and $R^b$ are independently selected from the group consisting of: hydrogen, alkyl, cycloalkane, aryl, arylalkyl, heteroaryl, heteroarylalkyl, acetyl, arylsulfonyl; wherein said alkyl, cycloalkane, aryl, arylalkyl, heteroaryl, heteroarylalkyl, acetyl or arylsulfonyl is optionally substituted with one or more substituents independently selected from: C1-C6 alkyl, nitro, amino, halogen and haloalkyl;
Y is absent or present and is selected from the group consisting of: hydrogen, alkyl, aryl and alkylamine; wherein when X is C—O-alkyl or C—$NR^aR^b$, Y is absent;
Q is a carbon or nitrogen atom, wherein when Q is a nitrogen atom, $R^3$ is absent;
n is 1;
m is 1;
or a pharmaceutically acceptable salt, tautomer, stereoisomer, deuterated derivative, thereof;
wherein the pathology is selected from the group consisting of: cystic fibrosis, limb-girdle muscular dystrophy (LGMD), congenital bilateral absence of vas deferens (CBAVD), acute, chronic, recurrent and/or autoimmune pancreatitis, disseminated bronchiectasis, asthma, allergic pulmonary aspergillosis, smoking-related lung pathology, dry eye syndrome, Sjogren's syndrome, chronic sinusitis, cholestatic jaundice, emphysema, idiopathic chronic pancreatitis, isolated obstructive azoospermia, sclerosing cholangitis, panbronchiolite, neonatal hypertripsinemia, adrenoleukodystrophy, Stargardt disease, Tangier disease, progressive familial intrahepatic cholestasis, Dubin-Johnson syndrome, elastic pseudoxantoma, persistent hyperinsulinemic hypoglycemia of infancy due to focal adenomatous hyperplasia, senile macular degeneration, retinitis pigmentosa and "cone-rod" retinal dystrophy.

2. The method according to claim 1, wherein $R^4$ is hydrogen.

3. The method according to claim 1, wherein B is a cycloalkyl or aryl ring.

4. The method according to claim 1, wherein n is 1 or 2.

5. The method according to claim 1, wherein A is a pentatomic aromatic heterocyclic ring comprising one or two nitrogen atoms.

6. The method according to claim 1, wherein X is C—O, C—OMe, C—$NH_2$ or C—$NHR^a$.

7. The method according to claim 1, wherein:
Q is a carbon atom, X is C—O and Y is hydrogen or alkyl, or
Q is a carbon atom, X is C—Oalkyl and Y is absent, or
Q is a nitrogen atom, X is C—$NR^aR^b$ and Y is absent.

8. The method according to claim 1 where the compound of formula (I) is selected from the group consisting of:

(II)

(III)

(IV)

-continued (V)
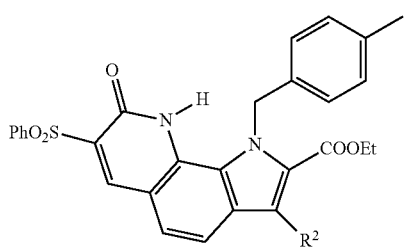

(VI)
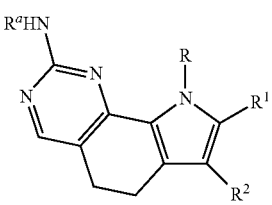

(VII)
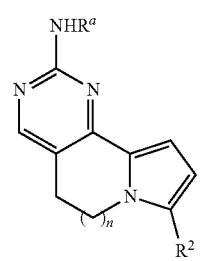

(VIII)
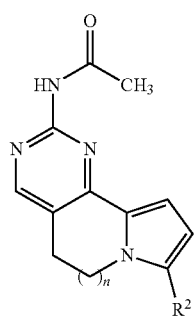

(IX)
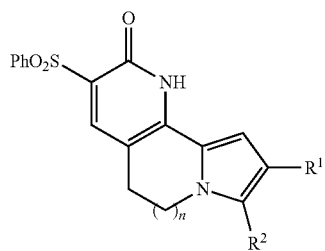

(X)
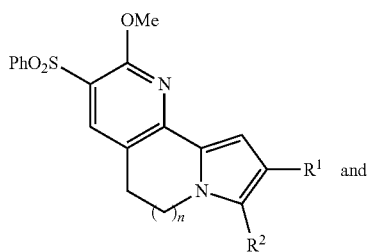
and

-continued (XI)
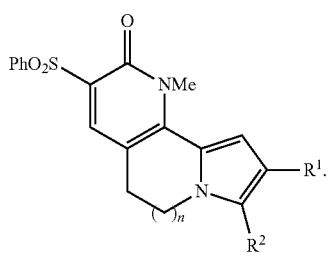

9. The method according to claim 1, wherein $R^1$ and/or $R^2$ is a carboxylic ester or a carboxamide from primary, secondary or tertiary amine.

10. The method according to claim 1, wherein $R^2$ is halogen.

11. The method according to claim 1, wherein $R^3$ is arylsulfonyl or $R^3$ is absent, Q is a nitrogen atom, X is C—$NR^aR^b$, $R^a$ is H and $R^b$ is arylsulfonyl.

12. The method according to claim 1, wherein the compound of formula (I) is selected from the group consisting of:

PP007
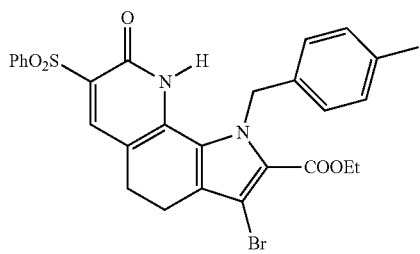

PP008
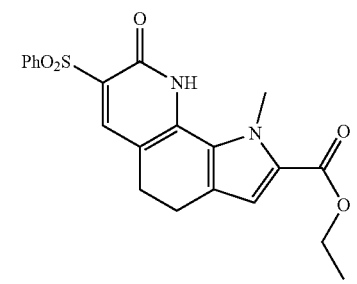

PP010
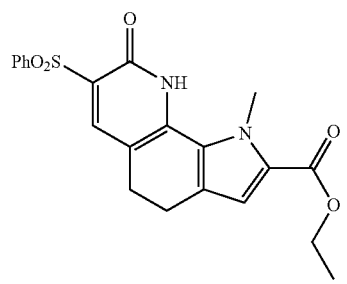

PP011
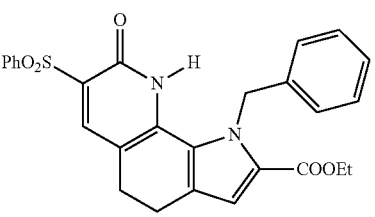

PP015
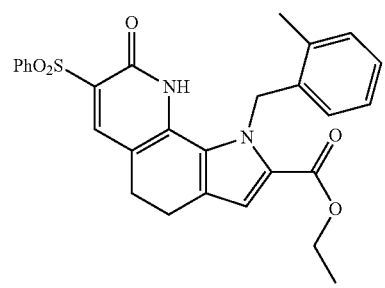
PP016
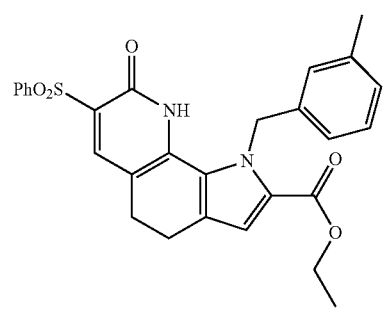
PP017
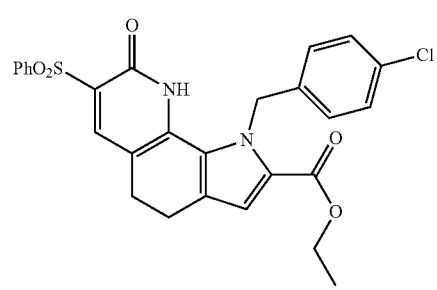
PP019
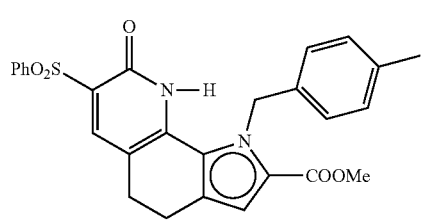
PP020
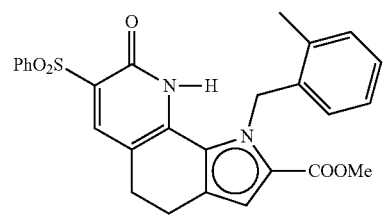
PP021
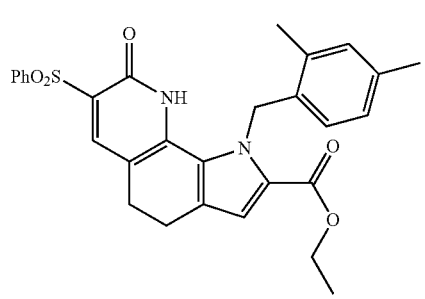
PP022
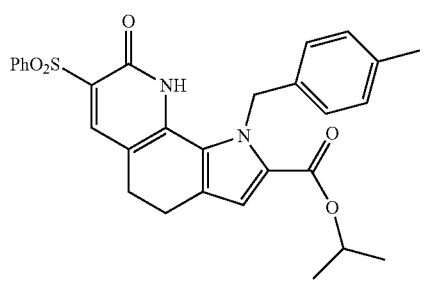
PP023
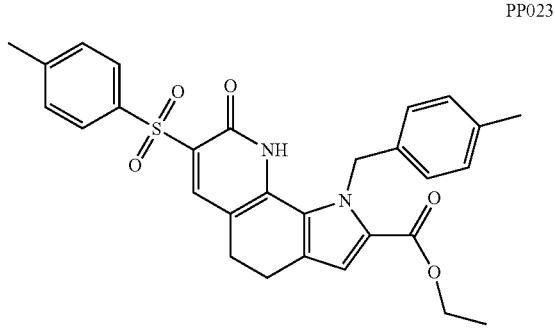
PP024
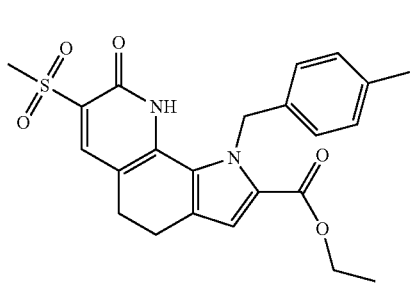
PP025
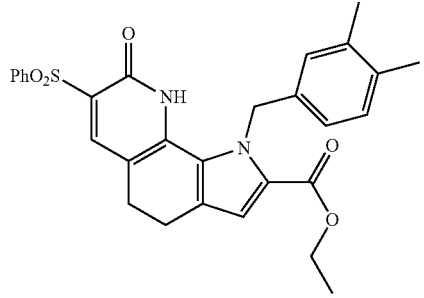
PP027
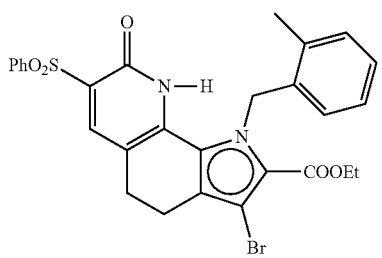

-continued
PP028
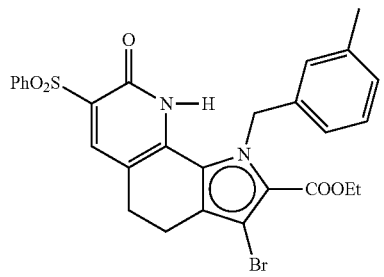
PP029
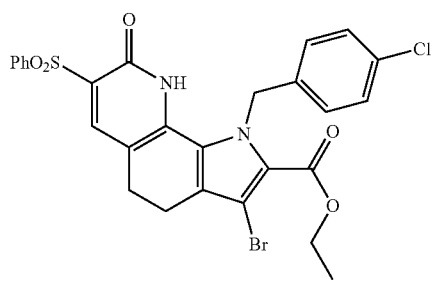
PP030
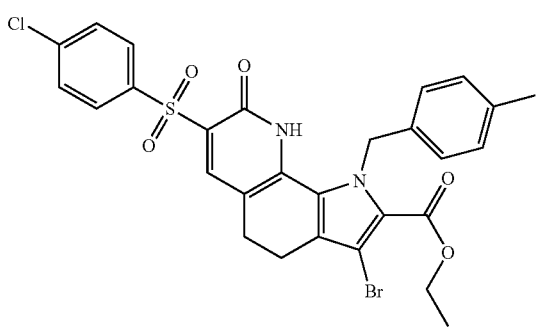
PP031
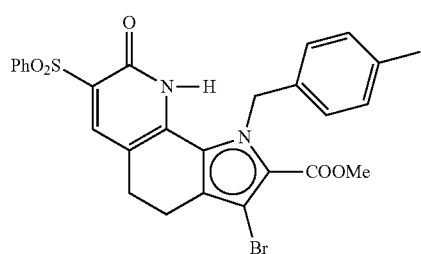
PP032
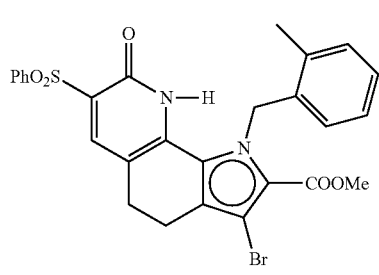
PP033
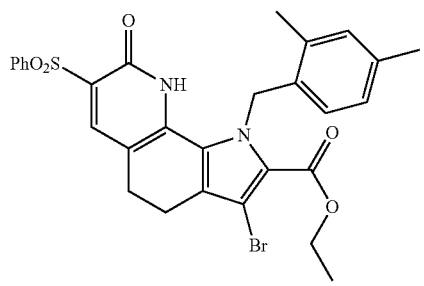
PP034
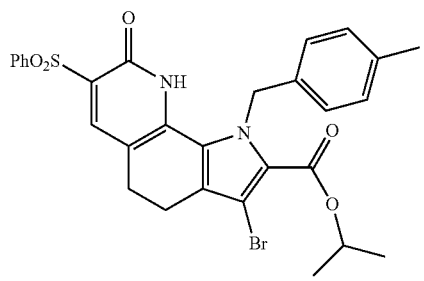
PP035
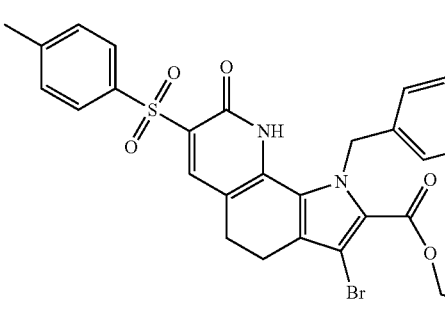
PP036
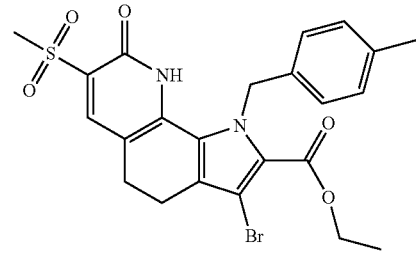
PP037
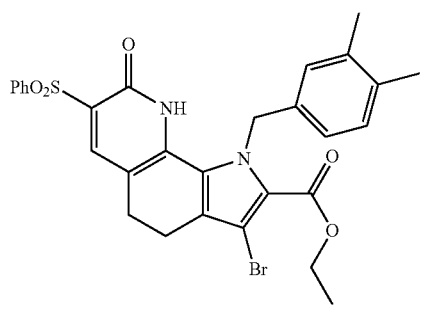

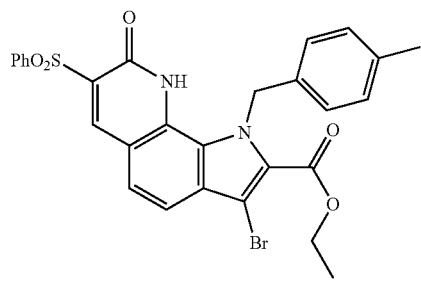
PP057
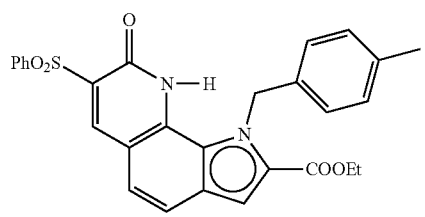
PP058
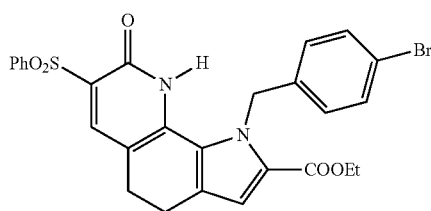
PP060
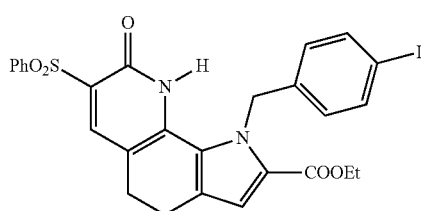
PP062
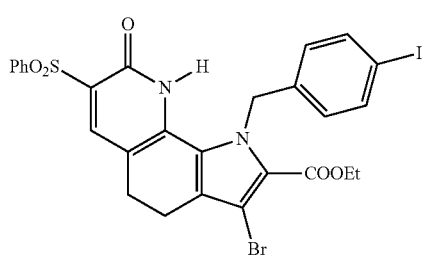
PP063
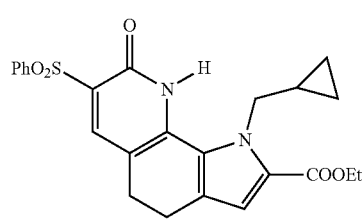
PP064
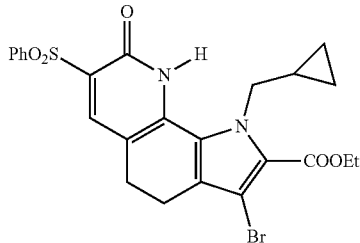
PP065
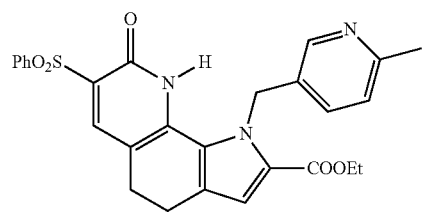
PP066
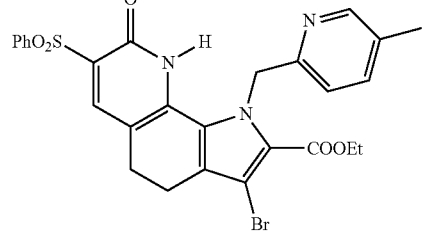
PP067
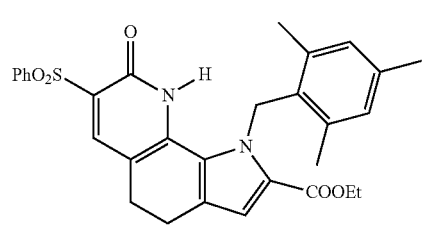
PP068
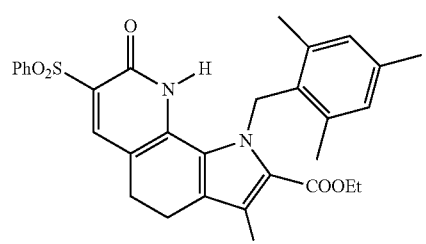
PP069
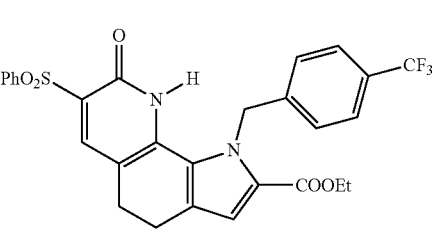
PP070

PP071 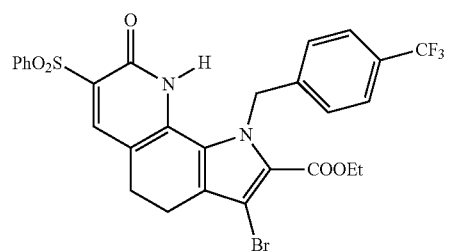
PP072 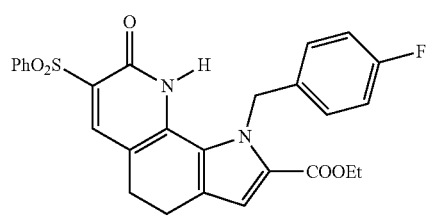
PP073 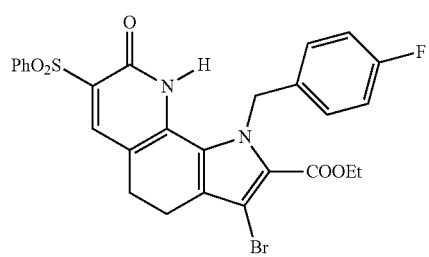
PP075 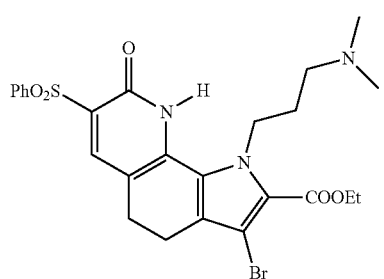
PP076 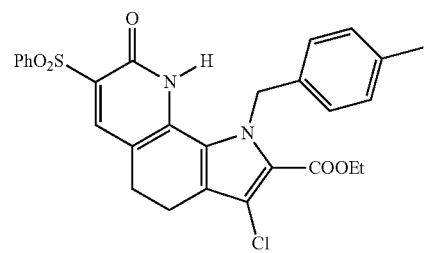
PP077 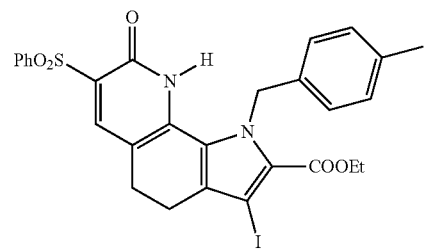
PP078 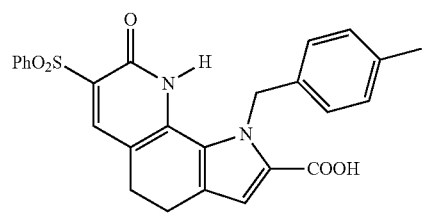
PP079 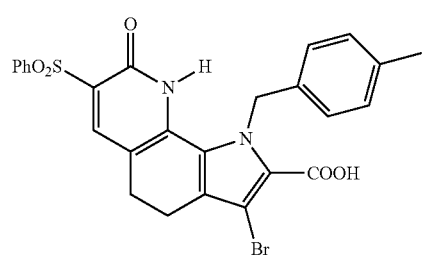
PP080 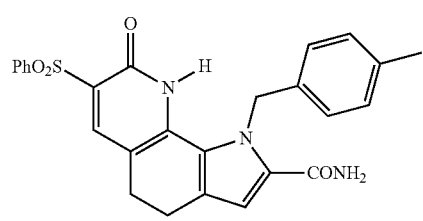
PP081 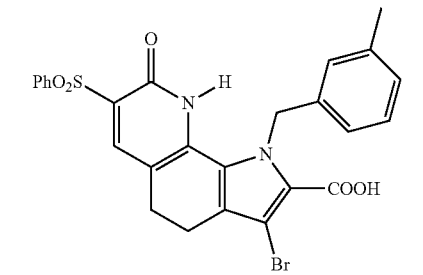
PP082 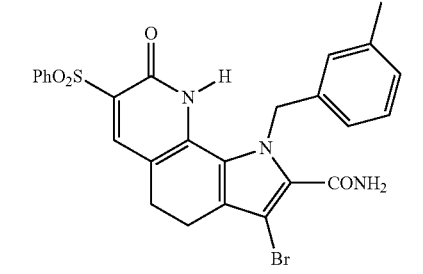
PP083 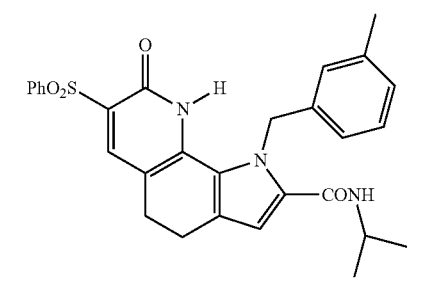

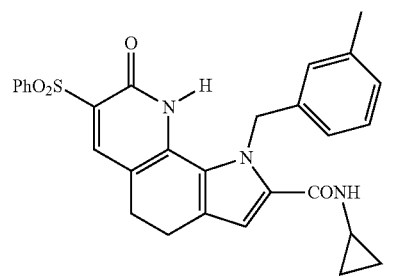
PP084
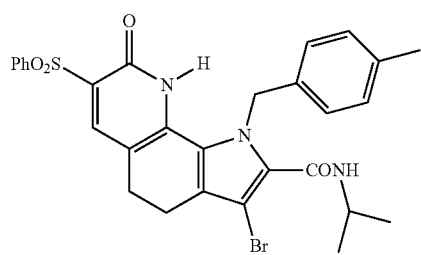
PP086
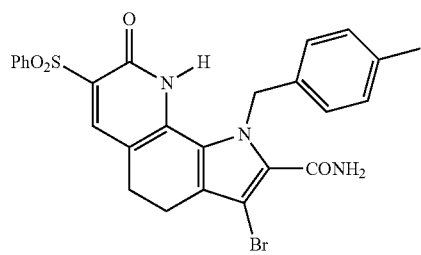
PP089
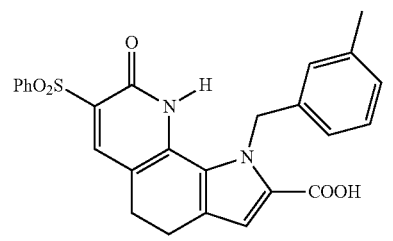
PP090
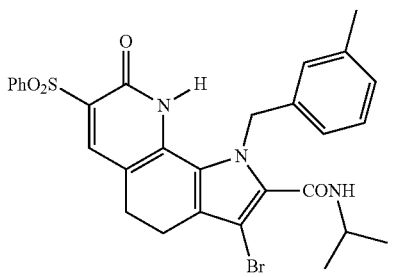
PP091
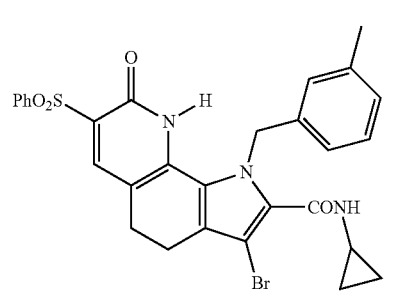
PP092
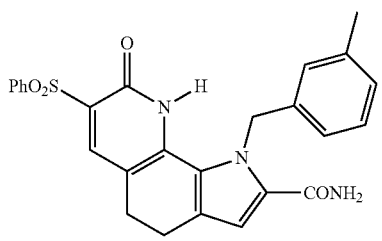
PP093
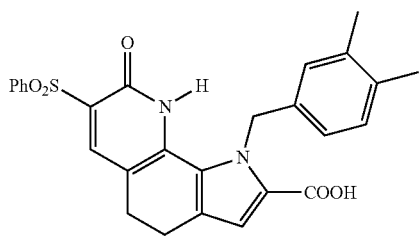
PP094
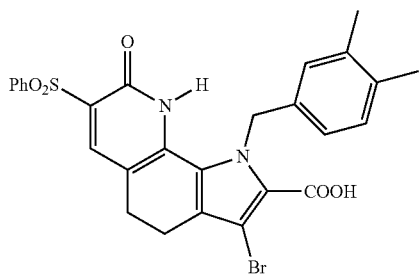
PP095
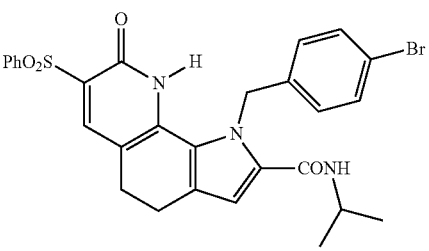
PP096
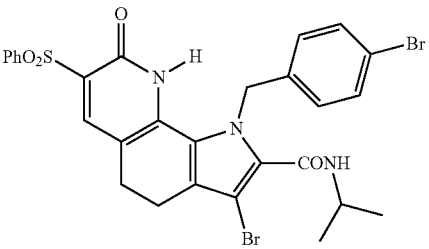
PP097
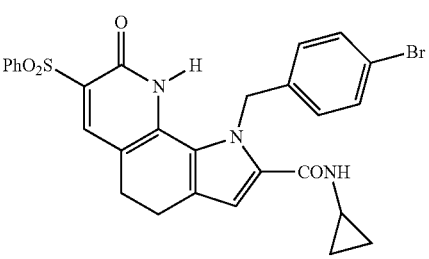
PP098

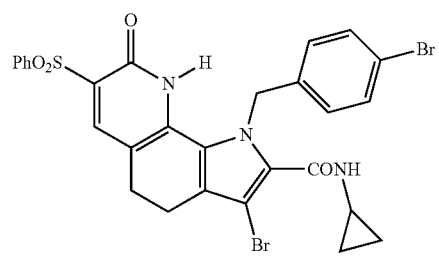
PP099
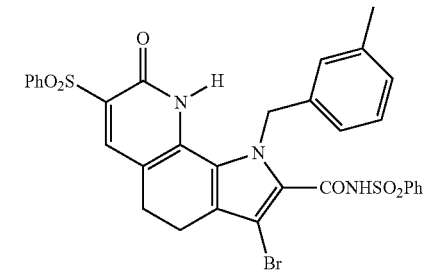
PP100
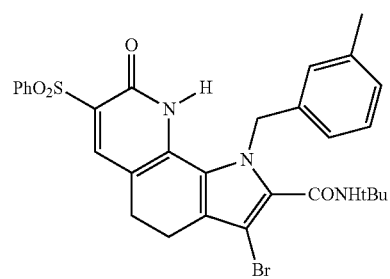
PP101
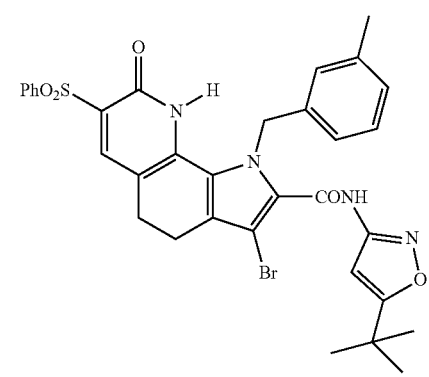
PP102
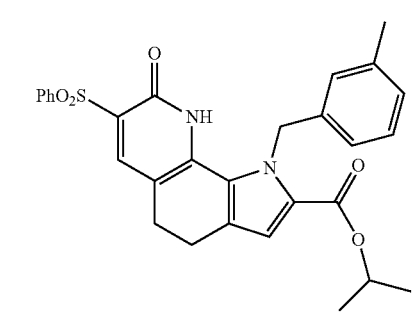
PP103
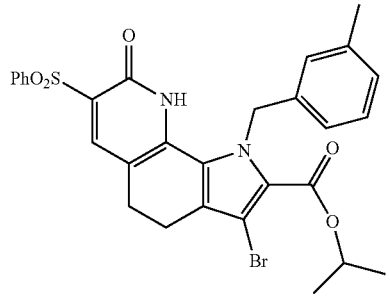
PP104
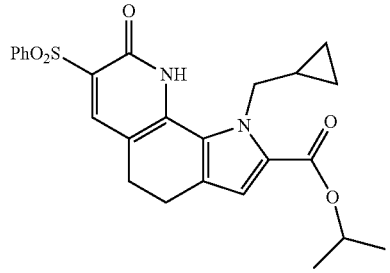
PP105
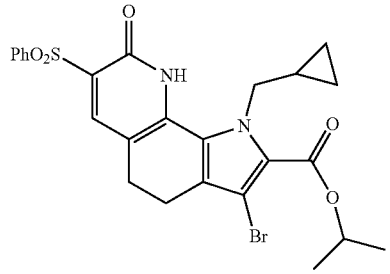
PP106
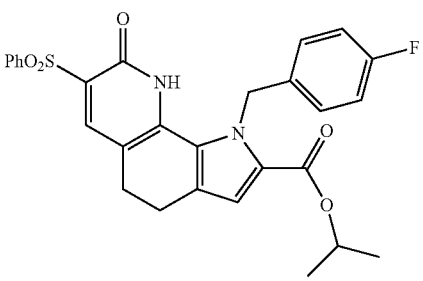
PP107
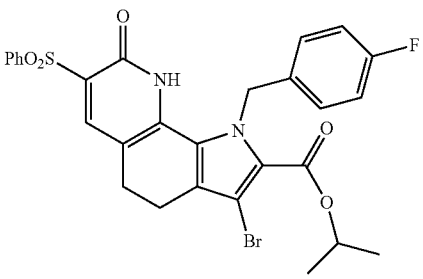
PP108

-continued
PP048
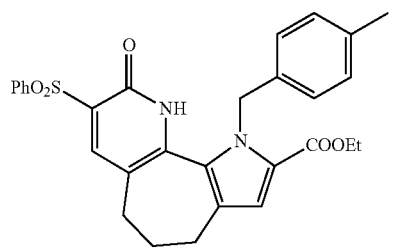
PP056
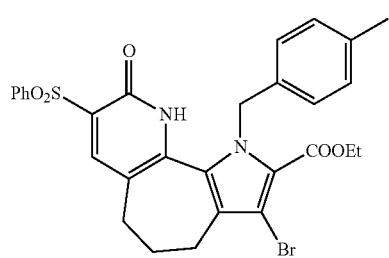
SVQ4
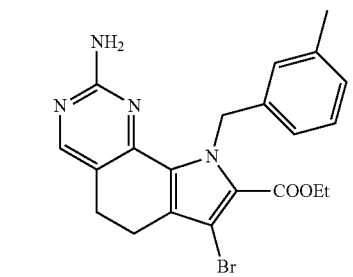
SVQ9
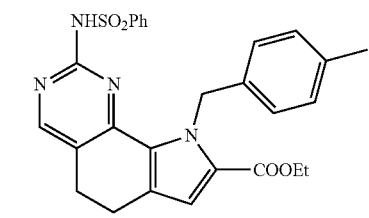
SVQ10
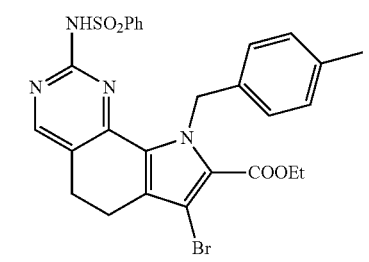
SVQ11
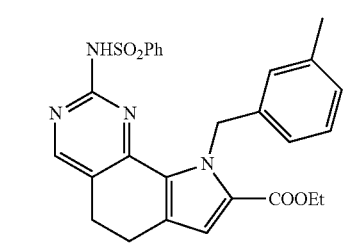
-continued
SVQ12
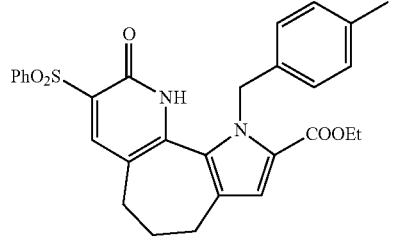
SVQ13
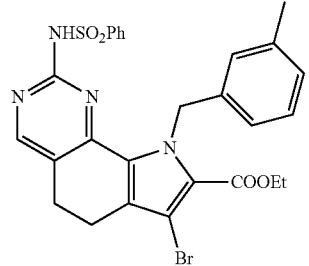
SVQ14
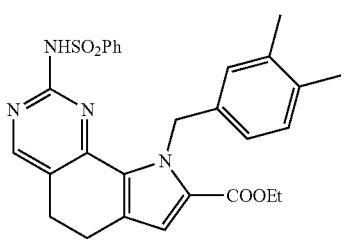
SVQ15
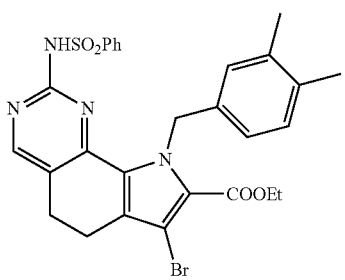
SVQ16
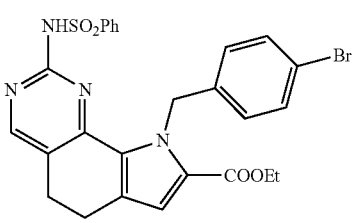
QZN2
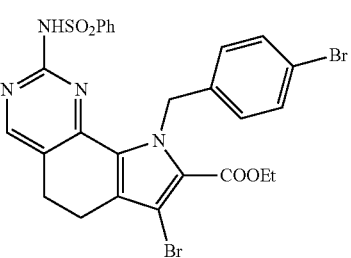

-continued
QZN5
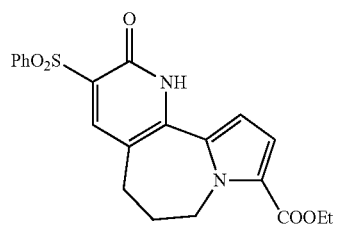
QZN6
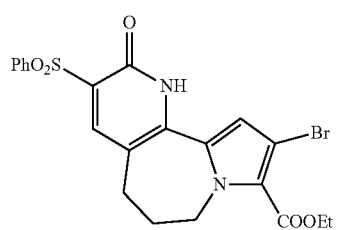
QZN10
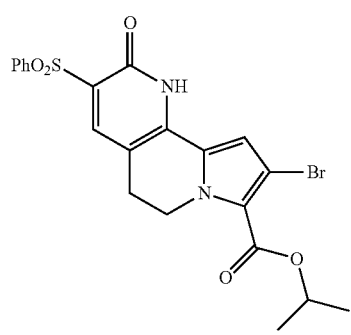
QZN13
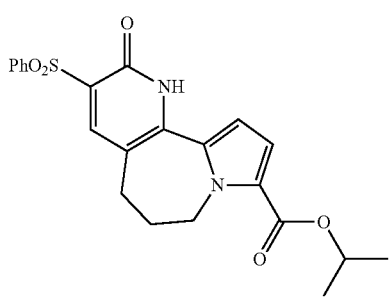
QZN14
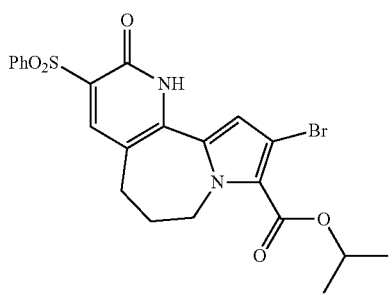
-continued
QZQ14
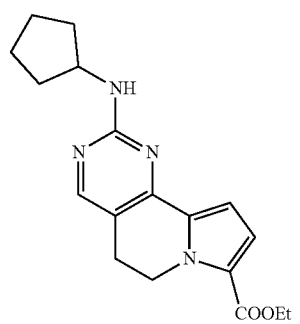
QZQ20
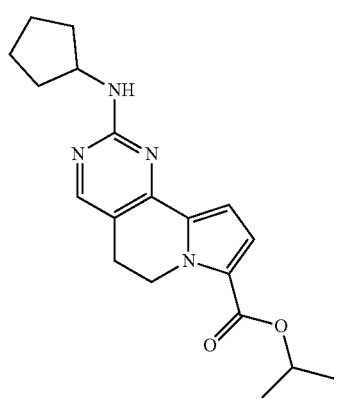
QZQ21
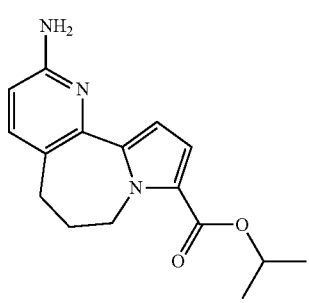
QZQ26
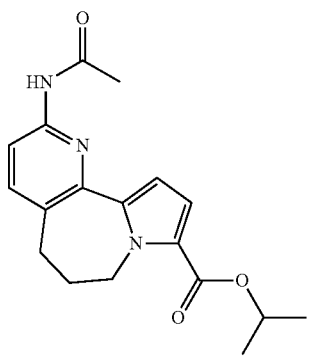
PZ1
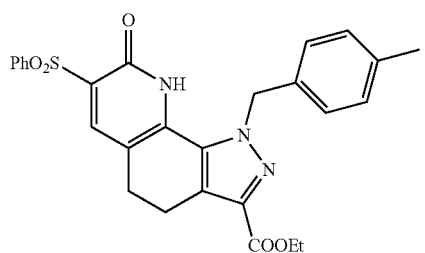

-continued

PZ3
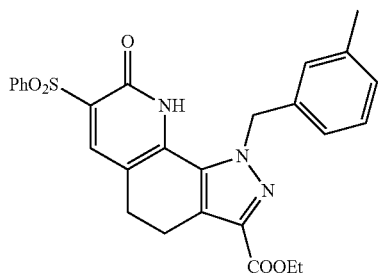

PZ5
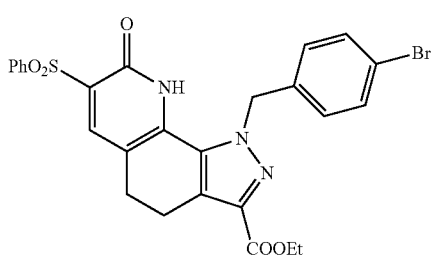

PZ7
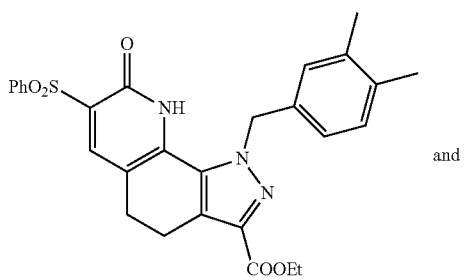
and

PZ8
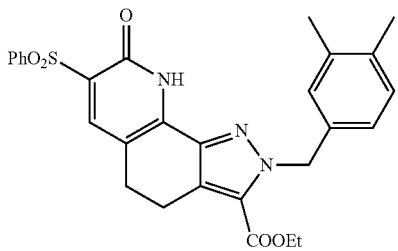

or a pharmaceutically acceptable salt, tautomer, stereoisomer, deuterated derivative, thereof.

13. The method according to claim 1, wherein said ABC (ATP-binding cassette) transporter is CFTR (Cystic Fibrosis Transmembrane conductance Regulator).

14. The method according to claim 1, wherein said pathology is cystic fibrosis.

15. The method according to claim 13, wherein the CFTR (Cystic Fibrosis Transmembrane conductance Regulator) protein bears the F508del mutation and/or the G542X premature stop codon mutation.

16. The method according to claim 3, wherein the cycloalkyl or aryl ring B is cyclohexyl, cycloheptyl or phenyl.

17. The method according to claim 5, wherein the pentatomic aromatic heterocyclic ring A is selected from the group consisting of:

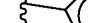

and

18. The method according to claim 1, wherein the pathology is smoking-related lung pathology and the smoking-related lung pathology is chronic obstructive pulmonary disease.

19. The method according to claim 1, wherein the defect in the ABC transporter is at least one of the following: protein mutation, protein misfolding, protein degradation, protein maturation, or protein trafficking.

* * * * *